US008518635B2

(12) United States Patent
Schwer et al.

(10) Patent No.: US 8,518,635 B2
(45) Date of Patent: Aug. 27, 2013

(54) REGULATION OF PROTEIN ACTIVITY BY REVERSIBLE ACETYLATION

(75) Inventors: Bjoern Schwer, Brookline, MA (US); Eric Verdin, San Francisco, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 445 days.

(21) Appl. No.: 11/761,198

(22) Filed: Jun. 11, 2007

(65) Prior Publication Data

US 2009/0061015 A1 Mar. 5, 2009

Related U.S. Application Data

(60) Provisional application No. 60/813,275, filed on Jun. 12, 2006.

(51) Int. Cl.
*C12Q 1/00* (2006.01)

(52) U.S. Cl.
USPC .............................................. 435/4; 435/7.72

(58) Field of Classification Search
USPC .................................................... 435/4, 7.72
See application file for complete search history.

(56) References Cited

U.S. PATENT DOCUMENTS

| | | | |
|---|---|---|---|
| 7,272,713 | B1 | 9/2007 | Verdin et al. |
| 7,351,542 | B2 | 4/2008 | Verdin et al. |
| 7,485,416 | B2 | 2/2009 | Ott et al. |
| 7,488,587 | B2 | 2/2009 | Verdin et al. |
| 2002/0120008 | A1 | 8/2002 | Benzer et al. |
| 2003/0082668 | A1 | 5/2003 | Tamal et al. |

FOREIGN PATENT DOCUMENTS

| | | |
|---|---|---|
| WO | WO 01/40506 | 6/2001 |
| WO | WO 02/102981 | 12/2002 |
| WO | WO 03/004621 | 1/2003 |
| WO | WO 03/099210 | 12/2003 |
| WO | WO 2004/065169 | 7/2004 |

OTHER PUBLICATIONS

Hallow et al. "Sirtuins deacetylate and activate mammalian acetyl-CoA synthetases", PNSA, 2006, 103(27):10230-10235.*

Nemoto et al "SIRT1 functionally interacts with the metabolic regulator and transcriptional coactivator PGC-1alpha", JBC, 2005, 280(16):16456-16460.*

Schwer, Bjoern et al.; "Reversible lysine acetylation controls the activity of the mitochondrial enzyme acetyl-CoA synthetase 2"; 2006, *PNAS,* vol. 103, No. 27, pp. 10224-10229.

Ait-Si-Ali S, et al. (1998) A rapid and sensitive assay for histone acetyl-transferase activity. Nucleic Acids Research 26: pp. 3869-3870.

Frye, RA (1999) Characterization of five human cDNAs with homology to the yeast SIR2 gene: Sir2-like proteins (Sirtuins) metabolize NAD and may have protein ADP-Ribosyltransferase activity. Biochemical and Biophysical Res Comm 260: 273-279.

Frye (2000) Biochem. Biophys. Res. Comm. 273:793-798.

Grozinger, Christina M. et al.; "Identification of a Class of Small Molecule Inhibitors of the Sirtuin Family of NAD-dependent Deacetylases by Phenotypic Screening"; 2001, *The Journal of Biochemical Chemistry,* vol. 276, No. 19, pp. 38837-38843.

Haigis MC et al (Sep. 8, 2006) SIRT4 inhibits glutamate dehydrogenase and opposes the effects of calorie restriction in pancreatic beta cells. Cell, vol. 126, pp. 941-954.

Imai S; Armstrong CM, Kaeberlein M, and Guarente L (2000) Transcriptional silencing and longevity protein Sir2 is an NAD-dependent histone deacetylase. Nature 403: pp. 795-800.

Landry J et al (May 23, 2000) The silencing protein SIR2 and its homologs are NAD-dependent protein deacetylases. Proc Natl Acad Sci, vol. 7, No. 11, pp. 5807-5811.

Landry et al., "Role of NAD+ in the Deacetylase Activity of the SIR2-like Proteins", Biochemical and Biophysical Research Communications, vol. 278, No. 3, (2000), pp. 685-690.

Moazed D (published online Mar. 7, 2001) Enzymatic activities of Sir2 and chromatin silencing. Curr Opin Cell Biol, vol. 13, pp. 232-238.

Onyango, Patrick et al.; "SIRT3, a human SIR2 homologue, is an NAD-dependent deacetylase localized to mitochondria"; 2002, *Proceedings of the National Academy of Science,* No. 99, No. 21, pp. 13653-13658.

Schwer et al., The human silent information regulator (Sir)2 homologue hSIRT3 is a mitochoncrial nicotinamide adenine dinucleotide-dependent deacetylase, Journal of Cell Biology, vol. 158, No. 4, (2002), pp. 647-657.

Sherman JM et al (Sep. 1999) The conserved core of a human SIR2 homologue functions in yeast silencing. Mol Biol Cell, vol. 10, pp. 3045-3059.

Shi, Tong et al.; "SIRT3, a Mitochondrial Sirtuin Deacetylase, Regulates Mitochondrial Function and Thermogenesis in Brown Adipocytes"; 2005, *The Journal of Biochemical Chemistry,* vol. 280, No. 14, pp. 13560-13567.

White DA, Belyaev ND, Turner BM (1999) Preparation of site-specific antibodies to acetylated histones. Methods 19: pp. 417-424.

Yang et al. (2000) Genomics 69:355-369.

Product Information: Histone from calf thymus Product No. H4380. Sigma online catalog, www.sigma-aldrich.com, 2006.

GenBank Accession No. NM_012239.

GenBank Accession No. AF083109.

Hallows, et al. Experimental Biology 2006: Meeting Abstracts, The FASEB Journal, Mar. 7, 2006, vol. 20, No. 5, pp. A959.

Michishita, et al., "Evolutionarily Conserved and Nonconserved Cellular Localizations and Functions of Human SIRT Proteins", 2005, Molecular Biology of the Cell, vol. 16, pp. 4623-4635.

* cited by examiner

*Primary Examiner* — Bin Shen

(74) *Attorney, Agent, or Firm* — Paula A. Borden; Bozicevic, Field & Francis LLP.

(57) ABSTRACT

This invention discloses the first cellular acetylated substrate protein of SIRT3, Acetyl-CoA synthetase 2 (AceCS2), which is a mitochondrial matrix protein. AceCS2 is reversibly acetylated at lysine 642 (Lys642) in the active site of the enzyme. The mitochondrial sirtuin SIRT3 interacts with AceCS2 and deacetylates Lys642 both in vitro and in vivo. Deacetylation of AceCS2 by SIRT3 activates the acetyl-CoA synthetase activity of AceCS2. Thus, a mammalian sirtuin directly controls the activity of a metabolic enzyme via reversible lysine acetylation. Modulators of the acetylation status or the activity of AceCS2 are useful for the treatment of pathological conditions, such as type II diabetes, hypercholesterolemia, hyperlipidemia, and obesity.

19 Claims, 7 Drawing Sheets

A.

B.

C.

A.

B.

A.

B.

SEQUENCE LISTING

```
<160> NUMBER OF SEQ ID NOS: 65

<210> SEQ ID NO 1
<211> LENGTH: 3
<212> TYPE: PRT
<213> ORGANISM: Homo sapiens

<400> SEQUENCE: 1

Ala Ala Ala
 1


<210> SEQ ID NO 2
<211> LENGTH: 3
<212> TYPE: PRT
<213> ORGANISM: Homo sapiens

<400> SEQUENCE: 2

Ala Ala Ala
 1


<210> SEQ ID NO 3
```

<211> LENGTH: 3
<212> TYPE: PRT
<213> ORGANISM: Homo sapiens

<400> SEQUENCE: 3

Ala Ala Ala
1

<210> SEQ ID NO 4
<211> LENGTH: 3
<212> TYPE: PRT
<213> ORGANISM: Homo sapiens

<400> SEQUENCE: 4

Ala Ala Ala
1

<210> SEQ ID NO 5
<211> LENGTH: 3
<212> TYPE: PRT
<213> ORGANISM: Homo sapiens

<400> SEQUENCE: 5

Ala Ala Ala
1

<210> SEQ ID NO 6
<211> LENGTH: 3
<212> TYPE: PRT
<213> ORGANISM: Homo sapiens

<400> SEQUENCE: 6

Ala Ala Ala
1

<210> SEQ ID NO 7
<211> LENGTH: 3
<212> TYPE: PRT
<213> ORGANISM: Homo sapiens

<400> SEQUENCE: 7

Ala Ala Ala
1

<210> SEQ ID NO 8
<211> LENGTH: 3
<212> TYPE: PRT
<213> ORGANISM: Homo sapiens

<400> SEQUENCE: 8

Ala Ala Ala
1

<210> SEQ ID NO 9
<211> LENGTH: 3
<212> TYPE: PRT
<213> ORGANISM: Homo sapiens

<400> SEQUENCE: 9

Ala Ala Ala
1

<210> SEQ ID NO 10
<211> LENGTH: 3
<212> TYPE: PRT
<213> ORGANISM: Homo sapiens

<400> SEQUENCE: 10

Ala Ala Ala
1

<210> SEQ ID NO 11
<211> LENGTH: 3
<212> TYPE: PRT
<213> ORGANISM: Homo sapiens

<400> SEQUENCE: 11

Ala Ala Ala
1

<210> SEQ ID NO 12
<211> LENGTH: 3
<212> TYPE: PRT
<213> ORGANISM: Homo sapiens

<400> SEQUENCE: 12

Ala Ala Ala
1

<210> SEQ ID NO 13
<211> LENGTH: 3
<212> TYPE: PRT
<213> ORGANISM: Homo sapiens

<400> SEQUENCE: 13

Ala Ala Ala
1

<210> SEQ ID NO 14
<211> LENGTH: 3
<212> TYPE: PRT
<213> ORGANISM: Homo sapiens

<400> SEQUENCE: 14

Ala Ala Ala
1

<210> SEQ ID NO 15
<211> LENGTH: 3
<212> TYPE: PRT
<213> ORGANISM: Homo sapiens

<400> SEQUENCE: 15

Ala Ala Ala
1

<210> SEQ ID NO 16
<211> LENGTH: 3
<212> TYPE: PRT
<213> ORGANISM: Homo sapiens

<400> SEQUENCE: 16

Ala Ala Ala
1

<210> SEQ ID NO 17
<211> LENGTH: 3
<212> TYPE: PRT
<213> ORGANISM: Homo sapiens

<400> SEQUENCE: 17

Ala Ala Ala
1

<210> SEQ ID NO 18
<211> LENGTH: 3
<212> TYPE: PRT
<213> ORGANISM: Homo sapiens

<400> SEQUENCE: 18

Ala Ala Ala
1

<210> SEQ ID NO 19
<211> LENGTH: 689
<212> TYPE: PRT
<213> ORGANISM: Homo sapiens

<400> SEQUENCE: 19

```
Met Ala Ala Arg Thr Leu Gly Arg Gly Val Gly Arg Leu Leu Gly Ser
 1              5                  10                  15

Leu Arg Gly Leu Ser Gly Gln Pro Ala Arg Pro Pro Cys Gly Val Ser
            20                  25                  30

Ala Pro Arg Arg Ala Ala Ser Gly Pro Ser Gly Ser Ala Pro Ala Val
        35                  40                  45

Ala Ala Ala Ala Ala Gln Pro Gly Ser Tyr Pro Ala Leu Ser Ala Gln
    50                  55                  60

Ala Ala Arg Glu Pro Ala Ala Phe Trp Gly Pro Leu Ala Arg Asp Thr
65                  70                  75                  80

Leu Val Trp Asp Thr Pro Tyr His Thr Val Trp Asp Cys Asp Phe Ser
                85                  90                  95

Thr Gly Lys Ile Gly Trp Phe Leu Gly Gly Gln Leu Asn Val Ser Val
            100                 105                 110

Asn Cys Leu Asp Gln His Val Arg Lys Ser Pro Glu Ser Val Ala Leu
        115                 120                 125

Ile Trp Glu Arg Asp Glu Pro Gly Thr Glu Val Arg Ile Thr Tyr Arg
    130                 135                 140

Glu Leu Leu Glu Thr Thr Cys Arg Leu Ala Asn Thr Leu Lys Arg His
145                 150                 155                 160

Gly Val His Arg Gly Asp Arg Val Ala Ile Tyr Met Pro Val Ser Pro
                165                 170                 175

Leu Ala Val Ala Ala Met Leu Ala Cys Ala Arg Ile Gly Ala Val His
            180                 185                 190

Thr Val Ile Phe Ala Gly Phe Ser Ala Glu Ser Leu Ala Gly Arg Ile
        195                 200                 205

Asn Asp Ala Lys Cys Lys Val Val Ile Thr Phe Asn Gln Gly Leu Arg
    210                 215                 220

Gly Gly Arg Val Val Glu Leu Lys Lys Ile Val Asp Glu Ala Val Lys
225                 230                 235                 240

His Cys Pro Thr Val Gln His Val Leu Val Ala His Arg Thr Asp Asn
                245                 250                 255

Lys Val His Met Gly Asp Leu Asp Val Pro Leu Glu Gln Glu Met Ala
            260                 265                 270

Lys Glu Asp Pro Val Cys Ala Pro Glu Ser Met Gly Ser Glu Asp Met
        275                 280                 285

Leu Phe Met Leu Tyr Thr Ser Gly Ser Thr Gly Met Pro Lys Gly Ile
    290                 295                 300

Val His Thr Gln Ala Gly Tyr Leu Leu Tyr Ala Ala Leu Thr His Lys
```

```
305                 310                 315                 320

Leu Val Phe Asp His Gln Pro Gly Asp Ile Phe Gly Cys Val Ala Asp
                325                 330                 335

Ile Gly Trp Ile Thr Gly His Ser Tyr Val Val Tyr Gly Pro Leu Cys
            340                 345                 350

Asn Gly Ala Thr Ser Val Leu Phe Glu Ser Thr Pro Val Tyr Pro Asn
        355                 360                 365

Ala Gly Arg Tyr Trp Glu Thr Val Glu Arg Leu Lys Ile Asn Gln Phe
    370                 375                 380

Tyr Gly Ala Pro Thr Ala Val Arg Leu Leu Leu Lys Tyr Gly Asp Ala
385                 390                 395                 400

Trp Val Lys Lys Tyr Asp Arg Ser Ser Leu Arg Thr Leu Gly Ser Val
                405                 410                 415

Gly Glu Pro Ile Asn Cys Glu Ala Trp Glu Trp Leu His Arg Val Val
            420                 425                 430

Gly Asp Ser Arg Cys Thr Leu Val Asp Thr Trp Trp Gln Thr Glu Thr
        435                 440                 445

Gly Gly Ile Cys Ile Ala Pro Arg Pro Ser Glu Glu Gly Ala Glu Ile
    450                 455                 460

Leu Pro Ala Met Ala Met Arg Pro Phe Phe Gly Ile Val Pro Val Leu
465                 470                 475                 480

Met Asp Glu Lys Gly Ser Val Val Glu Gly Ser Asn Val Ser Gly Ala
                485                 490                 495

Leu Cys Ile Ser Gln Ala Trp Pro Gly Met Ala Arg Thr Ile Tyr Gly
            500                 505                 510

Asp His Gln Arg Phe Val Asp Ala Tyr Phe Lys Ala Tyr Pro Gly Tyr
        515                 520                 525

Tyr Phe Thr Gly Asp Gly Ala Tyr Arg Thr Glu Gly Gly Tyr Tyr Gln
    530                 535                 540

Ile Thr Gly Arg Met Asp Asp Val Ile Asn Ile Ser Gly His Arg Leu
545                 550                 555                 560

Gly Thr Ala Glu Ile Glu Asp Ala Ile Ala Asp His Pro Ala Val Pro
                565                 570                 575

Glu Ser Ala Val Ile Gly Tyr Pro His Asp Ile Lys Gly Glu Ala Ala
            580                 585                 590

Phe Ala Phe Ile Val Val Lys Asp Ser Ala Gly Asp Ser Asp Val Val
        595                 600                 605

Val Gln Glu Leu Lys Ser Met Val Ala Thr Lys Ile Ala Lys Tyr Ala
    610                 615                 620

Val Pro Asp Glu Ile Leu Val Val Lys Arg Leu Pro Lys Thr Arg Ser
625                 630                 635                 640

Gly Lys Val Met Arg Arg Leu Leu Arg Lys Ile Ile Thr Ser Glu Ala
                645                 650                 655

Gln Glu Leu Gly Asp Thr Thr Thr Leu Glu Asp Pro Ser Ile Ile Ala
            660                 665                 670

Glu Ile Leu Ser Val Tyr Gln Lys Cys Lys Asp Lys Gln Ala Ala Ala
        675                 680                 685

Lys
```

<210> SEQ ID NO 20
<211> LENGTH: 682
<212> TYPE: PRT
<213> ORGANISM: Mus musculus

<400> SEQUENCE: 20

-continued

```
Met Ala Ala Arg Ser Leu Gly Ser Gly Val Gly Arg Leu Leu Arg Gly
 1               5                  10                  15

Leu Gln Gly Arg Ser Gly Gln Ser Gly Trp Ser Leu Ser Val Ser Arg
            20                  25                  30

Ser Thr Ala Thr Arg Leu Pro Gly Cys Val Pro Ala Ala Ala Gln Pro
        35                  40                  45

Gly Ser Tyr Pro Ala Leu Ser Ala Gln Ala Ala Gln Glu Pro Ala Ala
    50                  55                  60

Phe Trp Gly Pro Leu Ala Arg Asp Thr Leu Val Trp Asp Thr Pro Tyr
65                  70                  75                  80

His Thr Val Trp Asp Cys Asp Phe Arg Thr Gly Lys Ile Gly Trp Phe
                85                  90                  95

Leu Gly Gly Gln Leu Asn Val Ser Val Asn Cys Leu Asp Gln His Val
            100                 105                 110

Gln Lys Ser Pro Glu Thr Ile Ala Leu Ile Trp Glu Arg Asp Glu Pro
        115                 120                 125

Gly Thr Glu Val Arg Ile Thr Tyr Arg Glu Leu Leu Glu Thr Thr Cys
    130                 135                 140

Arg Leu Ala Asn Thr Leu Lys Arg His Gly Val His Arg Gly Asp Arg
145                 150                 155                 160

Val Ala Ile Tyr Met Pro Val Ser Pro Leu Ala Val Ala Ala Met Leu
                165                 170                 175

Ala Cys Ala Arg Ile Gly Ala Ile His Thr Val Val Phe Ala Gly Phe
            180                 185                 190

Ser Ala Glu Ser Leu Ala Gly Arg Ile Asn Asp Ala Lys Cys Lys Ala
        195                 200                 205

Val Ile Thr Phe Asn Gln Gly Leu Arg Gly Gly Arg Val Val Glu Leu
    210                 215                 220

Lys Lys Ile Val Asp Glu Ala Val Lys Ser Cys Pro Thr Val Gln His
225                 230                 235                 240

Val Leu Val Ala His Arg Thr Asp Thr Lys Val Pro Met Gly Ser Leu
                245                 250                 255

Asp Ile Pro Leu Glu Gln Glu Met Ala Lys Glu Ala Pro Val Cys Thr
            260                 265                 270

Pro Glu Ser Met Ser Ser Glu Asp Met Leu Phe Met Leu Tyr Thr Ser
        275                 280                 285

Gly Ser Thr Gly Thr Pro Lys Gly Leu Val His Thr Gln Ala Gly Tyr
    290                 295                 300

Leu Leu Tyr Ala Ala Met Thr His Lys Leu Val Phe Asp Tyr Gln Pro
305                 310                 315                 320

Gly Asp Val Phe Gly Cys Val Ala Asp Ile Gly Trp Ile Thr Gly His
                325                 330                 335

Ser Tyr Val Val Tyr Gly Pro Leu Cys Asn Gly Ala Thr Thr Val Leu
            340                 345                 350

Phe Glu Ser Thr Pro Val Tyr Pro Asp Ala Gly Arg Tyr Trp Glu Thr
        355                 360                 365

Val Gln Arg Leu Lys Ile Asn Gln Phe Tyr Gly Ala Pro Thr Ala Val
    370                 375                 380

Arg Leu Leu Leu Lys Tyr Gly Asp Ala Trp Val Lys Lys Tyr Asp Arg
385                 390                 395                 400

Ser Ser Leu Arg Thr Leu Gly Ser Val Gly Glu Pro Ile Asn His Glu
                405                 410                 415

Ala Trp Glu Trp Leu His Lys Val Val Gly Asp Gly Arg Cys Thr Leu
```

```
            420                 425                 430

Val Asp Thr Trp Trp Gln Thr Glu Thr Gly Gly Ile Cys Ile Ala Pro
        435                 440                 445

Arg Pro Ser Glu Asp Gly Ala Glu Ile Leu Pro Gly Met Ala Met Arg
    450                 455                 460

Pro Phe Phe Gly Ile Val Pro Val Leu Met Asp Glu Lys Gly Asn Val
465                 470                 475                 480

Leu Glu Gly Gly Asp Val Ser Gly Ala Leu Cys Ile Ser Gln Ala Trp
                485                 490                 495

Pro Gly Met Ala Arg Thr Ile Tyr Gly Asp His Gln Arg Phe Val Asp
            500                 505                 510

Ala Tyr Phe Arg Ala Tyr Pro Gly Tyr Tyr Phe Thr Gly Asp Gly Ala
        515                 520                 525

His Arg Thr Glu Gly Gly Tyr Tyr Gln Ile Thr Gly Arg Met Asp Asp
    530                 535                 540

Val Ile Asn Ile Ser Gly His Arg Leu Gly Thr Ala Glu Ile Glu Asp
545                 550                 555                 560

Ala Met Ala Asp His Pro Ala Val Pro Glu Thr Ala Val Ile Gly Tyr
                565                 570                 575

Pro His Asp Ile Lys Gly Glu Ala Ala Phe Ala Phe Ile Val Leu Lys
            580                 585                 590

Asp Asn Ile Ser Asp Glu Asn Met Val Val Asn Glu Leu Lys Leu Ser
        595                 600                 605

Val Ala Thr Lys Ile Ala Lys Tyr Ala Val Pro Asp Gln Ile Leu Val
    610                 615                 620

Val Lys Arg Leu Pro Lys Thr Arg Ser Gly Lys Val Met Arg Arg Leu
625                 630                 635                 640

Leu Arg Lys Ile Ile Thr Ser Arg Gly Gln Asp Leu Gly Asp Thr Thr
                645                 650                 655

Thr Leu Glu Asp Pro Ser Val Ile Thr Glu Ile Leu Ser Ala Phe Gln
            660                 665                 670

Lys Tyr Glu Glu Gln Arg Ala Ala Thr Asn
        675                 680


<210> SEQ ID NO 21
<211> LENGTH: 675
<212> TYPE: PRT
<213> ORGANISM: Bos taurus

<400> SEQUENCE: 21

Met Ala Ala Arg Cys Leu Gly Arg Gly Val Gly Arg Leu Leu Gly Gly
 1               5                  10                  15

Leu Arg Gly Val Gly Val Arg Ala Leu Ala Ala Pro Arg Leu Trp Ser
            20                  25                  30

Ser Ala Ser Ala Ser Val Ala Pro Pro Ser Ser Tyr Gln Glu Arg Ile
        35                  40                  45

Ala Leu Ala Ala Arg Glu Pro Ala Ala Phe Trp Gly Pro Leu Ala Arg
    50                  55                  60

Asp Ala Leu Val Trp Asp Thr Pro Tyr His Thr Val Ser Asp Cys Asp
65                  70                  75                  80

Phe Arg Ser Gly Arg Ile Ser Trp Phe Leu Gly Gly Gln Leu Asn Val
                85                  90                  95

Ser Val Asn Cys Leu Asp Gln His Val Gln Lys Ser Pro Glu Ser Ile
            100                 105                 110

Ala Leu Ile Trp Glu Arg Asp Glu Pro Gly Thr Glu Val Lys Ile Thr
```

-continued

```
        115                 120                 125

Tyr Arg Glu Leu Leu Glu Thr Thr Cys Arg Leu Ala Asn Thr Leu Lys
    130                 135                 140

Arg Tyr Gly Val Arg Arg Gly Asp Arg Val Ala Ile Tyr Met Pro Val
145                 150                 155                 160

Ser Pro Leu Ala Val Ala Ala Met Leu Ala Cys Ala Arg Ile Gly Ala
                165                 170                 175

Ile His Asn Val Ile Phe Ala Gly Phe Ser Val Gly Ser Leu Ala Gly
            180                 185                 190

Arg Ile Asn Asp Ala Gln Cys Lys Val Val Ile Thr Phe Asn Gln Gly
        195                 200                 205

Leu Arg Gly Gly Arg Val Val Gln Leu Lys Lys Ile Val Asp Glu Ala
    210                 215                 220

Ile Lys Val Cys Pro Ser Val Gln His Val Leu Val Ala His Arg Thr
225                 230                 235                 240

Asp Asn Lys Val His Met Gly His Leu Asp Val Ser Leu Glu Gln Glu
                245                 250                 255

Met Ala Lys Glu Glu Pro Val Cys Ala Pro Glu Ser Met Gly Ser Glu
            260                 265                 270

Asp Ile Leu Phe Leu Leu Tyr Thr Ser Gly Ser Thr Gly Lys Pro Lys
        275                 280                 285

Gly Leu Val His Thr Gln Ala Gly Tyr Leu Leu Tyr Ala Ala Leu Thr
    290                 295                 300

His Arg Leu Val Phe Asp Tyr Arg Pro Gly Asp Ile Phe Gly Cys Val
305                 310                 315                 320

Ala Asp Ile Gly Trp Ile Thr Gly His Ser Tyr Val Val Tyr Gly Pro
                325                 330                 335

Leu Cys Asn Gly Ala Thr Ser Val Leu Phe Glu Ser Thr Pro Val Tyr
            340                 345                 350

Pro Asp Ala Gly Arg Tyr Trp Glu Thr Val Gln Arg Leu Lys Ile Asn
        355                 360                 365

Gln Phe Tyr Gly Ala Pro Thr Ala Tyr Arg Leu Leu Leu Lys Phe Glu
    370                 375                 380

Asp Ser Trp Val Lys Lys Tyr Asp Arg Ser Ser Leu Arg Thr Leu Gly
385                 390                 395                 400

Ser Val Gly Glu Pro Ile Asn His Glu Ala Trp Glu Trp Leu His Arg
                405                 410                 415

Val Val Gly Asp Ser Arg Cys Thr Leu Val Asp Thr Trp Trp Gln Thr
            420                 425                 430

Glu Thr Gly Gly Ile Cys Ile Ser Pro Arg Pro Ser Glu Glu Gly Ala
        435                 440                 445

Glu Ile Leu Pro Cys Met Ala Met Arg Pro Leu Phe Gly Ile Val Pro
    450                 455                 460

Val Leu Met Asp Glu Lys Gly Asn Val Leu Glu Gly Gly Asp Val Ser
465                 470                 475                 480

Gly Ala Leu Cys Leu Ser Gln Ala Trp Pro Gly Met Ala Arg Thr Ile
                485                 490                 495

Tyr Gly Asp His Gln Arg Phe Leu Asp Ala Tyr Phe Glu Thr Tyr Pro
            500                 505                 510

Gly Tyr Tyr Phe Thr Gly Asp Gly Ala Tyr Arg Thr Glu Glu Gly Tyr
        515                 520                 525

Tyr Glu Ile Thr Gly Arg Met Asp Asp Val Ile Asn Ile Ser Gly His
    530                 535                 540
```

```
Arg Leu Gly Thr Ala Glu Ile Glu Asp Ala Met Ala Asp His Pro Ala
545                 550                 555                 560

Val Pro Glu Thr Ala Val Ile Gly Tyr Pro His Asp Ile Lys Gly Glu
                565                 570                 575

Ala Ala Phe Ala Phe Val Val Leu Lys Asp Asp Val Gly Asp Val Asp
            580                 585                 590

Val Val Val Lys Glu Leu Arg Ser Val Val Ala Asp Lys Ile Ala Lys
        595                 600                 605

Tyr Ala Val Pro Asp Gln Val Leu Val Val Lys Arg Leu Pro Lys Thr
    610                 615                 620

Arg Ser Gly Lys Val Met Arg Arg Leu Leu Arg Lys Ile Val Met Gly
625                 630                 635                 640

Arg Ala Gln Asp Leu Gly Asp Thr Thr Thr Leu Glu Asp Pro Gly Val
                645                 650                 655

Ile Thr Glu Ile Leu Ser Ala Tyr Gln Glu Tyr Lys Asp Lys Arg Gly
            660                 665                 670

Gly Ala Lys
        675


<210> SEQ ID NO 22
<211> LENGTH: 3649
<212> TYPE: DNA
<213> ORGANISM: Homo sapiens

<400> SEQUENCE: 22

gcactctggg agcacagaga gctcaggtag cctgcctaga tggcggcgcg caccctgggc     60

cgcggcgtcg ggaggctgct gggcagcctg cgagggctct cggggcagcc cgcgcggccg    120

ccgtgcgggg tgagcgcgcc gcgcagggcg gcctcgggac cctcgggcag cgctcccgca    180

gttgcagcag cagcagcaca gccaggctcg tatcccgcgc tgagtgcaca ggcagcccgg    240

gagccggccg ccttctgggg gcctctggcg cgggacactc tcgtgtggga caccccctac    300

cacaccgtct gggactgcga cttcagcact ggcaagatcg gctggttcct gggaggccag    360

ttaaatgtct ctgtcaactg cttggaccag catgttcgga agtcccccga gagcgttgct    420

ttgatctggg agcgcgatga gcctggaacg gaagtgagga tcacctacag ggaactactg    480

gagaccacgt gccgcctggc caacacgctg aagaggcatg gagtccaccg tggggaccgt    540

gttgccatct acatgcccgt gtccccattg gctgtggcag caatgctggc ctgtgccagg    600

atcggagctg tccacacagt catctttgct ggcttcagtg cggagtcctt ggctgggagg    660

atcaatgatg ccaagtgcaa ggtggttatc accttcaacc aaggactccg ggtgggcgc     720

gtggtggagc tgaagaaaat agtggatgag gctgtgaagc actgccccac cgtgcagcat    780

gtcctggtgg ctcacaggac agacaacaag gtccacatgg gggatctgga cgtcccgctg    840

gagcaggaaa tggccaagga ggaccctgtt tgcgccccag agagcatggg cagtgaggac    900

atgctcttca tgctgtacac ctcagggagc accggaatgc ccaagggcat cgtccatacc    960

caggcaggct acctgctcta tgccgccctg actcacaagc ttgtgtttga ccaccagcca   1020

ggtgacatct ttggctgtgt ggccgacatc ggttggatta caggacacag ctacgtggtg   1080

tatgggcctc tctgcaatgg tgccaccagc gtcctttttg agagcacccc agtttatccc   1140

aatgctggtc ggtactggga gacagtagag aggttgaaga tcaatcagtt ctatggcgcc   1200

ccaacggctg tccggctgtt gctgaaatac ggtgatgcct gggtgaagaa gtatgatcgc   1260

tcctccctgc ggaccctggg gtcagtggga gagcccatca actgtgaggc ctgggagtgg   1320

cttcacaggg tggtgggga cagcaggtgc acgctggtgg acacctggtg gcagacagaa    1380
```

-continued

```
acaggtggca tctgcatcgc accacggccc tcggaagaag gggcggaaat cctccctgcc   1440
atggcgatga ggcccttctt tggcatcgtc cccgtcctca tggatgagaa gggcagcgtc   1500
atggagggca gcaacgtctc cggggccctg tgcatctccc aggcctggcc gggcatggcc   1560
aggaccatct atggcgacca ccagcgattt gtggacgcct acttcaaggc ctacccaggc   1620
tattacttca ctggagacgg ggcttaccga actgagggcg gctattacca gatcacaggg   1680
cggatggatg atgtcatcaa catcagtggc caccggctgg ggaccgcaga gattgaggac   1740
gccatcgccg accaccctgc agtaccagaa agtgctgtca ttggctaccc ccacgacatc   1800
aaaggagaag ctgcctttgc cttcattgtg gtgaaagata gtgcgggtga ctcagatgtg   1860
gtggtgcagg agctcaagtc catggtggcc accaagatcg ccaaatatgc tgtgcctgat   1920
gagatcctgg tggtgaaacg tcttccaaaa accaggtctg ggaaggtcat gcggcggctc   1980
ctgaggaaga tcatcactag tgaggcccag gagctgggag acactaccac cttggaggac   2040
cccagcatca tcgcagagat cctgagtgtc taccagaagt gcaaggacaa gcaggctgct   2100
gctaagtgag ctggcacctt gtggggctct tgggatgggc gggcacccaa gccctggctt   2160
gtccttccca gaaggtaccc ctgaggttgg cgtcttccta cgtcccagaa gcagccccca   2220
ccccacacat gacccacacc gccctcacgt gaagctgggc tgagagccct ttctcccatc   2280
cattggaggt cccaggagtg tcacccatgg agaggctatg cgacatggct agggctggtt   2340
ctgccatctg agtttggttt cctggaatga aaaggcattg ccatctccat tcctctgccc   2400
tcttgagcca gcacaggaag gtgaggccct gggatagcgc gcctgctcag ataacacaga   2460
gctagttagc tagtagcaac cgtgttttct ccagatctgt ctagatacaa aggtcagaaa   2520
tcttattttt atacttttat attgtggaag aacagcatgc aacactcaca tgtagtgtgt   2580
ggatttactt gaacatgttc tttttaacat gtagttatga aaatctcctt ttttgcctct   2640
actggtgagg aaacatgagg atcagaggcc acatttttaa ttattgttag tgtatttgga   2700
agtctgaatt ggagatgttc gtacctctgt ctaaacagtt cccttgagaa cttccaagcc   2760
tccggcatct tttcctggtg agtgtttctc ctgtgcttgg ttgtgtataa tggagctaac   2820
tcctaagcgg tggggtgaat gtggccgcct tagttctgaa gctactccag ttatgttctg   2880
tttcttcaag ctgtgatcca gaaagatttt tgtgcccccca gatgcctctt gataggagag   2940
gcaacatact ccaaatagtt gggttcttca gggaagctat tagaaactca ggtgacttgt   3000
tagagcacta acttggtcag agccaaatcc tggcaaacgc tgcctgacct tcactctgtg   3060
gttggggcag tgagaaccac tgaggtccaa tgatgagact tggaggtctg gatccagtct   3120
ctctttgttt taatgtgact taggtgctgt caacattagc aagataatgg aaatcacgac   3180
gccagtgggt gcttacctcc ctgctaggca tgcaggggct ggcggttggc aggggaagga   3240
ggcccagtga gccgggtccc ttaggggagg gagagtttgt cctctttgcc ccacagtcta   3300
cccttcaggg ccttgtggca gtgccagtgt tcggggggtg tctgggccac tgagtaccca   3360
ctcggtcgtg gttgtgctgg cctcttgggt gagtgaacct gtgaagccca ggaggtggtg   3420
ttggctgcag ggtacacaaa tactgagtgg tggtcttttg ttacaggctt agcaacaaag   3480
ctgtgccctg ggcatggggg gctgtagtgt agctacagtt gtgcgtttgt gaaatggctt   3540
agctttccat gttgctgaga ggaacctgga catggtcccg ggcatctgaa tgatctgtag   3600
gggagggagt tcaaataaag ctttattttg ttcaaaaaaa aaaaaaaaa              3649
```

<210> SEQ ID NO 23
<211> LENGTH: 3584

-continued

<212> TYPE: DNA
<213> ORGANISM: Mus musculus

<400> SEQUENCE: 23

```
ggctaccgca cccgcgtggg gcgtcgggcg agatggcggc gcgcagcctc ggcagcggtg     60
tggggcgact gctgcgtggc ctgcaagggc gctctggaca atcggggtgg tcactgagcg    120
tgtcccgctc gaccgccacc cgactcccgg gctgcgttcc tgcagcagcg caaccaggct    180
cgtaccccgc gttgagcgct caggcagccc aggagccggc cgccttctgg gggccgctgg    240
cccgtgacac actagtttgg gacactcctt accatactgt ctgggactgt gacttcagga    300
cgggcaagat cggctggttc ctgggaggcc agttgaatgt gtctgtcaac tgcctggatc    360
agcatgtgca gaagtctcct gagaccatag ctttgatctg ggagagagat gaacctggga    420
cagaagtgag aatcacttac agggagcttc tggagaccac atgccgcctg gccaatacac    480
tgaagagaca tggagtgcac cgaggggacc gtgtggccat ctacatgcct gtgtccccac    540
tggctgtggc agcaatgctg gcctgtgcca ggattggagc tatccacaca gtggtatttg    600
ctggctttag tgcagagtcc ttggctggga ggatcaatga tgccaaatgc aaggctgtta    660
tcaccttcaa ccaaggactc aggggagggc gtgtggtgga gctgaagaaa atagtggatg    720
aagctgtgaa gagctgccca acagtccagc atgtcctggt ggctcacagg acggacacca    780
aggttcccat ggggagtctg gatatccccc ttgaacagga gatggccaag gaggcccctg    840
tttgcacccc tgagagcatg agcagtgaag acatgctctt tatgctctac acctcaggga    900
gcaccgggac acccaaggga ctcgttcata cacaggcagg ctatctactg tatgccgcca    960
tgacgcacaa gctcgtgttt gactaccagc caggtgatgt ctttggctgt gtggctgaca   1020
tcggttggat cacaggacac agctatgtgg tgtatggacc cctctgcaat ggagctacca   1080
cagtcctttt tgagagcacc ccagtttacc ctgatgctgg tcgttactgg gagacagtgc   1140
agaggctaaa gatcaaccag ttctatggtg ccccgacagc tgtccggctg ctgctgaagt   1200
atggggatgc ctgggtgaaa aagtatgacc gctcttccct gcgcacactg ggtcagtgg    1260
gagagcctat caaccacgaa gcctgggagt ggctccacaa agtcgtgggt gatggcagat   1320
gtacactggt ggacacttgg tggcaaacgg aaactggagg catctgcatt gcaccacggc   1380
cctcggaaga tggggcagag atcctcccgg gcatggccat gaggccgttt tttggcatcg   1440
ttcctgtact catggatgag aagggcaatg ttttggaggg tggagatgtc tctggggcct   1500
tgtgtatttc ccaagcttgg ccaggcatgg caaggaccat ctatggtgac caccagaggt   1560
tcgtagatgc ctacttcaga gcgtacccag gttattactt cactggagac ggagctcacc   1620
ggacagaggg tggctattac cagatcacgg ggcgcatgga tgatgtcatc aatatcagtg   1680
gtcatcgcct ggggactgca gagattgagg atgcaatggc tgaccatccc gctgttccag   1740
agactgctgt cattgggtac cctcatgata tcaaaggaga agctgcattt gccttcattg   1800
tgctgaaaga taacatcagt gatgagaaca tggtagtgaa tgaactcaaa ttgtcggtgg   1860
ccaccaagat cgccaagtat gctgtgcctg accagatcct ggtggtgaag cgtctcccca   1920
aaaccagatc tgggaaagtg atgaggagac tactgaggaa gatcatcacc agcaggggac   1980
aggatctagg ggacaccact accctggagg accccagcgt catcacagaa atcttgagtg   2040
ccttccagaa gtatgaagag cagcgggctg ctaccaactg agaggtgtgc ctctgtgttg   2100
ttcagacaag gctgcacagg accccctggac gtcctcaggg gaagcaactt caaaagtggc  2160
ttgtttcttc cgaacacatg acccatctac tgccctattt gaagctgaag cccctttttc   2220
tttctcctgg ggctcagagg gctgcttctg gaggctgggg gaaggccttt gtcatacatc   2280
```

tggtttccag aatcaagtca taattggcac taagccagca cagggtgacc agaggtctta 2340
gctccaaaac tgtcatgctt tctccagatg tgtttagata caaaacacaa attatttttt 2400
ttttgtactt tttctatttg gggagaatag cagaacattt gagtataatg tgaacattta 2460
gttacacaca cacacacaca cacacacaca cacacacaca ccgtgggaag aatctccctt 2520
cttacctccc caggggatga agataacaga atgcgctttt ttttaaaaat tttattacca 2580
ttcaatgtgc ttaaagtcca aaccagacat gtttgtgcct ctggcacata actctcctgc 2640
taatccaagt caccatgtcc aactcctgcg tctatttcat atttggttca tttggtttat 2700
tttatgatcg aacaaactgg acaattctta cattttgtat ggtaggaatt gcactcaggg 2760
cctcctgcac actaggcaag caagcgctct acctctgagc tgcacaccac acctctaact 2820
cccaagaaga cggagtgaat gtcctctcct ttacttgtga aatcatttgg gttcgtttct 2880
ctaagctgtg atctggaagg agtttctttc cccaaggtgc ctcatagtag gagatcatat 2940
tgcttcaaac gtgtgaggtt gttcatggta gccagtgaaa actcgggtgt ctttactaag 3000
cctctggtcc catctgaact gagatcctga agactctgcc tgtcctttct tttgtggttg 3060
gggcagcaag aactcactgt ggtccaatga cgatgacact tggtgctcct gagcaaggtc 3120
tcttttgatg tgccttaagt tctctggaca ttggtgagtg atgcaaatag tgaagtcatg 3180
aaaagcttat tttgcagcta gattgtggct aagcatggga gggctgaagg ggaggcagct 3240
ctgtgagcag ggcccctggg ggcaaaggaa gcctgttctg tctggtccac agaacttagc 3300
tatatgggtg tttcagggta tcttagctac tgcacactta ctgtctgtcc tgacgtcttg 3360
ggtaatgggg taaacatgct gacgctccca ggaggcggag cggttgtagt atgaacaaat 3420
cttaatagtc ctttgttaca atcagcagtg aagagccatg tgatggacgt ggctgagtat 3480
agttactgtg ccctttgaaa tggcctaggt ttctaggtta ctgatagaag ctctcggaat 3540
gatttataga aatatccaaa taaagcttta ttttgttcac tgtc 3584

<210> SEQ ID NO 24
<211> LENGTH: 2582
<212> TYPE: DNA
<213> ORGANISM: Bos taurus

<400> SEQUENCE: 24
atggcggcgc gctgcttggg ccgcggcgtc gggcggctac tgggcggcct ccgcggggtt 60
ggggtgcggg cgctggcggc cccccggctc tggagcagcg cctccgcctc cgtagcgcca 120
cccagctcct accaagagcg aatcgcgctt gcagctcgcg agcccgccgc cttctggggg 180
ccactggcgc gggacgctct cgtgtgggac accccttacc acacggtgag cgactgcgac 240
ttccgcagcg gcaggatcag ctggttcctg ggaggccagt taaacgtgtc tgtcaactgc 300
ttggatcagc acgttcagaa gtccccagag agcatcgctt tgatctggga gcgagatgag 360
cctggaactg aagtgaagat cacctacagg gagctactgg agaccacgtg ccgcctggcc 420
aacacactca agaggtatgg agtccgccga ggggaccgag tggccatcta catgcctgtc 480
tccccactgg ctgtggctgc catgctggcc tgtgccagga tcggagccat ccacaatgtc 540
atctttgctg gcttcagtgt ggggtccttg gctgggagga tcaacgatgc ccaatgcaag 600
gtggttatta ccttcaacca aggactccgg ggagggcgcg tggtgcagct gaagaagatc 660
gtggacgaag ccataaaggt ctgcccatcc gtccagcatg tcctggtggc tcacaggaca 720
gacaacaagg tccacatggg gcatctggat gtttcccttg agcaggagat ggccaaggag 780
gagccggtat gtgccccgga gagcatgggc agtgaggata tactcttcct cctgtacacc 840

-continued

```
tcggggagca ccgggaagcc caaggggctc gtccacaccc aggcgggtta cctgctctat    900
gctgccctga cgcaccggct tgtgtttgac taccggccag gtgacatctt cggctgcgtg    960
gctgatatcg gctggatcac gggacacagc tatgtggtgt acgggcccct ctgcaatgga   1020
gcgaccagtg tcctttttga gagcactccg gtttaccctg atgcgggtcg gtactgggag   1080
acggtgcaga ggctgaagat caatcagttc tatggcgccc cgacagccta ccggctgctg   1140
ctgaagttcg aggactcctg ggtgaagaag tatgaccgct cttctctgcg gaccctgggc   1200
tcagtgggag agccgatcaa ccacgaggcc tgggaatggc tgcacagggt ggtgggggac   1260
agccggtgca cgctggtaga cacctggtgg cagacagaaa cgggggggcat ctgcatctct   1320
ccacggccct cagaggaggg ggcagagatc ctgccctgca tggcgatgag gcccctgttt   1380
ggcattgttc ccgttctcat ggatgagaag ggaaatgtcc tggagggcgg agacgtgtct   1440
ggggctctgt gcctgtccca ggcctggccg ggcatggccc ggaccatcta cggagaccac   1500
cagcgattcc tggacgccta cttcgagacc taccctggct actacttcac aggagacggg   1560
gcttacagaa cagaggaggg ctactacgag atcactgggc gcatggacga cgttatcaac   1620
atcagtggcc accggctggg gaccgcggag attgaggacg ccatggctga ccaccccgcg   1680
gtgcccgaga ccgctgtcat tggctacccg catgacatca agggagaagc tgccttcgcc   1740
ttcgttgtgt tgaaagatga tgtgggtgat gtggacgtgg tggtgaagga gctccggtca   1800
gtggtggccg acaagatcgc caagtacgca gtgcccgatc aggtcctggt agtgaagcgt   1860
cttccaaaaa ctcggtctgg aaaagtcatg cggaggctcc tgaggaagat tgtcatgggc   1920
cgagctcagg acctggggga caccaccacc ctggaggacc ctggcgtcat cacggagatc   1980
ctgagtgcct accaggagta caaagacaag cggggaggtg ccaagtgatg gctctgctga   2040
gaccaggccc ctaatgcgtg ctcctagagc acagctcccg agtcggcttg ttcctagaca   2100
ccccagcaga acccaggctg ccctcctcgc gaagcctgaa gtccccgcct cccctcctgg   2160
ggacccacga caggtcctcg cccagggcga gcttcctccc gcttgtcccg aatctggttt   2220
cctggtgaaa agtccatccc cctgtcccct tgacagcaca ggaaggtgga gcccctgtgt   2280
ctgctcaggt ggactgggag caaacagcag tcatgtttcc tccagatgtt tctagaaaca   2340
aaaggtgaag attttatttt tatactttta tattttagaa gaaacatggt gcccacacac   2400
gtgcagtgta tgctgtactt gtacacactc ttcttaacag ttatgaaaag ctcctttttt   2460
gcctccgctc gtggggaagt gtggcgggct ggagggtgca atttgggtta ctgtttggct   2520
tgttggaaat ttaagttgga aatgtttgtg cctctgtctt aacacagcta tcttgaaacc   2580
tc                                                                  2582
```

<210> SEQ ID NO 25
<211> LENGTH: 503
<212> TYPE: PRT
<213> ORGANISM: Saccharomyces cerevisiae

<400> SEQUENCE: 25

```
Met Asn Ile Leu Leu Met Gln Arg Ile Val Ser Phe Ile Leu Val Val
 1               5                  10                  15

Ser Gln Gly Arg Tyr Phe His Val Gly Glu Leu Thr Met Thr Met Leu
            20                  25                  30

Lys Arg Pro Gln Glu Glu Glu Ser Asp Asn Asn Ala Thr Lys Lys Leu
        35                  40                  45

Lys Thr Arg Leu Thr Tyr Pro Cys Ile Leu Gly Lys Asp Lys Val Thr
    50                  55                  60
```

```
Gly Lys Phe Ile Phe Pro Ala Ile Thr Lys Asp Asp Val Met Asn Ala
65                  70                  75                  80

Arg Leu Phe Leu Lys Asp Asn Asp Leu Lys Thr Phe Leu Glu Tyr Phe
                85                  90                  95

Leu Pro Val Glu Val Asn Ser Ile Tyr Ile Tyr Phe Met Ile Lys Leu
            100                 105                 110

Leu Gly Phe Asp Val Lys Asp Lys Glu Leu Phe Met Ala Leu Asn Ser
        115                 120                 125

Asn Ile Thr Ser Asn Lys Glu Arg Ser Ser Ala Glu Leu Ser Ser Ile
    130                 135                 140

His Ala Lys Ala Glu Asp Glu Asp Glu Leu Thr Asp Pro Leu Glu Lys
145                 150                 155                 160

Lys His Ala Val Lys Leu Ile Lys Asp Leu Gln Lys Ala Ile Asn Lys
                165                 170                 175

Val Leu Ser Thr Arg Leu Arg Leu Pro Asn Phe Asn Thr Ile Asp His
            180                 185                 190

Phe Thr Ala Thr Leu Arg Asn Ala Lys Lys Ile Leu Val Leu Thr Gly
        195                 200                 205

Ala Gly Val Ser Thr Ser Leu Gly Ile Pro Asp Phe Arg Ser Ser Glu
    210                 215                 220

Gly Phe Tyr Ser Lys Ile Arg His Leu Gly Leu Glu Asp Pro Gln Asp
225                 230                 235                 240

Val Phe Asn Leu Asp Ile Phe Leu Gln Asp Pro Ser Val Phe Tyr Asn
                245                 250                 255

Ile Ala His Met Val Leu Pro Pro Glu Asn Met Tyr Ser Pro Leu His
            260                 265                 270

Ser Phe Ile Lys Met Leu Gln Asp Lys Gly Lys Leu Leu Arg Asn Tyr
        275                 280                 285

Thr Gln Asn Ile Asp Asn Leu Glu Ser Tyr Ala Gly Ile Asp Pro Asp
    290                 295                 300

Lys Leu Val Gln Cys His Gly Ser Phe Ala Thr Ala Ser Cys Val Thr
305                 310                 315                 320

Cys His Trp Gln Ile Pro Gly Glu Lys Ile Phe Glu Asn Ile Arg Asn
                325                 330                 335

Leu Glu Leu Pro Leu Cys Pro Tyr Cys Tyr Gln Lys Arg Lys Gln Tyr
            340                 345                 350

Phe Pro Met Ser Asn Gly Asn Asn Thr Val Gln Thr Asn Ile Asn Phe
        355                 360                 365

Asn Ser Pro Ile Leu Lys Ser Tyr Gly Val Leu Lys Pro Asp Met Thr
    370                 375                 380

Phe Phe Gly Glu Ala Leu Pro Ser Arg Phe His Lys Thr Ile Arg Lys
385                 390                 395                 400

Asp Ile Leu Glu Cys Asp Leu Leu Ile Cys Ile Gly Thr Ser Leu Lys
                405                 410                 415

Val Ala Pro Val Ser Glu Ile Val Asn Met Val Pro Ser His Val Pro
            420                 425                 430

Gln Ile Leu Ile Asn Arg Asp Met Val Thr His Ala Glu Phe Asp Leu
        435                 440                 445

Asn Leu Leu Gly Phe Cys Asp Asp Val Ala Ser Leu Val Ala Lys Lys
    450                 455                 460

Cys His Trp Asp Ile Pro His Lys Lys Trp Gln Asp Leu Lys Lys Ile
465                 470                 475                 480

Asp Tyr Asn Cys Thr Glu Ile Asp Lys Gly Thr Tyr Lys Ile Lys Lys
```

```
                485                 490                 495

Gln Pro Arg Lys Lys Gln Gln
            500


<210> SEQ ID NO 26
<211> LENGTH: 607
<212> TYPE: PRT
<213> ORGANISM: Caenorhabditis elegans

<400> SEQUENCE: 26

Met Ser Arg Asp Ser Gly Asn Asp Ser Glu Val Ala Val Thr His Gly
 1               5                  10                  15

Glu Val Gln Glu Ile Thr Glu Glu Asn Pro Glu Ile Gly Ser Met His
            20                  25                  30

Ile Thr Gln Glu Thr Asp Ile Ser Asp Ala Pro Glu Thr Asn Thr Asp
        35                  40                  45

Ser Ser Arg Gln Arg Thr Glu Ser Thr Thr Ser Val Ser Ser Glu Ser
    50                  55                  60

Trp Gln Asn Asn Asp Glu Met Met Ser Asn Leu Arg Arg Ala Gln Arg
65                  70                  75                  80

Leu Leu Asp Asp Gly Ala Thr Pro Leu Gln Ile Ile Gln Gln Ile Phe
                85                  90                  95

Pro Asp Phe Asn Ala Ser Arg Ile Ala Thr Met Ser Glu Asn Ala His
            100                 105                 110

Phe Ala Ile Leu Ser Asp Leu Leu Glu Arg Ala Pro Val Arg Gln Lys
        115                 120                 125

Leu Thr Asn Tyr Asn Ser Leu Ala Asp Ala Val Glu Leu Phe Lys Thr
    130                 135                 140

Lys Lys His Ile Leu Val Leu Thr Gly Ala Gly Val Ser Val Ser Cys
145                 150                 155                 160

Gly Ile Pro Asp Phe Arg Ser Lys Asp Gly Ile Tyr Ala Arg Leu Arg
                165                 170                 175

Ser Glu Phe Pro Asp Leu Pro Asp Pro Thr Ala Met Phe Asp Ile Arg
            180                 185                 190

Tyr Phe Arg Glu Asn Pro Ala Pro Phe Tyr Asn Phe Ala Arg Glu Ile
        195                 200                 205

Phe Pro Gly Gln Phe Val Pro Ser Val Ser His Arg Phe Ile Lys Glu
    210                 215                 220

Leu Glu Thr Ser Gly Arg Leu Leu Arg Asn Tyr Thr Gln Asn Ile Asp
225                 230                 235                 240

Thr Leu Glu His Gln Thr Gly Ile Lys Arg Val Val Glu Cys His Gly
                245                 250                 255

Ser Phe Ser Lys Cys Thr Cys Thr Arg Cys Gly Gln Lys Tyr Asp Gly
            260                 265                 270

Asn Glu Ile Arg Glu Glu Val Leu Ala Met Arg Val Ala His Cys Lys
        275                 280                 285

Arg Cys Glu Gly Val Ile Lys Pro Asn Ile Val Phe Phe Gly Glu Asp
    290                 295                 300

Leu Gly Arg Glu Phe His Gln His Val Thr Glu Asp Lys His Lys Val
305                 310                 315                 320

Asp Leu Ile Val Val Ile Gly Ser Ser Leu Lys Val Arg Pro Val Ala
                325                 330                 335

Leu Ile Pro His Cys Val Asp Lys Asn Val Pro Gln Ile Leu Ile Asn
            340                 345                 350

Arg Glu Ser Leu Pro His Tyr Asn Ala Asp Ile Glu Leu Leu Gly Asn
```

```
        355                 360                 365

Cys Asp Asp Ile Ile Arg Asp Ile Cys Phe Ser Leu Gly Gly Ser Phe
    370                 375                 380

Thr Glu Leu Ile Thr Ser Tyr Asp Ser Ile Met Glu Gln Gln Gly Lys
385                 390                 395                 400

Thr Lys Ser Gln Lys Pro Ser Gln Asn Lys Arg Gln Leu Ile Ser Gln
                405                 410                 415

Glu Asp Phe Leu Asn Ile Cys Met Lys Glu Lys Arg Asn Asp Asp Ser
            420                 425                 430

Ser Asp Glu Pro Thr Leu Lys Lys Pro Arg Met Ser Val Ala Asp Asp
        435                 440                 445

Ser Met Asp Ser Glu Lys Asn Asn Phe Gln Glu Ile Gln Lys His Lys
    450                 455                 460

Ser Glu Asp Asp Asp Asp Thr Arg Asn Ser Asp Asp Ile Leu Lys Lys
465                 470                 475                 480

Ile Lys His Pro Arg Leu Leu Ser Ile Thr Glu Met Leu His Asp Asn
                485                 490                 495

Lys Cys Val Ala Ile Ser Ala His Gln Thr Val Phe Pro Gly Ala Glu
            500                 505                 510

Cys Ser Phe Asp Leu Glu Thr Leu Lys Leu Val Arg Asp Val His His
        515                 520                 525

Glu Thr His Cys Glu Ser Ser Cys Gly Ser Ser Cys Ser Ser Asn Ala
    530                 535                 540

Asp Ser Glu Ala Asn Gln Leu Ser Arg Ala Gln Ser Leu Asp Asp Phe
545                 550                 555                 560

Val Leu Ser Asp Glu Asp Arg Lys Asn Thr Ile His Leu Asp Leu Gln
                565                 570                 575

Arg Ala Asp Ser Cys Asp Gly Asp Phe Gln Tyr Glu Leu Ser Glu Thr
            580                 585                 590

Ile Asp Pro Glu Thr Phe Ser His Leu Cys Glu Glu Met Arg Ile
        595                 600                 605


<210> SEQ ID NO 27
<211> LENGTH: 747
<212> TYPE: PRT
<213> ORGANISM: Homo sapiens

<400> SEQUENCE: 27

Met Ala Asp Glu Ala Ala Leu Ala Leu Gln Pro Gly Gly Ser Pro Ser
 1               5                  10                  15

Ala Ala Gly Ala Asp Arg Glu Ala Ala Ser Ser Pro Ala Gly Glu Pro
            20                  25                  30

Leu Arg Lys Arg Pro Arg Arg Asp Gly Pro Gly Leu Glu Arg Ser Pro
        35                  40                  45

Gly Glu Pro Gly Gly Ala Ala Pro Glu Arg Glu Val Pro Ala Ala Ala
    50                  55                  60

Arg Gly Cys Pro Gly Ala Ala Ala Ala Ala Leu Trp Arg Glu Ala Glu
65                  70                  75                  80

Ala Glu Ala Ala Ala Ala Gly Gly Glu Gln Glu Ala Gln Ala Thr Ala
                85                  90                  95

Ala Ala Gly Glu Gly Asp Asn Gly Pro Gly Leu Gln Gly Pro Ser Arg
            100                 105                 110

Glu Pro Pro Leu Ala Asp Asn Leu Tyr Asp Glu Asp Asp Asp Asp Glu
        115                 120                 125

Gly Glu Glu Glu Glu Glu Ala Ala Ala Ala Ala Ile Gly Tyr Arg Asp
```

```
    130                 135                 140

Asn Leu Leu Phe Gly Asp Glu Ile Ile Thr Asn Gly Phe His Ser Cys
145                 150                 155                 160

Glu Ser Asp Glu Glu Asp Arg Ala Ser His Ala Ser Ser Ser Asp Trp
                165                 170                 175

Thr Pro Arg Pro Arg Ile Gly Pro Tyr Thr Phe Val Gln Gln His Leu
            180                 185                 190

Met Ile Gly Thr Asp Pro Arg Thr Ile Leu Lys Asp Leu Leu Pro Glu
        195                 200                 205

Thr Ile Pro Pro Pro Glu Leu Asp Asp Met Thr Leu Trp Gln Ile Val
    210                 215                 220

Ile Asn Ile Leu Ser Glu Pro Pro Lys Arg Lys Lys Arg Lys Asp Ile
225                 230                 235                 240

Asn Thr Ile Glu Asp Ala Val Lys Leu Leu Gln Glu Cys Lys Lys Ile
                245                 250                 255

Ile Val Leu Thr Gly Ala Gly Val Ser Val Ser Cys Gly Ile Pro Asp
            260                 265                 270

Phe Arg Ser Arg Asp Gly Ile Tyr Ala Arg Leu Ala Val Asp Phe Pro
        275                 280                 285

Asp Leu Pro Asp Pro Gln Ala Met Phe Asp Ile Glu Tyr Phe Arg Lys
    290                 295                 300

Asp Pro Arg Pro Phe Phe Lys Phe Ala Lys Glu Ile Tyr Pro Gly Gln
305                 310                 315                 320

Phe Gln Pro Ser Leu Cys His Lys Phe Ile Ala Leu Ser Asp Lys Glu
                325                 330                 335

Gly Lys Leu Leu Arg Asn Tyr Thr Gln Asn Ile Asp Thr Leu Glu Gln
            340                 345                 350

Val Ala Gly Ile Gln Arg Ile Ile Gln Cys His Gly Ser Phe Ala Thr
        355                 360                 365

Ala Ser Cys Leu Ile Cys Lys Tyr Lys Val Asp Cys Glu Ala Val Arg
    370                 375                 380

Gly Asp Ile Phe Asn Gln Val Val Pro Arg Cys Pro Arg Cys Pro Ala
385                 390                 395                 400

Asp Glu Pro Leu Ala Ile Met Lys Pro Glu Ile Val Phe Phe Gly Glu
                405                 410                 415

Asn Leu Pro Glu Gln Phe His Arg Ala Met Lys Tyr Asp Lys Asp Glu
            420                 425                 430

Val Asp Leu Leu Ile Val Ile Gly Ser Ser Leu Lys Val Arg Pro Val
        435                 440                 445

Ala Leu Ile Pro Ser Ser Ile Pro His Glu Val Pro Gln Ile Leu Ile
    450                 455                 460

Asn Arg Glu Pro Leu Pro His Leu His Phe Asp Val Glu Leu Leu Gly
465                 470                 475                 480

Asp Cys Asp Val Ile Ile Asn Glu Leu Cys His Arg Leu Gly Gly Glu
                485                 490                 495

Tyr Ala Lys Leu Cys Cys Asn Pro Val Lys Leu Ser Glu Ile Thr Glu
            500                 505                 510

Lys Pro Pro Arg Thr Gln Lys Glu Leu Ala Tyr Leu Ser Glu Leu Pro
        515                 520                 525

Pro Thr Pro Leu His Val Ser Glu Asp Ser Ser Ser Pro Glu Arg Thr
    530                 535                 540

Ser Pro Pro Asp Ser Ser Val Ile Val Thr Leu Leu Asp Gln Ala Ala
545                 550                 555                 560
```

```
Lys Ser Asn Asp Asp Leu Asp Val Ser Glu Ser Lys Gly Cys Met Glu
                565                 570                 575

Glu Lys Pro Gln Glu Val Gln Thr Ser Arg Asn Val Glu Ser Ile Ala
            580                 585                 590

Glu Gln Met Glu Asn Pro Asp Leu Lys Asn Val Gly Ser Ser Thr Gly
        595                 600                 605

Glu Lys Asn Glu Arg Thr Ser Val Ala Gly Thr Val Arg Lys Cys Trp
    610                 615                 620

Pro Asn Arg Val Ala Lys Glu Gln Ile Ser Arg Arg Leu Asp Gly Asn
625                 630                 635                 640

Gln Tyr Leu Phe Leu Pro Pro Asn Arg Tyr Ile Phe His Gly Ala Glu
                645                 650                 655

Val Tyr Ser Asp Ser Glu Asp Asp Val Leu Ser Ser Ser Ser Cys Gly
            660                 665                 670

Ser Asn Ser Asp Ser Gly Thr Cys Gln Ser Pro Ser Leu Glu Glu Pro
        675                 680                 685

Met Glu Asp Glu Ser Glu Ile Glu Glu Phe Tyr Asn Gly Leu Glu Asp
    690                 695                 700

Glu Pro Asp Val Pro Glu Arg Ala Gly Gly Ala Gly Phe Gly Thr Asp
705                 710                 715                 720

Gly Asp Asp Gln Glu Ala Ile Asn Glu Ala Ile Ser Val Lys Gln Glu
                725                 730                 735

Val Thr Asp Met Asn Tyr Pro Ser Asn Lys Ser
            740                 745
```

<210> SEQ ID NO 28
<211> LENGTH: 2078
<212> TYPE: DNA
<213> ORGANISM: Homo sapiens

<400> SEQUENCE: 28

```
agagtattcg ggaggactac aactctctag ccgttcccac attttccggg cgccctttac      60

caacatggct gctgacgcca cgccttctgg gactcgtagt ccggtcctcg cgcgctttct     120

tacctaactg gggcgctctg ggtgttgtac gaaagcgcgt ctgcggccgc aatgtctgct     180

gagagttgta gttctgtgcc ctatcacggc cactcccatt tctggtgccg tcacgggaca     240

gagcagtcgg tgacaggaca gagcagtcgg tgacgggaca cagtggttgg tgacgggaca     300

gagcggtcgg tgacagcctc aagggcttca gcaccgcgcc catggcagag ccagaccgac     360

tcagattcag actctgaggg aggagccgct ggtggagaag cagacatgga cttcctgcgg     420

aacttattct cccagacgct cagcctgggc agccagaagg agcgtctgct ggacgagctg     480

accttggaag ggtggcccg gtacatgcag agcgaacgct gtcgcagagt catctgtttg     540

gtgggagctg gaatctccac atccgcaggc atccccgact ttcgctctcc atccaccggc     600

ctctatgaca acctagagaa gtaccatctt ccctacccag aggccatctt tgagatcagc     660

tatttcaaga aacatccgga acccttcttc gccctcgcca aggaactcta tcctgggcag     720

ttcaagccaa ccatctgtca ctacttcatg cgcctgctga aggacaaggg gctactcctg     780

cgctgctaca cgcagaacat agataccctg gagcgaatag ccgggctgga acaggaggac     840

ttggtggagg cgcacggcac cttctacaca tcacactgcg tcagcgccag ctgccggcac     900

gaatacccgc taagctggat gaaagagaag atcttctctg aggtgacgcc caagtgtgaa     960

gactgtcaga gcctggtgaa gcctgatatc gtcttttttg gtgagagcct cccagcgcgt    1020

ttcttctcct gtatgcagtc agacttcctg aaggtggacc tcctcctggt catgggtacc    1080
```

-continued

```
tccttgcagg tgcagccctt tgcctccctc atcagcaagg caccccctctc cacccctcgc   1140

ctgctcatca acaaggagaa agctggccag tcggaccctt tcctggggat gattatgggc   1200

ctcggaggag gcatggactt tgactccaag aaggcctaca gggacgtggc ctggctgggt   1260

gaatgcgacc agggctgcct ggcccttgct gagctccttg gatggaagaa ggagctggag   1320

gaccttgtcc ggagggagca cgccagcata gatgcccagt cgggggcggg ggtccccaac   1380

cccagcactt cagcttcccc caagaagtcc ccgccacctg ccaaggacga ggccaggaca   1440

acagagaggg agaaacccca gtgacagctg catctcccag gcgggatgcc gagctcctca   1500

gggacagctg agccccaacc gggcctggcc ccctcttaac cagcagttct tgtctgggga   1560

gctcagaaca tcccccaatc tcttacagct ccctccccaa aactggggtc ccagcaaccc   1620

tggcccccaa ccccagcaaa tctctaacac ctcctagagg ccaaggctta aacaggcatc   1680

tctaccagcc ccactgtctc taaccactcc tgggctaagg agtaacctcc ctcatctcta   1740

actgccccca cggggccagg gctaccccag aacttttaac tcttccagga cagggagctt   1800

cgggccccca ctctgtctcc tgcccccggg ggcctgtggc taagtaaacc atacctaacc   1860

taccccagtg tgggtgtggg cctctgaata taacccacac ccagcgtagg gggagtctga   1920

gccgggaggg ctcccgagtc tctgccttca gctcccaaag tgggtggtgg gccccccttca   1980

cgtgggaccc acttcccatg ctggatgggc agaagacatt gcttattgga gacaaattaa   2040

aaacaaaaac aactaacaat ccggaaaaaa aaaaaaaa                           2078
```

<210> SEQ ID NO 29
<211> LENGTH: 1963
<212> TYPE: DNA
<213> ORGANISM: Homo sapiens

<400> SEQUENCE: 29

```
gtgttgtacg aaagcgcgtc tgcggccgca atgtctgctg agagttgtag ttctgtgccc     60

tatcacggcc actcccattt ctggtgccgt cacgggacag agcagtcggt gacaggacag    120

agcagtcggt gacgggacac agtggttggt gacgggacag agcggtcggt gacagcctca    180

agggcttcag caccgcgccc atggcagagc cagacccctc tcaccctctg gagacccagg    240

cagggaaggt gcaggaggct caggactcag attcagactc tgagggagga gccgctggtg    300

gagaagcaga catggacttc ctgcggaact tattctccca gacgctcagc ctgggcagcc    360

agaaggagcg tctgctggac gagctgacct tggaaggggt ggcccggtac atgcagagcg    420

aacgctgtcg cagagtcatc tgtttggtgg gagctggaat ctccacatcc gcaggcatcc    480

ccgactttcg ctctccatcc accggcctct atgacaacct agagaagtac catcttccct    540

acccagaggc catctttgag atcagctatt tcaagaaaca tccggaaccc ttcttcgccc    600

tcgccaagga actctatcct gggcagttca agccaaccat ctgtcactac ttcatgcgcc    660

tgctgaagga caaggggcta ctcctgcgct gctacacgca gaacatagat accctggagc    720

gaatagccgg gctggaacag gaggacttgg tggaggcgca cggcaccttc tacacatcac    780

actgcgtcag cgccagctgc cggcacgaat acccgctaag ctggatgaaa gagaagatct    840

tctctgaggt gacgcccaag tgtgaagact gtcagagcct ggtgaagcct gatatcgtct    900

tttttggtga gagcctccca gcgcgtttct tctcctgtat gcagtcagac ttcctgaagg    960

tggacctcct cctggtcatg ggtacctcct tgcaggtgca gccctttgcc tccctcatca   1020

gcaaggcacc cctctccacc cctcgcctgc tcatcaacaa ggagaaagct ggccagtcgg   1080

acccttttcct ggggatgatt atgggcctcg gaggaggcat ggactttgac tccaagaagg   1140
```

```
cctacaggga cgtggcctgg ctgggtgaat gcgaccaggg ctgcctggcc cttgctgagc   1200

tccttggatg gaagaaggag ctggaggacc ttgtccggag ggagcacgcc agcatagatg   1260

cccagtcggg ggcgggggtc cccaacccca gcacttcagc ttcccccaag aagtccccgc   1320

cacctgccaa ggacgaggcc aggacaacag agagggagaa accccagtga cagctgcatc   1380

tcccaggcgg gatgccgagc tcctcaggga cagctgagcc ccaaccgggc ctggccccct   1440

cttaaccagc agttcttgtc tggggagctc agaacatccc ccaatctctt acagctccct   1500

ccccaaaact ggggtcccag caaccctggc ccccaacccc agcaaatctc taacacctcc   1560

tagaggccaa ggcttaaaca ggcatctcta ccagccccac tgtctctaac cactcctggg   1620

ctaaggagta acctccctca tctctaactg cccccacggg gccagggcta ccccagaact   1680

tttaactctt ccaggacagg gagcttcggg cccccactct gtctcctgcc cccgggggcc   1740

tgtggctaag taaaccatac ctaacctacc ccagtgtggg tgtgggcctc tgaatataac   1800

ccacacccag cgtaggggga gtctgagccg ggagggctcc cgagtctctg ccttcagctc   1860

ccaaagtggg tggtgggccc ccttcacgtg ggacccactt cccatgctgg atgggcagaa   1920

gacattgctt attggagaca aattaaaaac aaaaacaact aac                     1963
```

<210> SEQ ID NO 30
<211> LENGTH: 389
<212> TYPE: PRT
<213> ORGANISM: Homo sapiens

<400> SEQUENCE: 30

```
Met Ala Glu Pro Asp Pro Ser His Pro Leu Glu Thr Gln Ala Gly Lys
 1               5                  10                  15

Val Gln Glu Ala Gln Asp Ser Asp Ser Asp Ser Glu Gly Gly Ala Ala
            20                  25                  30

Gly Gly Glu Ala Asp Met Asp Phe Leu Arg Asn Leu Phe Ser Gln Thr
        35                  40                  45

Leu Ser Leu Gly Ser Gln Lys Glu Arg Leu Leu Asp Glu Leu Thr Leu
    50                  55                  60

Glu Gly Val Ala Arg Tyr Met Gln Ser Glu Arg Cys Arg Arg Val Ile
65                  70                  75                  80

Cys Leu Val Gly Ala Gly Ile Ser Thr Ser Ala Gly Ile Pro Asp Phe
                85                  90                  95

Arg Ser Pro Ser Thr Gly Leu Tyr Asp Asn Leu Glu Lys Tyr His Leu
            100                 105                 110

Pro Tyr Pro Glu Ala Ile Phe Glu Ile Ser Tyr Phe Lys Lys His Pro
        115                 120                 125

Glu Pro Phe Phe Ala Leu Ala Lys Glu Leu Tyr Pro Gly Gln Phe Lys
    130                 135                 140

Pro Thr Ile Cys His Tyr Phe Met Arg Leu Leu Lys Asp Lys Gly Leu
145                 150                 155                 160

Leu Leu Arg Cys Tyr Thr Gln Asn Ile Asp Thr Leu Glu Arg Ile Ala
                165                 170                 175

Gly Leu Glu Gln Glu Asp Leu Val Glu Ala His Gly Thr Phe Tyr Thr
            180                 185                 190

Ser His Cys Val Ser Ala Ser Cys Arg His Glu Tyr Pro Leu Ser Trp
        195                 200                 205

Met Lys Glu Lys Ile Phe Ser Glu Val Thr Pro Lys Cys Glu Asp Cys
    210                 215                 220

Gln Ser Leu Val Lys Pro Asp Ile Val Phe Phe Gly Glu Ser Leu Pro
225                 230                 235                 240
```

-continued

```
Ala Arg Phe Phe Ser Cys Met Gln Ser Asp Phe Leu Lys Val Asp Leu
                245                 250                 255

Leu Leu Val Met Gly Thr Ser Leu Gln Val Gln Pro Phe Ala Ser Leu
            260                 265                 270

Ile Ser Lys Ala Pro Leu Ser Thr Pro Arg Leu Leu Ile Asn Lys Glu
        275                 280                 285

Lys Ala Gly Gln Ser Asp Pro Phe Leu Gly Met Ile Met Gly Leu Gly
    290                 295                 300

Gly Gly Met Asp Phe Asp Ser Lys Lys Ala Tyr Arg Asp Val Ala Trp
305                 310                 315                 320

Leu Gly Glu Cys Asp Gln Gly Cys Leu Ala Leu Ala Glu Leu Leu Gly
                325                 330                 335

Trp Lys Lys Glu Leu Glu Asp Leu Val Arg Arg Glu His Ala Ser Ile
            340                 345                 350

Asp Ala Gln Ser Gly Ala Gly Val Pro Asn Pro Ser Thr Ser Ala Ser
        355                 360                 365

Pro Lys Lys Ser Pro Pro Pro Ala Lys Asp Glu Ala Arg Thr Thr Glu
    370                 375                 380

Arg Glu Lys Pro Gln
385
```

<210> SEQ ID NO 31
<211> LENGTH: 369
<212> TYPE: PRT
<213> ORGANISM: Homo sapiens

<400> SEQUENCE: 31

```
Met Pro Leu Ala Glu Cys Pro Ser Cys Arg Cys Leu Ser Ser Phe Arg
 1               5                  10                  15

Ser Val Asp Phe Leu Arg Asn Leu Phe Ser Gln Thr Leu Ser Leu Gly
            20                  25                  30

Ser Gln Lys Glu Arg Leu Leu Asp Glu Leu Thr Leu Glu Gly Val Ala
        35                  40                  45

Arg Tyr Met Gln Ser Glu Arg Cys Arg Arg Val Ile Cys Leu Val Gly
    50                  55                  60

Ala Gly Ile Ser Thr Ser Ala Gly Ile Pro Asp Phe Arg Ser Pro Ser
65                  70                  75                  80

Thr Gly Leu Tyr Asp Asn Leu Glu Lys Tyr His Leu Pro Tyr Pro Glu
                85                  90                  95

Ala Ile Phe Glu Ile Ser Tyr Phe Lys Lys His Pro Glu Pro Phe Phe
            100                 105                 110

Ala Leu Ala Lys Glu Leu Tyr Pro Gly Gln Phe Lys Pro Thr Ile Cys
        115                 120                 125

His Tyr Phe Met Arg Leu Leu Lys Asp Lys Gly Leu Leu Leu Arg Cys
    130                 135                 140

Tyr Thr Gln Asn Ile Asp Thr Leu Glu Arg Ile Ala Gly Leu Glu Gln
145                 150                 155                 160

Glu Asp Leu Val Glu Ala His Gly Thr Phe Tyr Thr Ser His Cys Val
                165                 170                 175

Ser Ala Ser Cys Arg His Glu Tyr Pro Leu Ser Trp Met Lys Glu Lys
            180                 185                 190

Ile Phe Ser Glu Val Thr Leu Lys Cys Glu Asp Cys Gln Ser Leu Val
        195                 200                 205

Lys Pro Asp Ile Val Phe Phe Gly Glu Ser Leu Pro Ala Arg Phe Phe
    210                 215                 220
```

```
Ser Cys Met Gln Ser Asp Phe Leu Lys Val Asp Leu Leu Leu Val Met
225                 230                 235                 240

Gly Thr Ser Leu Gln Val Gln Pro Phe Ala Ser Leu Ile Ser Lys Ala
                245                 250                 255

Pro Leu Ser Thr Pro Arg Leu Leu Ile Asn Lys Glu Lys Ala Gly Gln
            260                 265                 270

Ser Asp Pro Phe Leu Gly Met Ile Met Gly Leu Gly Gly Gly Met Asp
        275                 280                 285

Phe Asp Ser Lys Lys Ala Tyr Arg Asp Val Ala Trp Leu Gly Glu Cys
    290                 295                 300

Asp Gln Gly Cys Leu Ala Leu Ala Glu Leu Leu Gly Trp Lys Lys Glu
305                 310                 315                 320

Leu Glu Asp Leu Val Arg Arg Glu His Ala Ser Ile Asp Ala Gln Ser
                325                 330                 335

Gly Ala Gly Val Pro Asn Pro Ser Thr Ser Ala Ser Pro Lys Lys Ser
            340                 345                 350

Pro Pro Pro Ala Lys Asp Glu Ala Arg Thr Thr Glu Arg Glu Lys Pro
        355                 360                 365

Gln
```

<210> SEQ ID NO 32
<211> LENGTH: 747
<212> TYPE: PRT
<213> ORGANISM: Homo sapiens

<400> SEQUENCE: 32

```
Met Ala Asp Glu Ala Ala Leu Ala Leu Gln Pro Gly Gly Ser Pro Ser
 1               5                  10                  15

Ala Ala Gly Ala Asp Arg Glu Ala Ala Ser Ser Pro Ala Gly Glu Pro
            20                  25                  30

Leu Arg Lys Arg Pro Arg Arg Asp Gly Pro Gly Leu Glu Arg Ser Pro
        35                  40                  45

Gly Glu Pro Gly Gly Ala Ala Pro Glu Arg Glu Val Pro Ala Ala Ala
    50                  55                  60

Arg Gly Cys Pro Gly Ala Ala Ala Ala Ala Leu Trp Arg Glu Ala Glu
65                  70                  75                  80

Ala Glu Ala Ala Ala Ala Gly Gly Glu Gln Glu Ala Gln Ala Thr Ala
                85                  90                  95

Ala Ala Gly Glu Gly Asp Asn Gly Pro Gly Leu Gln Gly Pro Ser Arg
            100                 105                 110

Glu Pro Pro Leu Ala Asp Asn Leu Tyr Asp Glu Asp Asp Asp Asp Glu
        115                 120                 125

Gly Glu Glu Glu Glu Glu Ala Ala Ala Ala Ala Ile Gly Tyr Arg Asp
    130                 135                 140

Asn Leu Leu Phe Gly Asp Glu Ile Ile Thr Asn Gly Phe His Ser Cys
145                 150                 155                 160

Glu Ser Asp Glu Glu Asp Arg Ala Ser His Ala Ser Ser Ser Asp Trp
                165                 170                 175

Thr Pro Arg Pro Arg Ile Gly Pro Tyr Thr Phe Val Gln Gln His Leu
            180                 185                 190

Met Ile Gly Thr Asp Pro Arg Thr Ile Leu Lys Asp Leu Leu Pro Glu
        195                 200                 205

Thr Ile Pro Pro Pro Glu Leu Asp Asp Met Thr Leu Trp Gln Ile Val
    210                 215                 220
```

-continued

```
Ile Asn Ile Leu Ser Glu Pro Pro Lys Arg Lys Lys Arg Lys Asp Ile
225                 230                 235                 240

Asn Thr Ile Glu Asp Ala Val Lys Leu Leu Gln Glu Cys Lys Lys Ile
                245                 250                 255

Ile Val Leu Thr Gly Ala Gly Val Ser Val Ser Cys Gly Ile Pro Asp
            260                 265                 270

Phe Arg Ser Arg Asp Gly Ile Tyr Ala Arg Leu Ala Val Asp Phe Pro
        275                 280                 285

Asp Leu Pro Asp Pro Gln Ala Met Phe Asp Ile Glu Tyr Phe Arg Lys
    290                 295                 300

Asp Pro Arg Pro Phe Phe Lys Phe Ala Lys Glu Ile Tyr Pro Gly Gln
305                 310                 315                 320

Phe Gln Pro Ser Leu Cys His Lys Phe Ile Ala Leu Ser Asp Lys Glu
                325                 330                 335

Gly Lys Leu Leu Arg Asn Tyr Thr Gln Asn Ile Asp Thr Leu Glu Gln
            340                 345                 350

Val Ala Gly Ile Gln Arg Ile Ile Gln Cys His Gly Ser Phe Ala Thr
        355                 360                 365

Ala Ser Cys Leu Ile Cys Lys Tyr Lys Val Asp Cys Glu Ala Val Arg
    370                 375                 380

Gly Asp Ile Phe Asn Gln Val Val Pro Arg Cys Pro Arg Cys Pro Ala
385                 390                 395                 400

Asp Glu Pro Leu Ala Ile Met Lys Pro Glu Ile Val Phe Phe Gly Glu
                405                 410                 415

Asn Leu Pro Glu Gln Phe His Arg Ala Met Lys Tyr Asp Lys Asp Glu
            420                 425                 430

Val Asp Leu Leu Ile Val Ile Gly Ser Ser Leu Lys Val Arg Pro Val
        435                 440                 445

Ala Leu Ile Pro Ser Ser Ile Pro His Glu Val Pro Gln Ile Leu Ile
    450                 455                 460

Asn Arg Glu Pro Leu Pro His Leu His Phe Asp Val Glu Leu Leu Gly
465                 470                 475                 480

Asp Cys Asp Val Ile Ile Asn Glu Leu Cys His Arg Leu Gly Gly Glu
                485                 490                 495

Tyr Ala Lys Leu Cys Cys Asn Pro Val Lys Leu Ser Glu Ile Thr Glu
            500                 505                 510

Lys Pro Pro Arg Thr Gln Lys Glu Leu Ala Tyr Leu Ser Glu Leu Pro
        515                 520                 525

Pro Thr Pro Leu His Val Ser Glu Asp Ser Ser Ser Pro Glu Arg Thr
    530                 535                 540

Ser Pro Pro Asp Ser Ser Val Ile Val Thr Leu Leu Asp Gln Ala Ala
545                 550                 555                 560

Lys Ser Asn Asp Asp Leu Asp Val Ser Glu Ser Lys Gly Cys Met Glu
                565                 570                 575

Glu Lys Pro Gln Glu Val Gln Thr Ser Arg Asn Val Glu Ser Ile Ala
            580                 585                 590

Glu Gln Met Glu Asn Pro Asp Leu Lys Asn Val Gly Ser Ser Thr Gly
        595                 600                 605

Glu Lys Asn Glu Arg Thr Ser Val Ala Gly Thr Val Arg Lys Cys Trp
    610                 615                 620

Pro Asn Arg Val Ala Lys Glu Gln Ile Ser Arg Arg Leu Asp Gly Asn
625                 630                 635                 640

Gln Tyr Leu Phe Leu Pro Pro Asn Arg Tyr Ile Phe His Gly Ala Glu
                645                 650                 655
```

```
Val Tyr Ser Asp Ser Glu Asp Asp Val Leu Ser Ser Ser Ser Cys Gly
            660                 665                 670

Ser Asn Ser Asp Ser Gly Thr Cys Gln Ser Pro Ser Leu Glu Glu Pro
        675                 680                 685

Met Glu Asp Glu Ser Glu Ile Glu Glu Phe Tyr Asn Gly Leu Glu Asp
    690                 695                 700

Glu Pro Asp Val Pro Glu Arg Ala Gly Gly Ala Gly Phe Gly Thr Asp
705                 710                 715                 720

Gly Asp Asp Gln Glu Ala Ile Asn Glu Ala Ile Ser Val Lys Gln Glu
                725                 730                 735

Val Thr Asp Met Asn Tyr Pro Ser Asn Lys Ser
            740                 745


<210> SEQ ID NO 33
<211> LENGTH: 352
<212> TYPE: PRT
<213> ORGANISM: Homo sapiens

<400> SEQUENCE: 33

Met Asp Phe Leu Arg Asn Leu Phe Ser Gln Thr Leu Ser Leu Gly Ser
 1               5                  10                  15

Gln Lys Glu Arg Leu Leu Asp Glu Leu Thr Leu Glu Gly Val Ala Arg
            20                  25                  30

Tyr Met Gln Ser Glu Arg Cys Arg Arg Val Ile Cys Leu Val Gly Ala
        35                  40                  45

Gly Ile Ser Thr Ser Ala Gly Ile Pro Asp Phe Arg Ser Pro Ser Thr
    50                  55                  60

Gly Leu Tyr Asp Asn Leu Glu Lys Tyr His Leu Pro Tyr Pro Glu Ala
65                  70                  75                  80

Ile Phe Glu Ile Ser Tyr Phe Lys Lys His Pro Glu Pro Phe Phe Ala
                85                  90                  95

Leu Ala Lys Glu Leu Tyr Pro Gly Gln Phe Lys Pro Thr Ile Cys His
            100                 105                 110

Tyr Phe Met Arg Leu Leu Lys Asp Lys Gly Leu Leu Leu Arg Cys Tyr
        115                 120                 125

Thr Gln Asn Ile Asp Thr Leu Glu Arg Ile Ala Gly Leu Glu Gln Glu
    130                 135                 140

Asp Leu Val Glu Ala His Gly Thr Phe Tyr Thr Ser His Cys Val Ser
145                 150                 155                 160

Ala Ser Cys Arg His Glu Tyr Pro Leu Ser Trp Met Lys Glu Lys Ile
                165                 170                 175

Phe Ser Glu Val Thr Pro Lys Cys Glu Asp Cys Gln Ser Leu Val Lys
            180                 185                 190

Pro Asp Ile Val Phe Phe Gly Glu Ser Leu Pro Ala Arg Phe Phe Ser
        195                 200                 205

Cys Met Gln Ser Asp Phe Leu Lys Val Asp Leu Leu Leu Val Met Gly
    210                 215                 220

Thr Ser Leu Gln Val Gln Pro Phe Ala Ser Leu Ile Ser Lys Ala Pro
225                 230                 235                 240

Leu Ser Thr Pro Arg Leu Leu Ile Asn Lys Glu Lys Ala Gly Gln Ser
                245                 250                 255

Asp Pro Phe Leu Gly Met Ile Met Gly Leu Gly Gly Gly Met Asp Phe
            260                 265                 270

Asp Ser Lys Lys Ala Tyr Arg Asp Val Ala Trp Leu Gly Glu Cys Asp
        275                 280                 285
```

```
Gln Gly Cys Leu Ala Leu Ala Glu Leu Leu Gly Trp Lys Lys Glu Leu
    290                 295                 300

Glu Asp Leu Val Arg Arg Glu His Ala Ser Ile Asp Ala Gln Ser Gly
305                 310                 315                 320

Ala Gly Val Pro Asn Pro Ser Thr Ser Ala Ser Pro Lys Lys Ser Pro
                325                 330                 335

Pro Pro Ala Lys Asp Glu Ala Arg Thr Thr Glu Arg Glu Lys Pro Gln
            340                 345                 350


<210> SEQ ID NO 34
<211> LENGTH: 399
<212> TYPE: PRT
<213> ORGANISM: Homo sapiens

<400> SEQUENCE: 34

Met Ala Phe Trp Gly Trp Arg Ala Ala Ala Ala Leu Arg Leu Trp Gly
 1               5                  10                  15

Arg Val Val Glu Arg Val Glu Ala Gly Gly Gly Val Gly Pro Phe Gln
            20                  25                  30

Ala Cys Gly Cys Arg Leu Val Leu Gly Gly Arg Asp Asp Val Ser Ala
        35                  40                  45

Gly Leu Arg Gly Ser His Gly Ala Arg Gly Glu Pro Leu Asp Pro Ala
    50                  55                  60

Arg Pro Leu Gln Arg Pro Pro Arg Pro Glu Val Pro Arg Ala Phe Arg
65                  70                  75                  80

Arg Gln Pro Arg Ala Ala Ala Pro Ser Phe Phe Phe Ser Ser Ile Lys
                85                  90                  95

Gly Gly Arg Arg Ser Ile Ser Phe Ser Val Gly Ala Ser Ser Val Val
            100                 105                 110

Gly Ser Gly Gly Ser Ser Asp Lys Gly Lys Leu Ser Leu Gln Asp Val
        115                 120                 125

Ala Glu Leu Ile Arg Ala Arg Ala Cys Gln Arg Val Val Val Met Val
    130                 135                 140

Gly Ala Gly Ile Ser Thr Pro Ser Gly Ile Pro Asp Phe Arg Ser Pro
145                 150                 155                 160

Gly Ser Gly Leu Tyr Ser Asn Leu Gln Gln Tyr Asp Leu Pro Tyr Pro
                165                 170                 175

Glu Ala Ile Phe Glu Leu Pro Phe Phe Phe His Asn Pro Lys Pro Phe
            180                 185                 190

Phe Thr Leu Ala Lys Glu Leu Tyr Pro Gly Asn Tyr Lys Pro Asn Val
        195                 200                 205

Thr His Tyr Phe Leu Arg Leu Leu His Asp Lys Gly Leu Leu Leu Arg
    210                 215                 220

Leu Tyr Thr Gln Asn Ile Asp Gly Leu Glu Arg Val Ser Gly Ile Pro
225                 230                 235                 240

Ala Ser Lys Leu Val Glu Ala His Gly Thr Phe Ala Ser Ala Thr Cys
                245                 250                 255

Thr Val Cys Gln Arg Pro Phe Pro Gly Glu Asp Ile Arg Ala Asp Val
            260                 265                 270

Met Ala Asp Arg Val Pro Arg Cys Pro Val Cys Thr Gly Val Val Lys
        275                 280                 285

Pro Asp Ile Val Phe Phe Gly Glu Pro Leu Pro Gln Arg Phe Leu Leu
    290                 295                 300

His Val Val Asp Phe Pro Met Ala Asp Leu Leu Leu Ile Leu Gly Thr
305                 310                 315                 320
```

Ser Leu Glu Val Glu Pro Phe Ala Ser Leu Thr Glu Ala Val Arg Ser
325 330 335

Ser Val Pro Arg Leu Leu Ile Asn Arg Asp Leu Val Gly Pro Leu Ala
340 345 350

Trp His Pro Arg Ser Arg Asp Val Ala Gln Leu Gly Asp Val Val His
355 360 365

Gly Val Glu Ser Leu Val Glu Leu Leu Gly Trp Thr Glu Glu Met Arg
370 375 380

Asp Leu Val Gln Arg Glu Thr Gly Lys Leu Asp Gly Pro Asp Lys
385 390 395

<210> SEQ ID NO 35
<211> LENGTH: 314
<212> TYPE: PRT
<213> ORGANISM: Homo sapiens

<400> SEQUENCE: 35

Met Lys Met Ser Phe Ala Leu Thr Phe Arg Ser Ala Lys Gly Arg Trp
1 5 10 15

Ile Ala Asn Pro Ser Gln Pro Cys Ser Lys Ala Ser Ile Gly Leu Phe
20 25 30

Val Pro Ala Ser Pro Pro Leu Asp Pro Glu Lys Val Lys Glu Leu Gln
35 40 45

Arg Phe Ile Thr Leu Ser Lys Arg Leu Leu Val Met Thr Gly Ala Gly
50 55 60

Ile Ser Thr Glu Ser Gly Ile Pro Asp Tyr Arg Ser Glu Lys Val Gly
65 70 75 80

Leu Tyr Ala Arg Thr Asp Arg Arg Pro Ile Gln His Gly Asp Phe Val
85 90 95

Arg Ser Ala Pro Ile Arg Gln Arg Tyr Trp Ala Arg Asn Phe Val Gly
100 105 110

Trp Pro Gln Phe Ser Ser His Gln Pro Asn Pro Ala His Trp Ala Leu
115 120 125

Ser Thr Trp Glu Lys Leu Gly Lys Leu Tyr Trp Leu Val Thr Gln Asn
130 135 140

Val Asp Ala Leu His Thr Lys Ala Gly Ser Arg Arg Leu Thr Glu Leu
145 150 155 160

His Gly Cys Met Asp Arg Val Leu Cys Leu Asp Cys Gly Glu Gln Thr
165 170 175

Pro Arg Gly Val Leu Gln Glu Arg Phe Gln Val Leu Asn Pro Thr Trp
180 185 190

Ser Ala Glu Ala His Gly Leu Ala Pro Asp Gly Asp Val Phe Leu Ser
195 200 205

Glu Glu Gln Val Arg Ser Phe Gln Val Pro Thr Cys Val Gln Cys Gly
210 215 220

Gly His Leu Lys Pro Asp Val Val Phe Phe Gly Asp Thr Val Asn Pro
225 230 235 240

Asp Lys Val Asp Phe Val His Lys Arg Val Lys Glu Ala Asp Ser Leu
245 250 255

Leu Val Val Gly Ser Ser Leu Gln Val Tyr Ser Gly Tyr Arg Phe Ile
260 265 270

Leu Thr Ala Trp Glu Lys Lys Leu Pro Ile Ala Ile Leu Asn Ile Gly
275 280 285

Pro Thr Arg Ser Asp Asp Leu Ala Cys Leu Lys Leu Asn Ser Arg Cys
290 295 300

```
Gly Glu Leu Leu Pro Leu Ile Asp Pro Cys
305                 310


<210> SEQ ID NO 36
<211> LENGTH: 310
<212> TYPE: PRT
<213> ORGANISM: Homo sapiens

<400> SEQUENCE: 36

Met Arg Pro Leu Gln Ile Val Pro Ser Arg Leu Ile Ser Gln Leu Tyr
 1               5                  10                  15

Cys Gly Leu Lys Pro Pro Ala Ser Thr Arg Asn Gln Ile Cys Leu Lys
            20                  25                  30

Met Ala Arg Pro Ser Ser Ser Met Ala Asp Phe Arg Lys Phe Phe Ala
        35                  40                  45

Lys Ala Lys His Ile Val Ile Ile Ser Gly Ala Gly Val Ser Ala Glu
    50                  55                  60

Ser Gly Val Pro Thr Phe Arg Gly Ala Gly Gly Tyr Trp Arg Lys Trp
65                  70                  75                  80

Gln Ala Gln Asp Leu Ala Thr Pro Leu Ala Phe Ala His Asn Pro Ser
                85                  90                  95

Arg Val Trp Glu Phe Tyr His Tyr Arg Arg Glu Val Met Gly Ser Lys
            100                 105                 110

Glu Pro Asn Ala Gly His Arg Ala Ile Ala Glu Cys Glu Thr Arg Leu
        115                 120                 125

Gly Lys Gln Gly Arg Arg Val Val Val Ile Thr Gln Asn Ile Asp Glu
    130                 135                 140

Leu His Arg Lys Ala Gly Thr Lys Asn Leu Leu Glu Ile His Gly Ser
145                 150                 155                 160

Leu Phe Lys Thr Arg Cys Thr Ser Cys Gly Val Val Ala Glu Asn Tyr
                165                 170                 175

Lys Ser Pro Ile Cys Pro Ala Leu Ser Gly Lys Gly Ala Pro Glu Pro
            180                 185                 190

Gly Thr Gln Asp Ala Ser Ile Pro Val Glu Lys Leu Pro Arg Cys Glu
        195                 200                 205

Glu Ala Gly Cys Gly Gly Leu Leu Arg Pro His Val Val Trp Phe Gly
    210                 215                 220

Glu Asn Leu Asp Pro Ala Ile Leu Glu Glu Val Asp Arg Glu Leu Ala
225                 230                 235                 240

His Cys Asp Leu Cys Leu Val Val Gly Thr Ser Ser Val Val Tyr Pro
                245                 250                 255

Ala Ala Met Phe Ala Pro Gln Val Ala Ala Arg Gly Val Pro Val Ala
            260                 265                 270

Glu Phe Asn Thr Glu Thr Thr Pro Ala Thr Asn Arg Phe Arg Phe His
        275                 280                 285

Phe Gln Gly Pro Cys Gly Thr Thr Leu Pro Glu Ala Leu Ala Cys His
    290                 295                 300

Glu Asn Glu Thr Val Ser
305                 310


<210> SEQ ID NO 37
<211> LENGTH: 299
<212> TYPE: PRT
<213> ORGANISM: Homo sapiens

<400> SEQUENCE: 37
```

```
Met Arg Pro Leu Gln Ile Val Pro Ser Arg Leu Ile Ser Gln Leu Tyr
 1               5                  10                  15

Cys Gly Leu Lys Pro Pro Ala Ser Thr Arg Asn Gln Ile Cys Leu Lys
            20                  25                  30

Met Ala Arg Pro Ser Ser Ser Met Ala Asp Phe Arg Lys Phe Phe Ala
        35                  40                  45

Lys Ala Lys His Ile Val Ile Ile Ser Gly Ala Gly Val Ser Ala Glu
    50                  55                  60

Ser Gly Val Pro Thr Phe Arg Gly Ala Gly Gly Tyr Trp Arg Lys Trp
65                  70                  75                  80

Gln Ala Gln Asp Leu Ala Thr Pro Leu Ala Phe Ala His Asn Pro Ser
                85                  90                  95

Arg Val Trp Glu Phe Tyr His Tyr Arg Arg Glu Val Met Gly Ser Lys
            100                 105                 110

Glu Pro Asn Ala Gly His Arg Ala Ile Ala Glu Cys Glu Thr Arg Leu
        115                 120                 125

Gly Lys Gln Gly Arg Arg Val Val Val Ile Thr Gln Asn Ile Asp Glu
    130                 135                 140

Leu His Arg Lys Ala Gly Thr Lys Asn Leu Leu Glu Ile His Gly Ser
145                 150                 155                 160

Leu Phe Lys Thr Arg Cys Thr Ser Cys Gly Val Val Ala Glu Asn Tyr
                165                 170                 175

Lys Ser Pro Ile Cys Pro Ala Leu Ser Gly Lys Gly Ala Pro Glu Pro
            180                 185                 190

Gly Thr Gln Asp Ala Ser Ile Pro Val Glu Lys Leu Pro Arg Cys Glu
        195                 200                 205

Glu Ala Gly Cys Gly Gly Leu Leu Arg Pro His Val Val Trp Phe Gly
    210                 215                 220

Glu Asn Leu Asp Pro Ala Ile Leu Glu Glu Val Asp Arg Glu Leu Ala
225                 230                 235                 240

His Cys Asp Leu Cys Leu Val Val Gly Thr Ser Ser Val Val Tyr Pro
                245                 250                 255

Ala Ala Met Phe Ala Pro Gln Val Ala Ala Arg Gly Val Pro Val Ala
            260                 265                 270

Glu Phe Asn Thr Glu Thr Thr Pro Ala Thr Asn Arg Phe Ser His Leu
        275                 280                 285

Ile Ser Ile Ser Ser Leu Ile Ile Ile Lys Asn
    290                 295


<210> SEQ ID NO 38
<211> LENGTH: 355
<212> TYPE: PRT
<213> ORGANISM: Homo sapiens

<400> SEQUENCE: 38

Met Ser Val Asn Tyr Ala Ala Gly Leu Ser Pro Tyr Ala Asp Lys Gly
 1               5                  10                  15

Lys Cys Gly Leu Pro Glu Ile Phe Asp Pro Pro Glu Glu Leu Glu Arg
            20                  25                  30

Lys Val Trp Glu Leu Ala Arg Leu Val Trp Gln Ser Ser Ser Val Val
        35                  40                  45

Phe His Thr Gly Ala Gly Ile Ser Thr Ala Ser Gly Ile Pro Asp Phe
    50                  55                  60

Arg Gly Pro His Gly Val Trp Thr Met Glu Glu Arg Gly Leu Ala Pro
65                  70                  75                  80
```

```
Lys Phe Asp Thr Thr Phe Glu Ser Ala Arg Pro Thr Gln Thr His Met
                85                  90                  95

Ala Leu Val Gln Leu Glu Arg Val Gly Leu Leu Arg Phe Leu Val Ser
            100                 105                 110

Gln Asn Val Asp Gly Leu His Val Arg Ser Gly Phe Pro Arg Asp Lys
        115                 120                 125

Leu Ala Glu Leu His Gly Asn Met Phe Val Glu Glu Cys Ala Lys Cys
    130                 135                 140

Lys Thr Gln Tyr Val Arg Asp Thr Val Val Gly Thr Met Gly Leu Lys
145                 150                 155                 160

Ala Thr Gly Arg Leu Cys Thr Val Ala Lys Ala Arg Gly Leu Arg Ala
                165                 170                 175

Cys Arg Gly Glu Leu Arg Asp Thr Ile Leu Asp Trp Glu Asp Ser Leu
            180                 185                 190

Pro Asp Arg Asp Leu Ala Leu Ala Asp Glu Ala Ser Arg Asn Ala Asp
        195                 200                 205

Leu Ser Ile Thr Leu Gly Thr Ser Leu Gln Ile Arg Pro Ser Gly Asn
    210                 215                 220

Leu Pro Leu Ala Thr Lys Arg Arg Gly Gly Arg Leu Val Ile Val Asn
225                 230                 235                 240

Leu Gln Pro Thr Lys His Asp Arg His Ala Asp Leu Arg Ile His Gly
                245                 250                 255

Tyr Val Asp Glu Val Met Thr Arg Leu Met Lys His Leu Gly Leu Glu
            260                 265                 270

Ile Pro Ala Trp Asp Gly Pro Arg Val Leu Glu Arg Ala Leu Pro Pro
        275                 280                 285

Leu Pro Arg Pro Pro Thr Pro Lys Leu Glu Pro Lys Glu Glu Ser Pro
    290                 295                 300

Thr Arg Ile Asn Gly Ser Ile Pro Ala Gly Pro Lys Gln Glu Pro Cys
305                 310                 315                 320

Ala Gln His Asn Gly Ser Glu Pro Ala Ser Pro Lys Arg Glu Arg Pro
                325                 330                 335

Thr Ser Pro Ala Pro His Arg Pro Pro Lys Arg Val Lys Ala Lys Ala
            340                 345                 350

Val Pro Ser
        355


<210> SEQ ID NO 39
<211> LENGTH: 256
<212> TYPE: PRT
<213> ORGANISM: Homo sapiens

<400> SEQUENCE: 39

Met Glu Glu Arg Gly Leu Ala Pro Lys Phe Asp Thr Thr Phe Glu Ser
 1               5                  10                  15

Ala Arg Pro Thr Gln Thr His Met Ala Leu Val Gln Leu Glu Arg Val
            20                  25                  30

Gly Leu Leu Arg Phe Leu Val Ser Gln Asn Val Asp Gly Leu His Val
        35                  40                  45

Arg Ser Gly Phe Pro Arg Asp Lys Leu Ala Glu Leu His Gly Asn Met
    50                  55                  60

Phe Val Glu Glu Cys Ala Lys Cys Lys Thr Gln Tyr Val Arg Asp Thr
65                  70                  75                  80

Val Val Gly Thr Met Gly Leu Lys Ala Thr Gly Arg Leu Cys Thr Val
                85                  90                  95
```

```
Ala Lys Ala Arg Gly Leu Arg Ala Cys Arg Asn Ala Asp Leu Ser Ile
            100                 105                 110

Thr Leu Gly Thr Ser Leu Gln Ile Arg Pro Ser Gly Asn Leu Pro Leu
        115                 120                 125

Ala Thr Lys Arg Arg Gly Gly Arg Leu Val Ile Val Asn Leu Gln Pro
    130                 135                 140

Thr Lys His Asp Arg Tyr Ala Asp Leu Arg Ile His Gly Tyr Val Asp
145                 150                 155                 160

Glu Val Met Thr Arg Leu Met Lys His Leu Gly Leu Glu Ile Pro Ala
                165                 170                 175

Trp Asp Gly Pro Arg Val Leu Glu Arg Ala Leu Pro Pro Leu Pro Arg
            180                 185                 190

Pro Pro Thr Pro Lys Leu Glu Pro Lys Glu Glu Ser Pro Thr Arg Ile
        195                 200                 205

Asn Gly Ser Ile Pro Ala Gly Pro Lys Gln Glu Pro Cys Ala Gln His
    210                 215                 220

Asn Gly Ser Glu Pro Ala Ser Pro Lys Arg Glu Arg Pro Thr Ser Pro
225                 230                 235                 240

Ala Pro His Arg Pro Pro Lys Arg Val Lys Ala Lys Ala Val Pro Ser
                245                 250                 255
```

<210> SEQ ID NO 40
<211> LENGTH: 328
<212> TYPE: PRT
<213> ORGANISM: Homo sapiens

<400> SEQUENCE: 40

```
Met Ser Val Asn Tyr Ala Ala Gly Leu Ser Pro Tyr Ala Asp Lys Gly
 1               5                  10                  15

Lys Cys Gly Leu Pro Glu Ile Phe Asp Pro Pro Glu Glu Leu Glu Arg
            20                  25                  30

Lys Val Trp Glu Leu Ala Arg Leu Val Trp Gln Ser Ser Asn Val Val
        35                  40                  45

Phe His Thr Gly Ala Gly Ile Ser Thr Ala Ser Gly Ile Pro Asp Phe
    50                  55                  60

Arg Gly Pro His Gly Val Trp Thr Met Glu Glu Arg Gly Leu Ala Pro
65                  70                  75                  80

Lys Phe Asp Thr Thr Phe Glu Ser Ala Arg Pro Thr Gln Thr His Met
                85                  90                  95

Ala Leu Val Gln Leu Glu Arg Val Gly Leu Leu Arg Phe Leu Val Ser
            100                 105                 110

Gln Asn Val Asp Gly Leu His Val Arg Ser Gly Phe Pro Arg Asp Lys
        115                 120                 125

Leu Ala Glu Leu His Gly Asn Met Phe Val Glu Glu Cys Ala Lys Cys
    130                 135                 140

Lys Thr Gln Tyr Val Arg Asp Thr Val Val Gly Thr Met Gly Leu Lys
145                 150                 155                 160

Ala Thr Gly Arg Leu Cys Thr Val Ala Lys Ala Arg Gly Leu Arg Ala
                165                 170                 175

Cys Arg Asn Ala Asp Leu Ser Ile Thr Leu Gly Thr Ser Leu Gln Ile
            180                 185                 190

Arg Pro Ser Gly Asn Leu Pro Leu Ala Thr Lys Arg Arg Gly Gly Arg
        195                 200                 205

Leu Val Ile Val Asn Leu Gln Pro Thr Lys His Asp Arg His Ala Asp
    210                 215                 220
```

```
Leu Arg Ile His Gly Tyr Val Asp Glu Val Met Thr Arg Leu Met Lys
225                 230                 235                 240

His Leu Gly Leu Glu Ile Pro Ala Trp Asp Gly Pro Arg Val Leu Glu
                245                 250                 255

Arg Ala Leu Pro Pro Leu Pro Arg Pro Pro Thr Pro Lys Leu Glu Pro
            260                 265                 270

Lys Glu Glu Ser Pro Thr Arg Ile Asn Gly Ser Ile Pro Ala Gly Pro
        275                 280                 285

Lys Gln Glu Pro Cys Ala Gln His Asn Gly Ser Glu Pro Ala Ser Pro
    290                 295                 300

Lys Arg Glu Arg Pro Thr Ser Pro Ala Pro His Arg Pro Pro Lys Arg
305                 310                 315                 320

Val Lys Ala Lys Ala Val Pro Ser
                325


<210> SEQ ID NO 41
<211> LENGTH: 400
<212> TYPE: PRT
<213> ORGANISM: Homo sapiens

<400> SEQUENCE: 41

Met Ala Ala Gly Gly Leu Ser Arg Ser Glu Arg Lys Ala Ala Glu Arg
 1               5                  10                  15

Val Arg Arg Leu Arg Glu Glu Gln Gln Arg Glu Arg Leu Arg Gln Val
            20                  25                  30

Ser Arg Ile Leu Arg Lys Ala Ala Ala Glu Arg Ser Ala Glu Glu Gly
        35                  40                  45

Arg Leu Leu Ala Glu Ser Ala Asp Leu Val Thr Glu Leu Gln Gly Arg
    50                  55                  60

Ser Arg Arg Arg Glu Gly Leu Lys Arg Arg Gln Glu Glu Val Cys Asp
65                  70                  75                  80

Asp Pro Glu Glu Leu Arg Gly Lys Val Arg Glu Leu Ala Ser Ala Val
                85                  90                  95

Arg Asn Ala Lys Tyr Leu Val Val Tyr Thr Gly Ala Gly Ile Ser Thr
            100                 105                 110

Ala Ala Ser Ile Pro Asp Tyr Arg Gly Pro Asn Gly Val Trp Thr Leu
        115                 120                 125

Leu Gln Lys Gly Arg Ser Val Ser Ala Ala Asp Leu Ser Glu Ala Glu
    130                 135                 140

Pro Thr Leu Thr His Met Ser Ile Thr Arg Leu His Glu Gln Lys Leu
145                 150                 155                 160

Val Gln His Val Val Ser Gln Asn Cys Asp Gly Leu His Leu Arg Ser
                165                 170                 175

Gly Leu Pro Arg Thr Ala Ile Ser Glu Leu His Gly Asn Met Tyr Ile
            180                 185                 190

Glu Val Cys Thr Ser Cys Val Pro Asn Arg Glu Tyr Val Arg Val Phe
        195                 200                 205

Asp Val Thr Glu Arg Thr Ala Leu His Arg His Gln Thr Gly Arg Thr
    210                 215                 220

Cys His Lys Cys Gly Thr Gln Leu Arg Asp Thr Ile Val His Phe Gly
225                 230                 235                 240

Glu Arg Gly Thr Leu Gly Gln Pro Leu Asn Trp Glu Ala Ala Thr Glu
                245                 250                 255

Ala Ala Ser Arg Ala Asp Thr Ile Leu Cys Leu Gly Ser Ser Leu Lys
            260                 265                 270
```

```
Val Leu Lys Lys Tyr Pro Arg Leu Trp Cys Met Thr Lys Pro Pro Ser
        275                 280                 285

Arg Arg Pro Lys Leu Tyr Ile Val Asn Leu Gln Trp Thr Pro Lys Asp
    290                 295                 300

Asp Trp Ala Ala Leu Lys Leu His Gly Lys Cys Asp Asp Val Met Arg
305                 310                 315                 320

Leu Leu Met Ala Glu Leu Gly Leu Glu Ile Pro Ala Tyr Ser Arg Trp
                325                 330                 335

Gln Asp Pro Ile Phe Ser Leu Ala Thr Pro Leu Arg Ala Gly Glu Glu
            340                 345                 350

Gly Ser His Ser Arg Lys Ser Leu Cys Arg Ser Arg Glu Glu Ala Pro
        355                 360                 365

Pro Gly Asp Arg Gly Ala Pro Leu Ser Ser Ala Pro Ile Leu Gly Gly
    370                 375                 380

Trp Phe Gly Arg Gly Cys Thr Lys Arg Thr Lys Arg Lys Lys Val Thr
385                 390                 395                 400


<210> SEQ ID NO 42
<211> LENGTH: 2773
<212> TYPE: DNA
<213> ORGANISM: Homo sapiens

<400> SEQUENCE: 42

gcgagtccgg aggactcctt ggactgcgcg gaacatggcg ttctggggtt ggcgcgccgc     60

ggcagccctc cggctgtggg gccgggtagt tgaacgggtc gaggccgggg gaggcgtggg    120

gccgtttcag gcctgcggct gtcggctggt gcttggcggc agggacgatt attaaaggtg    180

gaagaaggtc catatctttt tctgtgggtg cttcaagtgt tgttggaagt ggaggcagca    240

gtgacaaggg gaagctttcc ctgcaggatg tagctgagct gattcgggcc agagcctgcc    300

agagggtggt ggtcatggtg ggggccggca tcagcacacc cagtggcatt ccagacttca    360

gatcgccggg gagtggcctg tacagcaacc tccagcagta cgatctcccg taccccgagg    420

ccatttttga actcccattc ttctttcaca accccaagcc ctttttcact ttggccaagg    480

agctgtaccc tggaaactac aagcccaacg tcactcacta ctttctccgg ctgcttcatg    540

acaaggggct gcttctgcgg ctctacacgc agaacatcga tgggcttgag agagtgtcgg    600

gcatccctgc ctcaaagctg gttgaagctc atggaacctt tgcctctgcc acctgcacag    660

tctgccaaag acccttccca ggggaggaca ttcgggctga cgtgatggca gacagggttc    720

cccgctgccc ggtctgcacc ggcgttgtga agcccgacat tgtgttcttt ggggagccgc    780

tgccccagag gttcttgctg catgtggttg atttccccat ggcagatctg ctgctcatcc    840

ttgggacctc cctggaggtg gagccttttg ccagcttgac cgaggccgtg cggagctcag    900

ttccccgact gctcatcaac cgggacttgg tggggccctt ggcttggcat cctcgcagca    960

gggacgtggc ccagctgggg gacgtggttc acggcgtgga aagcctagtg gagcttctgg   1020

gctggacaga agagatgcgg gaccttgtgc agcgggaaac tgggaagctt gatggaccag   1080

acaaatagga tgatggctgc ccccacacaa taaatggtaa cataggagac atccacatcc   1140

caattctgac aagacctcat gcctgaagac agcttgggca ggtgaaacca gaatatgtga   1200

actgagtgga cacccgaggc tgccactgga atgtcttctc aggccatgag ctgcagtgac   1260

tggtagggct gtgtttacag tcagggccac cccgtcacat atacaaagga gctgcctgcc   1320

tgtttgctgt gttgaactct tcactctgct gaagctccta atggaaaaag ctttcttctg   1380

actgtgaccc tcttgaactg aatcagacca actggaatcc cagaccgagt ctgctttctg   1440
```

tgcctagttg aacggcaagc tcggcatctg ttggttacaa gatccagact tgggccgagc 1500
ggtccccagc cctcttcatg ttccgaagtg tagtcttgag gccctggtgc cgcacttcta 1560
gcatgttggt ctcctttagt ggggctattt ttaatgagag aaaatctgtt ctttccagca 1620
tgaaatacat ttagtctcct caaagggact gcaggtgttg acatgagttg gaaagggaac 1680
cctgggatac gtggcgtccc ctctattgga acagtctgag gactgaaggc atttgtccct 1740
ggatttattg gagacggccc agctcctccc tctgaaggtg gtcacattct gttgactctc 1800
catactcagc ctctcctcca gaaacagatc tgttccagaa cattccagca ctttctatct 1860
ggcctccttg tccccacact acgccccccc accctcgcca gggcttcctc tagtgacact 1920
gttagagcta atctctgaga cagggaaggc attactcact taaaacccag gctgagtcct 1980
ggccacctgc tggattgtga cataggaggt ggaatccact gaactgctac ttctgcacag 2040
gctccttctc ctggggctgt acccaggccc agccctgatg gctcaccctg tcaggcacca 2100
gctgctccct cctgggctct cacccacctg cacatcctcc ttcctagcat cacattacct 2160
gcgtgtttcc ccagacaaaa gcacttccca ttcttgaacc ttgcctaccc tgggctgagc 2220
tgacggcaat agatttaatg acagtgactc ccaggaaggg ggtcctgtga ctttgcgcct 2280
taataagaac aaaaggtgga attggtgacc taggaaaact gttgaattct aaaaagaatg 2340
aagttagttt ctaaccctag ttaatgttcc ttttttattt tttgagtctt gccctgtcac 2400
tcagggtgga gtgcggtgtt atgatctcag ctcactgcaa cttccgcctc ccgggtttaa 2460
gcgattctcc tgggtagctg ggattacagg tgtgtcccac cacacctagc acatgggcat 2520
atttgtaata gagacaaggt tttgctatgt tggccaggct ggtctcgaac tcctggcttc 2580
aagtgatcca cccacctcgg cctcccaaag tgctgggatt acaggcatga gccactgtgc 2640
ctggcccctt tatttgataa tttacacata catttttgtc caaaactctt ctttatttca 2700
agatgatgtt tctgtggcta tgtgtggtat gtggtataaa tctcaatcta tggtcaaaaa 2760
aaaaaaaaaa aaa 2773

<210> SEQ ID NO 43
<211> LENGTH: 2919
<212> TYPE: DNA
<213> ORGANISM: Homo sapiens

<400> SEQUENCE: 43
gcgagtccgg aggactcctt ggactgcgcg gaacatggcg ttctggggtt ggcgcgccgc 60
ggcagccctc cggctgtggg gccgggtagt tgaacgggtc gaggccgggg gaggcgtggg 120
gccgtttcag gcctgcggct gtcggctggt gcttggcggc agggacgatg tgagtgcggg 180
gctgagaggc agccatgggg cccgcggtga gcccttggac ccggcgcgcc ccttgcagag 240
gcctcccaga cccgaggtgc ccagggcatt ccggaggcag ccgagggcag cagctcccag 300
tttcttcttt tcgagtatta aaggtggaag aaggtccata tctttttctg tgggtgcttc 360
aagtgttgtt ggaagtggag gcagcagtga caaggggaag ctttccctgc aggatgtagc 420
tgagctgatt cgggccagag cctgccagag ggtggtggtc atggtggggg ccggcatcag 480
cacacccagt ggcattccag acttcagatc gccggggagt ggcctgtaca gcaacctcca 540
gcagtacgat ctcccgtacc ccgaggccat ttttgaactc ccattcttct ttcacaaccc 600
caagcccttt ttcactttgg ccaaggagct gtaccctgga aactacaagc ccaacgtcac 660
tcactacttt ctccggctgc ttcatgacaa ggggctgctt ctgcggctct acacgcagaa 720
catcgatggg cttgagagag tgtcgggcat ccctgcctca aagctggttg aagctcatgg 780

-continued

```
aacctttgcc tctgccacct gcacagtctg ccaaagaccc ttcccagggg aggacattcg    840
ggctgacgtg atggcagaca gggttccccg ctgcccggtc tgcaccggcg ttgtgaagcc    900
cgacattgtg ttctttgggg agccgctgcc ccagaggttc ttgctgcatg tggttgattt    960
ccccatggca gatctgctgc tcatccttgg gacctccctg gaggtggagc cttttgccag   1020
cttgaccgag gccgtgcgga gctcagttcc ccgactgctc atcaaccggg acttggtggg   1080
gcccttggct tggcatcctc gcagcaggga cgtggcccag ctgggggacg tggttcacgg   1140
cgtggaaagc ctagtggagc ttctgggctg gacagaagag atgcgggacc ttgtgcagcg   1200
ggaaactggg aagcttgatg gaccagacaa ataggatgat ggctgccccc acacaataaa   1260
tggtaacata ggagacatcc acatcccaat tctgacaaga cctcatgcct gaagacagct   1320
tgggcaggtg aaaccagaat atgtgaactg agtggacacc cgaggctgcc actggaatgt   1380
cttctcaggc catgagctgc agtgactggt agggctgtgt ttacagtcag ggccaccccg   1440
tcacatatac aaaggagctg cctgcctgtt tgctgtgttg aactcttcac tctgctgaag   1500
ctcctaatgg aaaaagcttt cttctgactg tgaccctctt gaactgaatc agaccaactg   1560
gaatcccaga ccgagtctgc tttctgtgcc tagttgaacg gcaagctcgg catctgttgg   1620
ttacaagatc cagacttggg ccgagcggtc cccagccctc ttcatgttcc gaagtgtagt   1680
cttgaggccc tggtgccgca cttctagcat gttggtctcc tttagtgggg ctatttttaa   1740
tgagagaaaa tctgttcttt ccagcatgaa atacatttag tctcctcaaa gggactgcag   1800
gtgttgacat gagttggaaa gggaaccctg ggatacgtgg cgtcccctct attggaacag   1860
tctgaggact gaaggcattt gtccctggat ttattggaga cggcccagct cctccctctg   1920
aaggtggtca cattctgttg actctccata ctcagcctct cctccagaaa cagatctgtt   1980
ccagaacatt ccagcacttt ctatctggcc tccttgtccc cacactacgc ccccccaccc   2040
tcgccagggc ttcctctagt gacactgtta gagctaatct ctgagacagg gaaggcatta   2100
ctcacttaaa acccaggctg agtcctggcc acctgctgga ttgtgacata ggaggtggaa   2160
tccactgaac tgctacttct gcacaggctc cttctcctgg ggctgtaccc aggcccagcc   2220
ctgatggctc accctgtcag gcaccagctg ctccctcctg ggctctcacc cacctgcaca   2280
tcctccttcc tagcatcaca ttacctgcgt gtttccccag acaaaagcac ttcccattct   2340
tgaaccttgc ctaccctggg ctgagctgac ggcaatagat ttaatgacag tgactcccag   2400
gaagggggtc ctgtgacttt gcgccttaat aagaacaaaa ggtggaattg gtgacctagg   2460
aaaactgttg aattctaaaa agaatgaagt tagtttctaa ccctagttaa tgttcctttt   2520
ttattttttg agtcttgccc tgtcactcag ggtggagtgc ggtgttatga tctcagctca   2580
ctgcaacttc cgcctcccgg gtttaagcga ttctcctggg tagctgggat tacaggtgtg   2640
tcccaccaca cctagcacat gggcatattt gtaatagaga caaggttttg ctatgttggc   2700
caggctggtc tcgaactcct ggcttcaagt gatccaccca cctcggcctc ccaaagtgct   2760
gggattacag gcatgagcca ctgtgcctgg cccctttatt tgataattta cacatacatt   2820
tttgtccaaa actcttcttt atttcaagat gatgtttctg tggctatgtg tggtatgtgg   2880
tataaatctc aatctatggt caaaaaaaaa aaaaaaaaa                           2919
```

<210> SEQ ID NO 44
<211> LENGTH: 1798
<212> TYPE: DNA
<213> ORGANISM: Homo sapiens

<400> SEQUENCE: 44

-continued

```
ctcggactgc gcggaacatg gcgttctggg gttggcgcgc cgcggcagcc ctccggctgt      60
ggggccgggt agttgaacgg gtcgaggccg ggggaggcgt ggggccgttt caggcctgcg     120
gctgtcggct ggtgcttggc ggcagggacg atgtgagtgc ggggctgaga ggcagccatg     180
gggcccgcgg tgagcccttg gacccggcgc gccccttgca gaggcctccc agacccgagg     240
tgcccagggc attccggagg cagccgaggg cagcagctcc cagtttcttc ttttcgagta     300
ttaaaggtgg aagaaggtcc atatcttttt ctgtgggtgc ttcaagtgtt gttggaagtg     360
gaggcagcag tgacaagggg aagctttccc tgcaggatgt agctgagctg attcgggcca     420
gagcctgcca gagggtggtg gtcatggtgg gggccggcat cagcacaccc agtggcattc     480
cagacttcag atcgccgggg agtggcctgt acagcaacct ccagcagtac gatctcccgt     540
accccgaggc catttttgaa ctcccattct tctttcacaa ccccaagccc tttttcactt     600
tggccaagga gctgtaccct ggaaactaca agcccaacgt cactcactac tttctccggc     660
tgcttcatga caaggggctg cttctgcggc tctacacgca gaacatcgat gggcttgaga     720
gagtgtcggg catccctgcc tcaaagctgg ttgaagctca tggaaccttt gcctctgcca     780
cctgcacagt ctgccaaaga cccttcccag gggaggacat tcgggctgac gtgatggcag     840
acagggttcc ccgctgcccg gtctgcaccg gcgttgtgaa gcccgacatt gtgttctttg     900
gggagccgct gccccagagg ttcttgctgc atgtggttga tttccccatg gcagatctgc     960
tgctcatcct tgggacctcc ctggaggtgg agccttttgc cagcttgacc gaggccgtgc    1020
ggagctcagt tccccgactg ctcatcaacc gggacttggt ggggcccttg gcttggcatc    1080
ctcgcagcag ggacgtggcc cagctggggg acgtggttca cggcgtggaa agcctagtgg    1140
agcttctggg ctggacagaa gagatgcggg accttgtgca gcgggaaact gggaagcttg    1200
atggaccaga caaataggat gatggctgcc cccacacaat aaatggtaac ataggagaca    1260
tccacatccc aattctgaca agacctcatg cctgaagaca gcttgggcag gtgaaaccag    1320
aatatgtgaa ctgagtggac acccgaggct gccactggaa tgtcttctca ggccatgagc    1380
tgcagtgact ggtagggctg tgtttacagt cagggccacc ccgtcacata tacaaaggag    1440
ctgcctgcct gtttgctgtg ttgaactctt cactctgctg aagctcctaa tggaaaaagc    1500
tttcttctga ctgtgaccct cttgaactga atcagaccaa ctggaatccc agaccgagtc    1560
tgctttctgt gcctagttga acggcaagct cggcatctgt tggttacaag atccagactt    1620
gggccgagcg gtccccagcc ctcttcatgt tccgaagtgt agtcttgagg ccctggtgcc    1680
gcacttctag catgttggtc tcctttagtg gggctatttt taatgagaga aaatctgttc    1740
tttccagcat gaaatacatt tagtctcctc aaaaaaaaaa aaaaaaaaaa aaaaaaaa      1798
```

<210> SEQ ID NO 45
<211> LENGTH: 1869
<212> TYPE: DNA
<213> ORGANISM: Homo sapiens

<400> SEQUENCE: 45

```
ggcgccgggg gcgggggtgg gaggcggagg cggggccggg gcgccgcggg cggggcgccg      60
ggggcggggc gagtccggag gactcctcgg actgcgcgga acatggcgtt ctggggttgg     120
cgcgccgcgg cagccctccg gctgtggggc cgggtagttg aacgggtcga ggccggggga     180
ggcgtggggc cgtttcaggc ctgcggctgt cggctggtgc ttggcggcag ggacgatgtg     240
agtgcggggc tgagaggcag ccatggggcc cgcggtgagc ccttggaccc ggcgcgcccc     300
ttgcagaggc ctcccagacc cgaggtgccc agggcattcc ggaggcagcc gagggcagca     360
```

-continued

```
gctcccagtt tcttcttttc gagtattaaa ggtggaagaa ggtccatatc tttttctgtg    420
ggtgcttcaa gtgttgttgg aagtggaggc agcagtgaca aggggaagct ttccctgcag    480
gatgtagctg agctgattcg ggccagagcc tgccagaggg tggtggtcat ggtgggggcc    540
ggcatcagca cacccagtgg cattccagac ttcagatcgc cggggagtgg cctgtacagc    600
aacctccagc agtacgatct cccgtacccc gaggccattt ttgaactccc attcttcttt    660
cacaacccca agcccttttt cactttggcc aaggagctgt accctggaaa ctacaagccc    720
aacgtcactc actactttct ccggctgctt catgacaagg ggctgcttct gcggctctac    780
acgcagaaca tcgatgggct tgagagagtg tcgggcatcc ctgcctcaaa gctggttgaa    840
gctcatggaa cctttgcctc tgccacctgc acagtctgcc aaagaccctt cccaggggag    900
gacattcggg ctgacgtgat ggcagacagg gttccccgct gcccggtctg caccggcgtt    960
gtgaagcccg acattgtgtt ctttggggag ccgctgcccc agaggttctt gctgcatgtg   1020
gttgatttcc ccatggcaga tctgctgctc atccttggga cctccctgga ggtggagcct   1080
tttgccagct tgaccgaggc cgtgcggagc tcagttcccc gactgctcat caaccgggac   1140
ttggtggggc ccttggcttg gcatcctcgc agcagggacg tggcccagct gggggacgtg   1200
gttcacggcg tggaaagcct agtggagctt ctgggctgga cagaagagat gcgggacctt   1260
gtgcagcggg aaactgggaa gcttgatgga ccagacaaat aggatgatgg ctgcccccac   1320
acaataaatg gtaacatagg agacatccac atcccaattc tgacaagacc tcatgcctga   1380
agacagcttg ggcaggtgaa accagaatat gtgaactgag tggacacccg aggctgccac   1440
tggaatgtct tctcaggcca tgagctgcag tgactggtag ggctgtgttt acagtcaggg   1500
ccaccccgtc acatatacaa aggagctgcc tgcctgtttg ctgtgttgaa ctcttcactc   1560
tgctgaagct cctaatggaa aaagctttct tctgactgtg accctcttga actgaatcag   1620
accaactgga atcccagacc gagtctgctt tctgtgccta gttgaacggc aagctcggca   1680
tctgttggtt acaagatcca gacttgggcc gagcggtccc cagccctctt catgttccga   1740
agtgtagtct tgaggccctg gtgccgcact tctagcatgt tggtctcctt tagtggggct   1800
atttttaatg agagaaaatc tgttctttcc agcatgaaat acatttagtc tcctcaaaaa   1860
aaaaaaaca                                                            1869

<210> SEQ ID NO 46
<211> LENGTH: 257
<212> TYPE: PRT
<213> ORGANISM: Mus musculus

<400> SEQUENCE: 46

Met Val Gly Ala Gly Ile Ser Thr Pro Ser Gly Ile Pro Asp Phe Arg
1               5                   10                  15

Ser Pro Gly Ser Gly Leu Tyr Ser Asn Leu Gln Gln Tyr Asp Ile Pro
            20                  25                  30

Tyr Pro Glu Ala Ile Phe Glu Leu Gly Phe Phe Phe His Asn Pro Lys
        35                  40                  45

Pro Phe Phe Met Leu Ala Lys Glu Leu Tyr Pro Gly His Tyr Arg Pro
    50                  55                  60

Asn Val Thr His Tyr Phe Leu Arg Leu Leu His Asp Lys Glu Leu Leu
65                  70                  75                  80

Leu Arg Leu Tyr Thr Gln Asn Ile Asp Gly Leu Glu Arg Ala Ser Gly
                85                  90                  95

Ile Pro Ala Ser Lys Leu Val Glu Ala His Gly Thr Phe Val Thr Ala
            100                 105                 110
```

```
Thr Cys Thr Val Cys Arg Arg Ser Phe Pro Gly Glu Asp Ile Trp Ala
        115                 120                 125

Asp Val Met Ala Asp Arg Val Pro Arg Cys Pro Val Cys Thr Gly Val
    130                 135                 140

Val Lys Pro Asp Ile Val Phe Phe Gly Glu Gln Leu Pro Ala Arg Phe
145                 150                 155                 160

Leu Leu His Met Ala Asp Phe Ala Leu Ala Asp Leu Leu Leu Ile Leu
                165                 170                 175

Gly Thr Ser Leu Glu Val Glu Pro Phe Ala Ser Leu Ser Glu Ala Val
            180                 185                 190

Gln Lys Ser Val Pro Arg Leu Leu Ile Asn Arg Asp Leu Val Gly Pro
        195                 200                 205

Phe Val Leu Ser Pro Arg Arg Lys Asp Val Val Gln Leu Gly Asp Val
    210                 215                 220

Val His Gly Val Glu Arg Leu Val Asp Leu Leu Gly Trp Thr Gln Glu
225                 230                 235                 240

Leu Leu Asp Leu Met Gln Arg Glu Arg Gly Lys Leu Asp Gly Gln Asp
                245                 250                 255

Arg


<210> SEQ ID NO 47
<211> LENGTH: 257
<212> TYPE: PRT
<213> ORGANISM: Rattus norvegicus

<400> SEQUENCE: 47

Met Val Gly Ala Gly Ile Ser Thr Pro Ser Gly Ile Pro Asp Phe Arg
 1               5                  10                  15

Ser Pro Gly Ser Gly Leu Tyr Ser Asn Leu Gln Gln Tyr Asp Ile Pro
            20                  25                  30

Tyr Pro Glu Ala Ile Phe Glu Leu Gly Phe Phe Phe His Asn Pro Lys
        35                  40                  45

Pro Phe Phe Thr Leu Ala Lys Glu Leu Tyr Pro Gly His Tyr Arg Pro
    50                  55                  60

Asn Val Ala His Tyr Phe Leu Arg Leu Leu His Asp Lys Glu Leu Leu
65                  70                  75                  80

Leu Arg Leu Tyr Thr Gln Asn Ile Asp Gly Leu Glu Arg Ala Ser Gly
                85                  90                  95

Ile Pro Ala Ser Lys Leu Val Glu Ala His Gly Ser Phe Val Ser Ala
            100                 105                 110

Thr Cys Thr Val Cys Arg Arg Ser Phe Pro Gly Glu Asp Ile Arg Ala
        115                 120                 125

Asp Val Met Ala Asp Arg Val Pro Arg Cys Pro Val Cys Thr Gly Val
    130                 135                 140

Val Lys Pro Asp Ile Val Phe Phe Gly Glu Gln Leu Pro Ala Arg Phe
145                 150                 155                 160

Leu Leu His Val Ala Asp Phe Ala Leu Ala Asp Leu Leu Leu Ile Leu
                165                 170                 175

Gly Thr Ser Leu Glu Val Glu Pro Phe Ala Ser Leu Ser Glu Ser Val
            180                 185                 190

Gln Lys Ser Val Pro Arg Leu Leu Ile Asn Arg Asp Leu Val Gly Ser
        195                 200                 205

Phe Ala Leu Ser Pro Arg Arg Lys Asp Val Val Gln Leu Gly Asp Val
    210                 215                 220
```

Val Gln Gly Val Glu Arg Leu Val Asp Leu Leu Gly Trp Thr Gln Glu
225 230 235 240

Leu Gln Asp Leu Ile Gln Arg Glu Asn Gly Lys Leu Asp Gly Gln Asp
245 250 255

Gly

<210> SEQ ID NO 48
<211> LENGTH: 318
<212> TYPE: PRT
<213> ORGANISM: Bos taurus

<400> SEQUENCE: 48

Met Ala Leu Phe Pro Arg Ser Ala Val Pro Ala Leu Ser Ile Pro Gly
1 5 10 15

Gly Gly Trp Ser Ile Ser Cys Phe Ala Gly Ala Ser Ser Asp Thr Gly
20 25 30

Gly Gly Asp His Ser Gln Lys Lys Phe Leu Leu Gln Asp Ile Ala Glu
35 40 45

Leu Ile Lys Thr Arg Ala Cys Gln Lys Val Val Val Met Val Gly Ala
50 55 60

Gly Ile Ser Thr Pro Ser Gly Ile Pro Asp Phe Arg Ser Pro Gly Val
65 70 75 80

Gly Tyr Tyr Ser Ile Leu Gln Gln Tyr Lys Leu Pro Tyr Pro Glu Ala
85 90 95

Ile Phe Glu Leu Ser Phe Phe Phe His Asp Pro Lys Pro Phe Phe Thr
100 105 110

Phe Ala Lys Lys Leu Tyr Pro Gly Asn Tyr Arg Pro Asn Ala Thr His
115 120 125

Tyr Phe Leu Arg Leu Leu His Glu Lys Gly Leu Leu Leu Arg Leu Tyr
130 135 140

Thr Gln Asn Ile Asp Gly Leu Glu Arg Ala Ser Gly Ile Pro Asp Ser
145 150 155 160

Lys Leu Val Glu Ala His Gly Ser Leu Ala Ser Ala Thr Cys Thr Val
165 170 175

Cys Arg Arg Pro Tyr Pro Gly Glu Asp Phe Trp Ala Asp Val Met Ala
180 185 190

Asp Arg Val Pro Arg Cys Pro Val Cys Ser Gly Val Thr Lys Pro Asp
195 200 205

Ile Val Phe Phe Gly Glu Pro Leu Pro Ala Arg Phe Leu Leu His Leu
210 215 220

Ala Asp Phe Pro Met Ala Asp Leu Leu Leu Ile Leu Gly Thr Ser Leu
225 230 235 240

Glu Val Glu Pro Phe Ala Ser Leu Ser Asp Ala Val Arg Ser Ser Val
245 250 255

Pro Arg Leu Leu Ile Asn Arg Asp Leu Val Gly Ser Leu Ala Arg Asn
260 265 270

Pro Arg Gly Arg Asp Val Ala Gln Leu Gly Asp Val Val His Gly Val
275 280 285

Lys Arg Leu Val Glu Leu Leu Gly Trp Thr Asp Asp Ile Gln Asp Leu
290 295 300

Ile Gln Arg Glu Thr Gly Lys Phe Asp Gly Trp Asp Arg Leu
305 310 315

<210> SEQ ID NO 49
<211> LENGTH: 333
<212> TYPE: PRT

<213> ORGANISM: Bos taurus

<400> SEQUENCE: 49

```
Met Ala Leu Phe Pro Arg Ser Ala Val Pro Ala Leu Arg Phe Trp Gly
 1               5                  10                  15

Leu Arg Gly Ala Arg Ala Trp Thr Arg Trp Pro Arg Ile Pro Gly Gly
            20                  25                  30

Gly Trp Ser Ile Ser Cys Phe Ala Gly Ala Ser Ser Asp Thr Gly Gly
        35                  40                  45

Gly Asp His Ser Gln Lys Lys Phe Leu Leu Gln Asp Ile Ala Glu Leu
    50                  55                  60

Ile Lys Thr Arg Ala Cys Gln Lys Val Val Val Met Val Gly Ala Gly
65                  70                  75                  80

Ile Ser Thr Pro Ser Gly Ile Pro Asp Phe Arg Ser Pro Gly Val Gly
                85                  90                  95

Tyr Tyr Ser Ile Leu Gln Gln Tyr Lys Leu Pro Tyr Pro Glu Ala Ile
            100                 105                 110

Phe Glu Leu Ser Phe Phe Phe His Asp Pro Lys Pro Phe Phe Thr Phe
        115                 120                 125

Ala Lys Lys Leu Tyr Pro Gly Asn Tyr Arg Pro Asn Ala Thr His Tyr
    130                 135                 140

Phe Leu Arg Leu Leu His Glu Lys Gly Leu Leu Leu Arg Leu Tyr Thr
145                 150                 155                 160

Gln Asn Ile Asp Gly Leu Glu Arg Ala Ser Gly Ile Pro Asp Ser Lys
                165                 170                 175

Leu Val Glu Ala His Gly Ser Leu Ala Ser Ala Thr Cys Thr Val Cys
            180                 185                 190

Arg Arg Pro Tyr Pro Gly Glu Asp Phe Trp Ala Asp Val Met Ala Asp
        195                 200                 205

Arg Val Pro Arg Cys Pro Val Cys Ser Gly Val Thr Lys Pro Asp Ile
    210                 215                 220

Val Phe Phe Gly Glu Pro Leu Pro Ala Arg Phe Leu Leu His Leu Ala
225                 230                 235                 240

Asp Phe Pro Met Ala Asp Leu Leu Leu Ile Leu Gly Thr Ser Leu Glu
                245                 250                 255

Val Glu Pro Phe Ala Ser Leu Ser Asp Ala Val Arg Ser Ser Val Pro
            260                 265                 270

Arg Leu Leu Ile Asn Arg Asp Leu Val Gly Ser Leu Ala Arg Asn Pro
        275                 280                 285

Arg Gly Arg Asp Val Ala Gln Leu Gly Asp Val Val His Gly Val Lys
    290                 295                 300

Arg Leu Val Glu Leu Leu Gly Trp Thr Asp Asp Ile Gln Asp Leu Ile
305                 310                 315                 320

Gln Arg Glu Thr Gly Lys Phe Asp Gly Trp Asp Arg Leu
                325                 330
```

<210> SEQ ID NO 50
<211> LENGTH: 330
<212> TYPE: PRT
<213> ORGANISM: Canis lupus familiaris

<400> SEQUENCE: 50

```
Met Asp Met Gly Ala Ala Ser Leu Trp Gly Val Arg Lys Ala Pro Cys
 1               5                  10                  15

Ala Val Glu Leu Ala Val Leu Asn Ser Gly Ile Thr Gly Gly Arg Arg
            20                  25                  30
```

```
Pro Ile Ser Phe Ser Thr Arg Thr Ser Ser Ile Phe Gly Ser Gly Gly
        35                  40                  45

Asp His Lys Lys Lys Leu Phe Leu Gln Asp Ile Ala Glu Leu Ile Arg
    50                  55                  60

Ala Arg Ala Cys Gln Arg Val Leu Val Met Val Gly Ala Gly Ile Ser
65                  70                  75                  80

Thr Pro Ser Gly Ile Pro Asp Phe Arg Ser Pro Gly Ser Gly Leu Tyr
                85                  90                  95

Ser Asn Leu Gln Gln Tyr Asp Leu Pro Tyr Pro Glu Ala Val Phe Glu
            100                 105                 110

Leu Ala Phe Phe Ser His Asn Pro Lys Pro Phe Phe Thr Leu Ala Lys
        115                 120                 125

Glu Leu Tyr Leu Lys Asn Tyr Arg Pro Asn Ile Ile His Tyr Phe Leu
    130                 135                 140

Arg Leu Leu His Asp Lys Gly Leu Leu Leu Arg Leu Tyr Thr Gln Asn
145                 150                 155                 160

Ile Asp Gly Leu Glu Arg Val Ala Gly Ile Pro Ala Ser Lys Leu Val
                165                 170                 175

Glu Ala His Gly Ser Phe Ala Ser Ala Thr Cys Thr Val Cys Arg Arg
            180                 185                 190

Pro Ser Ser Gly Lys Asp Ile Trp Ala Asp Val Ser Met Asp Lys Ile
        195                 200                 205

Pro Arg Cys Pro Val Cys Thr Gly Val Leu Lys Pro Asp Ile Val Phe
    210                 215                 220

Phe Gly Glu Thr Leu Pro Gln Arg Phe Leu Leu His Val Leu Asp Phe
225                 230                 235                 240

Pro Met Ala Asp Met Leu Leu Ile Leu Gly Thr Ser Leu Glu Val Glu
                245                 250                 255

Pro Phe Ala Ser Leu Ser Glu Ala Val Arg Ser Ser Val Pro Arg Leu
            260                 265                 270

Leu Ile Asn Arg Asp Val Val Gly Pro Phe Ala Trp Cys Pro Arg Ser
        275                 280                 285

Arg Asp Val Val Gln Leu Gly Asp Val Val His Ser Val Glu Arg Leu
    290                 295                 300

Val Glu Leu Leu Gly Trp Arg Glu Glu Leu Gln Asp Leu Ile Gln Gln
305                 310                 315                 320

Glu Thr Glu Lys Leu Asp Gly Arg Asp Gly
                325                 330
```

<210> SEQ ID NO 51
<211> LENGTH: 372
<212> TYPE: PRT
<213> ORGANISM: Canis lupus familiaris

<400> SEQUENCE: 51

```
Met Thr Arg Cys Ala Arg Pro Ala Leu Ala Ala Leu Gly Leu Trp Gly
 1               5                  10                  15

Pro Ala Gly Trp Arg Ser Leu Tyr Thr Gly Val Arg Asp Val Leu Gly
            20                  25                  30

Glu Gly His Gln Arg Pro Ser Pro Gly Arg Met Asp Met Gly Ala Ala
        35                  40                  45

Ser Leu Trp Gly Val Arg Lys Ala Pro Cys Ala Val Glu Leu Ala Val
    50                  55                  60

Leu Asn Ser Gly Ile Thr Gly Gly Arg Arg Pro Ile Ser Phe Ser Thr
65                  70                  75                  80
```

```
Arg Thr Ser Ser Ile Phe Gly Ser Gly Gly Asp His Lys Lys Lys Leu
                85                  90                  95

Phe Leu Gln Asp Ile Ala Glu Leu Ile Arg Ala Arg Ala Cys Gln Arg
            100                 105                 110

Val Leu Val Met Val Gly Ala Gly Ile Ser Thr Pro Ser Gly Ile Pro
        115                 120                 125

Asp Phe Arg Ser Pro Gly Ser Gly Leu Tyr Ser Asn Leu Gln Gln Tyr
    130                 135                 140

Asp Leu Pro Tyr Pro Glu Ala Val Phe Glu Leu Ala Phe Phe Ser His
145                 150                 155                 160

Asn Pro Lys Pro Phe Phe Thr Leu Ala Lys Glu Leu Tyr Leu Lys Asn
                165                 170                 175

Tyr Arg Pro Asn Ile Ile His Tyr Phe Leu Arg Leu Leu His Asp Lys
            180                 185                 190

Gly Leu Leu Leu Arg Leu Tyr Thr Gln Asn Ile Asp Gly Leu Glu Arg
        195                 200                 205

Val Ala Gly Ile Pro Ala Ser Lys Leu Val Glu Ala His Gly Ser Phe
    210                 215                 220

Ala Ser Ala Thr Cys Thr Val Cys Arg Arg Pro Ser Ser Gly Lys Asp
225                 230                 235                 240

Ile Trp Ala Asp Val Ser Met Asp Lys Ile Pro Arg Cys Pro Val Cys
                245                 250                 255

Thr Gly Val Leu Lys Pro Asp Ile Val Phe Phe Gly Glu Thr Leu Pro
            260                 265                 270

Gln Arg Phe Leu Leu His Val Leu Asp Phe Pro Met Ala Asp Met Leu
        275                 280                 285

Leu Ile Leu Gly Thr Ser Leu Glu Val Glu Pro Phe Ala Ser Leu Ser
    290                 295                 300

Glu Ala Val Arg Ser Ser Val Pro Arg Leu Leu Ile Asn Arg Asp Val
305                 310                 315                 320

Val Gly Pro Phe Ala Trp Cys Pro Arg Ser Arg Asp Val Val Gln Leu
                325                 330                 335

Gly Asp Val Val His Ser Val Glu Arg Leu Val Glu Leu Leu Gly Trp
            340                 345                 350

Arg Glu Glu Leu Gln Asp Leu Ile Gln Gln Glu Thr Glu Lys Leu Asp
        355                 360                 365

Gly Arg Asp Gly
    370


<210> SEQ ID NO 52
<211> LENGTH: 374
<212> TYPE: PRT
<213> ORGANISM: Canis lupus familiaris

<400> SEQUENCE: 52

Met Thr Arg Cys Ala Arg Pro Ala Leu Ala Ala Leu Gly Leu Trp Gly
 1               5                  10                  15

Pro Ala Gly Trp Arg Ser Leu Tyr Thr Gly Val Arg Asp Val Leu Gly
            20                  25                  30

Glu Gly His Gln Arg Pro Ser Pro Gly Arg Met Asp Met Gly Ala Ala
        35                  40                  45

Ser Leu Trp Gly Val Arg Lys Ala Pro Cys Ala Val Glu Leu Ala Val
    50                  55                  60

Leu Asn Ser Gly Ile Thr Gly Gly Arg Arg Pro Ile Ser Phe Ser Thr
65                  70                  75                  80
```

```
Arg Thr Ser Ser Ile Phe Gly Ser Gly Gly Asp His Lys Lys Lys Leu
                85                  90                  95

Phe Leu Gln Asp Ile Ala Glu Leu Ile Arg Ala Arg Ala Cys Gln Arg
            100                 105                 110

Val Leu Val Met Val Gly Ala Gly Ile Ser Thr Pro Ser Gly Ile Pro
        115                 120                 125

Asp Phe Arg Ser Pro Gly Ser Gly Leu Tyr Ser Asn Leu Gln Gln Tyr
    130                 135                 140

Asp Leu Pro Tyr Pro Glu Ala Val Phe Glu Leu Ala Phe Phe Ser His
145                 150                 155                 160

Asn Pro Lys Pro Phe Phe Thr Leu Ala Lys Glu Leu Tyr Leu Lys Asn
                165                 170                 175

Tyr Arg Pro Asn Ile Ile His Tyr Phe Leu Arg Leu Leu His Asp Lys
            180                 185                 190

Gly Leu Leu Leu Arg Leu Tyr Thr Gln Asn Ile Asp Gly Leu Glu Arg
        195                 200                 205

Val Ala Gly Ile Pro Ala Ser Lys Leu Val Glu Ala His Gly Ser Phe
    210                 215                 220

Ala Ser Ala Thr Cys Thr Val Cys Arg Arg Pro Ser Ser Gly Lys Asp
225                 230                 235                 240

Ile Trp Val Thr Phe Asn Ile Phe Pro Ser Val Ile Pro Arg Cys Pro
                245                 250                 255

Val Cys Thr Gly Val Leu Lys Pro Asp Ile Val Phe Phe Gly Glu Thr
            260                 265                 270

Leu Pro Gln Arg Phe Leu Leu His Val Leu Asp Phe Pro Met Ala Asp
        275                 280                 285

Met Leu Leu Ile Leu Gly Thr Ser Leu Glu Val Glu Pro Phe Ala Ser
    290                 295                 300

Leu Ser Glu Ala Val Arg Ser Ser Val Pro Arg Leu Leu Ile Asn Arg
305                 310                 315                 320

Asp Val Val Gly Pro Phe Ala Trp Cys Pro Arg Ser Arg Asp Val Val
                325                 330                 335

Gln Leu Gly Asp Val Val His Ser Val Glu Arg Leu Val Glu Leu Leu
            340                 345                 350

Gly Trp Arg Glu Glu Leu Gln Asp Leu Ile Gln Gln Glu Thr Glu Lys
        355                 360                 365

Leu Asp Gly Arg Asp Gly
    370
```

<210> SEQ ID NO 53
<211> LENGTH: 357
<212> TYPE: PRT
<213> ORGANISM: Danio rerio

<400> SEQUENCE: 53

```
Met Leu Tyr Leu Asn Thr Phe Leu Pro Ser Val Cys Arg Arg Cys Phe
 1               5                  10                  15

Ala Glu Asn Leu Leu Trp Arg Arg Gly Leu Thr Thr Thr Gln Asn Leu
            20                  25                  30

Ser Arg Thr Lys Leu Val His Gln Lys Thr Leu Ser His Phe Pro His
        35                  40                  45

Ala Gln Lys Gly Ala Ala Phe Leu Ser Gln Phe Ile Tyr Cys Pro Ala
    50                  55                  60

Ala Phe Ile Lys Cys Gly Gly Thr Arg Gly Leu Phe Gly Gly Gly Arg
65                  70                  75                  80
```

```
Asp Asn Val His Gln Gln Thr Leu Glu Asp Ile Ala Glu Lys Ile Arg
                85                  90                  95

Glu Arg Lys Phe Lys Arg Ile Val Val Met Ala Gly Ala Gly Ile Ser
            100                 105                 110

Thr Pro Ser Gly Ile Pro Asp Phe Arg Ser Pro Gly Ser Gly Leu Tyr
        115                 120                 125

Asp Asn Leu Gln Gln Tyr Asn Leu Pro Tyr Ala Glu Ala Ile Phe Glu
    130                 135                 140

Ile Asn Tyr Phe His His Asn Pro Asn Pro Phe Phe Ala Leu Ala Lys
145                 150                 155                 160

Glu Leu Tyr Pro Gly Asn Tyr Gln Pro Asn Leu Thr His Tyr Phe Ile
                165                 170                 175

Arg Met Leu His Asp Lys Glu Gln Leu Leu Arg Met Tyr Thr Gln Asn
            180                 185                 190

Ile Asp Gly Leu Glu Arg Met Ala Gly Ile Pro Pro Lys Met Leu Val
        195                 200                 205

Glu Ala His Gly Thr Phe Ala Thr Ala Thr Cys Thr Val Cys Arg Arg
    210                 215                 220

Asp Tyr Lys Gly Glu Glu Leu Arg Asp Asp Ile Met Ala Gly Thr Val
225                 230                 235                 240

Pro Lys Cys Pro Thr Cys Lys Gly Ile Ile Lys Pro Asp Ile Val Phe
                245                 250                 255

Phe Gly Glu Glu Leu Pro Gln His Phe Phe Thr Tyr Leu Thr Asp Phe
            260                 265                 270

Pro Ile Ala Asp Leu Leu Ile Val Met Gly Thr Ser Leu Glu Val Glu
        275                 280                 285

Pro Phe Ala Ser Leu Ala Gly Ala Val Arg Gly Ser Val Pro Arg Leu
    290                 295                 300

Leu Ile Asn Arg Asp Leu Val Gly Pro Phe Ala Ser Gly Ser Gln Arg
305                 310                 315                 320

His Thr Asp Val Ala Glu Leu Gly Asp Val Val Asn Gly Val Lys Lys
                325                 330                 335

Leu Val Glu Leu Leu Gly Trp Lys Gln Glu Leu Glu Asp Leu Met Asn
            340                 345                 350

Val Gly Arg Asp Lys
        355


<210> SEQ ID NO 54
<211> LENGTH: 370
<212> TYPE: PRT
<213> ORGANISM: Danio rerio

<400> SEQUENCE: 54

Met Ser Lys Ala Arg Leu Ser Arg Asp Arg Arg Ala Ala Ser Val Gly
 1               5                  10                  15

Val Ser Arg Val Thr Arg Ser Ser Met Met Ser Pro Gln Asp Cys Glu
            20                  25                  30

Arg Ser Arg Ala Pro Asp Pro Gly Leu Leu Asp Glu Leu Ser Leu Met
        35                  40                  45

Ser Val Ser Glu Gln Gln Ala Ser Ala Thr Arg Lys Gly Ser Ser Lys
    50                  55                  60

Pro Ala Leu Ser Ser Pro Ser Gly Arg Ser Val Ser Arg Gly Ala Leu
65                  70                  75                  80

Glu Thr Ile Gly Arg Leu Met Lys Leu Gly Arg Val Arg Asn Ile Val
                85                  90                  95
```

```
Val Val Ala Gly Ala Gly Ile Ser Thr Ala Ser Gly Ile Pro Asp Phe
            100                 105                 110

Arg Thr Pro Gly Thr Gly Leu Tyr Ala Asn Leu Ala Lys Tyr Asp Ile
        115                 120                 125

Pro Tyr Pro Glu Ala Val Phe Asn Ile Asp Tyr Phe Ser Asp Asn Pro
    130                 135                 140

His Pro Phe Phe Ser Leu Ala Lys Glu Leu Tyr Pro Gly His His Arg
145                 150                 155                 160

Pro Asn Tyr Val His Tyr Phe Ile Arg Met Leu His Gln Lys Gly Leu
                165                 170                 175

Leu Leu Arg Met Tyr Thr Gln Asn Ile Asp Gly Leu Glu Lys Leu Cys
            180                 185                 190

Gly Ile Pro Asp Asp Lys Leu Val Glu Ala His Gly Ser Phe Ala Thr
        195                 200                 205

Ala Ala Cys His Leu Cys Tyr Thr Pro Tyr Pro Ala Glu Glu Ala Lys
    210                 215                 220

Gln Ala Ile Met Asn Gly Ser Val Pro Ile Cys Thr Phe Cys Ala Gly
225                 230                 235                 240

Ala Val Lys Pro Asn Val Val Phe Phe Gly Glu Asp Leu Pro Glu Lys
                245                 250                 255

Tyr Phe Gln His Ala Glu Asp Phe Pro Lys Ala Asp Leu Leu Ile Ile
            260                 265                 270

Met Gly Thr Ser Leu Lys Ile Glu Pro Phe Ala Ser Leu Ile Asn Thr
        275                 280                 285

Val Lys Ser Thr Val Pro Arg Leu Leu Leu Asn Arg Asp Ala Val Gly
    290                 295                 300

Pro Phe Glu Arg Arg Pro Leu Arg Arg Ala Asp Tyr Met Glu Leu Gly
305                 310                 315                 320

Asp Leu Ser Glu Ser Val Arg Lys Leu Ala Glu Ile Leu Gly Trp His
                325                 330                 335

Thr Glu Ile Gln Thr Leu Met Asn Ser His Glu Asn Gly Leu Tyr Ser
            340                 345                 350

Tyr Ile Ser Ser Ser Gly Glu Asn Ser Gly Asp Ser Glu Thr Asp Ser
        355                 360                 365

Met His
    370


<210> SEQ ID NO 55
<211> LENGTH: 774
<212> TYPE: DNA
<213> ORGANISM: Mus musculus

<400> SEQUENCE: 55

atggtggggg ccggcatcag cacacccagt ggcatcccgg acttcagatc cccagggagc      60

ggcctctaca gcaaccttca gcagtatgac atcccgtacc ctgaagccat ctttgaactt     120

ggctttttct ttcacaaccc caagcccttt ttcatgttgg ccaaggagct gtaccctggg     180

cactacaggc ccaatgtcac tcactacttc ctgaggctcc tccacgacaa ggagctgctt     240

ctgcggctct atacacagaa catcgacggg cttgagagag catctgggat ccctgcctca     300

aagctggttg aagcccacgg gacctttgta acagctacat gcacggtctg tcgaaggtcc     360

ttcccagggg aagacatatg ggctgatgtg atggcggaca gggtgccccg ctgccctgtc     420

tgtactggcg ttgtgaaacc cgacattgtg ttctttgggg agcagctgcc tgcaaggttc     480

ctactccata tggctgactt cgctttggca gatctgctac tcattcttgg gacctccctg     540
```

-continued gaggtggagc cttttgccag cttgtctgaa gcagtacaga aatcagtgcc ccgactgctc 600
atcaatcgag acttggtggg gccgttcgtt ctgagtcctc gaaggaaaga tgtggtccag 660
ctaggggatg tagttcatgg tgtggaaagg ctggtggacc tcctggggtg gacacaagaa 720
ctgctggatc ttatgcagcg ggaacgtggc aagctggatg gacaggacag atag 774

<210> SEQ ID NO 56
<211> LENGTH: 1372
<212> TYPE: DNA
<213> ORGANISM: Mus musculus

<400> SEQUENCE: 56
cgctaagcgg tcgactggca ttggccgcgc tcagactgtg ggtccggga gtgttacagg 60 tgggagaagg cccatatccc tctgtgtggg agcctcaggc ggctttggag gtggaggaag 120
cagtgagaag aagttttctc tgcaggatgt agctgagctg cttcggacca gagcctgcag 180
tagggtggtg gtcatggtgg gggccggcat cagcacaccc agtggcatcc cggacttcag 240
atccccaggg agcggcctct acagcaacct tcagcagtat gacatcccgt accctgaagc 300
catctttgaa cttggctttt tctttcacaa ccccaagccc tttttcatgt tggccaagga 360
gctgtaccct gggcactaca ggcccaatgt cactcactac ttcctgaggc tcctccacga 420
caaggagctg cttctgcggc tctatacaca gaacatcgac gggcttgaga gagcatctgg 480
gatccctgcc tcaaagctgg ttgaagccca cgggaccttt gtaacagcta catgcacggt 540
ctgtcgaagg tccttcccag gggaagacat atggctgat gtgatggcgg acagggtgcc 600
ccgctgccct gtctgtactg gcgttgtgaa acccgacatt gtgttctttg gggagcagct 660
gcctgcaagg ttcctactcc atatggctga cttcgctttg gcagatctgc tactcattct 720
tgggacctcc ctggaggtgg agccttttgc cagcttgtct gaagcagtac agaaatcagt 780
gccccgactg ctcatcaatc gagacttggt ggggccgttc gttctgagtc ctcgaaggaa 840
agatgtggtc cagctagggg atgtagttca tggtgtggaa aggctggtgg acctcctggg 900
gtggacacaa gaactgctgg atcttatgca gcgggaacgt ggcaagctgg atggacagga 960
cagataagac tatggcttct tcacctgggg aagtcacaca gcagatcatc ctatgtccag 1020
caagacttca tgcctgaaga cagctccaac acgtttacaa acatgaacca gaccacaaca 1080
tgtggcctgg acagtggtcc tccgaggctg cctttggaaa ggctgaccag ggatgtctac 1140
ccttggggcc cctccatgtg tgcgccctgt ccacctcatc actgctgaag gtgtagtgca 1200
ggtgctgctt tctgcagcgg cccttaagtt atcacgaggg cagcacagca cgcccgtcgc 1260
caggcaggcg atgcactagg gcaatctagc atgttgatcg gtaaagtggc atctttaact 1320
acaacatcat ttcttgcatg aaataaactt agtataaaaa aaaaaaaaaa aa 1372

<210> SEQ ID NO 57
<211> LENGTH: 1484
<212> TYPE: DNA
<213> ORGANISM: Mus musculus

<400> SEQUENCE: 57
acttccgcta aacttctccc gggtttctgg ccctgccctt gaggcattaa agagtagagg 60
tgcctgggga cagctagcca ctgactggtc acgtagcctc aagcctgcag acttgggtcc 120
tctgaaaccg gatggcgttt ggcgaggact agtgttacag gtgggagaag gcccatatcc 180
ctctgtgtgg gagcctcagg cggctttgga ggtggaggaa gcagtgagaa gaagttttct 240
ctgcaggatg tagctgagct gcttcggacc agagcctgca gtagggtggt ggtcatggtg 300

```
ggggccggca tcagcacacc cagtggcatc ccggacttca gatccccagg gagcggcctc    360
tacagcaacc ttcagcagta tgacatcccg taccctgaag ccatctttga acttggcttt    420
ttctttcaca accccaagcc ctttttcatg ttggccaagg agctgtaccc tgggcactac    480
aggcccaatg tcactcacta cttcctgagg ctcctccacg acaaggagct gcttctgcgg    540
ctctatacac agaacatcga cgggcttgag agagcatctg ggatccctgc ctcaaagctg    600
gttgaagccc acgggacctt tgtaacagct acatgcacgg tctgtcgaag gtccttccca    660
ggggaagaca tatgggctga tgtgatggcg gacagggtgc cccgctgccc tgtctgtact    720
ggcgttgtga aacccgacat tgtgttcttt ggggagcagc tgcctgcaag gttcctactc    780
catatggctg acttcgcttt ggcagatctg ctactcattc ttgggacctc cctggaggtg    840
gagcctttttg ccagcttgtc tgaagcagta cagaaatcag tgccccgact gctcatcaat    900
cgagacttgg tggggccgtt cgttctgagt cctcgaagga aagatgtggt ccagctaggg    960
gatgtagttc atggtgtgga aaggctggtg gacctcctgg ggtggacaca agaactgctg   1020
gatcttatgc agcgggaacg tggcaagctg gatggacagg acagataaga ctatggcttc   1080
ttcacctggg gaagtcacac agcagatcat cctatgtcca gcaagacttc atgcctgaag   1140
acagctccaa cacgtttaca aacatgaacc agaccacaac atgtggcctg gacagtggtc   1200
ctccgaggct gcctttggaa aggctgacca gggatgtcta cccttggggc ccctccatgt   1260
gtgcgccctg tccacctcat cactgctgaa ggtgtagtgc aggtgctgct ttctgcagcg   1320
gcccttaagt tatcacgagg gcagcacagc acgcccgtcg ccaggcaggc gatgcactag   1380
ggcaatctag catgttgatc ggtaaagtgg catctttaac tacaacatca tttcttgcat   1440
gaaataaact tagtataaaa acttggcaaa aaaaaaaaaa aaaa                     1484
```

<210> SEQ ID NO 58
<211> LENGTH: 1393
<212> TYPE: DNA
<213> ORGANISM: Rattus norvegicus

<400> SEQUENCE: 58

```
ggccgcgctc agactgtggg gtccgggagt attacaggtg ggagaaggcc catatccctc     60
tctgtgggag cctcaggcgg ctttggatgt ggaggacaca gtgagaagaa gctgtctctg    120
caggacgtag ctgagctgct tcggaccaga gcctgcagta gggttgtggt catggtgggg    180
gctggcatca gcacacccag tggtatccca gacttcagat ccccagggag tggcctctac    240
agcaaccttc agcagtatga catcccgtac cctgaggcca tctttgaact aggcttcttt    300
tttcacaacc ccaagccctt tttcacgttg gccaaggagc tgtaccctgg gcactacagg    360
cccaatgtcg ctcactactt ccttcggctg cttcacgaca aggagctgct tctgcggctc    420
tacacacaga acatcgacgg gcttgagaga gcatctggta tccctgcctc aaagctggtt    480
gaagctcatg ggtcctttgt atcagctacg tgcacggtct gtcgaaggtc cttcccaggg    540
gaagacatac gggctgacgt gatggcagac agggtgcccc gctgccctgt ctgtactggc    600
gttgtgaaac ctgacattgt gttctttggg gagcagctgc cagcaaggtt cttactacat    660
gtggctgatt tcgccttggc agatctgcta ctcattcttg ggacctccct ggaggtggag    720
ccttttgcca gcttgtctga atcggtacag aaatcagtgc cccgactgct catcaatcga    780
gacttggtgg ggtcctttgc tctgagtcct cgaaggaaag atgtggtcca gctaggggat    840
gtagtccagg gtgtggaaag gctggtggac ctcctggggt ggacacaaga gctgcaggat    900
ctcatccagc gggaaaatgg aaagctggat ggacaggacg gataagacag actatggctt    960
```

acttcttcac ctgcgggaaa gtcgcacagg agatcatcct attcccaggg agacctcatg 1020
tctgaaaaca gctccgacag gtttacaaac atgggccaga ccacaacatg tgtcctgggc 1080
agtagtccca aggctgcctt tgttaaggct gaccagggac ctttaccctt ggggccatgt 1140
gttaccatac aaaggagctc cacgtgtgtg ctctgtccac ccatcactgc tgaagcttgc 1200
agtacagtgc tgctttctga cagaggcctt agttaccaag agggcagggc agcatgccca 1260
tcgctagaca gctgatacgc taggctaatc tagcatgttg gtcggtaaag tggcatcttt 1320
aactgaaaaa tcatttttcg catgaaataa atttagtata aaaaaaaaaa aaaaaaaaaa 1380
aaaaaaaaaa aaa 1393

<210> SEQ ID NO 59
<211> LENGTH: 1459
<212> TYPE: DNA
<213> ORGANISM: Bos taurus

<400> SEQUENCE: 59
ctgggcacct gacattgcgc actgcggaga agcatggcgt tgtttcctcg ttcagctgtt 60
ccagccctca gtattccagg tggaggatgg tccatatctt gttttgctgg tgcctcaagt 120
gacactggag ggggagacca cagtcagaag aagtttctcc tgcaggacat cgctgagctg 180
attaagacca gagcctgcca gaaggtggtg gtcatggtgg gggccggcat cagcacaccc 240
agcggcatcc cagacttcag gtctccgggg gttggctact acagcatcct ccagcagtac 300
aagctcccct accctgaggc catttttgag ctctcctttt tctttcatga ccccaagcca 360
tttttcactt ttgccaagaa gctgtaccct gggaactata ggcccaatgc tactcactac 420
ttcctccgat tgctacacga gaaggggctg cttctgcggc tctacaccca gaacatcgac 480
gggctcgaga gagcatctgg catccctgac tcaaagctcg ttgaagctca tggatccctt 540
gcctctgcca cctgcaccgt ctgccgaaga ccctacccag gggaggactt ctgggccgac 600
gtgatggcgg acagggtccc ccgctgcccc gtctgctctg gcgtcacgaa gcctgacatc 660
gtgttcttcg gggagccgct gcctgctagg ttcctgctgc atctggctga cttccccatg 720
gcagacctgc tgctcatcct tgggacctcc ctggaggtgg aaccttttgc cagcttgtcc 780
gatgctgtgc ggagctcggt gccccgactg ctcatcaacc gggacttggt ggggtccttg 840
gctaggaatc ctcggggcag ggacgtggcc cagctggggg atgtggtcca tggtgtgaaa 900
aggctggtgg agcttctcgg ctggacagac gacatccagg acctcatcca gagggaaact 960
ggaaagtttg atggctggga cagactgtga ggaacgcctc tcacaccaga ggttacttgg 1020
gagtcaccgc ccatttctga tgaagacttc tgcttgaaga agagctcggg cacgtttaca 1080
aattgtggct gaaccaggac acgcaacctg aggctgcccc tggagtgtct tcccgggttg 1140
taaccccgtg cactcagggc cactcgccac agattaatgg cgctgcctgg gctgacgttg 1200
ctgtttaact cttcacgctg ctgaagctct caatgtcaga agctttctcc tgatggcgaa 1260
tctcttgaat cagactgcct agaaccccaa gttgggatcc atgtgaaggg caggatcaac 1320
atctgtccac tggggtgagc agctgcagcc gccttctggg agtgggtctg ggtcccaggt 1380
aacgcgctag tcttctggcc tctttagtag gcttattttt agtctgtcct tcttttccgg 1440
catgaaataa attttaatg 1459

<210> SEQ ID NO 60
<211> LENGTH: 1526
<212> TYPE: DNA
<213> ORGANISM: Bos taurus

<400> SEQUENCE: 60
ggcgcgcacg agacccctgg gcacctgaca ttgcgcactg cggagaagca tggcgttgtt 60
tcctcgttca gctgttccag ccctcaggtt ctggggcctg cgaggtgcgc gggcgtggac 120
ccgctggcct cgtattccag gtggaggatg gtccatatct tgttttgctg gtgcctcaag 180
tgacactgga gggggagacc acagtcagaa gaagtttctc ctgcaggaca tcgctgagct 240
gattaagacc agagcctgcc agaaggtggt ggtcatggtg ggggccggca tcagcacacc 300
cagcggcatc ccagacttca ggtctccggg ggttggctac tacagcatcc tccagcagta 360
caagctcccc taccctgagg ccatttttga gctctccttt ttctttcatg accccaagcc 420
atttttcact tttgccaaga agctgtaccc tgggaactat aggcccaatg ctactcacta 480
cttcctccga ttgctacacg agaaggggct gcttctgcgg ctctacaccc agaacatcga 540
cgggctcgag agagcatctg gcatccctga ctcaaagctc gttgaagctc atggatccct 600
tgcctctgcc acctgcaccg tctgccgaag accctaccca ggggaggact tctgggccga 660
cgtgatggcg gacagggtcc cccgctgccc cgtctgctct ggcgtcacga agcctgacat 720
cgtgttcttc ggggagccgc tgcctgctag gttcctgctg catctggctg acttccccat 780
ggcagacctg ctgctcatcc ttgggacctc cctggaggtg gaaccttttg ccagcttgtc 840
cgatgctgtg cggagctcgg tgccccgact gctcatcaac cgggacttgg tggggtcctt 900
ggctaggaat cctcggggca gggacgtggc ccagctgggg gatgtggtcc atggtgtgaa 960
aaggctggtg gagcttctcg gctggacaga cgacatccag gacctcatcc agagggaaac 1020
tggaaagttt gatggctggg acagactgtg aggaacgcct ctcacaccag aggttacttg 1080
ggagtcaccg cccatttctg atgaagactt ctgcttgaag aagagctcgg gcacgtttac 1140
aaattgtggc tgaaccagga cacgcaacct gaggctgccc ctggagtgtc ttcccgggtt 1200
gtaaccccgt gcactcaggg ccactcgcca cagattaatg gcgctgcctg ggctgacgtt 1260
gctgtttaac tcttcacgct gctgaagctc tcaatgtcag aagctttctc ctgatggcga 1320
atctcttgaa tcagactgcc tagaacccca agttgggatc catgtgaagg gcaggatcaa 1380
catctgtcca ctggggtgag cagctgcagc cgccttctgg gagtgggtct gggtcccagg 1440
taacgcgcta gtcttctggc ctctttagta ggcttatttt tagtctgtcc ttcttttccg 1500
gcatgaaata aattttaatg tagaaa 1526

<210> SEQ ID NO 61
<211> LENGTH: 1888
<212> TYPE: DNA
<213> ORGANISM: Canis lupus familiaris

<400> SEQUENCE: 61
cctcactgac cgtgtgtcca ctgggtgggt ctgcacagag cttgctgtgc cagttccgta 60
aggagcaaag gaatacaaca gacaaggagc aaacaggaga gtgagttggg gccatacttc 120
tagaagattc atactcttga attgttctga tgtgtatctg acaatgcgct tttagggtgc 180
ttatttcttg cctgcatcac aaatgagtaa aagaagtgct gtcagtttcc tgtctttatg 240
tctgtattca ctttagattc gtcactcatt tgaggagggt tgtcaattcc atttgttgaa 300
tctcttttcc catcagggtg gaggagtctc tataccggag tcagagatgt cctgggggag 360
ggtcatcaac ggccttctcc cggaagaatg gacatggggg ccgccagtct ttggggtgtg 420
agaaaggcgc cctgtgcagt ggagctggca gtcctgaact ctggcattac aggcggaaga 480
agacccatat ctttttccac tagaacctca agcatctttg gaagcggagg tgaccataag 540

```
aagaagcttt ttctgcagga tatagcagaa ctgattcgag ccagagcctg ccagagggtg    600
ctggtcatgg tgggggctgg catcagcacg cccagcggca ttccggactt caggtctccc    660
gggagcggcc tctatagcaa cctgcagcag tatgacctcc catacccega ggctgttttt    720
gagctggctt tcttctctca caaccccaag cccttttca ctttggccaa ggagctgtac     780
cttaagaact acaggcccaa catcatacac tacttcctcc gactgctcca cgacaagggg    840
ctgcttctgc ggctctacac gcagaatatt gatgggctcg agagagtagc tgggatccct    900
gcctcaaagc tggttgaagc tcatggatcc ttcgcctccg ccacatgcac tgtctgccga    960
agaccctcct cagggaagga catttgggcc gacgtgagca tggacaagat cccccgctgc   1020
ccagtgtgca ctggcgtttt gaagcctgac atcgtgttct ttggggagac actgcctcag   1080
aggttcctgc tgcatgtact tgatttccca atggcagata tgctgctcat cctcgggacc   1140
tccctggagg tagaaccttt cgccagcttg tctgaggctg tgcggagctc agtgccccga   1200
ctgctcatca accgggacgt ggtggggccc tttgcctggt gtcctcgcag cagggatgtg   1260
gtccagctgg gggatgtggt tcacagcgtg gaaaggctgg tggagcttct gggctggaga   1320
gaagagctgc aggacctcat ccagcaggaa accgaaaagc tcgatggacg ggacggatag   1380
gatcatggct ggtcccccac ccctcctggg aacagaaacg gttccaagga gtcactgccc   1440
acctctgagt aaacaatttt ggctgaacca ggaccggtgg cctgaggaag agtgtgaggc   1500
tgcccaagtc gtgttctgct cacgctgtgg gccaccccaa tcatgggtgc caagctgccg   1560
gcatctttct gctgtttgac tcttcaatct gaagctcttg atgccaaaca aaagctttct   1620
tctgacagtg accctcttga actcagacca gcaggaagcc cagactgaat ctgctcagtg   1680
tccaggtctc catccgaagg gcagactcag cctctgtccc ttagacctgg tcttgggctg   1740
agtggccaca gctgttccca aggcgtggtc ctgggtccga agtaatacaa tagggtccta   1800
tagcctgttg gcctcttttg tggggttatc tttaattagg gaaacattgt tcatttttgg   1860
catgaaataa acactgtggt ctcctcaa                                      1888
```

<210> SEQ ID NO 62
<211> LENGTH: 2021
<212> TYPE: DNA
<213> ORGANISM: Canis lupus familiaris

<400> SEQUENCE: 62

```
ccgggtgcgg ttggcccggt ttcccgcgcg ccggccgagc ggttccgcgg ttcgagagcc     60
tcgggccgcc cggccctctc ccggcttggt agccgacgtt ctccctccgt gggggcctcg    120
gtaggactgg cttccgcgga gcgtcgcgag gaccgccgaa gatgtgatgc cgggcgggag    180
tccgcggagc gtgcgcctcc cccgcccggc ggaaacggac ggggagcggg gcagagacac    240
gcaggctcct gctctggtct ccggggcgag aggcgggagc ccgaccggct aggaagccgc    300
cctcgcctgg cgtccgcccc agcctggctc gcggagcggg gcggacctgc gccctagggt    360
caaggctgcg ggcgggcggc ggcggagcgg ggccatgacg cggtgcgctc ggcctgctct    420
cgcggccctc gggctctggg gcccggcagg gtggaggagt ctctataccg gagtcagaga    480
tgtcctgggg gagggtcatc aacggccttc tcccggaaga atggacatgg gggccgccag    540
tctttggggt gtgagaaagg cgccctgtgc agtggagctg gcagtcctga actctggcat    600
tacaggcgga agaagaccca tatcttttc cactagaacc tcaagcatct ttggaagcgg     660
aggtgaccat aagaagaagc tttttctgca ggatatagca gaactgattc gagccagagc    720
ctgccagagg gtgctggtca tggtgggggc tggcatcagc acgcccagcg gcattccgga    780
```

```
cttcaggtct cccgggagcg gcctctatag caacctgcag cagtatgacc tcccataccc    840
cgaggctgtt tttgagctgg ctttcttctc tcacaacccc aagccctttt tcactttggc    900
caaggagctg taccttaaga actacaggcc caacatcata cactacttcc tccgactgct    960
ccacgacaag ggctgcttc tgcggctcta cacgcagaat attgatgggc tcgagagagt    1020
agctgggatc cctgcctcaa agctggttga agctcatgga tccttcgcct ccgccacatg   1080
cactgtctgc cgaagaccct cctcagggaa ggacatttgg gccgacgtga gcatggacaa   1140
gatcccccgc tgcccagtgt gcactggcgt tttgaagcct gacatcgtgt tctttgggga   1200
gacactgcct cagaggttcc tgctgcatgt acttgatttc ccaatggcag atatgctgct   1260
catcctcggg acctccctgg aggtagaacc tttcgccagc ttgtctgagg ctgtgcggag   1320
ctcagtgccc cgactgctca tcaaccggga cgtggtgggg ccctttgcct ggtgtcctcg   1380
cagcagggat gtggtccagc tgggggatgt ggttcacagc gtggaaaggc tggtggagct   1440
tctgggctgg agagaagagc tgcaggacct catccagcag gaaaccgaaa agctcgatgg   1500
acgggacgga taggatcatg gctggtcccc cacccctcct gggaacagaa acggttccaa   1560
ggagtcactg cccacctctg agtaaacaat tttggctgaa ccaggaccgg tggcctgagg   1620
aagagtgtga ggctgcccaa gtcgtgttct gctcacgctg tgggccaccc caatcatggg   1680
tgccaagctg ccggcatctt tctgctgttt gactcttcaa tctgaagctc ttgatgccaa   1740
acaaaagctt tcttctgaca gtgaccctct tgaactcaga ccagcaggaa gcccagactg   1800
aatctgctca gtgtccaggt ctccatccga agggcagact cagcctctgt cccttagacc   1860
tggtcttggg ctgagtggcc acagctgttc ccaaggcgtg gtcctgggtc cgaagtaata   1920
caatagggtc ctatagcctg ttggcctctt ttgtggggtt atctttaatt agggaaacat   1980
tgttcatttt tggcatgaaa taaacactgt ggtctcctca a                        2021
```

<210> SEQ ID NO 63
<211> LENGTH: 2027
<212> TYPE: DNA
<213> ORGANISM: Canis lupus familiaris

<400> SEQUENCE: 63

```
ccgggtgcgg ttggcccggt ttcccgcgcg ccggccgagc ggttccgcgg ttcgagagcc     60
tcgggccgcc cggccctctc ccggcttggt agccgacgtt ctccctccgt gggggcctcg    120
gtaggactgg cttccgcgga gcgtcgcgag gaccgccgaa gatgtgatgc cgggcgggag    180
tccgcggagc gtgcgcctcc cccgcccggc ggaaacggac ggggagcggg gcagagacac    240
gcaggctcct gctctggtct ccggggcgag aggcgggagc ccgaccggct aggaagccgc    300
cctcgcctgg cgtccgcccc agcctggctc gcggagcggg gcggacctgc gccctagggt    360
caaggctgcg ggcgggcggc ggcggagcgg ggccatgacg cggtgcgctc ggcctgctct    420
cgcggccctc gggctctggg gcccggcagg gtggaggagt ctctataccg gagtcagaga    480
tgtcctgggg gagggtcatc aacggccttc tcccggaaga atggacatgg gggccgccag    540
tctttggggt gtgagaaagg cgccctgtgc agtggagctg gcagtcctga actctggcat    600
tacaggcgga agaagaccca tatctttttc cactagaacc tcaagcatct ttggaagcgg    660
aggtgaccat aagaagaagc tttttctgca ggatatagca gaactgattc gagccagagc    720
ctgccagagg gtgctggtca tggtgggggc tggcatcagc acgcccagcg gcattccgga    780
cttcaggtct cccgggagcg gcctctatag caacctgcag cagtatgacc tcccataccc    840
cgaggctgtt tttgagctgg ctttcttctc tcacaacccc aagccctttt tcactttggc    900
```

caaggagctg taccttaaga actacaggcc caacatcata cactacttcc tccgactgct 960
ccacgacaag ggctgcttc tgcggctcta cacgcagaat attgatgggc tcgagagagt 1020
agctgggatc cctgcctcaa agctggttga agctcatgga tccttcgcct ccgccacatg 1080
cactgtctgc cgaagaccct cctcagggaa ggacatttgg gtgacattta atatatttcc 1140
cagtgttatc cccgctgcc cagtgtgcac tggcgttttg aagcctgaca tcgtgttctt 1200
tggggagaca ctgcctcaga ggttcctgct gcatgtactt gatttcccaa tggcagatat 1260
gctgctcatc ctcgggacct ccctggaggt agaacctttc gccagcttgt ctgaggctgt 1320
gcggagctca gtgccccgac tgctcatcaa ccgggacgtg gtggggccct ttgcctggtg 1380
tcctcgcagc agggatgtgg tccagctggg ggatgtggtt cacagcgtgg aaaggctggt 1440
ggagcttctg ggctggagag aagagctgca ggacctcatc cagcaggaaa ccgaaaagct 1500
cgatggacgg gacggatagg atcatggctg gtcccccacc cctcctggga acagaaacgg 1560
ttccaaggag tcactgccca cctctgagta aacaattttg gctgaaccag gaccggtggc 1620
ctgaggaaga gtgtgaggct gcccaagtcg tgttctgctc acgctgtggg ccaccccaat 1680
catgggtgcc aagctgccgg catctttctg ctgtttgact cttcaatctg aagctcttga 1740
tgccaaacaa aagctttctt ctgacagtga ccctcttgaa ctcagaccag caggaagccc 1800
agactgaatc tgctcagtgt ccaggtctcc atccgaaggg cagactcagc ctctgtccct 1860
tagacctggt cttgggctga gtggccacag ctgttcccaa ggcgtggtcc tgggtccgaa 1920
gtaatacaat agggtcctat agcctgttgg cctcttttgt ggggttatct ttaattaggg 1980
aaacattgtt catttttggc atgaaataaa cactgtggtc tcctcaa 2027

<210> SEQ ID NO 64
<211> LENGTH: 1627
<212> TYPE: DNA
<213> ORGANISM: Danio rerio

<400> SEQUENCE: 64
acaagcacag attcgatgca ataatgtgcg ccttttaaca aagcaggagc cttgctgtag 60
tcaattatgc tgtacttaaa taccttttg ccaagtgttt gcagacgctg ttttgcagag 120
aatctcttat ggagaagagg attgactact acacagaatc tgtcaagaac aaagctcgtt 180
catcaaaaga ctctgtcaca tttccctcat gcacagaagg gtgctgcatt tctttcacag 240
ttcatttatt gcccagctgc cttcattaaa tgtggtggaa caagaggcct gtttggagga 300
ggccgtgaca atgttcacca gcaaaccctt gaagacattg cagaaaaaat cagagaacgc 360
aagtttaaac gaattgtggt gatggcaggg gcaggcatca gcacaccaag tggaatccca 420
gacttcagat cacccggcag cggcctttat gataaccttc aacagtacaa tctaccctat 480
gctgaagcca tatttgaaat aaattatttc catcataatc ctaacccttt tttcgctctt 540
gccaaagagc tttatcctgg taattaccaa cccaacctga cgcactactt cattcgcatg 600
cttcacgata aggaacagct gctcaggatg tacacgcaaa acattgatgg acttgagcgc 660
atggctggca ttcctccaaa gatgcttgtg gaggcacatg gaacatttgc cactgccaca 720
tgcacagttt gtcggaggga ttacaaagga gaggaacttc gggatgacat catggcagga 780
acagtaccca aatgcccaac ttgtaaagga atcatcaagc ctgacattgt gttctttggt 840
gaggagcttc cacagcactt cttcacctac cttacagact tcccaatagc agacctgctc 900
attgtgatgg gaacatctct tgaggtggag ccctttgcaa gtttggctgg tgctgtgcgt 960
ggttctgtac caaggctttt gataaatcga gaccttgtgg ggccgtttgc ctcggggtcc 1020
caacgtcaca ctgacgtggc tgagctgggt gacgtggtta atggggtaaa aaagctggtg 1080
gagctcctgg gctggaagca ggaattagaa gacttaatga atgttggcag agacaagtag 1140
tcttcggtgg agagagagga gtgagcaagg aggagtgatg gagtgatgga gtcctgggac 1200
tagtttggtt tatttctgcc taatttactg aacattcact ggttggcgtg agttttagtt 1260
ggtgtcaaga agatgcactt gagtatatac tgggttgagg aagaagatcc aaatctactg 1320
taaataacca ggtcacctct acacacgcct ctacgaaatg tagtgtataa ttcacaagca 1380
aataatgatt tcaataatga tgcaaaacgc actaacattt tatcatttta gtttttatct 1440
tgaacagtat ggcagtggat atgattaatt tattctgtag ctaacagcaa tgttcagctg 1500
gtcagttaat ctcagtgagg ttactcacat aaagaaaacc ccactatgat gaaagaataa 1560
aacagctttt tctagaataa aaaaaaaaaa aaaaaaaaaa aaaaaaaaaa aaaaaaaaaa 1620
aaaaaaa 1627

<210> SEQ ID NO 65
<211> LENGTH: 1284
<212> TYPE: DNA
<213> ORGANISM: Danio rerio

<400> SEQUENCE: 65
ggaacgctgg acttgcacag attcaaacat gacatctatc tagcgttaga tgtcgcctac 60
attttccttt aactgacggt ttgctgtggt gagggatttc atcggtgccc tttgctcgtt 120
ttgacggtct tcccttcatc cctagtcggg taaacaaata caggtgtcgt gatgagcaag 180
gcgaggttga gcagagacag aagagcggca tcggttgggg tctccagagt cacccgcagc 240
tccatgatga gtcctcagga ctgtgagcgc agcagagctc cagaccccgg cctgctggac 300
gagctcagcc tcatgagtgt cagtgaacag caggcctcag ccacacggaa aggtagtagt 360
aagcctgctc tgtcctcacc ctctggacgc tcagtatcgc gcggggcttt ggaaaccatc 420
ggcaggctga tgaagcttgg tcgagtgcga aacattgtgg tagttgctgg agcaggaatc 480
agcacagcca gcgggatccc agacttcagg actccaggaa cggtctcta cgcaaaccta 540 gcaaagtacg acatccctta cccagaggcc gtctttaaca tcgactactt ttctgacaac 600
cctcatccct tcttctcact ggctaaagag ctttatcctg gacaccaccg gcccaactac 660
gtccactact tcatccgcat gctgcatcag aaaggcctgc tgctccgcat gtacacccag 720
aacatcgacg gtctcgaaaa actttgcggt atccctgatg acaaacttgt ggaggctcat 780
gggagttttg ccaccgctgc ctgtcacctc tgctatactc cttatcctgc agaggaagcc 840
aagcaagcta taatgaacgg gagtgttccc atctgcacat tctgcgctgg ggccgtcaaa 900
cctaatgttg tgttctttgg agaagatctg ccggaaaaat acttccaaca tgctgaagat 960
ttcccaaaag cagatcttct cataatcatg ggcacttctt taaagattga gccctttgcc 1020
agcttgataa acaccgtgaa gtccacagtt cctcgtctcc tgctgaaccg tgatgcagtc 1080
gggccctttg aacggaggcc cctgagaaga gccgactaca tggagctggg agatctgtcc 1140
gaatctgtac gcaaactggc agagatcctt ggatggcaca cggagatcca gaccctgatg 1200
aacagccatg agaacggtct ttattcatac atcagcagca gtggtgagaa cagcggagac 1260
tctgagacgg acagcatgca ctaa 1284

REGULATION OF PROTEIN ACTIVITY BY REVERSIBLE ACETYLATION

CROSS-REFERENCES TO RELATED APPLICATIONS

This application claims benefit of U.S. provisional application Ser. No. 60/813,275, filed Jun. 12, 2006, the disclosure of which is incorporated herein in its entirety by reference.

FIELD OF THE INVENTION

This invention discloses the first cellular acetylated substrate protein of SIRT3, Acetyl-CoA synthetase 2 (AceCS2), which is a mitochondrial matrix protein. The mitochondrial sirtuin SIRT3 interacts with AceCS2 and directly controls the activity of this metabolic enzyme via reversible lysine acetylation. Modulators of the acetylation status or the activity of AceCS2 are useful for the treatment of pathological conditions, such as type II diabetes, hypercholesterolemia, hyperlipidemia, and obesity.

BACKGROUND OF THE INVENTION

Reversible lysine acetylation is a highly regulated post-translational protein modification, which is controlled by protein deacetylases and acetyltransferases (Han and Martinage, 1992, *Int J Biochem* 24:19-28; Yang, 2004, *Bioessays* 26:1076-87). While originally linked to transcription and chromatin dynamics, reversible lysine acetylation is emerging as a regulator of cellular functions such as cell motility, immune synapse formation, programmed cell death, and protein trafficking (Hubbert et al., 2002, *Nature* 417:455-458; Kawaguchi et al., 2003, *Cell* 115:727-38; Serrador et al., 2004, *Immunity* 20:417-28; Cohen et al., 2004, *Science* 305: 390-2; Cohen et al., 2004, *Mol Cell* 13:627-38). While the importance of reversible lysine acetylation of nuclear non-histone and histone proteins is well established, the role of protein modification by reversible lysine acetylation in mitochondria is unknown. However, the importance of post-translational modification of mitochondrial proteins such as phosphorylation and ADP-ribosylation, is becoming increasingly clear, and it is likely that reversible acetylation of mitochondrial proteins also plays an important role in the regulation of mitochondrial functions.

The nicotinamide (NAM) adenine dinucleotide $NAD^+$-dependent deacetylase silent information regulator 2 (Sir2) is an important mediator of longevity in response to caloric restriction (CR) signals in *Saccharomyces cerevisiae, Caenorhabditis elegans* and *Drosophila melanogaster* (Kaeberlein et al., 1999, *Genes Dev* 13:2570-80; Tissenbaum and Guarente, 2001, *Nature* 410:227-30; Lin et al., 2000, *Science* 289:2126-8; Rogina and Helfand, 2004, *Proc Natl Acad Sci USA* 101: 15998-6003; Lin et al., 2004, *Genes Dev* 18:12-6; Lin et al., 2002, *Nature* 418:344-8; Anderson et al., 2003, *Nature* 423: 181-5). Seven mammalian Sir2 homologs (SIRT1-7) are known (Frye, 1999, *Biochem Biophys Res Commun* 260:273-9; Frye, 2000 *Biochem Biophys Res Commun* 273:793-8; Blander and Guarente, 2004, *Annu Rev Biochem* 73:417-35; North and Verdin, 2004, *Genome Biol* 5:224). The recent discovery that SIRT3, SIRT4 and SIRT5 are found in mitochondria (Shi et al., 2005, *J Biol Chem* 280:13560-7; Michishita et al., 2005, *Mol Biol Cell* 16:4623-35; Onyango et al., 2002, *Proc Natl Acad Sci USA* 99, 13653-8; Schwer et al., 2002, *J Cell Biol* 158:647-57) suggests the existence of mitochondrial sirtuin substrate proteins.

The present invention discloses the identification of the first cellular acetylated substrate protein of SIRT3, Acetyl-CoA synthetase 2 (AceCS2), which is a mitochondrial matrix protein.

AceCS catalyzes the ligation of acetate with CoA to produce acetyl-CoA, an essential molecule utilized in various metabolic pathways including fatty acid and cholesterol synthesis and the tricarboxylic acid cycle (for review, see, Bremer and Osmundsen, 1984, in *Fatty Acid Metabolism and Its Regulation* (Numa, S. ed), 113-154, Elsevier Science Publisher, Amsterdam).

AceCS from various microorganisms and higher organisms indicates a superfamily (Toh, 1990, *Protein Sequences Data Anal* 3:517-521; Toh, 1991, *Protein Sequences Data Anal* 4:111-117), including the mammalian long chain acyl-CoA synthetases, ACS1-ACS5 (Fujino and Yamamoto, 1992, *J Biochem* 111:197-203; Fujino et al., *J Biol Chem* 271: 16748-16752; Kang et al., 1997, *Proc Natl. Acad Sci USA* 94:2880-2884; Suzuki et al., 1990, *J Biol Chem* 265:8681-8685; Oikawa et al., 1998, *J Biochem* 124:679-685). All enzymes in this superfamily contain a common sequence motif of Ser-Gly-(small hydrophilic residue)$_2$-Gly-(any residue)-Pro-Lys-Gly (SEQ ID NO:1) and catalyze common two-step reactions: adenylation of substrates and subsequent thioester formation (Toh, 1990, *Protein Sequences Data Anal* 3:517-521; Toh, 1991, *Protein Sequences Data Anal* 4:111-117).

Recently bovine and murine AceCS cDNAs were cloned and characterized. Two functionally distinct murine AceCSs were described: a cardiac AceCS and a hepatic AceCS. The hepatic type enzyme, termed AceCS1, is a cytosolic enzyme, whereas the cardiac enzyme, termed AceCS2, is located in the mitochondrial matrix (Fujino et al., 2001, *J Biol Chem* 276: 11420-11426). Based on the finding that AceCS2 mRNA is induced after fasting, it was suggested that AceCS2 provides acetyl-CoA that is utilized mainly for oxidation under ketogenic conditions, such as starvation and diabetes (Fujino et al., 2001, *J Biol Chem* 276:11420-11426). This suggestion is supported by the finding that the level of AceCS2 mRNA in Zucker diabetic rats is increased (Fujino et al., 2001, *J Biol Chem* 276:11420-11426). While Fujino et al. described the induction of AceCS2 under certain conditions, they did not investigate the precise function and regulation of AceCS2 (Fujino et al., 2001, *J Biol Chem* 276:11420-11426).

In order to better understand and treat pathological conditions, such as ketogenic conditions, characterized by elevated levels of acetate, a substrate for AceCS2, it is important to elucidate these regulatory mechanisms. The present invention provides one such regulatory mechanism by identifying Acetyl-CoA synthetase 2 (AceCS2) as a mitochondrial enzyme and as a cellular acetylated substrate of the mitochondrial sirtuin SIRT3. AceCS2 is reversibly acetylated at lysine 642 (Lys642) in the active site of the enzyme. SIRT3 interacts with AceCS2 and deacetylates Lys642 both in vitro and in vivo. Deacetylation of AceCS2 by SIRT3 activates the acetyl-CoA synthetase activity of AceCS2.

It would be advantageous to identify agents that activate a level or deacetylase activity of SIRT3 or agents that modulate a level, acetylation status, or activity of AceCS2. Such agents would have therapeutic utility in treating pathological conditions characterized by elevated levels of acetate and other diseases or disorders that are at least partially caused by such elevated acetate levels. Here, the present invention provides methods for the identification of such agents, compositions comprising such agents and methods using such agents for the treatment of type II diabetes, hypercholesterolemia, hyperlipidemia, and obesity.

BRIEF SUMMARY OF THE INVENTION

The present invention discloses that a mammalian sirtuin, SIRT3, directly controls the activity of a metabolic enzyme, acetyl-CoA synthetase 2 (AceCS2), via reversible lysine acetylation. Provided herein are methods, compositions and kits for identifying agents that increase a level or deacetylase activity of a SIRT3 polypeptide. The invention also provides methods, compositions and kits for identifying agents that modulate a level, acetylation status, or activity of an acetyl-CoA synthetase 2 (AceCS2) polypeptide. The invention also relates to the use of such agents in methods, compositions and kits for reducing acetate levels in an individual and for the treatment of a disorder characterized by elevated levels of acetate, such as Type II diabetes, hypercholesterolemia, hyperlipidemia, or obesity.

More specifically, in one aspect, the present invention provides a method for identifying an agent that increases a level or deacetylase activity of a SIRT3 polypeptide. In a preferred embodiment of the present invention, this method comprises the steps of (a) contacting a cell expressing a SIRT3 polypeptide and an AceCS2 polypeptide with a candidate agent and (b) determining the effect, if any, of the candidate agent on the level of acetylated AceCS2 in the cell. Step (b) may comprises an immunological assay using an antibody specific for acetylated AceCS2. Optionally, this method comprises the step of identifying a structure or sequence of the candidate agent.

A preferred cell is a mammalian cell, preferably a human cell. In some embodiments, the mammalian cell is selected from the group consisting of a heart cell, a muscle cell, and a brain cell.

In another aspect of the present invention, the method for identifying an agent that increases a level or deacetylase activity of a SIRT3 polypeptide comprises the steps of (a) contacting a SIRT3 polypeptide and an acetylated AceCS2 polypeptide in an assay mixture comprising $NAD^+$ with a candidate agent and (b) determining the effect, if any, of the candidate agent on the level of acetylated AceCS2 in the assay mixture. A decrease in a first level of acetylated AceCS2 in the assay mixture relative to a second level of acetylated AceCS2 in an assay mixture, which has not been treated with the candidate agent, is indicative of an agent that increases the level or deacetylase activity of the SIRT3 polypeptide.

In a preferred embodiment of this method, the acetylated AceCS2 polypeptide comprises a $^{14}C$-labeled acetyl group and step (b) is performed by measuring release of the $^{14}C$-labeled acetyl group.

In another aspect of the present invention, a method for identifying an agent that modulates a level, acetylation status, or activity of an AceCS2 polypeptide, is provided. In a preferred embodiment of the present invention, this method comprises the steps of (a) contacting a cell expressing an AceCS2 polypeptide with a candidate agent and (b) determining the effect, if any, of the candidate agent on the level, acetylation status, or activity of the AceCS2 in the cell.

In another aspect of the present invention, the method for identifying an agent that modulates a level, acetylation status, or activity of an AceCS2 polypeptide comprises the steps of (a) contacting an AceCS2 polypeptide in an assay mixture with a candidate agent and (b) determining the effect, if any, of the candidate agent on the level, acetylation status, or activity of the AceCS2 in the assay mixture.

In a further aspect of the present invention, biologically active agents identified by one of the subject screening methods of the present invention, are provided.

In yet another aspect, the present invention provides a method for modulating the acetylation status of an AceCS2 polypeptide. In a preferred embodiment of the present invention, this method comprises the step of contacting a cell expressing an AceCS2 polypeptide with an agent obtainable according to a subject method of the present invention, such as a method for identifying an agent that increases a level or deacetylase activity of a SIRT3 polypeptide or a method for identifying an agent that modulates a level, acetylation status, or activity of an AceCS2 polypeptide.

This invention also provides a method for treatment of a pathological condition in an individual, wherein the pathological condition is characterized by an elevated acetate level. In a preferred embodiment of the present invention, this method comprises the step of administering to the individual a therapeutically effective amount of an agent that increases a level or deacetylase activity of a SIRT3 polypeptide which deacetylates AceCS2. Thereby the pathological condition is treated.

In a preferred embodiment of the present invention, the pathological condition is selected from the group consisting of type II diabetes, hypercholesterolemia, hyperlipidemia, and obesity.

Preferably the individual treated is a human or non-human animal.

In yet another aspect, the present invention provides a pharmaceutical composition for increasing a level or deacetylase activity of SIRT3. In a preferred embodiment of the present invention, a pharmaceutical composition comprises (i) an agent obtainable according to a subject method of the present invention, such as a method for identifying an agent that increases a level or deacetylase activity of a SIRT3 polypeptide, and (ii) a pharmaceutically acceptable carrier.

This invention also provides pharmaceutical compositions for modulating a level, acetylation status or activity of an AceCS2 polypeptide. In a preferred embodiment of the present invention, a pharmaceutical composition comprises (i) an agent obtainable according to a subject method of the present invention, such as a method for identifying an agent that modulates a level, acetylation status, or activity of an AceCS2 polypeptide, and (ii) a pharmaceutically acceptable carrier.

In yet another aspect of the present invention, kits are provided. A preferred kit for increasing a level or deacetylase activity of SIRT3 comprises (i) a container containing an agent obtainable according to a method of the present invention, such as a method for identifying an agent that increases a level or deacetylase activity of a SIRT3 polypeptide, and (ii) instructions for contacting the agent to a cell expressing a SIRT3 polypeptide and an AceCS2 polypeptide and determining the effect, if any, of the agent on the level of acetylated AceCS2 in the cell.

In another aspect of the present invention, a kit for modulating a level, acetylation status, or activity of an AceCS2 polypeptide is provided. In a preferred embodiment of the present invention, the kit comprises (i) a container containing an agent obtainable according to a subject method of the present invention, such as a method for identifying an agent that modulates a level, acetylation status, or activity of an AceCS2 polypeptide, and (ii) instructions for contacting a cell expressing an AceCS2 polypeptide and determining the effect, if any, of the agent on the level, acetylation status, or activity of the AceCS2.

Useful agents to be included in pharmaceutical compositions and kits are agents that increase a level or deacetylase activity of a SIRT3 polypeptide and agents that modulate a level, acetylation status, or activity of an AceCS2 polypeptide.

Methods, compositions, and kits of the present invention embrace the specifics as fully described herein.

DETAILED DESCRIPTION OF THE INVENTION

I. Definitions

Figure 1:
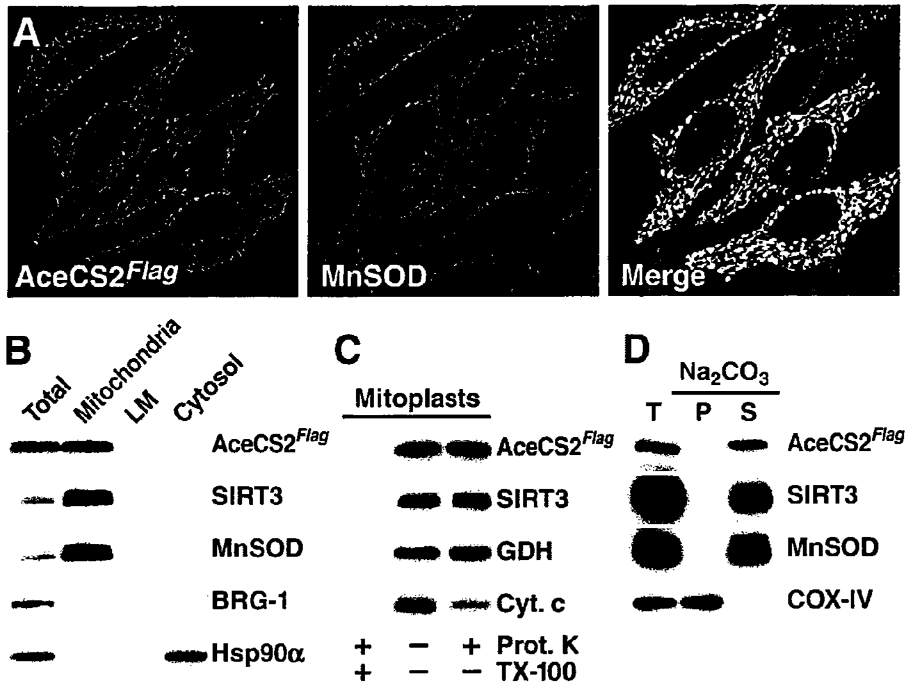
FIG. 1 shows that human Acetyl-CoA Synthetase 2 (AceCS2) is a soluble mitochondrial protein. (A) Human AceCS2$^{Flag}$ was transfected into Hela cells. Cells were co-stained with anti-Flag antibodies and antibodies against the endogenous mitochondrial marker protein MnSOD and analyzed by confocal laser scanning microscopy. The fluorescent signals from AceCS2$^{Flag}$ (left) and MnSOD (middle) in the same focal plane are shown. (Right) The merged image demonstrates that AceCS2$^{Flag}$ localizes to the mitochondria. (B) Subcellular fractions were prepared from HEK293 cells stably expressing AceCS2$^{Flag}$. Equal amounts (30 μg) of total cell extract (Total), mitochondria, light membranes (LM) and cytosolic proteins were analyzed by immunoblotting using the antibodies indicated. (C) Submitochondrial localization of AceCS2$^{Flag}$. Mitochondria from HEK293 cells stably expressing AceCS2$^{Flag}$ were converted into mitoplasts by hypotonic swelling and treated with proteinase K. After incubation (20 min at 0° C.), mitoplasts were reisolated by centrifugation and analyzed by immunoblotting using the antibodies indicated. Rupture of the outer mitochondrial membrane was confirmed by immunoblotting against the intermembrane space protein cytochrome c (Cyt. C). The integrity of the inner mitochondrial membrane was confirmed by immunoblotting against the matrix protein markers SIRT3 and GDH. AceCS2$^{Flag}$ was detected with anti-Flag antibodies. (D) AceCS2$^{Flag}$ is a soluble protein. Mitochondria were isolated from HEK293 cells stably expressing AceCS2$^{Flag}$ and either directly solubilized in SDS sample buffer (T, total) or extracted with sodium carbonate ($Na_2CO_3$, pH 11.5). The alkaline extract was separated into a membrane fraction (P, pellet) and a fraction containing sodium carbonate soluble proteins (S, supernatant) by ultracentrifugation. The efficiency of the alkaline extraction was followed or monitored by immunoblotting of the different fractions for the presence of the well-characterized marker proteins COX-IV, MnSOD, and SIRT3. Details are presented in Example 3.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics,* 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used herein "AceCS2" means acetyl CoA synthetase 2.

As used herein, "AceCS2" or "Acetyl CoA Synthetase 2" refers to and includes mammalian AceCS2 polypeptides and nucleic acids encoding mammalian AceCS2 polypeptides. In certain embodiments, an AceCS2 polypeptide or AceCS2 nucleic acid is from yeast, *Drosophila*, zebrafish, trypanosome, *C. elegans*, and others. Exemplary AceCS2 polypeptide sequences can be found at GenBank, for example, human (GenBank accession number Q9NUB1) (SEQ ID NO: 19); mouse (GenBank accession number BAB21612) (SEQ ID NO: 20); bovine (GenBank accession number BAB21611) (SEQ ID NO: 21). Exemplary AceCS2 nucleic acid sequences can be found at GenBank, for example, human (GenBank accession number BC039261) (SEQ ID NO: 22); mouse (GenBank accession number AB046742) (SEQ ID NO: 23), and bovine (GenBank accession number AB046741) (SEQ ID NO: 24).

As used herein, "acetylation status" refers to the presence or absence of an acetyl group on a polypeptide, preferably an acetyl CoA synthetase 2 (AceCS2) polypeptide.

As used herein, "activator" refers to an agent that, e.g., induces or activates the expression of a polypeptide of the invention or binds to, stimulates, increases, opens, activates, facilitates, or enhances activation, sensitizes or up regulates the activity of a polypeptide of the invention. Activators include nucleic acids that encode SIRT3 or AceCS2, as well as naturally occurring and synthetic compounds or agents, small chemical molecules and the like. Assays for activators include, e.g., applying a candidate agent to a cell expressing SIRT3 or AceCS2 and then determining the functional effects. Samples or assays comprising SIRT3 or AceCS2 that are treated with a potential activator are compared to control samples without the activator to examine the extent of the effect. Control samples (untreated with candidate agents) are assigned a relative activity value of 100%. Activation of the polypeptide is achieved when the polypeptide activity value relative to the control is 110%, optionally 130%, 150%, optionally 200%, 300%, 400%, 500%, or 1000-3000% or more higher.

As used herein, "activity of AceCS2" or "activity of an AceCS2 polypeptide" refers to (i) binding of AceCS2 to a polypeptide or peptide, preferably a SIRT3 polypeptide, (ii) interaction of AceCS2 with a polypeptide or peptide, preferably a SIRT3 polypeptide, (iii) assembly of AceCS2 into a multiprotein complex, comprising a SIRT3 polypeptide, (iv) localization of AceCS2 in mitochondria, or (v) enzymatic conversion of acetate, ATP and CoA into acetyl-CoA and AMP (adenosine monophosphate), i.e., using acetate, ATP and CoA as a substrate to generate acetyl-CoA and AMP.

As used herein, "activity of SIRT3" or "activity of a SIRT3 polypeptide" refers to (i) binding of SIRT3 to a polypeptide or peptide, preferably an AceCS2 polypeptide, (ii) interaction of a SIRT3 with a polypeptide or peptide, preferably an AceCS2 polypeptide, (iii) assembly of SIRT3 into a multiprotein complex, comprising an AceCS2 polypeptide, (iv) localization of SIRT3 in mitochondria, (v) deacetylation of a polypeptide or peptide, preferably an AceCS2 polypeptide, or (vi) ADP-ribosylation of a polypeptide or peptide, preferably an AceCS2 polypeptide.

As used herein, an "agent" or "candidate agent" can be any chemical compound, for example, a macromolecule or a small molecule. The candidate agent can have a formula weight of less than about 10,000 grams per mole, less than 5,000 grams per mole, less than 1,000 grams per mole, or less than about 500 grams per mole. The candidate agent can be naturally occurring (e.g., a herb or a nature product), synthetic, or both. Examples of macromolecules are proteins, protein complexes, and glycoproteins, nucleic acids, e.g., DNA, RNA and PNA (peptide nucleic acid). Examples of small molecules are peptides, peptidomimetics (e.g., peptoids), amino acids, amino acid analogs, polynucleotides, polynucleotide analogs, nucleotides, nucleotide analogs, organic or inorganic compounds e.g., heteroorganic or organometallic compounds. A candidate agent can be the only substance assayed by the method described herein. Alternatively, a collection of candidate agents can be assayed either consecutively or concurrently by the methods described herein.

Candidate agents encompass numerous chemical classes, typically synthetic, semi-synthetic, or naturally-occurring inorganic or organic molecules. Candidate agents may be small organic compounds having a molecular weight of more than 50 and less than about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

As used herein, "antagonist" means a chemical substance that diminishes, abolishes or interferes with the physiological action of a polypeptide. The antagonist may be, for example, a chemical antagonist, a pharmacokinetic antagonist, a non-competitive antagonist, or a physiological antagonist, such as a biomolecule, e.g., a polypeptide. A preferred antagonist diminishes, abolishes or interferes with the physiological action of an AceCS2 polypeptide.

Specifically, an antagonist may act at the level of the interaction between a first polypeptide, e.g., a SIRT3 polypeptide and a second polypeptide, for example, a binding partner, such as an AceCS2 polypeptide. The antagonist, for example, may competitively or non-competitively (e.g., allosterically) inhibit binding of the first polypeptide to the second polypeptide. A "pharmacokinetic antagonist" effectively reduces the concentration of the active drug at its site of action, e.g., by increasing the rate of metabolic degradation of the first polypeptide. A "competitive antagonist" is a molecule which binds directly to the first polypeptide in a manner that sterically interferes with the interaction of the first polypeptide with the second polypeptide. Non-competitive antagonism describes a situation where the antagonist does not compete directly with the binding, but instead blocks a point in the signal transduction pathway subsequent to the binding of the first polypeptide to the second polypeptide. Physiological antagonism loosely describes the interaction of two substances whose opposing actions in the body tend to cancel each other out. An antagonist can also be a substance that diminishes or abolishes expression of a first polypeptide. Thus, an AceCS2 antagonist can be, for example, a substance that diminishes or abolishes: (i) the expression of the gene encoding AceCS2, (ii) the translation of AceCS2 mRNA, (iii) the post-translational modification of AceCS2, or (iv) the interaction of AceCS2 with other polypeptides in the formation of a multi-protein complex.

The term "antisense-oligonucleotides" as used herein encompasses both nucleotides that are entirely complementary to a target sequence and those having a mismatch of one or more nucleotides, so long as the antisense-oligonucleotides can specifically hybridize to the target sequence. For example, the antisense-oligonucleotides of the present invention include polynucleotides that have a homology (also referred to as sequence identity) of at least 70% or higher, preferably 80% or higher, more preferably 90% or higher, even more preferably 95% or higher over a span of at least 15 continuous nucleotides up to the full length sequence of any of the nucleotide sequences of an AceCS2 gene. Algorithms known in the art can be used to determine the homology. Furthermore, derivatives or modified products of the antisense-oligonucleotides can also be used as antisense-oligonucleotides in the present invention. Examples of such modified products include lower alkyl phosphonate modifications such as methyl-phosphonate-type or ethyl-phosphonate-type, phosphorothioate modifications and phosphoroamidate modifications.

As used herein, "associated with" means contact, interact or bind to.

As used herein, the term "biologically active" when referring to an agent is art-recognized and refers to a form of an agent that allows for it, or a portion of the amount of agent administered, to be absorbed by, incorporated to, or otherwise physiologically available to a subject or patient to whom it is administered.

As used herein, "biological sample" means a sample of biological tissue or fluid that contains nucleic acids or polypeptides. Such samples are typically from humans, but include tissues isolated from non-human primates, or rodents, e.g., mice, and rats. Biological samples may also include sections of tissues such as biopsy and autopsy samples, frozen sections taken for histological purposes, cerebral spinal fluid, blood, plasma, serum, sputum, stool, tears, mucus, hair, skin, etc. Biological samples also include explants and primary and/or transformed cell cultures derived from patient tissues. A “biological sample” also refers to a cell or population of cells or a quantity of tissue or fluid from an animal. Most often, the biological sample has been removed from an animal, but the term “biological sample” can also refer to cells or tissue analyzed in vivo, i.e., without removal from the animal. Typically, a “biological sample” will contain cells from the animal, but the term can also refer to noncellular biological material, such as noncellular fractions of blood, serum, saliva, cerebral spinal fluid or urine, that can be used to measure expression level of a polynucleotide or polypeptide. Numerous types of biological samples can be used in the present invention, including, but not limited to, a tissue biopsy or a blood sample. As used herein, a “tissue biopsy” refers to an amount of tissue removed from an animal, preferably a human, for diagnostic analysis. “Tissue biopsy” can refer to any type of biopsy, such as needle biopsy, fine needle biopsy, surgical biopsy, etc.

“Providing a biological sample” means to obtain a biological sample for use in methods described in this invention. Most often, this will be done by removing a sample of cells from a subject, but can also be accomplished by using previously isolated cells (e.g., isolated by another person, at another time, and/or for another purpose), or by performing the methods of the invention in vivo. Archival tissues, having treatment or outcome history, will be particularly useful.

As used herein, “CoA” means coenzyme A.

As used herein, a “combinatorial chemical library” refers to a collection of diverse chemical compounds generated by either chemical synthesis or biological synthesis, by combining a number of chemical “building blocks” such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

As used herein, the term “decreased expression” refers to the level of a gene expression product that is lower and/or the activity of the gene expression product is lowered. Preferably, the decrease is at least 20%, more preferably, the decrease is at least 30%, at least 40%, at least 50%, at least 60%, at least 70%, at least 80%, or at least 90% and most preferably, the decrease is at least 100%, relative to a control.

Synonyms of the term, “determining” are contemplated within the scope of the present invention and include, but are not limited to, detecting, measuring, assaying, or testing for the presence, absence, amount or concentration of a molecule, such as a an AceCS2, a SIRT3, a label, or a small molecule of the invention and the like. The term refers to both qualitative and quantitative determinations.

As used herein, “determining the effect” or “determining the functional effect” means assaying for an agent that increases or decreases a parameter that is indirectly or directly under the influence of the agent, e.g., functional, enzymatic, physical and chemical effects. Such effects can be measured by any means known to those skilled in the art, e.g., changes in spectroscopic characteristics (e.g., fluorescence, absorbance, refractive index), hydrodynamic (e.g., shape), chromatographic, or solubility properties for the protein, measuring inducible markers or transcriptional activation of a gene, such as SIRT3 or AceCS2; measuring binding activity, e.g., binding of a SIRT3 to an AceCS2; assaying for deacetylation activity of SIRT3; determining the acetylation status of an AceCS2; measuring cellular proliferation, measuring apoptosis, measuring subcellular localization of a polypeptide, such as SIRT3 or AceCS2; measuring the production of acetyl-CoA or AMP; measuring the reduction of an acetate level, ATP level or CoA level, or the like. Determination of the functional effect of an agent on a disease, disorder, cancer or other pathology can also be performed using assays known to those of skill in the art such as in vitro assays, e.g., cellular proliferation; growth factor or serum dependence; mRNA and protein expression in cells, and other characteristics of cells. The effects can be evaluated by many means known to those skilled in the art, e.g., microscopy for quantitative or qualitative measures of alterations in morphological features, measurement of changes in RNA or protein levels, measurement of RNA stability, identification of downstream or reporter gene expression (CAT, luciferase, β-gal, GFP and the like), e.g., via chemiluminescence, fluorescence, colorimetric reactions, antibody binding, inducible markers, ligand binding assays, apoptosis assays, measuring the production of acetyl-CoA and AMP, and the like. “Functional effects” include in vitro, in vivo, and ex vivo activities.

As used herein, “disorder”, “disease” or “pathological condition” are used inclusively and refer to any deviation from the normal structure or function of any part, organ or system of the body (or any combination thereof). A specific disease is manifested by characteristic symptoms and signs, including biological, chemical and physical changes, and is often associated with a variety of other factors including, but not limited to, demographic, environmental, employment, genetic and medically historical factors. Certain characteristic signs, symptoms, and related factors can be quantitated through a variety of methods to yield important diagnostic information.

Figure 11:
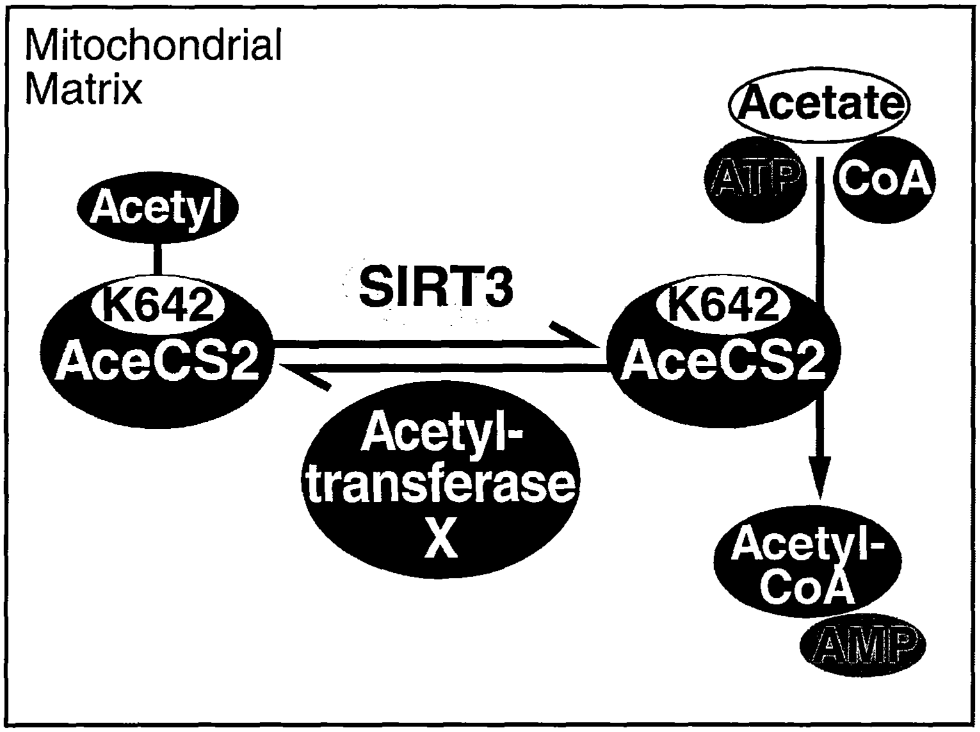
FIG. 11 shows a schematic illustration of AceCS2 regulation by reversible lysine acetylation of Lys642. Deacetylation of AceCS2 by SIRT3 activates its acetyl-CoA synthetase activity. The identity of the protein acetyltransferase of AceCS2 is unknown and is therefore labeled Acetyltransferase X. Details are presented in Example 13.

As used herein, “effective amount”, “effective dose”, “sufficient amount”, “amount effective to”, “therapeutically effective amount” or grammatical equivalents thereof mean a dosage sufficient to produce a desired result, to ameliorate, or in some manner, reduce a symptom or stop or reverse progression of a condition. In some embodiments, the desired result is an increase in mitochondrial localization of a SIRT3. In other embodiments, the desired result is an increase in mitochondrial localization of a AceCS2. In yet other embodiments, the desired result is an increase in the deacetylation activity of SIRT3. In another embodiment, the desired result is an increase or decrease in the acetylation status of AceCS2. In yet other embodiments, the desired result is an increase or decrease in the generation of acetyl-CoA and AMP using acetate, ATP and CoA as a substrate (see FIG. 11). In yet another embodiment, the desired result is a decrease in the level of acetate. Amelioration of a symptom of a particular condition by administration of a pharmaceutical composition described herein refers to any lessening, whether permanent or temporary, lasting or transient that can be associated with the administration of the pharmaceutical composition. An “effective amount” can be administered in vivo and in vitro.

A “full length” polypeptide or nucleic acid refers to a polypeptide or polynucleotide sequence, or a variant thereof, that contains all of the elements normally contained in one or more naturally occurring polynucleotide or polypeptide sequences. The “full length” may be prior to, or after, various stages of post-translation processing or splicing, including alternative splicing and signal peptide cleavage.

The term “heterologous” when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein)

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as *E. coli*, or eukaryotic cells such as yeast, insect cells, amphibian cells, or mammalian cells such as CHO, 293, 3T3, HeLa, and the like (see, e.g., the American Type Culture Collection catalog).

For the purposes of this invention the terms "hybridize" or "hybridize specifically" are used to refer to the ability of two nucleic acid molecules to hybridize under "stringent hybridization conditions." The phrase "stringent hybridization conditions" refers to conditions under which a nucleic acid molecule will hybridize to its target sequence, typically in a complex mixture of nucleic acids, but not detectably to other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 50° C. The antisense-oligonucleotides and derivatives thereof act on cells producing, e.g., a protein encoded by an AceCS2 gene, by binding to the DNA or mRNA encoding the protein, inhibiting transcription or translation thereof, promoting the degradation of the mRNAs and inhibiting the expression of the protein, thereby resulting in the inhibition of the protein function.

The term "hypercholesterolemia" refers to a state in a subject in which the level of cholesterol in the bloodstream is abnormally high.

The term "hyperlipidemia" refers to a state in a subject in which the level of fatty substances in the blood is higher than normal. Fatty substances include cholesterol, cholesterol esters, phospholipids, and triglycerides.

The terms "individual," "subject," "host," and "patient," used interchangeably herein, refer to a mammal, including, but not limited to, murines, simians, felines, canines, equines, bovines, mammalian farm animals, mammalian sport animals, and mammalian pets and humans. Preferred is a human. In certain embodiments, the terms also include *Xenopus*, zebrafish, trypanosome, *C. elegans, Drosophila*, and yeast.

As used herein, "inhibitor" refers to an agent that, e.g., represses or inactivates the expression of a polypeptide of the invention or binds to, decreases, closes, inactivates, impedes, or reduces activation, desensitizes or down regulates the activity of a polypeptide of the invention. Inhibitors include nucleic acids such as siRNA, antisense RNA, and ribozymes that interfere with the expression of, e.g., AceCS2 as well as naturally occurring and synthetic compounds and agents, small chemical molecules and the like. Assays for activators (see above and herein) can also be used as assays for inhibitors. Samples or assays comprising AceCS2 that are treated with a potential inhibitor are compared to control samples without the inhibitor to examine the extent of the effect. Control samples (untreated with candidate agents) are assigned a relative activity value of 100%. Inhibition of the polypeptide is achieved when the activity value relative to the control is reduced by 10%, optionally 20%, optionally 30%, optionally 40%, optionally 50%, 60%, 70%, 80%, or 90-100%.

As used herein, "in vitro" means outside the body of the organism from which a cell or cells is obtained or from which a cell line is isolated.

As used herein, "in vivo" means within the body of the organism from which a cell or cells is obtained or from which a cell line is isolated.

As used herein, the term "ketogenic condition" refers to a condition in an individual characterized by the liver releasing substantial amounts of acetate into the bloodstream (Buckley and Williamson, 1977*, Biochem J* 166:539-45; Seufert et al., 1974*, Biochem Biophys Res Commun* 57:901-9; Yamashita et al., 2001*, Biochim Biophys Acta* 1532:79-87). A ketogenic condition can be the effect of prolonged fasting or diabetes. In addition, the hepatic acetyl-CoA hydrolase, which produces acetate, is activated under ketogenic conditions (Matsunaga et al., 1985*, Eur J Biochem* 152, 331-6).

A "label" or a "detectable moiety" is a composition detectable by spectroscopic, photochemical, biochemical, immunochemical, chemical, or other physical means. For example, useful labels include $^{3}H$, $^{125}I$, $^{32}P$ $^{14}C$, fluorescent dyes, electron-dense reagents, enzymes (e.g., as commonly used in an ELISA), biotin, digoxigenin, or haptens and proteins or other entities which can be made detectable, e.g., by incorporating a radiolabel into a SIRT3, an AceCS2, a substrate of SIRT3 (e.g., NAD or a polypeptide) or a substrate of AceCS2 (e.g., acetate), or a small molecule compound. A preferred label is $^{14}C$, preferably in an acetyl group.

As used herein, "level of an mRNA" in a biological sample refers to the amount of mRNA transcribed from a gene that is present in a cell or a biological sample. The mRNA generally encodes a functional protein, although mutations may be present that alter or eliminate the function of the encoded protein. A "level of mRNA" need not be quantified, but can simply be detected, e.g., a subjective, visual detection by a human, with or without comparison to a level from a control sample or a level expected of a control sample. A preferred mRNA is a SIRT3 mRNA or an AceCS2 mRNA.

As used herein, "level of a polypeptide" in a biological sample refers to the amount of polypeptide translated from an mRNA that is present in a cell or biological sample. The polypeptide may or may not have protein activity. A "level of a polypeptide" need not be quantified, but can simply be detected, e.g., a subjective, visual detection by a human, with or without comparison to a level from a control sample or a level expected of a control sample. A preferred polypeptide is a SIRT3 or an AceCS2 polypeptide.

As used herein, "mammal" or "mammalian" means or relates to the class mammalia including the orders carnivore (e.g., dogs and cats), rodentia (e.g., mice, guinea pigs, and rats), and primates (e.g., humans, chimpanzees, and monkeys).

The terms "modulate," "modulation," or "modulating" are art-recognized and refer to up-regulation (i.e., activation, stimulation, increase), or down regulation (i.e., inhibition, suppression, reduction, or decrease) of a response, or the two in combination or apart.

As used herein a "modulator" of the level or activity of a polypeptide, such as an AceCS2, includes an activator and/or inhibitor of that polypeptide and is used to refer to agents that activate or inhibit the level of expression of the polypeptide or an activity of the polypeptide. A preferred polypeptide is AceCS2.

As used herein, a "multi-protein complex" refers to the binding and non-covalent attachment of two or more polypeptides to each other.

As used herein, a "naturally-occurring" nucleic acid molecule refers to an RNA or DNA molecule having a nucleotide sequence that occurs in nature. For example a naturally occurring nucleic acid molecule can encode a natural protein.

As used herein, a "naturally-occurring" polypeptide refers to a polypeptide molecule having an amino acid sequence that occurs in nature.

As used herein, "nucleic acid" or "oligonucleotide" or "polynucleotide" or grammatical equivalents thereof, means at least two nucleotides covalently linked together. Oligonucleotides are typically from about 5, 6, 7, 8, 9, 10, 12, 15, 25, 30, 40, 50 or more nucleotides in length, up to about 100 nucleotides in length. Nucleic acids and polynucleotides are polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphosphoroamidite linkages (see, Eckstein, *Oligonucleotides and Analogues: A Practical Approach*, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580*, Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g. to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

A variety of references disclose such nucleic acid analogs, including, for example, phosphoramidate (Beaucage et al., *Tetrahedron* 49(10):1925 (1993) and references therein; Letsinger, *J. Org. Chem.* 35:3800 (1970); Sprinzl et al., *Eur. J. Biochem.* 81:579 (1977); Letsinger et al., *Nucl. Acids Res.* 14:3487 (1986); Sawai et al., *Chem. Lett.* 805 (1984), Letsinger et al., *J. Am. Chem. Soc.* 110:4470 (1988); and Pauwels et al., *Chemica Scripta* 26:141 91986)), phosphorothioate (Mag et al., *Nucleic Acids Res.* 19:1437 (1991); and U.S. Pat. No. 5,644,048), phosphorodithioate (Briu et al., *J. Am. Chem. Soc.* 111:2321 (1989), O-methylphosphoroamidite linkages (see, Eckstein, *Oligonucleotides and Analogues: A Practical Approach*, Oxford University Press) and peptide nucleic acid backbones and linkages (see, Egholm, *J. Am. Chem. Soc.* 114:1895 (1992); Meier et al., *Chem. Int. Ed. Engl.* 31:1008 (1992); Nielsen, *Nature* 365:566 (1993); Carlson et al., *Nature* 380:207 (1996), all of which are incorporated by reference). Other analog nucleic acids include those with positive backbones (Denpcy et al., *Proc. Natl. Acad. Sci. USA* 92:6097 (1995), non ionic backbones (U.S. Pat. Nos. 5,386,023, 5,637,684, 5,602,240, 5,216,141 and 4,469,863; Kiedrowshi et al., *Angew. Chem. Intl. Ed. English* 30:423 (1991); Letsinger et al., *J. Am. Chem. Soc.* 110:4470 (1988); Letsinger et al., *Nucleoside & Nucleotide* 13:1597 (1994); Chapters 2 and 3, ASC Symposium Series 580*, "Carbohydrate Modifications in Antisense Research"*, Ed. Y. S. Sanghui and P. Dan Cook; Mesmaeker et al., *Bioorganic & Medicinal Chem. Lett.* 4:395 (1994); Jeffs et al., *J. Biomolecular NMR* 34:17 (1994); *Tetrahedron Lett.* 37:743 (1996)) and non ribose backbones, including those described in U.S. Pat. Nos. 5,235,033 and 5,034,506, and Chapters 6 and 7, ASC Symposium Series 580*, "Carbohydrate Modifications in Antisense Research"*, Ed. Y. S. Sanghui and P. Dan Cook. Nucleic acids containing one or more carbocyclic sugars are also included within one definition of nucleic acids (see, Jenkins et al., *Chem. Soc. Rev*. pp 169 176 (1995)). Several nucleic acid analogs are described in Rawls, *C & E News* Jun. 2, 1997 page 35. All of these references are hereby expressly incorporated by reference.

Other analogs include peptide nucleic acids (PNA) which are peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature ($T_m$) for mismatched versus perfectly matched base pairs. DNA and RNA typically exhibit a 2-4° C. drop in $T_m$ for an internal mismatch. With the non-ionic PNA backbone, the drop is closer to 7-9° C. Similarly, due to their non-ionic nature, hybridization of the bases attached to these backbones is relatively insensitive to salt concentration. In addition, PNAs are not degraded by cellular enzymes, and thus can be more stable.

The nucleic acids may be single stranded or double stranded, as specified, or contain portions of both double stranded or single stranded sequence. As will be appreciated by those in the art, the depiction of a single strand also defines the sequence of the complementary strand; thus the sequences described herein also provide the complement of the sequence. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. "Transcript" typically refers to a naturally occurring RNA, e.g., a pre-mRNA, hnRNA, or mRNA. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g., the individual units of a peptide nucleic acid, each containing a base, are referred to herein as a nucleoside.

As used herein, "pharmaceutically acceptable" refers to compositions that are physiologically tolerable and do not typically produce an allergic or similar untoward reaction when administered to a subject, preferably a human subject. Preferably, as used herein, the term "pharmaceutically acceptable" means approved by a regulatory agency of a Federal or state government or listed in the U.S. Pharmacopeia or other generally recognized pharmacopeia for use in animals, and more particularly in humans.

As used herein, "polypeptide" and "protein" are used interchangeably herein to refer to a polymer of amino acid residues. The terms also apply to amino acid polymers in which one or more amino acid residues is an artificial chemical mimetic of a corresponding naturally occurring amino acid, as well as to naturally occurring amino acid polymers, those containing modified residues, and non-naturally occurring amino acid polymers. Preferred polypeptides are SIRT3 and AceCS2.

The term "promoter" refers to a nucleic acid sequence comprising one or more regulatory regions that control transcription of a SIRT3 gene or an AceCS2 gene. In some embodiments, a promoter is a human promoter.

A "purified" or "isolated" polypeptide or protein is substantially free of cellular material or other contaminating proteins from the cell or tissue source from which the protein is derived, or substantially free from chemical precursors or other chemicals when chemically synthesized. "Substantially free" means that the protein of interest in the preparation is at least 10% pure. In one embodiment, the preparation of the protein has less than about 30%, 20%, 10% and more preferably 5% (by dry weight), of a contaminating component (e.g., a protein not of interest, chemical precursors, and so forth). When the protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The term "recombinant" when used with reference to, e.g., a cell, nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under-expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operable linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

As used herein, the term "salts" refers to salts of an active compound or agent of the present invention, such as a SIRT3 activator or an AceCS2 modulator, which are prepared with relatively nontoxic acids or bases, depending on the particular substituents found on the compounds described herein. When compounds, agents, and small molecules of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds, agents, and small molecules of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., 1977, *J Pharm Science* 66:1-19). Certain specific agents of the present invention contain both basic and acidic functionalities that allow the agents to be converted into either base or acid addition salts.

The neutral forms of the agents and small molecules of the present invention may be regenerated by contacting the salt with a base or acid and isolating the parent compound in the conventional manner. The parent form of the agent and small molecule differs from the various salt forms in certain physical properties, such as solubility in polar solvents, but otherwise the salts are equivalent to the parent form of the compound, agent, and small molecule for the purposes of the present invention.

As used herein, the term "sirtuin" refers to a member of the sirtuin deacetylase protein family, preferably to the Sir2 family, which includes yeast Sir2 (e.g., GenBank Accession No. P53685) (SEQ ID NO: 25), *C. elegans* Sir-2.1 (e.g., GenBank Accession No. NP_01912) (SEQ ID NO: 26), and human SIRT1 (e.g., GenBank Accession Nos. Q96EB6 (SEQ ID NO: 27), NP_036370 (SEQ ID NO: 27), and AAD40849 (SEQ ID NO: 27)), and human SIRT2 (e.g., GenBank Accession Nos. NM_030593 (SEQ ID NO: 28), AF083107 (SEQ ID NO: 29), AAD40850 (SEQ ID NO: 30), CAD43717 (SEQ ID NO: 31), ABB72675 (SEQ ID NO: 32), NP_085096 (SEQ ID NO: 33), AAH03547 (SEQ ID NO: 33)) proteins. Other family members include the four additional yeast Sir2-like genes termed "HST genes" (homologues of Sir2) HST1, HST2, HST3 and HST4, and the five other human homologues hSIRT3 (e.g., GenBank Accession Nos. NP_036371 (SEQ ID NO: 34), AAH01042 (SEQ ID NO: 34), AAD40851 (SEQ ID NO: 34), and Q9NTG7 (SEQ ID NO: 34)), hSIRT4 (e.g., GenBank Accession Nos. NP_036372 (SEQ ID NO: 35), AAI09321 (SEQ ID NO: 35), AAI09320 (SEQ ID NO: 35), AAD40852 (SEQ ID NO: 35), and Q9Y6E7 (SEQ ID NO: 35)), hSIRT5 (e.g., GenBank Accession Nos. CAI19838 (SEQ ID NO: 36), CAI19837 (SEQ ID NO: 37), NP_112534 (SEQ ID NO: 37), and NP_036373 (SEQ ID NO: 36), hSIRT6 (e.g., GenBank Accession Nos. NP_057623 (SEQ ID NO: 38), AAH05026 (SEQ ID NO: 38), AAH04218 (SEQ ID NO: 39), and AAH28220 (SEQ ID NO: 40)), and hSIRT7 (e.g., GenBank Accession Nos. NP_057622 (SEQ ID NO: 41), AAH17305 (SEQ ID NO: 41), AAI01794 (SEQ ID NO: 41), and AAI01792 (SEQ ID NO: 41)) (Brachmann et al., 1995, *Genes Dev* 9:2888-902 and Frye, 1999, *Biochem Biophys Res Commun* 260(1):273-279; Frye, 2000, *Biochem Biophys Res Commun* 273(2):793-798). Preferred sirtuins are those that share more similarities with SIRT3, more preferably a hSIRT3.

As used herein, the term "SIRT3" refers to nucleic acids, polypeptides and polymorphic variants, alleles, mutants, and interspecies homologues thereof and as further described herein, that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 75, 100, 150, 200, 250, 300, 350, or 400 or more amino acids, to a SIRT3 sequence as deposited under GenBank Accession Nos. NP__036371 (SEQ ID NO: 34), AAH01042 (SEQ ID NO: 34), AAD40851 (SEQ ID NO: 34), NM__001017524 (SEQ ID NO: 42), or Q9NTG7 (SEQ ID NO: 34); (2) bind to antibodies, e.g., polyclonal antibodies, raised against an immunogen comprising an amino acid sequence as deposited under GenBank Accession Nos. NP__036371 (SEQ ID NO: 34), AAH01042 (SEQ ID NO: 34), AAD40851 (SEQ ID NO: 34), NM__001017524 (SEQ ID NO: 42), or Q9NTG7 (SEQ ID NO: 34) or conservatively modified variants thereof or a fragment thereof; (3) bind to an AceCS2 polypeptide; (4) modulate at least partially and indirectly the production of acetyl-CoA and AMP; (5) deacetylate an acetylated AceCS2 polypeptide, (6) specifically hybridize under stringent hybridization conditions to a nucleic acid sequence as deposited under GenBank Accession Nos. NP__036371 (SEQ ID NO: 34), AAH01042 (SEQ ID NO: 34), AAD40851 (SEQ ID NO: 34), and Q9NTG7 (SEQ ID NO: 34), or conservatively modified variants thereof; (7) have a nucleic acid sequence that has greater than about 90%, preferably greater than about 96%, 97%, 98%, 99%, or higher nucleotide sequence identity, preferably over a region of at least about 30, 50, 100, 200, 500, 1000, 1,500, 2000 or more nucleotides, to nucleic acid sequences as deposited under GenBank Accession Nos. NM-012239 (SEQ ID NO: 43), BC001042 (SEQ ID NO: 44), or AF083108 (SEQ ID NO: 45); (8) have at least 25, often 50, 75, 100, 150, 200, 250, 300, 350, or 400 contiguous amino acid residues of a polypeptide the sequence of which is deposited under GenBank Accession Nos. NP__036371 (SEQ ID NO: 34), AAH01042 (SEQ ID NO: 34), AAD40851 (SEQ ID NO: 34), or Q9NTG7 (SEQ ID NO: 34); and/or at least 25, often 50, 75, 100, 150, 200, 250, 300, 350, 400, 500, 600, 700, 800, 900, 1,000, 1,200, 1,500, 2,000 or more contiguous nucleotides of a nucleic acid sequence as deposited under GenBank Accession Nos. NM__012239 (SEQ ID NO: 43), BC001042 (SEQ ID NO: 44), or AF083108 (SEQ ID NO: 45).

A SIRT3 polynucleotide or polypeptide sequence is typically from a human, but may be from other mammals, but not limited to, a non-human primate, a rodent, e.g., a rat, mouse, or hamster; a cow, a pig, a horse, a sheep, or other mammal. In certain embodiments, it is desirable to use a SIRT3 from yeast, *Drosophila*, trypanosome, chicken, *C. elegans*, or *Xenopus*. A "SIRT3" polypeptide and polynucleotide includes both naturally occurring or recombinant forms. Therefore, in some embodiments, a SIRT3 polypeptide and a SIRT3 subdomain polypeptide as described herein can comprise a sequence that corresponds to a human SIRT3 polypeptide sequence. Thus, exemplary SIRT3 polypeptide sequences are provided herein and are known in the art. For example, GenBank accession numbers for human SIRT3 polypeptides are NP__036371 (SEQ ID NO: 34), AAH01042 (SEQ ID NO: 34), AAD40851 (SEQ ID NO: 34), NM__001017524 (SEQ ID NO: 42), and Q9NTG7 (SEQ ID NO: 34). GenBank accession numbers for mouse SIRT3 polypeptides are, for example, CAJ18608 (SEQ ID NO: 46), Q8R104 (SEQ ID NO: 46), AAH25878 (SEQ ID NO: 46), and NP__071878 (SEQ ID NO: 46); for rat SIRT3, XP__215124 (SEQ ID NO: 47); for bovine SIRT3, XP 869883 (SEQ ID NO: 48) and XP__879073 (SEQ ID NO: 49); for dog SIRT3, XP 848300 (SEQ ID NO: 50), XP 855809 (SEQ ID NO: 51), and XP__856096 (SEQ ID NO: 52); for zebrafish SIRT3, XP 684225 (SEQ ID NO: 53) and XP690925 (SEQ ID NO: 54). Exemplary SIRT3 polynucleotide sequences are provided herein and are known in the art. For example, GenBank accession numbers for human SIRT3 nucleic acids are NM__012239 (SEQ ID NO: 43), BC001042 (SEQ ID NO: 44), NM__001017524 (SEQ ID NO: 42), and AF083108 (SEQ ID NO: 45). GenBank accession numbers for mouse SIRT3 nucleic acids are, for example, CT010402 (SEQ ID NO: 55), BCO25878 (SEQ ID NO: 56), and NM__022433 (SEQ ID NO: 57); for rat SIRT3, XM__215124 (SEQ ID NO: 58); for bovine SIRT3, XM__864790 (SEQ ID NO: 59) and XM__873980 (SEQ ID NO: 60); for dog SIRT3, XM__843207 (SEQ ID NO: 61), XM__850716 (SEQ ID NO: 62), and XM__851003 (SEQ ID NO: 63); and for zebrafish SIRT3, XM__679133 (SEQ ID NO: 64) and XM__685833 (SEQ ID NO: 65).

In some embodiments the SIRT3 polypeptide can be a "full length" SIRT3 polypeptide. The term "full length" as used herein refers to a polypeptide that has at least the length of a naturally occurring SIRT3 polypeptide. A "full-length" SIRT3 polypeptide or a fragment thereof can also include other sequences, e.g., a purification tag (such as FLAG or HA), or other attached compounds (such as an attached fluorophore, a label, or cofactor).

By "small interfering RNA", "short interfering RNA", or "siRNA" is meant an isolated RNA molecule, preferably greater than 10 nucleotides in length, more preferably greater than 15 nucleotides in length, and most preferably 18, 19, 20, 21, 22, 23, 24, 25, 26, 27, 28, 29, or 30 nucleotides in length that functions as a key intermediate in triggering sequence-specific RNA degradation. A range of 19-25 nucleotides is the most preferred size for siRNAs. siRNAs can also include short hairpin RNAs (shRNA) in which both strands of an siRNA duplex are included within a single RNA molecule. Double-stranded siRNAs generally consist of a sense and anti-sense strand. Single-stranded siRNAs generally consist of only the antisense strand that is complementary to the target gene or mRNA. siRNA includes any form of RNA, preferably dsRNA (proteolytically cleaved products of larger dsRNA, partially purified RNA, essentially pure RNA, synthetic RNA, recombinantly produced RNA) as well as modified RNA that differs from naturally occurring RNA by the addition, deletion, substitution, and/or alteration of one or more nucleotides.

A "small molecule" is a molecule having a molecular weight of less than 5, 2, 1, or 0.5 kDa. In many embodiments, such small molecules do not include a peptide bond or a phosphodiester bond. For example, they can be non-polymeric. In some embodiments, the molecule has a molecular weight of at least 50, 100, 200, or 400 Daltons.

The terms "subdomain", "domain", "functional domain", or grammatical equivalents thereof in the context of a protein, such as a SIRT3 or AceCS2, refer to a fragment of that protein, such as a fragment of SIRT3 or AceCS2, which participates in an interaction, e.g., an intra-molecular or an inter-molecular interaction, e.g., a binding or catalytic interaction. An inter-molecular interaction can be a specific binding interaction or an enzymatic interaction (e.g., the interaction can be transient and a covalent bond is formed or broken). An inter-molecular interaction can be between the protein and another protein, between the protein and another compound, or between a first molecule and a second molecule of the protein (e.g., a dimerization interaction). Biologically active portions/functional domains of a protein include peptides comprising amino acid sequences sufficiently homologous to or derived from the amino acid sequence of the protein which include fewer amino acids than the full length, natural protein, and exhibit at least one activity of the natural protein. Biologically active portions/functional domains can be identified by a variety of techniques including truncation analysis, site-directed mutagenesis, and proteolysis. Mutants or proteolytic fragments can be assayed for activity by an appropriate biochemical or biological (e.g., genetic) assay. In some embodiments, a functional domain is independently folded. Typically, biologically active fragments comprise a domain or motif with at least one activity of the proteins, e.g., a SIRT3 or AceCS2 core catalytic domain. A biologically active portion/functional domain of a protein can be a polypeptide which is, for example, 10, 25, 50, 100, 200 or more amino acids in length. Biologically active portions/functional domain of a protein, such as a SIRT3 (i) can bind to an AceCS2 polypeptide, (ii) have deacetylation activity, (iii) assemble into a multiprotein complex, comprising e.g., AceCS2 or (iv) can deacetylate AceCS2. Biologically active portions/functional domain of a protein, such as an AceCS2 (i) can bind to a SIRT3 polypeptide, (ii) have enzymatic activity, (iii) assemble into a multiprotein complex, comprising e.g., SIRT3, (iv) generate acetyl-CoA and AMP using acetate, ATP and CoA as a substrate, or locate to the mitochondria.

A "related" polypeptide as used herein, refers to a homolog, an isoform, an ortholog, a fusion protein or fragments of a polypeptide or any combination thereof.

A "SIRT3 homolog" or "AceCS2 homolog" refers to a polypeptide that comprises an amino acid sequence similar to that of SIRT3 or AceCS2, respectively, but does not necessarily possess a similar or identical function as SIRT3 or AceCS2.

A "SIRT3 isoform" or "AceCS2 isoform" refers to a variant of SIRT3 or AceCS2, respectively, that is encoded by the same gene, but differs in its pI or MW, or both. Such isoforms can differ in their amino acid composition (e.g., as a result of alternative splicing or limited proteolysis) and in addition, or in the alternative, may arise from differential post-translational modification (e.g., glycosylation, acetylation or phosphorylation).

A "SIRT3 ortholog" or "AceCS2 ortholog" as used herein refers to a non-human polypeptide that (i) comprises an amino acid sequence similar to that of human SIRT3 or human AceCS2, respectively and (ii) possesses a similar or identical function to that of human SIRT3 or human AceCS2, respectively.

A "SIRT3 fusion protein" as used herein refers to a polypeptide that comprises (i) an amino acid sequence of a SIRT3, a SIRT3 fragment, a SIRT3 subdomain polypeptide, a SIRT3 related polypeptide or a fragment of a SIRT3 related polypeptide and (ii) an amino acid sequence of a heterologous polypeptide (i.e., a non-SIRT3, non-SIRT3 fragment or non-SIRT3 related polypeptide). Similarly, an "AceCS2 fusion protein" as used herein refers to a polypeptide that comprises (i) an amino acid sequence of an AceCsS, an AceCS2 fragment, an AceCS2 subdomain polypeptide, an AceCS2 related polypeptide or a fragment of an AceCS2 related polypeptide and (ii) an amino acid sequence of a heterologous polypeptide (i.e., a non-AceCS2, non-AceCS2 fragment or non-AceCS2 related polypeptide).

As used herein, the term "solvate" refers to compounds, agents, and small molecules of the present invention that are complexed to a solvent. Solvents that can form solvates with the compounds, agents, and small molecules of the present invention include common organic solvents such as alcohols (methanol, ethanol, etc.), ethers, acetone, ethyl acetate, halogenated solvents (methylene chloride, chloroform, etc.), hexane and pentane. Additional solvents include water. When water is the complexing solvent, the complex is termed a "hydrate."

As used herein, "subject" or "patient" to be treated for a pathological condition, disorder, or disease by a subject method means either a human or non-human animal in need of treatment for a pathological condition, disorder, or disease. The term "non-human animal" includes all vertebrates, e.g., mammals, such as non-human primates (particularly higher primates), sheep, dog, rodent (e.g., mouse or rat), guinea pig, goat, pig, cat, rabbit, cow, and non-mammals, such as chickens, amphibians, reptiles, etc. In a preferred embodiment, the subject is a human. In another embodiment, the subject is an experimental animal or animal suitable as a disease model.

As used herein, the terms "treat", "treating", and "treatment" include: (1) preventing a pathological condition, disorder, or disease, i.e. causing the clinical symptoms of the pathological condition, disorder, or disease not to develop in a subject that may be predisposed to the pathological condition, disorder, or disease but does not yet experience any symptoms of the pathological condition, disorder, or disease; (2) inhibiting the pathological condition, disorder, or disease, i.e. arresting or reducing the development of the pathological condition, disorder, or disease or its clinical symptoms; or (3) relieving the pathological condition, disorder, or disease, i.e. causing regression of the pathological condition, disorder, or disease or its clinical symptoms. These terms encompass also prophylaxis, therapy and cure. Treatment means any manner in which the symptoms of a pathological condition, disorder, or disease are ameliorated or otherwise beneficially altered. Preferably, the subject in need of such treatment is a mammal, more preferable a human.

II. Identification and Testing of Activators for SIRT3 and Modulators for AceCS2

The present invention identified AceCS2 as the first cellular target for SIRT3. In addition, the present invention also discloses that SIRT3 deacetylates AceCS2 in vitro and in vivo. Further, it is described herein that the acetylation status of AceCS2 determines the enzymatic activity of AceCS2, i.e., generating acetyl-CoA and AMP using acetate, ATP and CoA as a substrate. Based on the findings described herein, the present inventors have devised a variety of methods for identifying agents increasing a level or activity of SIRT3 and agents modulating a level, acetylation status, or activity of AceCS2.

Agents activating a SIRT3 or agents modulating an AceCS2 are identified using methods known in the art and described herein. A number of different screening protocols can be utilized to identify agents that increase a level or activity of a SIRT3 or modulate a level or activity of an AceCS2. The terms "identifying" and "screening" are used herein interchangeably.

Preferred are agents that selectively increase, selectively activate or selectively modulate a level, acetylation status, or activity of a subject polypeptide. Thus, in certain embodiments, an agent which is suitable for use in a subject treatment method as described herein and which increases (i) a level or activity of SIRT3 or (ii) modulates a level, acetylation status, or activity of AceCS2, is a selective activator of SIRT3 or a selective modulator of AceCS2, respectively. Thus, an agent that is a selective activator of SIRT3 is an agent that does not substantially inhibit or activate other enzymes, including, e.g., other sirtuins, e.g., at the $IC_{50}$ for SIRT3, the agent does not result in more than about 5%, more than about 10%, or more than about 25% inhibition or activation of another sirtuin enzymatic activity. Further, an agent that is a selective modulator of AceCS2 is an agent that does not substantially inhibit or activate other enzymes, including, e.g., other AMP-forming enzymes, e.g., at the $IC_{50}$ for AceCS2, the agent does not result in more than about 5%, more than about 10%, or more than about 25% inhibition or activation of other AMP forming enzymes.

In certain embodiments of the present invention, a screening protocol is used in vitro. Other preferred screening protocols can be used in cells, particularly mammalian cells, and preferably in human cells. Particularly preferred cells for use in the screening methods of the present invention are a heart cell, a muscle cell, or a brain cell.

The subject polypeptides used in the method of the present invention may be naturally occurring polypeptides or recombinant polypeptides. In certain embodiments the subject polypeptide is a SIRT3 related polypeptide and/or an AceCS2 polypeptide.

As described herein, a SIRT3 or AceCS2 polypeptide for use in a subject method can be from various species, including, but not limited to, human, mouse, or rat. Preferred SIRT3 and AceCS2 polypeptides are human SIRT3 and AceCS2 polypeptides.

Figure 3:
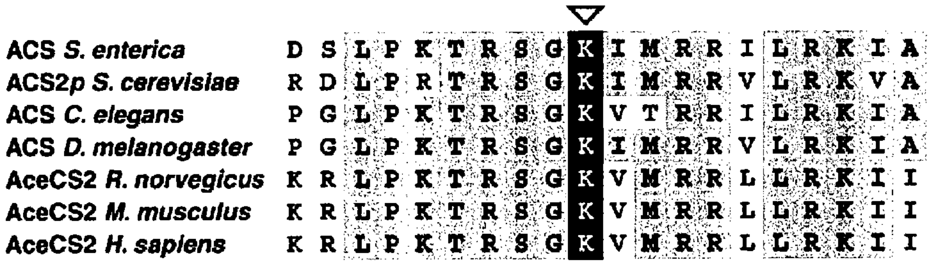
FIG. 3 shows that mutation of the conserved Lys642 in AceCS2 abolishes AceCS2 enzymatic activity. (A) Multiple sequence alignment of the active site region of acetyl-CoA synthetases from different species (ACS *S. enterica*, SEQ ID NO:3; ACS2p *S. cerevisiae*, SEQ ID NO:4; ACS *C. elegans*, SEQ ID NO:5; ACS *D. melanogaster*, SEQ ID NO:6; AceCS2 *R. norvegicus* and AceCS2 *M. musculus*, SEQ ID NO:7) and human AceCS2 (SEQ ID NO:7). The active site lysine is marked by an open triangle. (B) Lys642 is critical for AceCS2 function. Mutation of Lys642 of AceCS2 inactivates the enzyme. AceCS2 HA or AceCS2-K642Q$^{HA}$ (a mutant of AceCS2 in which Lys642 had been replaced by glutamine (Q)) were expressed in HEK293 cells, immunoprecipitated, and the specific acetyl-CoA synthetase (ACS) activity was determined. Data are means±SD from three independent acetyl-CoA synthetase activity assays. (C) Coomassie blue staining of immunoprecipitated AceCS2$^{HA}$ and AceCS2-K642Q$^{HA}$. AceCS2$^{HA}$ or AceCS2-K642Q$^{HA}$ were indistinguishable by Coomassie blue staining and were expressed at equal levels. Details are presented in Example 5.
Figure 3:
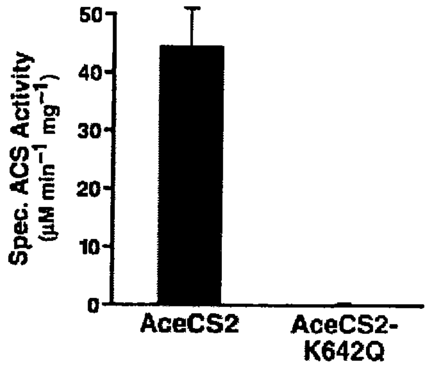
Figure 3:
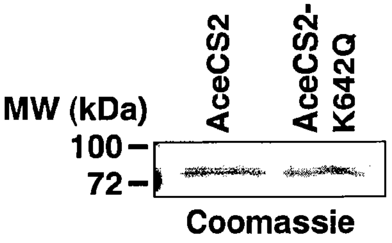

As further described herein, a SIRT3 or AceCS2 polypeptide may be a full-length SIRT3 or AceCS2 or a fragment or domain thereof. In addition, a SIRT3 and AceCS2 related polypeptide, SIRT3 and AceCS2 homologs, SIRT3 and AceCS2 isoforms or SIRT3 and AceCS2 orthologs can be used to practice methods and compositions of the present invention. A preferred AceCS2 polypeptide fragment of the present invention comprises the sequence $NH_2$-KRLPKTRSGKVMRRLLRKII-COOH (SEQ ID NO:7) (FIG. 3A). In other preferred embodiments, an AceCS2 polypeptide comprises the sequence $NH_2$-CPKTRSG(ac)KVMRRLL-COOH (SEQ ID NO:11) having an acetylated lysine (acK642) or $NH_2$-CPKTRSGKVMRRLL-COOH (SEQ ID NO:12).

Assays of the invention usually include one or more controls. Thus, a test sample includes a candidate agent, and a control sample has all the components of the test sample except for the candidate agent. Generally a plurality of assay mixtures is run in parallel with different agent concentrations to obtain a differential response to the various concentrations. Typically, one of these concentrations serves as a negative control, i.e. at zero concentration or below the level of detection.

As one of ordinary skill in the art will appreciate, screening assays may comprise a variety of reagents, other than the subject polypeptides. These reagents include buffers, salts, stabilizing agents, detergents, protease inhibitors, nuclease inhibitors, anti-microbial agents, etc. as described in the Examples herein and known in the art.

Candidate agents for increasing a level or activity of a SIRT3 or candidate agents modulating a level, acetylation, or activity of an AceCS2 as described herein can be identified, tested and verified using a variety of assays as described herein, These assays include, but are not limited to, for example, (i) Northern blot assays, (ii) in situ hybridization, (iii) Western blot assays, (iv) immunoprecipitation assays, (v) immunohistochemistry, (vi) cell-based assay, and (vii) an in vivo assay, and the like. In vitro assays may use a purified SIRT3 and/or AceCS2 polypeptide or a multiprotein complex comprising a SIRT3 and/or AceCS2 polypeptide as further described herein.

Agents that increase or decrease an activity of a subject polypeptide to the desired extent may be selected for further study, and assessed for cellular availability, cytotoxicity, biocompatibility, etc.

A candidate agent is assessed for any cytotoxic activity it may exhibit toward the cell used in the assay, using well-known assays, such as trypan blue dye exclusion, an MTT ([3-(4,5-dimethylthiazol-2-yl)-2,5-diphenyl-2H-tetrazolium bromide]) assay, and the like. Agents that do not exhibit cytotoxic activity or agents that do not exhibit a significant cytotoxic activity are preferred.

Once a candidate agent has been identified in one of the screening methods of the present invention, and is further used in a method, composition or kit of the present invention, it is typically referred to as an agent or as a biologically active agent, rather than a candidate agent.

In some embodiments, of particular interest is an agent which (i) increases SIRT3 activity, (ii) increases a level of a SIRT3 polypeptide in a cell, or (iii) increases a level of a SIRT3 mRNA in a cell. Also of particular interest is an agent which (i) increases AceCS2 activity, (ii) increases a level of an AceCS2 polypeptide in a cell, or (iii) increases a level of an AceCS2 mRNA in a cell. Such agents are useful for treating pathological conditions characterized by an aberrant high level of acetate or aberrant low level of acetyl-CoA, e.g., type II diabetes, hypercholesterolemia, hyperlipidemia, and obesity.

In some embodiments, of particular interest is an agent which (i) decreases AceCS2 activity, (ii) decreases a level of an AceCS2 polypeptide in a cell, or (iii) decreases a level of an AceCS2 mRNA in a cell. Such agents are useful for treating pathological conditions characterized by an aberrant high level of acetyl-CoA.

A. Agents Activating SIRT3

In general terms, the screening methods for identifying an agent that increases a level or activity of a SIRT3, preferably a deacetylase activity of SIRT3, involve screening a variety of agents. A screening method generally comprises the step of (a) contacting a candidate agent with (i) a SIRT3 and/or an AceCS2, (ii) with a biological sample comprising a SIRT3 and/or an AceCS2 or (iii) a mammalian cell expressing a SIRT3 and/or an AceCS2; and (b) assaying a level or activity of the SIRT3 and/or a level or activity of an AceCS2 in the presence of the candidate agent. An increase in the level or activity of SIRT3 measured in comparison to the activity of the SIRT3 in a suitable control (e.g., a SIRT3 in the absence of the candidate agent, a biological sample comprising a SIRT3 in the absence of the candidate agent or a mammalian cell expressing a SIRT3 in the absence of the candidate compound) is an indication that the candidate agent activates an activity of the SIRT3.

In one aspect, the screening methods involve screening candidate agents to identify an agent that increases a level or activity of a SIRT3. The term "increase a level or activity of a SIRT3" encompasses an increase in the measured level of a SIRT3 polypeptide, a SIRT3 nucleic acid, or SIRT3 activity, e.g., a SIRT3 deacetylase activity, when compared to a suitable control.

In one aspect, the present invention provides a method for identifying an agent that increases a level or deacetylase activity of a SIRT3 polypeptide. In a preferred embodiment of the present invention, this method comprises the steps of (a) contacting a cell expressing a SIRT3 polypeptide and an AceCS2 polypeptide with a candidate agent and (b) determining the effect, if any, of the candidate agent on the level of acetylated AceCS2 in the cell. Thereby a candidate agent increasing a level or deacetylase activity of a SIRT3 polypeptide is identified.

In another aspect of the present invention, a method for identifying an agent that increases a level or deacetylase activity of a SIRT3 polypeptide comprises the steps of (a) contacting a SIRT3 polypeptide and an acetylated AceCS2 polypeptide in an assay mixture with a candidate agent and (b) determining the effect, if any, of the candidate agent on the level of acetylated AceCS2 in the assay mixture. Thereby a candidate agent increasing a level or deacetylase activity of a SIRT3 polypeptide is identified. A decrease in a first level of acetylated AceCS2 in the assay mixture relative to a second level of acetylated AceCS2 in an assay mixture, which has not been treated with the candidate agent, is indicative of an agent that increases the level or deacetylase activity of the SIRT3 polypeptide.

In a preferred embodiment, the assay mixture comprises $NAD^+$.

Determining the effect of the candidate agent on the level of acetylated AceCS2 in the cell or in an assay mixture can be performed in a variety of ways. In a preferred embodiment, this step comprises an immunological assay using an antibody specific for acetylated AceCS2 as described herein. A decrease of acetylated AceCS2 polypeptide in the presence of a candidate agent is indicative of an agent activating a SIRT3.

In another preferred embodiment of the present invention, the AceCS2 comprises a label, such as labeled acetyl group, preferably a $^{14}C$-labeled acetyl group. Thus, in this embodiment, the step of determining the effect of the candidate agent on the level of acetylated AceCS2 in the cell or in an assay mixture is performed by measuring release of the $^{14}C$-labeled acetyl group from the labeled AceCS2 polypeptide. The released $^{14}C$ label can be routinely measured, e.g., by chromatography followed by scintillation counting. An increase of released $^{14}C$ label in the presence of a candidate agent is indicative of an agent activating a SIRT3.

Optionally, the method for identifying an agent that increases a level or activity of a SIRT3 comprises the step of identifying a structure or sequence of the candidate agent.

A candidate agent of interest is one that increases a level or activity of SIRT3 by at least about 10%, at least about 20%, at least about 30%, at least about 40%, at least about 50%, at least about 60%, at least about 70%, at least about 80%, at least about 90%, at least about 100%, at least about 150%, at least about 200%, at least about 500% or more relative to a suitable control, preferably a control in the absence of the candidate agent.

B. Agents Modulating Acetyl-CoA Synthetase 2

Inhibitors and activators, referred to herein as modulators of level, acetylation status, or activity of AceCS2, are identified using methods known in the art and described herein. A number of different screening protocols can be utilized to identify agents that modulate a level, acetylation status, or activity of an AceCS2. The term "modulate" encompasses an increase or a decrease in the measured level, acetylation status or activity of an AceCS2 when compared to a suitable control. Preferred are activators of AceCS2. However, in certain embodiments it may be desirous to inhibit an AceCS2.

In general terms, the screening methods involve screening a variety of agents to identify an agent that modulates a level, acetylation status or activity of an AceCS2. The method generally comprises the step of (a) contacting a candidate agent with (i) an AceCS2, (ii) with a biological sample comprising an AceCS2 or (iii) a mammalian cell expressing an AceCS2; and (b) assaying a level, acetylation status or an activity of the AceCS2 in the presence of the candidate agent. An increase or a decrease in the level, acetylation status or activity measured in comparison to the level, acetylation status or activity of the AceCS2 in a suitable control (e.g., an AceCS2 in the absence of the candidate agent, a biological sample comprising an AceCS2 in the absence of the candidate agent or a mammalian cell expressing an AceCS2 in the absence of the candidate compound) is an indication that the candidate agent modulates a level, acetylation status or activity of the AceCS2.

1. Agents Modulating a Level, Acetylation Status or an Activity of Acetyl-CoA Synthetase 2

In one aspect of the present invention, a method for identifying an agent that modulates a level, acetylation status, or activity of an AceCS2 polypeptide, is provided. In a preferred embodiment of the present invention, this method comprises the steps of (a) contacting a cell expressing an AceCS2 polypeptide with a candidate agent and (b) determining the effect, if any, of the candidate agent on the level, acetylation status, or activity of the AceCS2 in the cell. Thereby a candidate agent modulating a level, acetylation status, or activity of an AceCS2 polypeptide is identified.

In another aspect of the present invention, the method for identifying an agent that modulates a level, acetylation status, or activity of an AceCS2 polypeptide comprises the steps of (a) contacting an AceCS2 polypeptide in an assay mixture with a candidate agent and (b) determining the effect, if any, of the candidate agent on the level, acetylation status, or activity of the AceCS2 in the assay mixture. Thereby a candidate agent modulating a level, acetylation status, or activity of an AceCS2 polypeptide is identified.

In a preferred embodiment, the cell or assay mixture comprises a substrate for the AceCS2 polypeptide. A preferred substrate is acetate, which may be labeled. In such embodiments, the step of determining the effect of the candidate agent on the activity of the AceCS2 may comprises measuring the level of acetyl-CoA and AMP synthesized by the AceCS2.

A preferred activity of AceCS2 is the enzymatic conversion of acetate, ATP and CoA into acetyl-CoA and AMP. Thus, in one aspect, the present invention provides a method for identifying a candidate agent which modulates AceCS2 enzymatic activity is provided. In a preferred embodiment, this method comprises the steps of (a) contacting an AceCS2 polypeptide in the presence of a substrate with a candidate agent and (b) assaying AceCS2 enzymatic activity to identify the candidate agent which modulates AceCS2 enzymatic activity. Thereby a candidate agent modulating an enzymatic activity of an AceCS2 polypeptide is identified.

A preferred substrate is acetate, ATP and/or CoA. Assays for determining AceCS2 enzymatic activity are described herein.

Agents that modulate a level of AceCS2 include (i) agents that modulate an AceCS2 mRNA level, e.g., by activating or inhibiting AceCS2 gene expression and (ii) agents that modulate an AceCS2 polypeptide level. Methods for determining levels of mRNA and polypeptide are provided herein.

2. Agents Binding to Acetyl-CoA Synthetase 2

The present invention also provides methods for identifying an agent that binds to acetyl-CoA synthetase 2 (AceCS2). In one aspect of the present invention, a method for identifying an agent that binds to AceCS2 polypeptide is provided. In a preferred embodiment of the present invention, this method comprises the steps of (a) contacting a cell expressing an AceCS2 polypeptide with a candidate agent and (b) determining if the candidate agent binds to AceCS2. Thereby a candidate agent binding to an AceCS2 polypeptide is identified.

In another aspect of the present invention, the method for identifying an agent that binds to an AceCS2 polypeptide comprises the steps of (a) contacting an AceCS2 polypeptide in an assay mixture with a candidate agent and (b) determining if the candidate agent binds to AceCS2. Thereby a candidate agent binding to an AceCS2 polypeptide is identified.

Useful AceCS2 polypeptides for practicing a subject method of the present invention are naturally occurring AceCS2 polypeptides or recombinantly produced AceCS2.

Binding of a candidate agent to an AceCS2 polypeptide can be detected using a variety of methods as described herein and known in the art.

The AceCS2 polypeptide may be bound to a solid support prior to the contacting with a candidate agent. Coupling of subject polypeptides to solid supports, solid supports and their use in subject methods of the present invention are described herein.

3. Agents Modulating the Interaction between AceCS2 and SIRT3

The present inventors have shown that AceCS2 interacts with SIRT3. Thus, the present invention also provides a method for identifying agents that modulate the interaction between and AceCS2 polypeptide and a SIRT3 polypeptide.

In one aspect of the present invention, a method for identifying an agent that modulates the interaction between an AceCS2 polypeptide and a SIRT3 polypeptide is provided. In a preferred embodiment of the present invention, this method comprises the steps of (a) contacting a cell expressing an AceCS2 polypeptide and a SIRT3 polypeptide with a candidate agent and (b) determining the effect, if any, of the candidate agent on the interaction of AceCS2 and the SIRT3 polypeptide. Thereby a candidate agent modulating the interaction between an AceCS2 polypeptide and a SIRT3 polypeptide is identified.

In another embodiment of the present invention, the method for identifying an agent that modulates the interaction between an AceCS2 polypeptide and a SIRT3 polypeptide comprises the steps of (a) contacting an assay mixture comprising an AceCS2 polypeptide and a SIRT3 polypeptide with a candidate agent and (b) determining the effect, if any, of the candidate agent on the interaction of AceCS2 and the SIRT3 polypeptide. Thereby a candidate agent modulating the interaction between an AceCS2 polypeptide and a SIRT3 polypeptide is identified.

Figure 9:
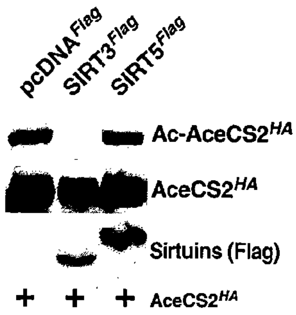
FIG. 9 shows that SIRT3 coimmunoprecipitates with AceCS2 and deacetylates AceCS2 in cells. (A) Overexpression of SIRT3 decreases the acetylation of ectopically expressed AceCS2. COS-1 cells were co-transfected with AceCS2$^{HA}$ and either pcDNA$^{Flag}$, SIRT3$^{Flag}$ or SIRT5$^{Flag}$. Acetylation of immunoprecipitated AceCS2$^{HA}$ was analyzed by immunoblotting with antibodies to acetylated lysine (Ac-AceCS2$^{HA}$). Membranes were stripped and reprobed for total AceCS2 amounts (AceCS2$^{HA}$) by probing with an anti-HA antibody. The expression of SIRT3$^{Flag}$ and SIRT5$^{Flag}$ in the total cell lysate was verified by immunoblotting with anti-Flag antibodies (Sirtuins (Flag)). (B) AceCS2 and SIRT3 co-immunoprecipitate from cells. Anti-Flag immune complexes from HEK293 cell lines stably expressing AceCS2$^{Flag}$ or an empty Flag-control vector (pcDNA$^{Flag}$) were analyzed for the presence of endogenous SIRT3. Details are presented in Example 11.
Figure 9:
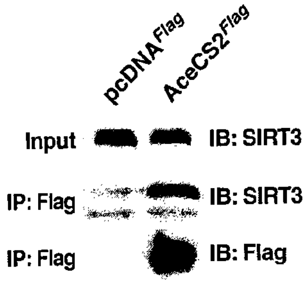
Figure 10:
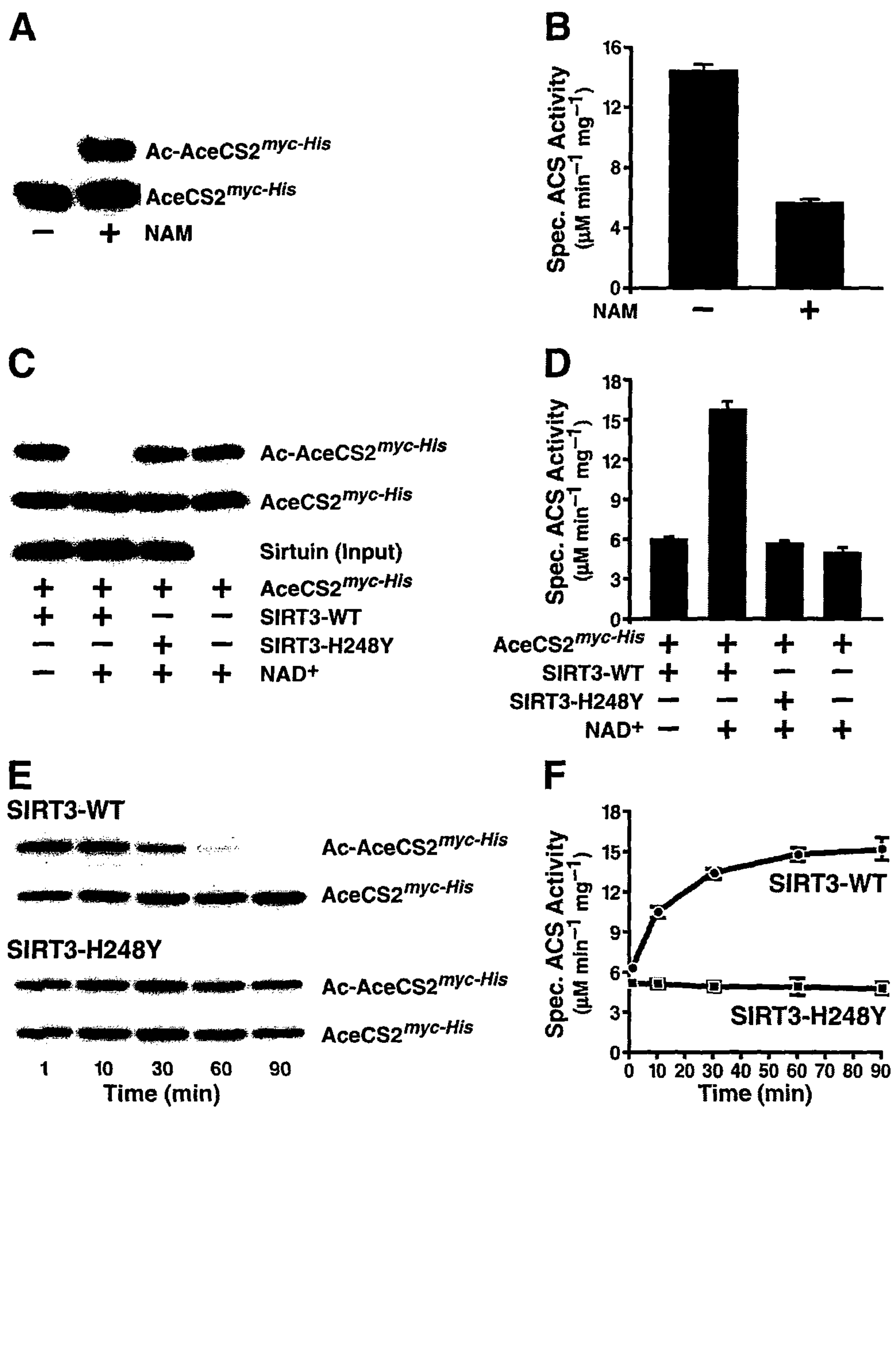
FIG. 10 shows that acetylation of Lys642 controls the acetyl-CoA synthetase activity of human AceCS2. (A) Recombinant human AceCS2 was expressed in bacteria in the presence or absence of nicotinamide (NAM). Acetylation levels and total amounts of AceCS2 were analyzed by immunoblotting with acetyl-lysine-specific antibodies or anti-myc antibodies. (B) Specific activity of purified AceCS2 expressed in the presence or absence of NAM. The data are means±SD from three independent experiments. (C) $NAD^+$-dependent deacetylation of AceCS2 by SIRT3 but not by SIRT3-H248Y. The lower panel indicates that equal amounts of SIRT3 or SIRT3-H248Y were added to the deacetylation reactions. (D) Deacetylation of AceCS2 by SIRT3 activates its acetyl-CoA synthetase activity. Equal amounts of AceCS2 were incubated in the absence or presence of SIRT3 or a catalytically inactive SIRT3 mutant (SIRT3-H248Y). Where indicated, $NAD^+$ (1 mM) was added during the incubation. After 3 h at 32° C., the deacetylation reaction was stopped by the addition of nicotinamide (NAM; 10 mM) and the specific activity of AceCS2 was determined. Data are means±SD from three independent activity determinations. (E) Time-dependent activation of AceCS2 by SIRT3. Recombinant human AceCS2 purified from NAM-treated bacteria was incubated with recombinant SIRT3 or SIRT3-H248Y. Samples were brought to 32° C. and $NAD^+$ (1 mM) was added. At the indicated time points, aliquots of the reaction were removed, mixed with NAM and incubated on ice. The immunoblots show the progressive deacetylation of AceCS2 by SIRT3 but not by SIRT3-H248Y. (F) The specific activity of AceCS2 after incubation with recombinant SIRT3 or SIRT3-H248Y for the indicated time was determined. Means±SD from three independent activity assays are shown. Details are presented in Example 12.

4. Agents Modulating the Assembly of Acetyl-CoA Synthetase 2 into a Multiprotein Complex The present inventors have shown that AceCS2 forms a multi-protein complex comprising SIRT3 (e.g., Example 11, FIG. 9). Thus, the present invention also provides a method for identifying agents modulating the assembly of AceCS2 into a multiprotein complex. Preferably the multiprotein complex comprises a SIRT3 polypeptide.

In one aspect of the present invention, a method for identifying an agent that modulates the assembly of an AceCS2 into a multiprotein complex is provided. In a preferred embodiment of the present invention, this method comprises the steps of (a) contacting a cell expressing an AceCS2 polypeptide and a SIRT3 polypeptide with a candidate agent and (b) determining the effect, if any, of the candidate agent on the assembly of AceCS2 into a multiprotein complex comprising the SIRT3 polypeptide. Thereby a candidate agent modulating the assembly of an AceCS2 polypeptide into a multiprotein complex is identified.

In another aspect of the present invention, a method for identifying an agent that modulates the assembly of an AceCS2 polypeptide into a multiprotein complex comprising the AceCS2 polypeptide and at least one second polypeptide, is provided. This method comprises the steps of (a) contacting an assay mixture comprising an AceCS2 polypeptide and a second polypeptide with a candidate agent and (b) determining the effect, if any, of the candidate agent on the assembly of the AceCS2 polypeptide into a multiprotein complex in the assay mixture. Thereby a candidate agent modulating the assembly of an AceCS2 polypeptide into a multiprotein complex is identified.

In a preferred embodiment of this method, the second polypeptide is a SIRT3 polypeptide.

In another preferred embodiment of the present invention, the AceCS2 comprises an epitope-tag, such as Flag, hemagglutinin (HA) or a 6×His-tag (SEQ ID NO: 13), as described herein. In other embodiments, a SIRT3 polypeptide comprises an epitope tag. Epitope tags allow easy detection and purification of polypeptides attached to these tags. Detection and purification is performed using an anti-Flag antibody, an anti-HA antibody or an anti-6×His-antibody and routine methods known in the art.

Determining the effect of the candidate agent on the assembly of AceCS2 into a multiprotein complex in the assay mixture can be done using a variety of methods. A preferred method is column chromatography or immunoprecipitation as described herein. In this method an antibody, such as an anti-AceCS2 is used to immunoprecipitate AceCS2 and any other polypeptide binding to it. The polypeptides binding to AceCS2, and thus forming a multiprotein complex with AceCS2, can be visualized by e.g., SDS-PAGE, mass spectrometry, or immunoblotting. Binding of a SIRT3 polypeptide to AceCS2 can be determined using an anti-SIRT3 antibody.

The method for identifying an agent that modulates the assembly of AceCS2 into a multiprotein complex can also be used to identify cellular proteins other than SIRT3 that bind to AceCS2. For example, antibodies which immunoprecipitate AceCS2 or an epitope-tagged AceCS2 from cells can be used to detect and purify cellular polypeptides binding to AceCS2. Polypeptides binding to AceCS2 are detected by, e.g., SDS-PAGE or mass spectrometry and may be identified further by peptide fingerprinting as described herein and known in the art. One such polypeptide that may be identified using this method is an acetyltransferase polypeptide which acetylates an AceCS2 polypeptide.

In a preferred embodiment, the agent for (i) modulating a level, acetylation status, or activity of an AceCS2 polypeptide, (ii) binding to an AceCS2 polypeptide, (iii) modulating the assembly of AceCS2 into a multiprotein complex, or (iv) modulating the cellular localization of AceCS2, is a SIRT3 polypeptide. The SIRT3 polypeptide may be a naturally occurring SIRT3 polypeptide or a fragment thereof. The SIRT3 polypeptide may also be a recombinantly expressed SIRT3 polypeptide or a fragment thereof. Further, the SIRT3 polypeptide may be a SIRT3 related polypeptide or a fragment thereof.

5. Agents Modulating the Cellular Localization of Acetyl-CoA Synthetase 2

The present inventors have shown herein that AceCS2 and SIRT3 localize to the mitochondria. Because of the important role of SIRT3 in deacetylating AceCS2, modulating AceCS2 and/or SIRT3 localization to the mitochondria may be important in controlling AceCS2 enzymatic activity.

Thus, in another aspect of the present invention, a method is provided for identifying an agent modulating the cellular localization of a SIRT3 polypeptide or an AceCS2 polypeptide. In a preferred embodiment of the present invention, this method comprises the steps of (a) contacting a cell expressing a SIRT3 polypeptide and/or an AceCS2 polypeptide with a candidate agent and (b) determining the cellular localization of the SIRT3 polypeptide and/or AceCS2 polypeptide wherein an agent modulating the cellular localization of the SIRT3 polypeptide and/or AceCS2 polypeptide is identified.

A preferred agent is an agent that increases the localization of a SIRT3 polypeptide and/or AceCS2 to mitochondria. Increasing the localization of a SIRT3 polypeptide and/or AceCS2 polypeptide includes prolonged retention of a SIRT3 polypeptide and/or AceCS2 polypeptide at the desired cellular location.

Cellular localization of a SIRT3 or AceCS2 polypeptide can de determined by a variety of methods known in the art. A preferred method is immunohistochemistry or analysis of mitochondrial fractions by immunoblotting using anti-SIRT3 antibodies and anti-AceCS2 antibodies (e.g., see FIG. 1 and corresponding Example).

The effect of a candidate agent on the (i) level, acetylation status or activity of an AceCS2 polypeptide, (ii) binding to an AceCS2 polypeptide, (iii) the interaction between an AceCS2 polypeptide and a SIRT3 polypeptide, (iv) on the assembly of AceCS2 into a multiprotein complex or (v) on the cellular localization of an AceCS2 polypeptide can be determined using a variety of methods as described herein and known in the art.

A candidate agent of interest is one that increases a level, acetylation status or activity of AceCS2 by at least about 10%, at least about 20%, at least about 30%, at least about 40%, at least about 50%, at least about 60%, at least about 70%, at least about 80%, at least about 90%, at least about 100%, at least about 150%, at least about 200%, at least about 500% or more relative to a suitable control, preferably a control in the absence of the candidate agent.

C. Assays Using Purified Proteins or Multi-Protein Complexes

Assays for identifying selective SIRT3 activating agents or selective AceCS2 modulating agents (activating or inhibiting agents) versus general activators or inhibitors may be conducted in a cell-based or cell-free format. For example, an assay may comprise incubating (or contacting) a subject polypeptide or subject nucleic acid, with a test agent under conditions in which a level or an activity of the subject polypeptide or subject nucleic acid can be activated, and monitoring or determining the level of activation in the presence of the test agent relative to that present in the absence of the test agent.

AceCS2 can be a naturally occurring AceCS2 or a recombinant AceCS2. Also, a SIRT3 can be a naturally occurring SIRT3 or a recombinant SIRT3. A naturally occurring AceCS2 or SIRT3 can be purified, e.g., from human or mouse tissue or e.g., from human or mouse cells. Recombinant AceCS2 and SIRT3 can be purified from any suitable expression system as known in the art, e.g., purification of recombinant proteins from a host cell, preferably a mammalian host cell.

AceCS2 and SIRT3 can be purified to substantial purity by standard techniques, e.g., including, but not limited to column chromatography, immunopurification methods, selective precipitation using ammonium sulfate, and others.

In certain embodiments of the present invention, the screening methods and test assays comprise using a multi-protein complex, comprising (i) at least AceCS2 and SIRT3, or (ii) AceCS2 and a second polypeptide, or (iii) SIRT3 and a second polypeptide. As for the isolated proteins, proteins of such multi-protein complexes can be obtained from, e.g., human or mouse tissues, human or mouse cells, or prepared recombinantly. When prepared recombinantly, the subject proteins are typically assembled into a multiprotein complex prior to using them in one of the subject methods. This can be done using a variety of methods known in the art.

For in vitro assays, the subject polypeptides may be, but need not be purified. Purification of subject proteins is done using methods known in the art. Purification of subject polypeptides from cells or host cells can be partial, preferred, however, are subject polypeptides that are at least 90% pure as determined by standard SDS-PAGE.

D. Cell-Based Assays

Identification and testing of candidate agents for activating a level or activity of a SIRT3 and agents for modulating a level, acetylation status, or activity of a AceCS2 can also be performed using cell-based assays (e.g., see Examples 5, 6, 9, and 11). Further, *E. coli* based assays, as described herein, can be used for identifying and/or testing candidate agents (see Examples 7, 8, and 12)

For cell-based assays, typically, eukaryotic cells, such as mammalian cells are used. In certain embodiments, yeast cells may be used. The cell can be a primary cell isolated from a donor biological sample. Alternatively, the cell can be an established cell line as made available by the American Type Culture Collection.

As described herein (see Examples), a cell can also be a cell that is transiently or stably transfected with an expression construct, such as an AceCS2 expression construct or a SIRT3 expression construct.

E. In Vivo Assays

Identification and testing of candidate agents for activating a level or activity of a SIRT3 and agents for modulating a level, acetylation status, or activity of a AceCS2 can also be performed in vivo. In this method, an agent is administered to an animal, preferably a mouse, and blood samples or tissue samples are taken from the animal at various times after administration of the agent and tested for the presence of e.g., (i) acetyl-CoA level, (ii) ATP level, (iii) level, acetylation status, or activity of AceCS2, or (iv) level or activity of SIRT3.

F. Detection of mRNA

Methods for testing and assaying compounds, agents or antagonists identified by methods described herein, are provided herein and involve a variety of accepted tests to determine whether a given candidate agent, or small molecule is useful to practice a method of the present invention. Methods of the present invention may optionally comprise the step of detecting a nucleic acid, such as an mRNA or a polypeptide. In one embodiment, such a method comprises determining or detecting an mRNA, preferably a SIRT3 mRNA or an AceCS2 mRNA. Other mRNAs encoding polypeptides described herein can also be determined using the following methods. Methods of evaluating mRNA expression of a particular gene are well known to those of skill in the art, and include, inter alia, hybridization and amplification based assays.

1. Direct Hybridization-based Assays

Methods of detecting and/or quantifying the level of a gene transcript (mRNA or cDNA made therefrom) using nucleic acid hybridization techniques are known to those of skill in the art. For example, one method for evaluating the presence, absence, or quantity of a polynucleotide involves a Northern blot. Gene expression levels can also be analyzed by techniques known in the art, e.g., dot blotting, in situ hybridization, RNase protection, probing DNA microchip arrays, and the like (e.g., see Sambrook, J., Fritsch, E. F., and Maniatis, "Molecular Cloning A Laboratory Manual" published by Cold Spring Harbor Laboratory Press, 2nd edition, 1989).

2. Amplification-Based Assays

In another embodiment, amplification-based assays are used to measure the expression level of a gene. In such an assay, the nucleic acid sequences act as a template in an amplification reaction (e.g., Polymerase Chain Reaction, or PCR). In a quantitative amplification, the amount of amplification product will be proportional to the amount of template in the original sample. Comparison to appropriate controls provides a measure of the level of an mRNA in the sample. Methods of quantitative amplification are well known to those of skill in the art. Detailed protocols for quantitative PCR are provided, e.g., in Innis et al. (1990) *PCR Protocols, A Guide to Methods and Applications*, Academic Press, Inc. N.Y.).

In one embodiment, a TaqMan based assay is used to quantify a polynucleotide. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, e.g., AmpliTaq, results in the cleavage of the TaqMan probe. This cleavage separates the 5' fluorescent dye and the 3' quenching agent, thereby resulting in an increase in fluorescence as a function of amplification (see, for example, Heid et al., 1996, *Genome Res* 6(10):986-94; Morris et al., 1996, *J Clin Microbiol* 34(12):2933-6).

Other suitable amplification methods include, but are not limited to, ligase chain reaction (LCR) (see, Wu and Wallace, 1989, *Genomics* 4:560; Landegren et al., 1988, *Science* 241: 1077; and Barringer et al., 1990, *Gene* 89:117), transcription amplification (Kwoh et al., 1989, *Proc Natl Acad Sci USA* 86:1173), self-sustained sequence replication (Guatelli et al., 1990, *Proc Nat Acad Sci USA* 87: 1874), dot PCR, and linker adapter PCR, etc.

G. Detection of Polypeptide

The methods of the present invention described above may optionally comprise the step of determining or detecting a polypeptide, such as an AceCS2 or SIRT3 polypeptide. Other polypeptides described herein can also be determined using the following methods.

Determining or detecting a polypeptide, such as an AceCS2, a SIRT3 and others may be done in a variety of ways, including, but not limited to, detecting the respective polypeptides in a biological sample, a cell, an organ, or in an animal, including human and non-human animals.

The expression level of a polypeptide may be determined by a variety of methods, including, but not limited to, affinity capture, mass spectrometry, traditional immunoassays and immunoprecipitation assays, PAGE, Western Blotting, RIA, or HPLC as further described herein (e.g., see FIGS. 1, and 3-10 and the corresponding Examples) or as known by one of skill in the art.

Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Using, e.g., antibodies, such as the anti-AceCS2 antibodies raised against acetylated AceCS2 peptides and described herein, the modulation of acetylation status of an AceCS2 polypeptide in the absence or presence of a candidate agent can be assessed (e.g., see FIG. 5B and corresponding Example). Other antibodies described herein are useful for detecting the level of AceCS2 expression or the level of SIRT3 expression.

H. Detection of Enzymatic Activity

1. Detecting SIRT3 Deacetylase Activity

Various assays have been described to detect sirtuin deacetylase activity. For example, Imai et al., and Frye reported assays for detecting NAD-dependent deacetylase activity of yeast Sir2 and human SIRT2 using histones as a substrate (Imai et al., 2000, *Nature* 403(6771):795-800; Frye 1999, *Biochem Biophys Res Comm* 260:273-279). However, neither Imai et al. nor Frye test sirtuin deacetylase activity on a cellular polypeptide.

The present invention describes the first cellular SIRT3 target polypeptide, AceCS2, which is deacetylated both in vitro and in vivo by SIRT3. As further described herein, the AceCS2 polypeptide is associated with SIRT3. Thus, in a preferred embodiment of the present invention, enzymatic activity of a SIRT3 polypeptide is determined in the presence of the substrate AceCS2 as described herein. This assay can be used to assess SIRT3 deacetylase activity in the absence or presence of a candidate agent.

SIRT3 deacetylating activity of AceCS2 can be monitored by, e.g., immunoblotting using an anti-AceCS2 antibody detecting both acetylated and deacetylated AceCS2 and an antibody which is specific for acetylated AceCS2. Alternatively, SIRT3 deacetylation activity of AceCS2 can also be monitored by determining AceCS2 enzymatic activity as described herein. Also, LC-MS/MS analysis can be used to determine acetylation status of AceCS2 as described herein (e.g., FIGS. 4 and 6; Examples 6 and 8).

2. Detecting AceCS2 Enzymatic Activity

Assays for testing the activity of AceCS2 are described herein (e.g., see Example 1) and are known in the art. AceCS2 enzymatic activity can also be determined, e.g., by isotopic or spectrophotometric methods (Fujino et al., 2001, *J Biol Chem* 276:11420-11426).

The standard reaction mixture for the isotopic method contains 100 mM Tris-HCl, pH 8.5, 10 mM $MgCl_2$, 10 mM ATP, 1 mM CoA and 10 mM [$^{14}C$]acetate (940 dpm/nmol) in a total volume of 0.2 mL. After 1 min of preincubation at 37° C., the reaction is initiated by the addition of AceCS2. After a 30 min incubation, the reaction is terminated by adding 50 μl of ice-cold glacial acetic acid. The reaction product ([$^{14}C$] acetyl-CoA) is isolated by spotting onto a piece of chromatography media (ITLC-SG type, Gelman Sciences) and extensive washing with water-saturated ether/formic acid (7:1) for measurement of radioactivity (Fujino et al., 2001, *J Biol Chem* 276:11420-11426).

The spectrometric method is based on the formation of AMP using adenylate kinase, pyruvate kinase, and lactate dehydrogenase. The standard reaction mixture for the spectrophotometric method contains 100 mM Tris-HCl, pH 8.5, 1 mM DTT, 15 mM $MgCl_2$, 10 mM ATP, 0.25 mM potassium phosphoenolpyruvate, 1 mM acetate, 0.3 mM NADH, 80 units of adenylate kinase (Roche Molecular Biochemicals), 17 units of lactate dehydrogenase (Roche Molecular Biochemicals) and 6 units of pyruvate kinase (Roche Molecular Biochemicals) in a total volume of 1 mL. After a 1 min preincubation at 37° C., the reaction is started by adding 24 μL of 25 mM CoA. The oxidation of NADH is measured at 340 nm on a recording spectrophotometer. The formation of 1 mol of ADP corresponds to the oxidation of 2 mol of NADH (Fujino et al., 2001, *J Biol Chem* 276:11420-11426). Other suitable spectrometric methods are known in the art (Jones & Lipmann, 1955, in *Methods in Enzymology* (Academic Press, Vol. 1, pp. 585-591; Barak et al., 2004, *J Mol Biol* 342:383-401).

Another useful assay to detect AceCS2 enzymatic activity is incubation of cells with [$^{14}$C]acetate and the subsequent analysis of $^{14}$C into $CO_2$ and lipids (Fujiino et al., 2001, *J Biol Chem* 276:11420-11426).

I. Two-Hybrid Assays

In another embodiment of the screening methods of the present invention, a two-hybrid system utilizing cells may be used ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); see also Dalton and Treisman, 1992, *Cell* 68: 597-612; Fields and Sternglanz, 1994, *Trends Genet.* 10:286-92).

In the two-hybrid system, for example, a SIRT3, preferably, a SIRT3 polypeptide, is fused to the SRF-binding region or GAL4-binding region and expressed in yeast cells. An AceCS2 polypeptide that binds to a SIRT3 polypeptide is fused to the VP16 or GAL4 transcriptional activation region and also expressed in the yeast cells in the existence of a test compound. Alternatively, the AceCS2 polypeptide that binds to the SIRT3 polypeptide may be fused to the SRF-binding region or GAL4-binding region, and the SIRT3 polypeptide to the VP16 or GAL4 transcriptional activation region. The binding of the two polypeptides activates a reporter gene, making positive clones detectable. As a reporter gene, for example, Ade2 gene, lacZ gene, CAT gene, luciferase gene and such can be used besides HIS3 gene.

A candidate agent that does not bind to SIRT3 or AceCS2 does not affect the activation of the reporter gene. However, an agent that increases the binding of SIRT3 to AceCS2 results in a stronger activation of the reporter gene. Conversely, a candidate agent that inhibits the binding between SIRT3 and AceCS2 leads to a lesser activation or no activation of the reporter gene.

J. Detection of Interaction Between Two Molecules

The interaction between two molecules, such as AceCS2 and SIRT3, AceCS2 and a candidate agent or SIRT3 and a candidate agent can also be detected, e.g., using a fluorescence assay in which at least one molecule is fluorescently labeled. One example of such an assay includes fluorescence energy transfer (FET or FRET for fluorescence resonance energy transfer) (see, for example, Lakowicz et al., U.S. Pat. No. 5,631,169; Stavrianopoulos et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor.' Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A FET binding event can be conveniently measured through standard fluorimetric detection means well known in the art (e.g., using a fluorimeter.

Another example of a fluorescence assay is fluorescence polarization (FP). For FP, only one component needs to be labeled. A binding interaction is detected by a change in molecular size of the labeled component. The size change alters the tumbling rate of the component in solution and is detected as a change in FP (see, e.g., Nasir et al., 1999, *Comb Chem HTS* 2:177-190; Jameson et al., 1995, *Methods Enzymol* 246:283; Seethala et al., 1998, *Anal Biochem* 255:257. Fluorescence polarization can be monitored in multiwell plates, e.g., using the Tecan Polarion™ reader (see, e.g., Parker et al., 2000, *J Biomol Screen* 5:77-88; and Shoeman, et al., 1999, *Biochemistry* 38:16802-16809).

In another embodiment, determining the ability of a protein to bind to a target molecule or the ability of a candidate agent to bind to a subject polypeptide can be accomplished using real-time Biomolecular Interaction Analysis (BIA) (see, e.g., Sjolander and Urbaniczky, 1991, *Anal Chem* 63:2338-2345; Szabo et al., 1995, *Curr Opin Struct Biol* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

K. Computer-Based Assays

It is also possible to use structure-activity relationships (SAR) and structure-based design principles to identify agents increasing a level or activity of SIRT3 or modulating a level, acetylation status, or activity of AceCS2. SARs provide information about the activity of related agents in at least one relevant assay. Correlations are made between structural features of an agent of interest and an activity. For example, it may be possible by evaluating SARs for a family of agents that interact with a SIRT3 polypeptide and/or an AceCS2 polypeptide to identify one or more structural features required for activity. A library of agents can then be produced that vary these features and then the library is screened. Structure-based design can include determining a structural model of the physical interaction of the agent and its target, such as a SIRT3 polypeptide and/or an AceCS2 polypeptide. The structural model can indicate how an antagonist of the target can be engineered. Such antagonist may be useful in altering lifespan regulation.

Both the SAR and the structure-based design approach can be used to identify a pharmacophore. Pharmacophores are a highly valuable and useful concept in drug discovery and drug-lead optimization. A pharmacophore is defined as a distinct three dimensional (3D) arrangement of chemical groups essential for biological activity. Since a pharmaceutically active molecule must interact with one or more molecular structures within the body of the subject in order to be effective, and the desired functional properties of the molecule are derived from these interactions, each active compound must contain a distinct arrangement of chemical groups which enable this interaction to occur. The chemical groups, commonly termed descriptor centers, can be represented by (a) an atom or group of atoms; (b) pseudo-atoms, for example a center of a ring, or the center of mass of a molecule; (c) vectors, for example atomic pairs, electron lone pair directions, or the normal to a plane. Once formulated a pharmacophore can be used to search a database of chemical compounds, e.g., for those having a structure compatible with the pharmacophore (see, for example, U.S. Pat. No. 6,343,257; Martin, 1992, *J Med Chem* 35, 2145-54). Database search queries are based not only on chemical property information but also on precise geometric information.

Computer-based approaches can use database searching to find matching templates (Martin, 1992, *J Med Chem* 35:2145-54, which is herein incorporated by reference). Existing methods for searching 2-D and 3-D databases of compounds are applicable. Lederle of American Cyanamid (Pearl River, N.Y.) has pioneered molecular shape-searching, 3D searching and trend-vectors of databases. Commercial vendors and other research groups also provide searching capabilities (MACSS-3D, Molecular Design Ltd. (San Leandro, Calif.); CAVEAT, Lauri, G et al., University of California (Berkeley, Calif.); CHEM-X, Chemical Design, Inc. (Mahwah, N.J.)). Software for these searches can be used to analyze databases of potential drug compounds indexed by their significant chemical and geometric structure (e.g., the Standard Drugs File (Derwent Publications Ltd., London, England), the Bielstein database (Bielstein Information, Frankfurt, Germany or Chicago) and the Chemical Registry database (CAS, Columbus, Ohio)).

Once a compound is identified that matches the pharmacophore, it can be tested for activity, e.g., for binding to a polypeptide and/or for modulating a biological activity of a polypeptide, e.g., increasing the enzymatic activity of a SIRT3 polypeptide and/or an AceCS2 polypeptide Further, structures have been determined for three class III enzymes, namely *E. coli* CobB (Zhao et al. 2004, *J Mol Biol* 337:731-741) and both *A. fulgidus* sirtuins, Sir2-Af1 (Min et al., 2001, *Cell* 105:269-279) and Sir2-Af2 (Avalos, 2002, *Mol Cell* 10:523-535). With respect to SIRT5, crystal structure information has been deposited at GenBank Accession Nos. 2FZQA, 2FZQB, 2B4YA, 2B4YB, 2B4YC, and 2B4YD. Other structural data are available for Sir2-P53 Peptide-Nicotinamide (GenBank Accession No. 1YC5), Sir2af2-NAD-ADPribose-Nicotinamide (GenBank Accession No. 1YC2), structural basis for nicotinamide cleavage and ADP-ribose transfer by $NAD^+$-dependent Sir2 Histone Protein Deacetylase (GenBank Accession Nos. 1SZD and 1SZC); structural basis for the mechanism and regulation of Sir2 enzymes (GenBank Accession No. 1S7G); and human SIRT2 Histone Deacetylase (1J8F). A 1.7 Å crystal structure of the 323 amino acid catalytic core of human SIRT2, revealing an NAD-binding domain, which is a variant of the Rossmann fold, and a smaller domain composed of helical module and a zinc-binding module was reported by Finnin et al. (Finnin et al. 2001, *Nat Struct Biol* 8(7):621-5). Finnin et al. also described a conserved large groove at the interface of the two domains and suggested this to be the likely site of catalysis. Intersecting this large groove, there is a pocket formed by the helical module. This pocket is lined with hydrophobic residues, which interestingly are conserved within each of the five Sir2 classes, suggesting that it is a class-specific protein binding site (Finnin et al. 2001, *Nat Struct Biol* 8(7):621-5).

A crystal structure of the coiled-coil dimerization motif of yeast Sir4, which interacts with Sir3, is provided at GenBank Accession No. 1NYH_A. Further, Chang et al. reported the X-ray structure of the coiled-coil dimerization motif within the C-terminus of Sir4 and showed that it formed a stable 1:1 complex with a dimeric fragment of Sir3 (residues 464-978). (Chang et al., 2003, *Structure* 11(6):637-649; incorporated herein by reference in its entirety). In addition, Murphy et al. provided a 2.5 Å resolution X-ray crystal structure of a Sir4 CT fragment (Sir4p 1217-1358) revealing a 72 residue homodimeric parallel coiled coil (GenBank Accession Nos. 1PL5S and 1PL5A; Murphy et al., 2003, *J Mol Biol* 334(4): 769-80, incorporated herein by reference in its entirety). This set of data can be used to design agents binding to a SIRT3 polypeptide and/or an AceCS2 polypeptide, interacting with a SIRT3 polypeptide and/or an AceCS2 polypeptide or increasing a level or activity of a SIRT3 polypeptide or modulating a level, acetylation status or activity of an AceCS2 polypeptide.

Thus, in one aspect of the present invention, an agent is identified that is designed to interact with a SIRT3 polypeptide and/or an AceCS2 polypeptide or binds to a SIRT3 polypeptide and/or an AceCS2 polypeptide by employing a structure of a SIRT3 polypeptide and/or an AceCS2 polypeptide or that of another sirtuin or AceCS2 polypeptide showing homology to SIRT3 and/or AceCS2 within one or more domains.

Thus, identification of structurally defined class III enzymes having overlapping patterns of activation provides a useful tool for identifying activators for mammalian sirtuins, in particular SIRT3. For example, SIRT3 can be co-crystallized with a SIRT3 activating agent and the three-dimensional structure of the complex can be determined. Information relating to the interactions between the SIRT3 activating agent and SIRT3 amino acid residues and/or the shape of the modulator binding site can then be entered into computer modeling programs to design new and potentially more potent activators of SIRT3. As will be understood by one of skill in the art upon reading this disclosure, AceCS2 activating and inhibiting agents can be designed in such manner.

Thus, another assay for candidate agents that activate the level or activity of a SIRT3 polypeptide or for agents that modulate a level, acetylation status or activity of an AceCS2 polypeptide involves computer assisted drug design, in which a computer system is used to generate a three-dimensional structure of SIRT3 or AceCS2 based on the structural information encoded by its amino acid sequence. The input amino acid sequence interacts directly and actively with a pre-established algorithm in a computer program to yield secondary, tertiary, and quaternary structural models of the protein. The models of the protein structure are then examined to identify regions of the structure that have the ability to bind, e.g., another polypeptide or a candidate agent. These regions are then used to identify activators that activate a level or activity of SIRT3 or a modulator that modulates a level, acetylation status or activity of an AceCS2 polypeptide.

The three-dimensional structural model of the protein is generated by entering protein amino acid sequences of at least 10 amino acid residues or corresponding nucleic acid sequences encoding a SIRT3 or AceCS2 into the computer system. The amino acid sequences encoded by the nucleic acid sequences provided herein represent the primary sequences or subsequences of the proteins, which encode the structural information of the proteins. At least 10 residues of an amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential modulator binding regions are identified by the computer system. Three-dimensional structures for potential modulators are generated by entering amino acid or nucleotide sequences or chemical formulas of compounds, as described herein. The three-dimensional structure of the potential ligand is then compared to that of SIRT3 or AceCS2 to identify binding sites on SIRT3 or AceCS2. Binding affinity between the protein and modulators is determined using energy terms to determine which modulators have an enhanced probability of binding to the protein.

Computer systems are also used to screen for mutations, polymorphic variants, alleles and interspecies homologs of genes encoding a SIRT3 or AceCS2 polypeptide of the invention. Such mutations can be associated with disease states or genetic traits. In addition, GeneChip™ and related technology can also be used to screen for mutations, polymorphic variants, alleles and interspecies homologs. Once the variants are identified, diagnostic assays can be used to identify patients, e.g., diabetics or individuals at risk for diabetes, hypercholesterolemia, hyperlipidemia, or obesity, having such mutated or allelic variant genes. Identification of such SIRT3 and/or AceCS2 genes involves receiving input of a first amino acid sequence of a SIRT3 or AceCS2 (or of a first nucleic acid sequence encoding a SIRT3 or AceCS2). The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in various SIRT3 or AceCS2 genes, and mutations associated with disease states and genetic traits.

L. High Throughput Assays

In one preferred embodiment, high throughput screening methods involve providing a combinatorial chemical or peptide library containing a large number of potential therapeutic compounds (potential modulator or ligand compounds). Such “combinatorial chemical libraries” or “ligand libraries” are then screened in one or more assays, as described herein, to identify those library members (particular chemical species or subclasses) that display a desired characteristic activity. The agents thus identified can serve as conventional “lead agents” or can themselves be used as potential or actual therapeutics.

Preparation and screening of combinatorial chemical libraries is well known to those of skill in the art. Such combinatorial chemical libraries include, but are not limited to, peptide libraries (see, e.g., U.S. Pat. No. 5,010,175, Furka, 1991, *Int J Pept Prot Res* 37:487-493 (1991) and Houghton et al., 1991, *Nature* 354:84-88). Other chemistries for generating chemical diversity libraries can also be used. Such chemistries include, but are not limited to, peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., 1993, *Proc Natl Acad Sci USA* 90:6909-6913), vinylogous polypeptides (Hagihara et al., 1992, *J Amer Chem Soc* 114:6568), nonpeptidal peptidomimetics with glucose scaffolding (Hirschmann et al., 1992, *J Amer Chem Soc* 114:9217-9218), analogous organic syntheses of small compound libraries (Chen et al., 1994, *J Amer Chem Soc* 116:2661), oligocarbamates (Cho et al., 1993, *Science* 261:1303), and/or peptidyl phosphonates (Campbell et al, 1994, *J Org Chem* 59:658), nucleic acid libraries (see Ausubel, Berger and Sambrook), peptide nucleic acid libraries (see, e.g., U.S. Pat. No. 5,539,083), antibody libraries (see, e.g., Vaughn et al., 1996, *Nature Biotechnology* 14(3):309-314 and PCT/US96/10287), carbohydrate libraries (see, e.g., Liang et al., 1996, *Science,* 274: 1520-1522 and U.S. Pat. No. 5,593,853), small organic molecule libraries (see, e.g., benzodiazepines, Baum C&EN, Jan. 18, 1993, page 33; isoprenoids, U.S. Pat. No. 5,569,588; thiazolidinones and metathiazanones, U.S. Pat. No. 5,549, 974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like). Additional examples of methods for the synthesis of molecular libraries can be found in the art, for example in: DeWitt et al., 1993, *Proc Natl Acad Sci USA* 90:6909; Erb et al., 1994, *Proc Natl Acad Sci USA* 91:11422; Zuckemmann et al., 1994, *J Med Chem* 37:2678; Cho et al., 1993, *Science* 261:1303; Carrell et al., 1994, *Angew Chem Int Ed Engl* 33:2059; Carell et al., 1994, *Angew Chem Int Ed Engl.* 33:2061; and Gallop et al., 1994, *J Med. Chem.* 37:1233.

High throughput assays are often used in screening for modulators. Thus, in high throughput assays for identifying (i) activators for SIRT3 and (ii) modulators for AceCS2, it is possible to screen up to several thousand different candidate agents or ligands in a single day. In particular, each well of a microtiter plate can be used to run a separate assay against a selected potential agent, or, if concentration or incubation time effects are to be observed, every 5-10 wells can test a single agent. Thus, a single standard microtiter plate can assay about 100 (e.g., 96) agents. If 1536 well plates are used, then a single plate can easily assay from about 100 to about 1500 different agents. It is possible to assay several different plates per day; assay screens for up to about 6,000-20,000 different agents are possible using the integrated systems of the invention. More recently, microfluidic approaches to reagent manipulation have been developed.

The molecule of interest can be bound to the solid state component, directly or indirectly, via covalent or non covalent linkage, e.g., via a tag. The tag can be any of a variety of components. In general, a molecule that binds the tag (a tag binder) is fixed to a solid support, and the tagged molecule of interest (e.g., SIRT3 or AceCS2) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin and appropriate tag binders are also widely available (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs, such as agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, *The Adhesion Molecule Facts Book I* (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly Gly sequences of between about 5 and 200 amino acids (SEQ ID NO:14). Such flexible linkers are known to those of skill in the art. For example, poly(ethylene glycol) linkers are available from Shearwater Polymers, Inc., Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature (see, e.g., Merrifield, 1965, *Endeavour* 24:3-7; Merrifield, 1964, *Biochemistry* 3:1385-90; Merrifield and Stewart, 1965, *Nature* 207(996):522-3; Merrifield, 1965, *Science* 150 (693): 178-85 (describing solid phase synthesis of, e.g., peptides); Geysen et al., 1987, *J Immun Meth* 102:259-274 (describing synthesis of solid phase components on pins); Frank and Doring, 1988, *Tetrahedron* 44:6031-6040 (describing synthesis of various peptide sequences on cellulose disks); Fodor et al., 1991, *Science* 251:767-777; Sheldon et al., 1993, *Clinical Chemistry* 39(4):718-719; and Kozal et al., 1996, *Nature Medicine* 2(7):753-759 (all describing arrays of biopolymers fixed to solid substrates). Non-chemical approaches for fixing tag binders to substrates include other common methods, such as heat, cross-linking by UV radiation, and the like.

The invention provides in vitro assays for identifying, in a high throughput format, agents that can increase a level or activity of SIRT3 or agents that modulate a level, acetylation status or activity of AceCS2. Control reactions that measure a level or activity of SIRT3 or a level, acetylation status or activity of AceCS2 in a reaction that does not include a potential activator/modulator are optional, as the assays are highly uniform. Such optional control reactions are appropriate and increase the reliability of the assay. Accordingly, in some embodiments, the methods of the invention include such a control reaction. For each of the assay formats described, "no activator" or "no modulator" control reactions which do not include an activator of SIRT3 or a modulator of AceCS2 provide a background level of binding activity.

III. Activators for SIRT3 and Modulators for AceCS2

Any candidate agent, for example, cell extracts, cell culture supernatants, products of fermenting microorganism, extracts from marine organism, plant extracts, purified or crude proteins, peptides, non-peptide compounds, nucleic acids, saccharides, lipids, synthetic micromolecular compounds and natural compounds and the like, can be used in the screening methods of the present invention. The candidate agent of the present invention can also be obtained using any of the numerous approaches in combinatorial library searching described herein and methods known in the art, including (1) biological libraries, (2) spatially addressable parallel solid phase or solution phase libraries, (3) synthetic library methods requiring deconvolution, (4) the "one-bead one-compound" library method and (5) synthetic library methods using affinity chromatography selection. The biological library methods using affinity chromatography selection is limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art (DeWitt et al., 1993, *Proc Natl Acad Sci USA* 90: 6909; Erb et al., 1994, *Pro. Natl Acad Sci USA* 91:11422; Zuckermann et al., 1994, *J Med Chem* 37:2678; Cho et al., 1993, *Science* 261:1303; Carell et al., 1994, *Angew Chem. Int. Ed Engl.* 33:2059; Carell et al., 1994, *Angew Chem Int Ed. Engl.* 33:2061; Gallop et al., 1994, *J Med Chem* 37:1233). Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

Libraries of compounds may be presented in solution (see Houghten, 1992, *Bio/Techniques* 13:412) or on beads (Lam, 1991, *Nature* 354: 82), chips (Fodor, 1993, *Nature* 364:555), bacteria (U.S. Pat. No. 5,223,409), spores (U.S. Pat. Nos. 5,571,698; 5,403,484, and 5,223,409), plasmids (Cull et al., 1992, *Proc Natl Acad Sci USA* 89:1865) or phage (Scott and Smith, 1990, *Science* 249:386; Devlin, 1990, *Science* 249: 404; Cwirla et al., 1990, *Proc Natl Acad Sci USA* 87:6378; Felici, 1991, *J Mol Biol* 222 301; US Pat. Application 20020103360). The candidate agent exposed to a cell or protein according to the screening methods of the present invention may be a single agent or a combination of agents. When a combination of agents is used in the screening methods of the invention, the agent may be contacted to the cell or protein sequentially or simultaneously.

An agent isolated by the screening methods of the present invention is a candidate for drugs which activate a level or activity of a SIRT3 or is a candidate drug for modulating a level, acetylation status or activity of an AceCS2. The candidate drugs are useful for treating or preventing a pathological condition, disorder, or disease as described herein. An agent in which a part of the structure of the agent obtained by a screening method of the present invention is converted by addition, deletion and/or replacement, is included in the agents obtained by the screening methods of the present invention. An agent effective in activating a level or activity of a SIRT3 or an agent modulating a level, acetylation status, or activity of an AceCS2 can be further tested for its ability to treat or prevent a disorder, disease or pathological condition in animal models or test subjects.

Agents identified by any of the subject methods described herein are useful as biologically active agents. In a preferred embodiment the biologically agent activates a level or activity of a SIRT3 as described herein. In another preferred embodiment the biologically active gent modulates a level, acetylation status or activity of an AceCS2, as described herein.

In addition, prodrugs are also included within the context of this invention. Prodrugs are any covalently bonded carriers that release an agent of the present invention in vivo when such prodrug is administered to a patient. Prodrugs are generally prepared by modifying functional groups in a way such that the modification is cleaved, either by routine manipulation or in vivo, yielding the parent agent.

A variety of agents that modulate one or more of a level, acetylation status, or activity of an AceCS2 as described herein, can be used. They include siRNA, antisense RNA, ribozymes, small molecules, and dominant negative proteins. Small molecules are also useful as agents for the activation of a level or activity of a SIRT3.

As described herein, modulators for AceCS2 include activators and inhibitors (e.g., an antagonist) of AceCS2. SiRNA, antisense RNA, ribozymes, and dominant negative proteins are particularly useful for inhibiting an activity of a nucleic acid or polypeptide. Thus, in one embodiment, the present invention provides compositions comprising siRNA, antisense RNA, ribozymes, dominant negative proteins for inhibiting an AceCS2 nucleic acid or an AceCS2 polypeptide and methods for using siRNA, antisense RNA, ribozymes, dominant negative proteins for inhibiting an AceCS2 nucleic acid or an AceCS2 polypeptide both in vitro and in vivo. These methods and compositions are useful for the treatment of pathological conditions, disorders, or diseases, and interfering with AceCS2 activity. A preferred pathological condition, disorder, or disease is characterized by, caused by or associated with an elevated level of acetyl-CoA relative to normal. Upon administration of an siRNA, an antisense RNA, a ribozyme, or a dominant negative protein for inhibiting an AceCS2 nucleic acid or an AceCS2 polypeptide as described herein to an individual having such pathological condition, disorder, or disease, the elevated level of acetyl-CoA in the individual is reduced, preferably reduced to a normal level.

A. Small Molecules

In a preferred embodiment the agent is a small molecule which can be identified as described herein. Useful small molecules and combinatorial libraries comprising them are described herein. Particular useful are small molecule agents that activate a level or activity of a SIRT3 or which modulate a level, acetylation status, or activity of an AceCS2m as described herein.

B. SiRNA

In a preferred embodiment of the present invention, an agent modulating one or more of a level, acetylation status, or activity of an AceCS2 as described herein is a short interfering RNA (siRNA). See, e.g., PCT applications WO0/44895, WO99/32619, WO01/75164, WO01/92513, WO01/29058, WO01/89304, WO02/16620, and WO02/29858; and U.S. Patent Publication No. 20040023390 for descriptions of siRNA technology.

In a preferred embodiment the agent is an siRNA directed against an AceCS2 mRNA.

Thus, agents of the present invention that are useful for practicing the methods of the present invention include, but are not limited to siRNAs of AceCS2. Typically, such agents are capable of (i) binding to AceCS2 mRNA, (ii) interfere with translation of AceCS2 mRNA or (iii) lead to degradation of AceCS2 mRNA. The present invention provides compositions and methods using RNA interference to modulate AceCS2 expression.

In many species, introduction of double-stranded RNA (dsRNA) which may alternatively be referred to herein as small interfering RNA (siRNA), induces potent and specific gene silencing, a phenomena called RNA interference or RNAi. This phenomenon has been extensively documented in the nematode *C. elegans* (Fire et al., 1998, *Nature,* 391:806-811), but is widespread in other organisms, ranging from trypanosomes to mouse. Depending on the organism being discussed, RNA interference has been referred to as "cosuppression", "post-transcriptional gene silencing", "sense suppression" and "quelling." RNAi is an attractive biotechnological tool because it provides a means for knocking out the activity of specific genes. It is particularly useful for knocking out gene expression in species that were not previously considered to be amenable to genetic analysis or manipulation.

RNAi is usually described as a post-transcriptional gene-silencing (PTGS) phenomenon in which dsRNAs trigger degradation of homologous mRNA in the cytoplasm. The basic process involves a dsRNA that is processed into shorter units (called short or small interfering RNAs (siRNAs)) that guide recognition and targeted cleavage of homologous messenger RNA (mRNA). The dsRNAs that (after processing) trigger RNAi/PTGS can be made in the nucleus or cytoplasm in a number of ways. The processing of dsRNA into siRNAs, which in turn degrade mRNA, is a two-step RNA degradation process. The first step involves a dsRNA endonuclease (ribonuclease III-like; RNase III-like) activity that processes dsRNA into sense and antisense RNAs which are 21 to 25 nucleotides (nt) long (i.e., siRNA). In *Drosophila*, this RNase III-type protein is termed Dicer. In the second step, the antisense siRNAs produced combine with, and serve as guides for, a different ribonuclease complex called RNA-induced silencing complex (RISC), which cleaves the homologous single-stranded mRNAs. RISC cuts the mRNA approximately in the middle of the region paired with the antisense siRNA, after which the mRNA is further degraded. dsRNAs from different sources can enter the processing pathway leading to RNAi/PTGS.

Thus, in a preferred embodiment of the present invention, the agent for use in the methods of the present invention is a siRNA of AceCS2. siRNA can be used to reduce the expression level of AceCS2. An siRNA of AceCS2 hybridizes to an AceCS2 mRNA and thereby decreases or inhibits production of AceCS2 polypeptides.

In designing RNAi experiments there are several factors that need to be considered such as the nature of the siRNA, the durability of the silencing effect, and the choice of delivery system. To produce an RNAi effect, the siRNA that is introduced into the organism should preferably contain exonic sequences. However, siRNAs directed against e.g., exon/intron splice sequences may also be chosen. Furthermore, the RNAi process is homology dependent, so the sequences must be carefully selected so as to maximize gene specificity, while minimizing the possibility of cross-interference between homologous, but not gene-specific sequences. Preferably the siRNA exhibits greater than 90% or even 100% identity between the sequence of the siRNA and the gene to be inhibited. Sequences less than about 80% identical to the target gene are substantially less effective. Thus, the greater homology between the siRNA of AceCS2 and the AceCS2 gene whose expression is to be inhibited, the less likely expression of unrelated genes will be affected.

In addition, the size of the siRNA is important. Generally, the present invention relates to siRNA molecules of AceCS2, which are double or single stranded and comprise at least about 19-25 nucleotides, and are able to modulate the gene expression of AceCS2. In the context of the present invention, the siRNA is preferably less than 500, 200, 100, 50 or 25 nucleotides in length. More preferably, the siRNA is from about 19 nucleotides to about 25 nucleotides in length.

In one aspect, the invention generally features an isolated siRNA molecule of at least 19 nucleotides, having at least one strand that is substantially complementary to at least ten but no more than thirty consecutive nucleotides of AceCS2 and that reduces the expression of AceCS2 gene or protein.

Therefore, a composition comprising an siRNA as described herein is useful in a method for modulating a level, acetylation status or activity of an AceCS2 in a mammalian cell or in a method for the treatment of a pathological condition, disorder or disease as described herein.

1. Selection of SiRNA Target Sites

Nucleic acid sequences encoding AceCS2 are described in the art and are available at GenBank. For example, human nucleic acid sequences for AceCS2 can be found, e.g., at GenBank Accession No. BC039261; mouse AceCS2 nucleic acid sequences can be found, e.g., at GenBank Accession No. AB046742; and bovine AceCS2 nucleic acid sequences can be found, e.g., at GenBank Accession No. AB046741.

Human nucleic acid sequences for SIRT3 can be found, e.g., at GenBank Accession Nos. NM_001017524, NM_012239, BC001042, and AF083108; mouse SIRT3 nucleic acid sequences can be found, e.g., at GenBank Accession Nos. CT010402, BC025878, and NM_022433; rat SIRT3 nucleic acid sequences can be found, e.g., at GenBank Accession No. XM_215124; bovine SIRT3 nucleic acid sequences can be found, e.g., at GenBank Accession Nos. XM_864790 and XM_873980; dog SIRT3 nucleic acid sequences can be found, e.g., at GenBank Accession Nos. XM_843207, XM_850716, and XM_851003; and zebrafish SIRT3 nucleic acid sequences can be found, e.g., at GenBank Accession Nos. XM_679133 and XM_685833.

Having these sequences at hand, a skilled artisan can readily identify without undue experimentation by using, e.g., the disclosure provided herein, siRNAs for practicing methods and compositions of the present invention.

In a preferred embodiment of the present invention, the siRNA molecule has at least one strand that is substantially complementary to at least ten but no more than thirty consecutive nucleotides of an AceCS2. Using such oligonucleotides, expression of AceCS2 can be drastically reduced. In other embodiments of the present invention, n siRNA for inhibiting AceCS2 expression from an AceCS2 mRNA comprises an siRNA obtained from any one of the AceCS2 sequences disclosed herein (see GenBank accession numbers provided herein).

Without undue experimentation and using the disclosure of this invention, it is understood that additional siRNAs of AceCS2 that modulate AceCS2 expression can be designed and used to practice the methods of the invention.

A preferable siRNA used in the present invention has the general formula:

5'-[A]-[B]-[A']-3' wherein [A] is a ribonucleotide sequence corresponding to a target sequence of an AceCS2 gene; [B] is a ribonucleotide sequence consisting of about 3 to about 23 nucleotides; and [A'] is a ribonucleotide sequence complementary to [A]. Herein, the phrase a "target sequence of an AceCS2 gene" refers to a sequence that, when introduced into a mammalian cell, is effective for inhibiting or reducing the translation of an AceCS2 mRNA.

Other than the siRNAs disclosed herein, siRNAs useful to practice a method of the present invention can be identified as follows. Beginning with the AUG start codon of the transcript (e.g., an AceCS2 mRNA), the transcript is scanned downstream for AA dinucleotide sequences. The occurrence of each AA and the 3' adjacent 19 nucleotides as potential siRNA target sites are recorded. It may not be recommended to design siRNAs against the 5' and 3' untranslated regions (UTRs) and regions near the start codon (within 75 bases) as these may be richer in regulatory protein binding sites, and thus the complex of endonuclease and siRNAs that were designed against these regions may interfere with the binding of UTR-binding proteins and/or translation initiation complexes (Tuschl, et al. 1999, *Genes Dev* 13(24):3191-7). The potential target sites are then compared to the human genome database or other mammalian sequences, depending on the species in which expression of the AceCS2 is to be modulated. Any target sequences with significant homology to other coding sequences are eliminated from consideration. The homology search can be performed using BLAST (Altschul et. al., 1997, *Nucleic Acids Res* 25:3389-402; Altschul et. al., 1990, *J Mol Biol* 215:403-10). Next, qualifying target sequences are selected for synthesis. On the website of Ambion, several preferable target sequences can be selected along the length of the gene for evaluation.

The double-stranded molecule of the present invention comprises a sense strand and an antisense strand, wherein the sense strand comprises a ribonucleotide sequence corresponding to an AceCS2 target sequence, and wherein the antisense strand comprises a ribonucleotide sequence which is complementary to said sense strand, wherein said sense strand and said antisense strand hybridize to each other to form said double-stranded molecule, and wherein said double-stranded molecule, when introduced into a cell expressing an AceCS2 gene, inhibits expression of said gene.

The double-stranded molecule of the present invention may be a polynucleotide derived from its original environment (i.e., when it is a naturally occurring molecule, the natural environment), physically or chemically altered from its natural state, or chemically synthesized. According to the present invention, such double-stranded molecules include those composed of DNA, RNA, and derivatives thereof. A DNA is suitably composed of bases such as A, T, C and G, and T is replaced by U in an RNA.

SiRNAs may be expressed from a vector. The vector preferably comprises a regulatory sequence adjacent to the region encoding the present double-stranded molecule that directs the expression of the molecule in an adequate cell. For example, the double-stranded molecules of the present invention are intracellularly transcribed by cloning their coding sequence into a vector containing, e.g., an RNA polymerase III transcription unit from the small nuclear RNA (snRNA) U6 or the human H1 RNA promoter.

Alternatively, the present vectors are produced, for example, by cloning the target sequence into an expression vector so the objective sequence is operatively-linked to a regulatory sequence of the vector in a manner to allow expression thereof (transcription of the DNA molecule) (Lee et al., 2002, *Nature Biotechnology* 20:500-505). For example, the transcription of an RNA molecule having an antisense sequence to the target sequence is driven by a first promoter (e.g., a promoter sequence linked to the 3'-end of the cloned DNA) and that having the sense strand to the target sequence by a second promoter (e.g., a promoter sequence linked to the 5'-end of the cloned DNA). The expressed sense and antisense strands hybridize to each other in vivo to generate an siRNA construct to silence a gene that comprises the target sequence. Furthermore, two constructs (vectors) may be utilized to respectively produce the sense and anti-sense strands of an siRNA construct.

For introducing the vectors into a cell, a transfection-enhancing agent can be used. FuGENE6 (Roche Diagnostics), Lipofectamine 2000 (Invitrogen), Oligofectamine (Invitrogen), and Nucleofector (Wako pure Chemical) are useful as the transfection-enhancing agent. Transfection of vectors expressing siRNA polynucleotides of the invention can be used to inhibit an AceCS2 in a mammalian cell. Thus, it is another aspect of the present invention to provide a double-stranded molecule comprising a sense-strand and antisense-strand which molecule functions as an siRNA for AceCS2, and a vector encoding the double-stranded molecule.

The siRNA may also comprise an alteration of one or more nucleotides. Such alterations can include the addition of non-nucleotide material, such as to the end(s) of the 19 to 25 nucleotide RNA or internally (at one or more nucleotides of the RNA). In a preferred embodiment, the RNA molecule contains a 3'-hydroxyl group. Nucleotides in the RNA molecules of the present invention can also comprise non-standard nucleotides, including non-naturally occurring nucleotides or deoxyribonucleotides. The double-stranded oligonucleotide may contain a modified backbone, for example, phosphorothioate, phosphorodithioate, or other modified backbones known in the art, or may contain non-natural internucleoside linkages. Additional modifications of siRNAs (e.g., 2'-O-methyl ribonucleotides, 2'-deoxy-2'-fluoro ribonucleotides, "universal base" nucleotides, 5-C-methyl nucleotides, one or more phosphorothioate internucleotide linkages, and inverted deoxyabasic residue incorporation) can be found in the U.S. Patent Application No. 20040019001 and U.S. Pat. No. 6,673,611 (incorporated by reference). Collectively, all such altered RNAs described above are referred to as modified siRNAs.

Preferably, RNAi is capable of decreasing the expression of AceCS2 in a cell by at least 10%, 20%, 30%, or 40%, more preferably by at least 50%, 60%, or 70%, and most preferably by at least 75%, 80%, 90%, 95% or more.

Introduction of siRNA into cells can be achieved by methods known in the art and disclosed herein, including for example, microinjection, electroporation, or transfection of a vector comprising a nucleic acid from which the siRNA can be transcribed. Alternatively, an siRNA for AceCS2 can be directly introduced into a cell in a form that is capable of binding to an AceCS2 mRNA transcript. To increase durability and membrane-permeability the siRNA may be combined or modified with liposomes, poly-L-lysine, lipids, cholesterol, lipofectine or derivatives thereof. Preferred are cholesterol-conjugated siRNA for AceCS2 (see, Song et al., *Nature Med.* 9:347-351 (2003)).

SiRNAs and vectors comprising siRNA nucleic acid sequences and methods for preparing and using same are described, for example, in U.S. Patent Application No. 20060051815, which is incorporated herewith in its entirety by reference.

C. Antisense RNA And Ribozymes

A variety of agents can be used to modulate the level, acetylation status, or activity of an AceCS2 as described herein. For example, the expression of AceCS2 can be modulated, preferably inhibited, by administering to a cell or a subject a nucleic acid that inhibits or antagonizes the expression of an AceCS2 gene. In addition to siRNAs, described above, antisense oligonucleotides or ribozymes which disrupt the expression of an AceCS2 gene can be used for modulating the level or activity of an AceCS2. In a preferred embodiment the modulator, preferably an inhibitor, is an anti-sense RNA, which can be identified as described herein.

As noted above, antisense-oligonucleotides corresponding to any of the nucleotide sequence of an AceCS2 gene can be used to reduce the expression level of the gene. Specifically, an antisense-oligonucleotide against an AceCS2 gene may act by binding to any of the AceCS2 mRNAs, thereby inhibiting the transcription or translation of an AceCS2 gene, promoting the degradation of an AceCS2 mRNA, and/or inhibiting the expression of proteins encoded by an AceCS2 gene, and finally inhibiting the function of an AceCS2 protein.

Anti-sense oligonucleotides and siRNAs of the invention can also be defined by their ability to hybridize specifically to mRNA or cDNA from the genes disclosed herein.

An antisense-oligonucleotide and derivatives thereof can be made into an external preparation, such as a liniment or a poultice, by mixing with a suitable base material which is inactive against the derivative.

The antisense-oligonucleotides of the invention inhibit the expression of a protein encoded by an AceCS2 gene, and thus are useful for suppressing the biological activity of an AceCS2 or of a multiprotein complex comprising one of AceCS2 or SIRT3 polypeptides.

Generally, ribozymes are classified into large ribozymes and small ribozymes. A large ribozyme is known as an enzyme that cleaves the phosphate ester bond of nucleic acids. After the reaction with the large ribozyme, the reacted site consists of a 5'-phosphate and 3'-hydroxyl group. The large ribozyme is further classified into (1) group I intron RNA catalyzing transesterification at the 5'-splice site by guanosine; (2) group II intron RNA catalyzing self-splicing through a two step reaction via lariat structure; and (3) RNA component of the ribonuclease P that cleaves the tRNA precursor at the 5' site through hydrolysis. On the other hand, small ribozymes have a smaller size (about 40 bp) compared to the large ribozymes and cleave RNAs to generate a 5'-hydroxyl group and a 2'-3' cyclic phosphate. Hammerhead type ribozymes (Koizumi et al., 1988, *FEBS Lett.* 228:225) and hairpin type ribozymes (Buzayan, 1986, *Nature* 323:349; Kikuchi and Sasaki, 1991, *Nucleic Acids Res.* 19: 6751) are included in the small ribozymes. Methods for designing and constructing ribozymes are known in the art (see Koizumi et al., 1988, *FEBS Lett.* 228:225; Koizumi et al., 1989, *Nucleic Acids Res.* 17:7059; Kikuchi and Sasaki, 1991, *Nucleic Acids Res.* 19: 6751) and ribozymes inhibiting the expression of an AceCS2 polypeptide can be constructed based on the sequence information of the nucleotide sequence encoding an AceCS2 polypeptide according to conventional methods for producing ribozymes.

D. Dominant Negative Proteins

A variety of agents can be used to inhibit a level, acetylation status, or an activity of an AceCS2. In a preferred embodiment the inhibitor is a dominant negative protein which can be identified as described herein.

As described by the present inventors, an AceCS2 polypeptide assembles into a multiprotein complex. Thus, in a preferred embodiment, a dominant negative protein inhibiting the level, acetylation status or activity of an AceCS2 or an active fragment thereof modulating, preferably inhibiting, the assembly of an AceCS2 polypeptide into a biological active multiprotein complex. Upon inhibition of the assembly of the biologically active complex, one or more activities of an AceCS2 polypeptide may be inhibited or reduced, such as the enzymatic activity of converting acetate, ATP, and CoA into acetyl-CoA and AMP or the localization to the mitochondria.

Other dominant negative proteins for AceCS2 may be identified using methods known in the art and the assays disclosed herein.

When the candidate compound is a protein, the amino acid sequence of the obtained protein is analyzed, an oligo DNA is synthesized based on the sequence, and cDNA libraries are screened using the oligo DNA as a probe to obtain a DNA encoding the protein.

IV. Methods for Using Agents

The agents identified herein find use in a variety of methods, for example agents can be used for (i) activating a level or activity of SIRT3, (ii) modulating a level, acetylation status, or activity of AceCS2, or (iii) treatment of a pathological condition, disorder or disease. These methods can be practiced in vitro and in vivo. Preferably, patients treated by any one of the methods are humans and non-human animals.

A. Increasing a Level or Activity of SIRT3

Using agents identified or identifiable by a screening method of the present invention, a level or activity of SIRT3 can be increased, i.e., stimulated or activated, in vitro or in vivo. Thus, in one aspect of the present invention, a method for increasing a level or an activity of a SIRT3 is provided. In a preferred embodiment of the present invention, this method comprises the step of contacting a SIRT3 with an agent obtained or obtainable by a screening method of the present invention, wherein the level or activity of SIRT3 is increased.

The SIRT3 may be in a cell, preferably a mammalian cell and more preferred in a human cell. A preferred activity of SIRT3 is the deacetylase activity of SIRT3, preferably the deacetylation of AceCS2.

The effect of the agents in vitro or in vivo can be assayed as described herein.

B. Modulation of Level, Acetylation Status or Activity of Acetyl-CoA Synthetase 2

In yet another aspect, the present invention provides a method for modulating a level, acetylation status, or activity of an AceCS2. In a preferred embodiment of the present invention, this method comprises the step of contacting an AceCS2 polypeptide with an agent obtained or obtainable by a screening method of the present invention, such as a method for identifying an agent that increases a level, acetylation status, or activity of AceCS2, wherein the level, acetylation status, or activity of an AceCS2 is modulated.

The AceCS2 may be in a cell, preferably a mammalian cell and more preferred in a human cell. A preferred activity of AceCS2 is an enzymatic activity, preferably the generation of acetyl-CoA as described herein.

The effect of the agents in vitro or in vivo can be assayed as described herein.

C. Treatment of a Pathological Condition

The present invention also provides methods for the treatment of a pathological condition, disorder or disease.

Under some circumstances in mammals, large amounts of acetate are produced that need to be activated by acetyl-CoA synthetase. For example, under ketogenic conditions such as prolonged fasting or diabetes, the liver releases substantial amounts of acetate into the bloodstream (Buckley and Williamson, 1977, *Biochem J* 166:539-45; Seufert et al., 1974, *Biochem Biophys Res Commun* 57:901-9; Yamashita et al., 2001, *Biochim Biophys Acta* 1532:79-87). In addition, the hepatic acetyl-CoA hydrolase, which produces acetate, is activated under ketogenic conditions (Matsunaga et al., 1985, *Eur J Biochem* 152, 331-6). Utilization of the released acetate in extrahepatic tissues requires the action of acetyl-CoA synthetases. The findings that AceCS2 is abundant in heart and skeletal muscle but absent from the liver and induced under ketogenic conditions, suggest that AceCS2 plays an important role in acetate conversion for energy production under ketogenic conditions (Fujino et al., 2001, *J Biol Chem* 276, 11420-6). Thus, a preferred pathological condition, disorder or disease that can be treated according to the present invention is a ketogenic condition. In addition, disorders related to, associated with or caused (directly or indirectly) by a ketogenic condition, are also amenable to treatment using a method according to the present invention.

Thus, in one aspect, the present invention provides a method for the treatment of an individual having a ketogenic condition. In a preferred embodiment, this method comprises the step of administering to an individual having a ketogenic condition a therapeutically effective amount of an agent that increases a level or deacetylase activity of SIRT3, wherein SIRT3 deacetylates AceCS2, and wherein the individual having the ketogenic condition is treated. The agent that increases a level or deacetylase activity of SIRT3 is obtained or is obtainable using a screening method of the present invention.

In another embodiment of the present invention, the method for the treatment of an individual having a ketogenic condition comprises the step of administering to an individual having a ketogenic condition a therapeutically effective amount of an agent that increases a level, acetylation status, or activity of AceCS2, wherein the individual having the ketogenic condition is treated. The agent that increases a level, acetylation status, or activity of AceCS2 is obtained or is obtainable using a screening method of the present invention.

In another preferred embodiment, the method for the treatment of an individual having a ketogenic condition comprises the step of administering a pharmaceutical composition to the individual; wherein the pharmaceutical composition comprises a biologically active agent obtainable according to a subject method for identifying such an agent and wherein the ketogenic condition is treated.

A preferred agent for the treatment of a ketogenic condition, and in particular for reducing a higher than normal level of acetate in the blood of an individual, is an agent which increases the affinity of AceCS2 for acetate, i.e., an agent that lowers the $K_m$.

Without being bound by theory, it is believed that increased mitochondrial AceCS2 activity can funnel acetate towards oxidation and away from cytosolic AceCS1 and might therefore reduce AceCS1-mediated lipid and cholesterol synthesis, thereby improving conditions, including, but not limited to, hypercholesterolemia, hyperlipidemia, obesity, and possibly type II diabetes.

Treatment of a ketogenic condition as described herein may result in a lower level of acetate in the bloodstream of an individual. Thus, treatment of a ketogenic condition as described herein can be monitored by measuring the acetate level in the blood of an individual treated according to the present invention.

Preferably the elevated acetate level in the blood of an individual being diagnosed with a ketogenic condition is reduced by at least about 10%, at least about 20%, at least about 30%, at least about 40%, at least about 50%, at least about 60%, at least about 70%, at least about 80%, at least about 90% or more relative to the elevated acetate level in the individual prior to the treatment. Preferably the elevated acetate level in the patient is reduced to the level of acetate in the blood of a healthy individual.

1. Type II Diabetes

Type II diabetes usually occurs in adulthood and is characterized by a lower than normal insulin level in the blood leading to increased glucose levels in the blood Buckley and Williamson reported that diabetic rats also have an elevated blood acetate concentration (Buckley and Williamson, 1977, *Biochem J* 166:5239-545). In addition, Fujino et al. reported that the level of AceCS2 mRNA in Zucker diabetic rats is increased (Fujino et al., 2001, *J Biol Chem* 276:11420-11426).

Thus, in one aspect, the present invention provides a method for the treatment of type II diabetes. In a preferred embodiment, this method comprises the step of administering to an individual having type II diabetes a therapeutically effective amount of an agent that increases a level or deacetylase activity of SIRT3, wherein SIRT3 deacetylates AceCS2, and wherein the individual having type II diabetes is treated. The agent that increases a level or deacetylase activity of SIRT3 is obtained or is obtainable using a screening method of the present invention.

In another embodiment of the present invention the method for the treatment of type II diabetes comprises the step of administering to an individual having type II diabetes a therapeutically effective amount of an agent that increases a level, acetylation status, or activity of AceCS2, wherein the individual having type II diabetes is treated. The agent that increases a level, acetylation status, or activity of AceCS2 is obtained or is obtainable using a screening method of the present invention.

Optionally, methods for treating diabetes comprise the step of administering to an individual an existing hypoglycemic agent, i.e., an agent that lowers circulating glucose concentrations. While current agents for treating type 2 diabetes may lower blood glucose levels without correcting underlying biochemical defects in this disease, it may be desirable in certain instances to combine an agent identified herein with an existing hypoglycemic agent. Such agents are known in the art and, for example, include (i) an agent of the sulfonylurea class, (ii) an agent of the more recently developed non-sulfonylurea class of agents that close the potassium/ATP channel, (iii) an agent that supplies substrates for mitochondrial metabolism (e.g., KCl, α-ketoisocaproic acid or leucine), insulin sensitizers (e.g., thiazolidinediones), inhibitors of hepatic glucose output (e.g., metformin) or (iv) glucose uptake blockers (e.g., acarbose).

2. Hypercholesterolemia

Hypercholesterolemia refers to an abnormally high concentration of cholesterol in the bloodstream. In individuals suffering from hypercholesterolemia the high levels of cholesterol can lead to heart disease, hardening of the arteries, heart attacks, and strokes. For total cholesterol, a blood cholesterol level of more than 240 mg/dL is considered abnormally high. A blood cholesterol level of between 200 and 239 mg/dL is considered borderline high. A blood cholesterol level of below 200 mg/dL is desirable.

Also individuals having familial hypercholesterolemia can be treated with agents identified herein. Affected people have consistently high levels of low-density lipoprotein (LDL or "bad" cholesterol), which leads to premature atherosclerosis of the coronary arteries. Typically in affected men, heart attacks occur in their 40s to 50s, and 85% of men with this disorder have experienced a heart attack by age 60. The incidence of heart attacks in women with this disorder is also increased, but happens 10 years later than in men.

Thus, in one aspect, the present invention provides a method for the treatment of hypercholesterolemia. In a preferred embodiment, this method comprises the step of administering to an individual having hypercholesterolemia a therapeutically effective amount of an agent that increases a level or deacetylase activity of SIRT3, wherein SIRT3 deacetylates AceCS2, and wherein the individual having hypercholesterolemia is treated. The agent that increases a level or deacetylase activity of SIRT3 is obtained or is obtainable using a screening method of the present invention.

In another embodiment of the present invention the method for the treatment of hypercholesterolemia comprises the step of administering to an individual having hypercholesterolemia a therapeutically effective amount of an agent that increases a level, acetylation status, or activity of AceCS2, wherein the individual having hypercholesterolemia is treated. The agent that increases a level, acetylation status, or activity of AceCS2 is obtained or is obtainable using a screening method of the present invention.

Treatment of hypercholesterolemia as described herein results in a lower level of cholesterol in the bloodstream of an individual. Preferably the blood cholesterol level is reduced from more than 240 mg/dL to a level of between 200 and 239 mg/dL, more preferably to a level of below 200 mg/dL.

3. Hyperlipidemia

Hyperlipidemia, also known as hyperlipoproteinemia, is a lipid disorder characterized by a high level of fatty substances, such as cholesterol and triglycerides, in the blood. Individuals suffering from hyperlipidemia are more likely to develop atherosclerosis and heart disease. For example, triglyceride levels of less than 150 mg/dL are considered normal, triglyceride levels of between 150-199 mg/dL are considered borderline high, triglyceride levels of between 200-499 mg/dL are considered high, and triglyceride levels of 500 mg/dL or above are considered very high.

Thus, in a further aspect, the present invention provides a method for the treatment of hyperlipidemia. In a preferred embodiment, this method comprises the step of administering to an individual having hyperlipidemia a therapeutically effective amount of an agent that increases a level or deacetylase activity of SIRT3, wherein SIRT3 deacetylates AceCS2, and wherein the individual having hyperlipidemia is treated. The agent that increases a level or deacetylase activity of SIRT3 is obtained or is obtainable using a screening method of the present invention.

In another embodiment of the present invention the method for the treatment of hyperlipidemia comprises the step of administering to an individual having hyperlipidemia a therapeutically effective amount of an agent that increases a level, acetylation status, or activity of AceCS2, wherein the individual having hyperlipidemia is treated. The agent that increases a level, acetylation status, or activity of AceCS2 is obtained or is obtainable using a screening method of the present invention.

Treatment of hyperlipidemia as described herein results in a lower level of triglycerides in the bloodstream of an individual. Preferably the blood cholesterol level is reduced from a level of above 500 mg/dL to a level of between 200 and 499 mg/dL, more preferably to a level of between 150 and 199 mg/dL, and most preferably to a level of below 150 mg/dL.

4. Obesity

Obesity is defined as BMI (body mass index) over 30 $kg/m^2$. Patients with a BMI between 25 and 29.9 are considered overweight, but not obese. A BMI of between 18.5 and 24.9 is considered normal and a BMI of 18.5 or less would be considered underweight. More than half of the U.S. population is overweight and rates of obesity are climbing. Obesity increases a person's risk of illness and death due to diabetes, stroke, coronary artery disease, hypertension, high cholesterol, and kidney and gallbladder disorders. Obesity may increase the risk for some cancer and is also a risk factor for the development of osteoarthritis and sleep apnea.

Thus, in a another aspect, the present invention provides a method for the treatment of obesity. In a preferred embodiment, this method comprises the step of administering to an individual being diagnosed with obesity a therapeutically effective amount of an agent that increases a level or deacetylase activity of SIRT3, wherein SIRT3 deacetylates AceCS2, and wherein the individual being diagnosed with obesity is treated. The agent that increases a level or deacetylase activity of SIRT3 is obtained or is obtainable using a screening method of the present invention.

In another embodiment of the present invention the method for the treatment of obesity comprises the step of administering to an individual being diagnosed with obesity a therapeutically effective amount of an agent that increases a level, acetylation status, or activity of AceCS2, wherein the individual being diagnosed with obesity is treated. The agent that increases a level, acetylation status, or activity of AceCS2 is obtained or is obtainable using a screening method of the present invention.

Treatment of obesity as described herein results in a lower BMI. Preferably the BMI is reduced from a level of above over 30 $kg/m^2$ to a level of between 25 and 29.9 $kg/m^2$, more preferably to a level of between 18.5 and 24.9 $kg/m^2$.

V. Pharmaceutical Compositions

In one aspect, the present invention provides a pharmaceutical composition or a medicament comprising at least an agent that modulates the level, acetylation status or activity of AceCS2 and a pharmaceutically acceptable carrier. In a preferred embodiment, the agent increases the level, or activity of a AceCS2 or reduces the acetylation status of AceCS2.

In another aspect, the present invention provides a pharmaceutical composition or a medicament comprising at least an agent that increases the level or activity, preferably the deacetylase activity of SIRT3 and a pharmaceutically acceptable carrier.

A pharmaceutical composition or medicament can be administered to a subject for the treatment of, for example, a pathological condition or disease as described herein.

A. Formulation And Administration

Compounds, agents, and small molecules identified by a method of the present invention, are useful in the manufacture of a pharmaceutical composition or a medicament comprising an effective amount thereof in conjunction or mixture with excipients or carriers suitable for either enteral or parenteral application.

A preferred pharmaceutical composition for (i) increasing a level or activity of SIRT3 or (ii) modulating a level, acetylation status, or activity of AceCS2 comprises (i) an agent obtained or obtainable according to a subject screening method described herein, and (ii) a pharmaceutical acceptable carrier. The agent may be provided in a therapeutically effective dose for use in a method for treatment as described herein.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E.W. Martin. Compounds, agents, and small molecules of the present invention and their physiologically acceptable salts and solvates can be formulated for administration by any suitable route, including via inhalation, topically, nasally, orally, parenterally, or rectally. Thus, the administration of the pharmaceutical composition may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices. Transdermal administration is also contemplated, as are inhalation or aerosol administration. Tablets and capsules can be administered orally, rectally or vaginally.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., a small molecule compound of the present invention, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Compounds, agents, and small molecules of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the compounds, agents, and small molecules may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

Suitable formulations for transdermal application include an effective amount of a compound, agent, and small molecules of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The compounds, agents, and small molecules can also be formulated in rectal compositions, for example, suppositories or retention enemas, for example, containing conventional suppository bases, for example, cocoa butter or other glycerides.

Furthermore, the compounds, agents, and small molecules can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

In one embodiment of the present invention, a pharmaceutical composition or medicament comprises an effective amount of an agent that (i) increases a level or activity of SIRT3 or (ii) modulates a level, acetylation status, or activity of AceCS2 as described herein, and another therapeutic agent. When used with a compound, an agent, or small molecule of the present invention, such therapeutic agent may be used individually, sequentially, or in combination with one or more other such therapeutic agents (e.g., a first therapeutic agent, a second therapeutic agent, and a compound of the present invention). Administration may be by the same or different route of administration or together in the same pharmaceutical formulation.

B. Therapeutic Effective Amount and Dosing

In one embodiment of the present invention, a pharmaceutical composition or medicament is administered to a subject, preferably a human or a non-human animal, at a therapeutically effective dose to prevent, treat, or control a pathological condition or disease as described herein. The pharmaceutical composition or medicament is administered to a subject in an amount sufficient to elicit an effective therapeutic response in the subject. An effective therapeutic response is a response that at least partially arrests or slows the symptoms or complications of the pathological condition, disorder, or disease. An amount adequate to accomplish this is defined as "therapeutically effective dose" also referred to as "therapeutically effective amount."

The dosage of active agents administered is dependent on the species of warm-blooded animal (mammal), the body weight, age, individual condition, surface area or volume of the area to be treated and on the form of administration. The size of the dose also will be determined by the existence, nature, and extent of any adverse effects that accompany the administration of a particular small molecule compound in a particular subject. A unit dosage for oral administration to a mammal of about 50 to 70 kg may contain between about 5 and 500 mg of the active ingredient. Typically, a dosage of the active compounds of the present invention, is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies and repetition rates.

The dosage of active agents administered is also dependent on the nature of the agent. For example, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks.

Exemplary doses of small molecules include milligram or microgram amounts of the small molecule per kilogram of subject or sample weight (e.g., about 1 microgram per-kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate a level, acetylation status, or activity of an AceCS2 polypeptide or nucleic acid or in order to activate a level or activity of a SIRT3 polypeptide or nucleic acid, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

In one embodiment of the present invention, a pharmaceutical composition or medicament comprising compounds, agents or small molecules of the present invention is administered in a daily dose in the range from about 1 mg of each compound per kg of subject weight (1 mg/kg) to about 1 g/kg for multiple days. In another embodiment, the daily dose is a dose in the range of about 5 mg/kg to about 500 mg/kg. In yet another embodiment, the daily dose is about 10 mg/kg to about 250 mg/kg. In another embodiment, the daily dose is about 25 mg/kg to about 150 mg/kg. A preferred dose is about 10 mg/kg. The daily dose can be administered once per day or divided into subdoses and administered in multiple doses, e.g., twice, three times, or four times per day. However, as will be appreciated by a skilled artisan, compounds, agents, or small molecules identified by methods of the present invention may be administered in different amounts and at different times. The skilled artisan will also appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments.

To achieve the desired therapeutic effect, compounds, agents or small molecules may be administered for multiple days at the therapeutically effective daily dose. Thus, therapeutically effective administration of compounds to treat a pathological condition or disease described herein in a subject requires periodic (e.g., daily) administration that continues for a period ranging from three days to two weeks or longer. Typically, agents will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every other day, every third day, or, if higher dose ranges are employed and tolerated by the subject, once a week.

Optimum dosages, toxicity, and therapeutic efficacy of such compounds, agents and small molecules may vary depending on the relative potency of individual compounds, agents or small molecules and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While agents that exhibit toxic side effects can be used, care should be taken to design a delivery system that targets such agents to the site of affected tissue to minimize potential damage to normal cells and, thereby, reduce side effects.

The data obtained from, for example, cell culture assays and animal studies can be used to formulate a dosage range for use in humans. The dosage of such small molecule agents lies preferably within a range of circulating concentrations that include the $ED_{50}$ with little or no toxicity. The dosage can vary within this range depending upon the dosage form employed and the route of administration. For any agents used in the methods of the invention, the therapeutically effective dose can be estimated initially from cell culture assays. A dose can be formulated in animal models to achieve a circulating plasma concentration range that includes the $IC_{50}$ (the concentration of the agent that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of agents is from about 1 ng/kg to 100 mg/kg for a typical subject.

Following successful treatment, it may be desirable to have the subject undergo maintenance therapy to prevent the recurrence of the condition or disease treated.

C. Food, Drink, and Feed

Furthermore, the present invention relates to food, drink or feed with an activity to modulate a level, acetylation, or activity of an AceCS2 or with an activity to increase a level or activity of a SIRT3. Such food drink or feed can be produced by a general method for producing foods and drinks or feeds, including, adding an active agent, e.g., an agent that modulates a level, acetylation status, or activity of an AceCS2 or a level or activity of a SIRT3, to a raw or cooked material of the food, drink or feed. The food, drink or feed in accordance with the present invention can be molded and granulated in the same manner as generally used for foods, drinks or feeds.

The concentration of the active agent is preferably 0.001 to 10% by weight, more preferably 0.01 to 10% by weight and most preferably 0.1 to 10% by weight of the food, drink or feed comprising such active agent.

Specific foods or drinks, to which the active agent is added, include, for example, juices, refreshing drinks, soups, teas, sour milk beverages, dairy products such as fermented milks, ices, butter, cheese, yogurt, processed milk and skim milk, meat products such as ham, sausage, and hamburger, fish meat, cereal, bran, cake products, egg products such as seasoned egg rolls and egg curd, confectioneries such as cookie, jelly, snacks, and chewing gum, breads, noodles, pickles, smoked products, dried fishes, soy sauce-seasoned boiled foods and seasonings.

Food, drinks and feed with an activity to modulate a level, acetylation, or activity of an AceCS2 or with an activity to increase a level or activity of a SIRT3 may be further supplemented with a nutritious composition (protein, lipid, saccharide, vitamins and/or mineral).

VI. Kits

For use in diagnostic, research, and therapeutic applications described above, kits are also provided by the present invention. In the diagnostic and research applications such kits may include any or all of the following: assay reagents, buffers, a compound, agent or small molecule of the present invention, a SIRT3 polypeptide, an AceCS2 polypeptide or any other polypeptide described herein, a SIRT3 nucleic acid, an AceCS2 nucleic acid or any other nucleic acid described herein, an anti-SIRT3 antibody, an anti-AceCS2 antibody, an anti-acetyl-lysine antibody, or any other antibody described herein, hybridization probes and/or primers detecting a SIRT3 nucleic acid, an AceCS2 nucleic acid or any other nucleic acid described herein, a SIRT3 expression construct, an AceCS2 expression construct or an expression construct for any other polypeptide described herein, acetate, NAD or any other compound or composition described herein, etc. A therapeutic product may include sterile saline or another pharmaceutically acceptable emulsion and suspension base.

Reference to particular buffers, media, reagents, cells, culture conditions and the like, or to some subclass of the same, is not intended to be limiting, but should be read to include all such related materials that one of ordinary skill in the art would recognize as being of interest or value in the particular context in which they are presented. For example, it is often possible to substitute one buffer system or culture medium for another, such that a different but known way is used to achieve the same goals as those to which the use of a suggested method, material or composition is directed.

Typically, the components of a kit are provided in a container. In a preferred embodiment of the present invention, a kit for increasing a level or activity of a SIRT3 or a kit for modulating a level, acetylation status, or activity of an AceCS2 comprises a container containing an agent obtained or obtainable according to a subject screening method.

In addition, a kit may include instructional materials containing directions (i.e., protocols) for the practice of the methods of this invention. The instructions may be present in the subject kits in a variety of forms, one or more of which may be present in the kit. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

In a preferred embodiment of the present invention, the kit comprises an instruction for contacting the agent to a mammalian cell for increasing a level or activity of a SIRT3 or an instruction for contacting the agent to a mammalian cell modulating a level, acetylation status, or activity of an AceCS2. In a preferred embodiment, an agent stimulates a level, acetylation status, or activity of an AceCS2. In another embodiment, an agent inhibits a level, acetylation status, or activity of an AceCS2

Optionally, the instruction comprises warnings of possible side effects and drug-drug or drug-food interactions.

A wide variety of kits and components can be prepared according to the present invention, depending upon the intended user of the kit and the particular needs of the user.

In a preferred embodiment of the present invention, the kit is a pharmaceutical kit and comprises a pharmaceutical composition comprising (i) an agent that increases a level or activity of a SIRT3, and (ii) a pharmaceutical acceptable carrier. In another preferred embodiment of the present invention, the kit is a pharmaceutical kit and comprises a pharmaceutical composition comprising (i) an agent that modulates a level, acetylation status, or activity of an AceCS2, and (ii) a pharmaceutical acceptable carrier. Pharmaceutical kits optionally comprise an instruction stating that the pharmaceutical composition can or should be used for treating a pathological condition, disorder or disease or any other subject method described herein.

Additional kit embodiments of the present invention include optional functional components that would allow one of ordinary skill in the art to perform any of the method variations described herein.

Although the forgoing invention has been described in some detail by way of illustration and example for clarity and understanding, it will be readily apparent to one of ordinary skill in the art in light of the teachings of this invention that certain variations, changes, modifications and substitutions of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature, including accession numbers to GenBank database sequences, referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As can be appreciated from the disclosure above, the present invention has a wide variety of applications. The invention is further illustrated by the following examples, which are only illustrative and are not intended to limit the definition and scope of the invention in any way.

VII. Examples

Example 1

General Methods

A. Cell Culture and Transfection

HEK293, COS-1 and HeLa cells were cultured in DMEM supplemented with 10% FCS, 2 mM L-glutamine, 100 U/mL penicillin, and 100 μg/mL streptomycin and grown in 5% $CO_2$ at 37° C. Calcium phosphate transfection was used to transfect HEK293 cells (Chen & Okayama, 1987, *Mol Cell Biol* 7:2745-52). Hela and Cos-1 cells were transfected with Fugene 6 (Roche). HEK293 cell lines stably expressing AceCS2$^{Flag}$, SIRT3$^{Flag}$, SIRT3-H248Y$^{Flag}$ or SIRT5$^{Flag}$ or containing the empty $^{Flag}$-control vector pcDNA$^{Flag}$ were generated by selection in complete DME growth medium containing 800 μg/mL geneticin (Invitrogen).

B. Plasmids and Mutagenesis

All expression constructs were generated using PCR-based standard cloning strategies and all expression constructs were verified by DNA sequencing. The human AceCS2 coding sequence was PCR amplified from human full-length Mammalian Gene Collection (MGC) cDNA (Genbank accession number BC039261; obtained through Open Biosystems) using the PCR primers 5'-CGGAATTCCATGGCGGCGCGCACCCTGGGC-3' (SEQ ID NO:15) and 5'-CGGAATTCCTTAGCAGCAGCCTGCTTGTCCTTGC-3' (SEQ ID NO: 16) (each comprising an EcoRI restriction site (underlined)). The PCR product was then cloned into the pcDNA3.1+ (Invitrogen)-derived vectors pcDNA$^{Flag}$ or pcDNA$^{HA}$ to yield AceCS2 with a C-terminal Flag- or hemagglutinin (HA)-tag. Based on N-terminal protein sequencing results, the open reading frame corresponding to mature AceCS2 (amino acid residues 38 to 689) was cloned into pTrcHis2C (Invitrogen). Recombinant expression vectors encoding mature human SIRT3 (amino acid residues 102-

399, (Schwer et al., 2002, *J Cell Biol* 158:647-57) or SIRT5 (amino acid residues 12-310 or amino acid residues 39-310) were constructed by PCR amplification and cloning into pTrcHis2C. The templates used for PCR amplification of the SIRT3 and SIRT5 coding sequences were as described (Schwer et al., 2002, *J Cell Biol* 158:647-57; North et al., 2003, *Mol Cell* 11437-44). Primers for the PCR amplification other than those described herein, can be deduced by one of ordinary skill in the art from corresponding nucleic acid sequences deposited at GenBank and described herein.

Site-directed mutagenesis (QuickChange™ Mutagenesis Kit; Stratagene) was used to construct AceCS2-K642Q$^{HA}$, pTrcHis2C-AceCS2-K642R and pTrcHis2C-SIRT3-H248Y (102-399).

C. Expression and Purification of Recombinant Proteins

*E. coli* DH5α bacteria (Invitrogen) transformed, e.g., with either pTrcHis2C-SIRT3(102-399), pTrcHis2C-SIRT3-H248Y(102-399), pTrcHis2C-SIRT5(12-310), pTrcHis2C-SIRT5(39-310) or pTrcHis2C-AceCS2(38-689) were grown to an A600 nm=0.4, and induced with 0.5 mM isopropyl-β-D-thiogalactopyranoside (IPTG) at 25° C. for 16 h. 6×His-tagged proteins were purified under native conditions at 4° C. using Ni-NTA agarose (Qiagen, Valencia, Calif.). Purified proteins were dialyzed (e.g., against sirtuin storage buffer mM Tris-HCl (pH 9.0), 4 mM $MgCl_2$, 50 mM NaCl, 0.5 mM DTT, 5% glycerol (v/v) or AceCS2 storage buffer [50 mM Tris-HCl (pH 8.0), 4 mM $MgCl_2$, 10% glycerol (v/v)], adjusted to 0.5 g/L and stored frozen at −80° C. To induce acetylation of recombinant AceCS2, nicotinamide (50 mM) was added during protein expression (16 h, 25° C.).

Parental *E. coli* K-12 BW25113 and a CobB-deficient single-gene knockout (KO) mutant (JW1106) of the same strain (Datsenko & Wanner, 2000, *Proc Natl Acad Sci USA* 97:6640-5) were obtained from the *Systematic Knock Out Strains of E. coli K*-12 *Collection* of GenoBase. The CobB-deficient KO mutant was colony-purified once non-selectively at 37° C. and then tested for ampicillin sensitivity to test for loss of the ampicillin-resistance conferring helper plasmid used in the single-gene knockout procedure (Datsenko & Wanner, 2000, *Proc Natl Acad Sci USA* 97:6640-5). Ampicillin-sensitive colonies were expanded, made chemically competent (Sambrock and Russell, 2001, in Molecular Cloning: A Laboratory Manual (Cold Spring Harbor Laboratory Press, Cold Spring Harbor), Vol. 1, pp. 1.116-1.118) and transformed with pTrcHis2C-AceCS2(38-689) or pTrcHis2C-AceCS2-K642R(38-689), which contain an ampicillin-resistance gene. 6×His-tagged proteins were expressed and purified as described above.

D. Antibodies

Antibodies used for immunoblotting and immunoprecipitations were anti-mtHsp70 (Clone JGI; Affinity Bioreagents, Neshanic Station, N.J.), anti-Hsp90α (StressGen) and anti-manganese superoxide dismutase (MnSOD) (StressGen Biotechnologies, Victoria, Canada), anti-cytochrome c oxidase subunit IV (Clone 20E8-C12; Molecular Probes), anti-Flag M2 or rabbit polyclonal anti-Flag (Sigma-Aldrich), anti-HA (12CA5 and 3F10; Roche Diagnostics), acetylated-lysine polyclonal antibody (Cell Signaling Technology, Beverly, Mass.), anti-actin C4 (ICN Biomedicals), anti-cytochrome c (clone 7H8.2; C12; Pharmingen), anti-BRG-1 (H88; Santa Cruz Biotechnology) and anti-c-myc (9E10; Santa Cruz Biotechnology). SIRT3 antiserum was raised as described (Schwer et al., 2002, *J Cell Biol* 158:647-57).

E. SDS-PAGE and Western Blotting

Immunoblots were developed with enhanced chemiluminescence (Amersham Pharmacia Biosciences) or West Super-Signal reagent (Pierce). Membranes were either nitrocellulose or polyvinylidene fluoride (PVDF) (Immun-Blot; Bio-Rad Laboratories).

F. Immunoprecipitation

Cells were lysed in ice-cold NP1 buffer (1% NP-40, 150 mM NaCl, 0.5 mM EDTA, 50 mM Tris-HCl, pH 7.4) containing protease inhibitor cocktail (Roche). Lysates were centrifuged at 16,200×g for 10 min at 4° C., and anti-FLAG monoclonal antibody M2 covalently coupled to agarose was added. Flag-tagged proteins were immunoprecipitated and washed four times in NP1 buffer.

In co-immunoprecipitation experiments, NP1 buffer containing 300 mM NaCl was used. Immunoprecipitated Flag-tagged sirtuins to be used in deacetylation assays were washed three times in NP1 buffer containing 500 mM NaCl and twice in sirtuin deacetylase buffer (SDAC) (50 mM Tris-HCl (pH 9.0), 4 mM $MgCl_2$, 50 mM NaCl, 0.5 mM DTT). Flag-tagged proteins were eluted from the beads into SDAC buffer with Flag-peptide (Sigma) for 1 h at 4° C.

G. Confocal Microscopy

HeLa cells were grown on coverslips, transfected with Fugene 6 (Roche) and 48 h later fixed in 3.7% formaldehyde/PBS. Cells were permeabilized with 05% Triton X-100/PBS for 5 min at room temperature (Schwer et al., 2002, *J Cell Biol* 158:647-57). Cells were blocked with 1% bovine serum albumin and co-stained with monoclonal anti-Flag M2 (1:500) and polyclonal anti-MnSOD (1:300) antibodies, followed by incubation with anti-mouse-Cy2-conjugated anti-mouse immunoglobulin G and Cy5-conjugated anti-rabbit immunoglobulin G secondary antibodies suitable for multi-labeling experiments (Jackson ImmunoResearch Laboratories). Coverslips were mounted on glass slides and images were acquired on a BioRad Radiance 2000 laser scanning microscope equipped with an Olympus Bx60 microscope and an Olympus PlanApo 60×/1.40 oil objective.

H. Subcellular Fractionation and Submitochondrial Localization

Subcellular fractionation was performed as described (Schwer et al., 2002, *J Cell Biol* 158:647-57; Yang et al., 1997, *Science* 275:1129-32). All steps were performed at 4° C. In brief, cells were homogenized in ice-cold buffer A (250 mM sucrose, 10 mM KCl, 1.5 mM $MgCl_2$, 1 mM EDTA, 1 mM EGTA, 1 mM dithiothreithol, 0.1 mM phenylmethylsulfonyl fluoride, 20 mM Hepes-KOH, pH 7.5) and homogenized in a Dounce homogenizer (Wheaton). Homogenization was checked by phase-contrast microscopy. The homogenate was centrifuged twice for 5 min at 960×g to remove all nuclei and unbroken cells. Mitochondria were isolated by centrifugation (7,000×g, 15 min) washed twice with buffer A, and finally lysed in NP1/150 buffer (1% NP-40 (v/v), 150 mM NaCl, 0.5 mM EDTA, 50 mM Tris-HCl, pH 7.4) supplemented with protease inhibitors. The postmitochondrial supernatant was fractionated into a light-membrane fraction (LM, pellet) and a cytosolic fraction (S-100, supernatant) by ultracentrifugation at 100,000×g for 30 min. The protein concentration of each fraction was determined (DC Protein Assay Bio-Rad Laboratoroies) and equal amounts of each fraction were analyzed by immunoblotting.

Mitoplast formation and protease accessibility experiments were performed according to published protocols (Schwer et al., 2002, *J Cell Biol* 158:647-57; Ryan et al., 2001, in *Mitochondria*, eds. Pon & Schon (Academic Press, Vol. 65, pp. 190-213). Mitoplasts were treated with proteinase K (150 μg/mL) for 15 min at 0° C. Protease digestion was stopped by adding 2 mM PMSF, and mitoplasts were reisolated by centrifugation, washed, and lysed in sample buffer.

Fractionation of mitochondrial proteins by alkaline treatment was performed as described (Schwer et al., 2002, *J Cell Biol* 158:647-57; Fujiki et al., 1982, *J Cell Biol* 93:97-102). Washed mitochondrial pellets were resuspended in freshly prepared 0.1 M sodium carbonate (pH 11.5) at 250 μg/mL and incubated at 0° C. for 30 min. Mitochondrial membranes were sedimented by ultracentrifugation (100,000×g, 30 min, 4° C.). The pellet was resuspended in SDS sample buffer, and soluble proteins in the supernatant were concentrated by trichloroacetate precipitation and resuspended in SDS sample buffer (Schwer et al., 2002, *J Cell Biol* 158:647-57; Fujiki et al., 1982, *J Cell Biol* 93:97-102).

I. N-Terminal Protein Sequencing

HEK293 cells stably expressing AceCS2$^{Flag}$ were lysed and subject to anti-Flag immunoprecipitation. After washing, immunoprecipitated AceCS2 μg was subjected to SDS-PAGE, transferred to poly(vinylidene difluoride) (PVDF) membrane, visualized by Ponceau S staining (Sigma), cut and submitted to the Stanford PAN Facility for N-terminal sequencing by Edman degradation according to standard protocols.

J. Protein Enzymatic Assays

1. In Vitro Deacetylation Assays

Equimolar amounts of purified recombinant AceCS2 and purified recombinant sirtuins were incubated in SDAC deacetylation buffer (50 mM Tris-HCl (pH 9.0), 4 mM $MgCl_2$, 50 mM NaCl, 0.5 mM DTT) in the presence or absence of $NAD^+$ (1 mM), in the presence or absence of nicotinamide (NAM, 10 mM), in the presence of trichostatin A (500 nM) for 3 h at 32° C. For time course deacetylation experiments, aliquots of the deacetylation reaction were removed at the indicated time points, mixed with 10 mM nicotinamide and incubated on ice until further analysis. Reactions were analyzed by SDS-PAGE and immunoblotting.

2. Acetyl-CoA Synthetase Activity

The activity of purified AceCS2 was measured as described (Jones & Lipmann, 1955, in *Methods in Enzymology* (Academic Press, Vol. 1, pp. 585-591; Barak et al., 2004, *J Mol Biol* 342:383-401). Each reaction (0.5 mL) contained 100 mM hydroxylamine (pre-neutralized with KOH), 50 mM Tris-HCl (pH 8.0), 20 mM potassium acetate, 10 mM $MgCl_2$, 10 mM ATP, 2 mM DTT and 1 mM CoA. All chemicals (Sigma) were of the highest purity available. Reactions were pre-incubated at 35° C. for 5 min before the addition of purified AceCS2 (6 μg). After 30 min of incubation, 0.5 mL stop solution (10% (w/v) $FeCl_3$, 3.3% (w/v) trichloroacetic acid in 2 N HCl) were added and reactions were incubated on ice for 2 min. The samples were centrifuged for 2 min at 16,200×g to remove turbidity and the generated color was measured at 540 nm. Samples without AceCS2 served as a blank and formation of acetylhydroxamate by acetyl-phosphate (Sigma) served as a standard (Barak et al., 2004, *J Mol Biol* 342:383-401). No acetyl-CoA synthetase activity was detectable in the absence of CoA.

K. SiRNA Inhibition—Depletion of SIRT3

Double-stranded siRNAs (100 nM; Dharmacon; Individual siGENOME duplex D-004827-04-0050, Human SIRT3, NM_012239) directed against human SIRT3 or firefly luciferase GL3 control siRNAs were transfected into HEK293 using oligofectamine (Invitrogen) according to the manufacturer's recommendations. Five days after transfection, cells were lysed in NP1/300 buffer containing protease inhibitors, 1 μM TSA and 10 mM nicotinamide. AceCS2$^{Flag}$ was immunoprecipitated and prepared for mass spectrometry.

The sequence of SIRT3 siRNA duplex was as follows:

```
Sense Sequence:
5'-GGAGUGGCCUGUACAGCAAUU-3'     (SEQ ID NO: 17)

Antisense Sequence:
5'-UUGCUGUACAGGCCACUCCUU-3'     (SEQ ID NO: 18)
```

Oligonucleotides used in siRNA experiments may be phosphorylated at their 5' ends.

Luciferase GL3 duplex D-001400-01-20 is described in Elbashir et al, "Duplexes of 21-nucleotide RNAs mediate RNA interference in cultured mammalian cells." *Nature* 411: 494-498 (2001).

L. Nanoscale Liquid Chromatography Mass Spectrometry

Immunoprecipitates were separated by SDS-PAGE and in-gel digestion was performed essentially as described (Hojrup, 2004, *Methods Mol Biol* 251:227-44). The tryptic digests were separated by reversed phase chromatography using an Agilent 1100 nanoflow system (Agilent Technologies, Palo Alto, Calif.) and electrosprayed directly into a 7-tesla Finnigan LTQ-FT mass spectrometer (Thermo Electron, Breme, Germany) equipped with a nanoelectrospray ion source (Proxeon Biosystems, Odense, Denmark). A 15-cm home-pulled fused silica emitter (75 μm inner diameter) packed with ReproSil-Pur C18-AQ 3 μm resin (Dr. Maisch GmbH, Ammerbuch-Entringen, Germany) served as reversed phase column. The protein digests were injected onto the column with a flow of 500 nl/min and subsequently eluted with a flow of 250 nl/min with a gradient from 5-40% MeCN in 0.5% acetic acid. For the initial analysis the mass spectrometer was opened in a data-dependent mode essentially as described (Olson and Mann, 2004, *Proc Natl Acad Sci USA* 101:13417-22). Briefly, a survey MS spectrum of the mass range m/z 300-1600 was acquired by Fourier transform ion cyclotron resonance (FTICR; resolution 50,000 at m/z 400) and the three most intense ions were selected for accurate mass determination using a selected ion monitoring (SIM) scan in the FTICR, while MS/MS and MS/MS/MS was performed using the linear ion trap.

Directed experiments of selected ions were performed using FTICR SIM scan at the m/z range of interest followed by $MS^2$ and $MS^3$ of predetermined m/z values. The centroided and merged MS/MS spectra were searched against the Uniprot database using the MASCOT search engine (Matrix Science, Boston) with a peptide mass tolerance of 5 ppm and fragment ion tolerance of 0.6Da. Carbamidomethylation of cysteines was set as a fixed modification while N-terminal protein acetylation, methionine oxidation and lysine acetylation were allowed as variable modifications. Peptides were required to be tryptic with at the most 3 missed cleavage sites. All identified peptides were manually validated using both the $MS^2$ and $MS^3$ spectra.

Example 2

Identification of Acetyl-CoA Synthetase (AceCS2) as a Cellular Target for SIRT3

As a strategy to identify lysine acetylated mitochondrial proteins that could be targeted by SIRT3, 4 or 5, a search for human proteins with sequence similarity to the region surrounding the acetylated lysine residue found in acetyl-CoA synthetase (ACS) from *Salmonella enterica* was performed. The acetyl-lysine containing region of *Salmonella enterica* ACS was chosen because it is a known substrate for the sirtuin CobB (Starai et al., 2003, *Genetics* 163:545-55; Starai et al., 2002, *Science* 298:2390-2). In a second step, human proteins showing high similarity were analyzed for their mitochondrial localization probability using MITOPROT II and PREDOTAR Ver. 1.03 subcellular prediction software (Small et al., 2004, *Proteomics* 4:1581-90; Claros and Vincens, 1996, *Eur J Biochem* 241:779-86). The search yielded a human acetyl-CoA synthetase protein with a high probability of being localized to mitochondria (MITOPROT II: 0.997; PREDOTAR: 0.94; max. score=1), which displayed high sequence similarity to the murine acetyl-CoA synthetase, AceCS2 (Claros and Vincens, 1996, *Eur J Biochem* 241:779-86).

Example 3

Identification of Mitochondrial Localization for AceCS2

To test whether the human AceCS2 enzyme is a mitochondrial protein, the open reading frame of human AceCS2 was cloned and expressed in HeLa cells as a Flag-tagged protein. Confocal laser scanning microscopy showed a mitochondrial staining pattern for AceCS2$^{Flag}$ that overlapped with the staining pattern observed for the endogenous mitochondrial matrix protein manganese superoxide dismutase (MnSOD; FIG. 1A).

To further verify the mitochondrial localization of human AceCS2, subcellular fractions were prepared from human embryonic kidney 293 (HEK293) cells stably expressing AceCS2$^{Flag}$. AceCS2$^{Flag}$ was detected in the mitochondrial fraction along with SIRT3 and MnSOD, as expected (FIG. 1B). Immunoblotting of each fraction for the nuclear marker protein BRG-1 and the cytosolic marker protein Hsp90α confirmed the purity of the fractions (FIG. 1B).

To further define the submitochondrial localization of AceCS2, mitoplasts were prepared from mitochondria containing AceCS2. Mitoplast preparation ruptures the outer mitochondrial membrane and makes the intermembrane space accessible to proteinase K. Treatment of mitoplasts with proteinase K led to a loss of the intermembrane space protein cytochrome c (Cyt. c), while it did not affect the mitochondrial matrix proteins glutamate dehydrogenase (GDH) and SIRT3 (FIG. 1C). AceCS2$^{Flag}$ was also not affected by proteinase K treatment of mitoplasts, suggesting that it was localized in the mitochondrial matrix, like GDH and SIRT3 (FIG. 1C). All proteins were completely digested by proteinase K when the non-ionic detergent TX-100 was added during the incubation of the mitoplasts with proteinase K (FIG. 1C; left lane).

To determine whether AceCS2 is integrally attached to the inner side of the inner mitochondrial membrane or soluble in the mitochondrial matrix, mitochondria were extracted with sodium carbonate (pH 11.5). This treatment releases soluble proteins but not integral membrane proteins. AceCS2 was completely released by sodium carbonate treatment and exhibited a distribution pattern like the soluble matrix proteins SIRT3 and MnSOD (FIG. 1D). Under the conditions used, the integral membrane protein COX-IV stayed associated with the membranes (FIG. 1D).

Example 4

N-Terminal Sequencing of AceCS2

Figure 2:
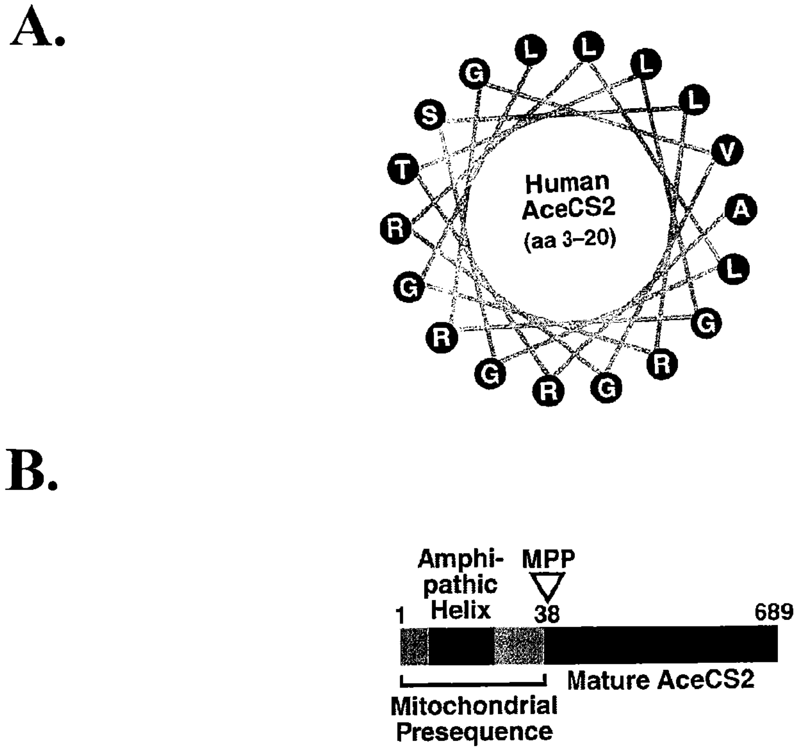
FIG. 2 shows the identification of the N-terminal sequence of human AceCS2. (A) The N-terminus of human AceCS2 contains an amphipathic α-helix. A region of AceCS2 (amino acid residues 3-20; SEQ ID NO:2) predicted by computational secondary structure analysis to form an α-helix was plotted as a helical wheel. R, basic residues; T, L, V, and A, hydrophobic residues; G and S, neutral residues. (B) Illustration of the mitochondrial presequence and cleavage site of human AceCS2 as determined by N-terminal protein sequencing and LC/MS-MS analysis. MPP, mitochondrial matrix processing peptidase. Details are presented in Example 4.

Nuclear-encoded proteins destined for the mitochondrial matrix often carry an N-terminal presequence, which is recognized by the mitochondrial translocase of the outer membrane (TOM) complex and is cleaved off after import into the matrix (Rehling et al., 2004, *Nat Rev Mol Cell Biol* 5:519-30). This N-terminal presequence often contains an α-helix and several basic residues. These characteristics are found in the N-terminus of human AceCS2, including several arginine residues (FIG. 2A).

N-terminal sequencing of immunoprecipitated AceCS2$^{Flag}$ by Edman degradation revealed that the first 37 amino acid residues of the open reading frame were missing from the protein, consistent with N-terminal processing of AceCS2 in the mitochondrial matrix. The identification of alanine 38 as the N-terminal amino acid of immunoprecipitated AceCS2$^{Flag}$ by liquid chromatography coupled tandem mass spectrometry (LC-MS/MS) confirmed the protein sequencing results (data not shown). The existence of a mitochondrial matrix processing peptidase (MPP) R-2 motif immediately upstream of the N-terminus of the mature AceCS2 protein suggests that AceCS2 is processed by MPP in the mitochondrial matrix FIG. 2B; Ito, 1999, *Biochem Biophys Res Commun* 265:611-6). These findings confirm the existence of a human mitochondrial acetyl-CoA synthetase located in the mitochondrial matrix.

Example 5

Mutation of the Conserved Lys642 Amino Acid Residue Abolishes AceCS2 Enzymatic Activity Based on the conservation of the active site region of *Salmonella enterica* ACS with human and murine AceCS2 and acetyl-CoA synthetases from other species (FIG. 3A), it was tested whether mutation of Lys642 would affect the acetyl-CoA synthetase activity of overexpressed human AceCS2 immunoprecipitated from HEK293 cells. Replacement of Lys642 with glutamine, which mimics a constitutively acetylated lysine residue, yielded a completely inactive AceCS2 protein (FIG. 3B), indicating that Lys642 is of critical importance for AceCS2 function. Both wild-type AceCS2 and mutant AceCS2-K642Q were expressed at similar levels (FIG. 3C).

Example 6

Human AceCS2 is Acetylated In Vivo

Figure 4:
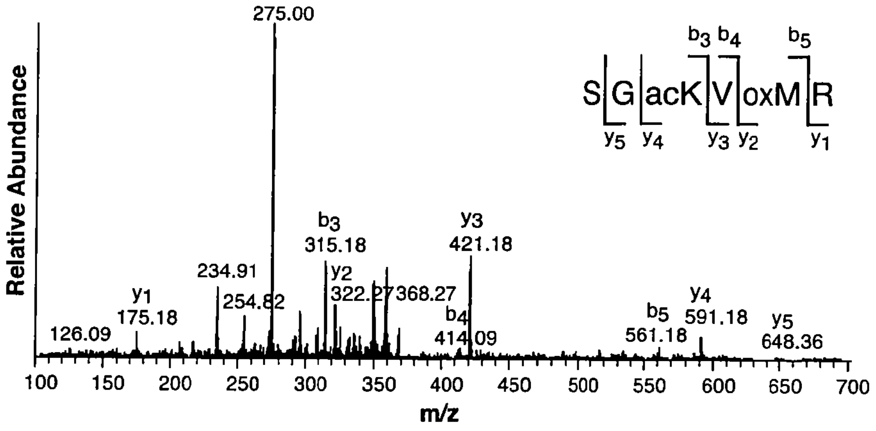
FIG. 4 shows that human AceCS2 is acetylated in vivo at Lys642. HEK293 cells stably expressing AceCS2$^{Flag}$ were transfected with SIRT3-specific siRNAs and AceCS2FLAG was immunoprecipitated five days later. Immunoprecipitated AceCS2$^{Flag}$ was separated by SDS-PAGE and prepared for mass spectrometry. Liquid chromatography coupled tandem mass spectrometry (LC/MS-MS) was performed on tryptic digests to identify lysine acetylation sites. acK, acetylated lysine. SGacKVoxMR, SEQ ID NO:8. Details are presented in Example 6.
Figure 5:
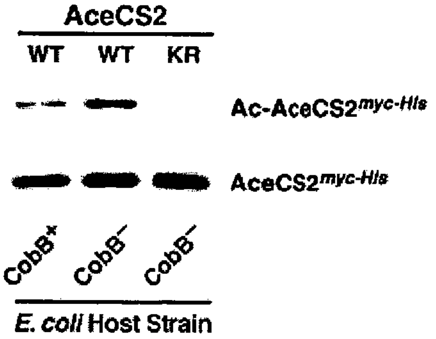
FIG. 5 shows that human AceCS2 expressed in *E. coli* lacking the sirtuin CobB gene or protein is hyperacetylated. (A) Removal or inhibition of the bacterial sirtuin CobB results in hyperacetylation of the active site lysine of human AceCS2 in bacteria. Knockout mutant or wild-type *E. coli* K-12 were used to express C-terminally myc-His-tagged recombinant human AceCS2 (AceCS2:KR). Equal amounts of purified recombinant human myc-His-tagged AceCS2 (WT) or AceCS2-K642R (KR) from $CobB^-$ or $CobB^+$ *E. coli* were analyzed by immunoblotting with an acetyl-lysine-specific antibody (Ac-AceCS2$^{myc\text{-}His}$). Blots were stripped and reprobed with α-myc antibodies to show total levels of AceCS2 (AceCS2$^{myc\text{-}His}$). (B) The anti-acetyl-lysine antibody specifically recognizes a synthetic peptide of AceCS2 containing an acetylated Lys642 residue (acK642) but does not crossreact with a non-acetylated Lys642 containing peptide (K642). Synthetic peptides (Elim Biopharmaceuticals, Inc., Hayward, Calif.) were coupled to carrier protein CP39 using a peptide coupling kit (NEB). The AceCS2 peptides used were: $NH_2$-CPKTRSG(ac)KVMRRLL-$CONH_2$ (acK642, SEQ ID NO:9) and $NH_2$-CPKTRSGKVMRRLL-$CONH_2$ (K642, SEQ ID NO: 10). The N-terminal cysteine residue was added for coupling purposes. 150 ng of CP39-coupled K642 or acK642 were resolved by SDS-PAGE and analyzed by immunoblotting using a polyclonal anti-acetyl-lysine antibody (Cell Signaling Technology, Beverly, Mass.). Details are presented in Example 7.
Figure 5:
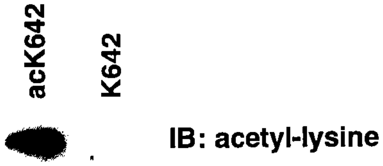
Figure 6:
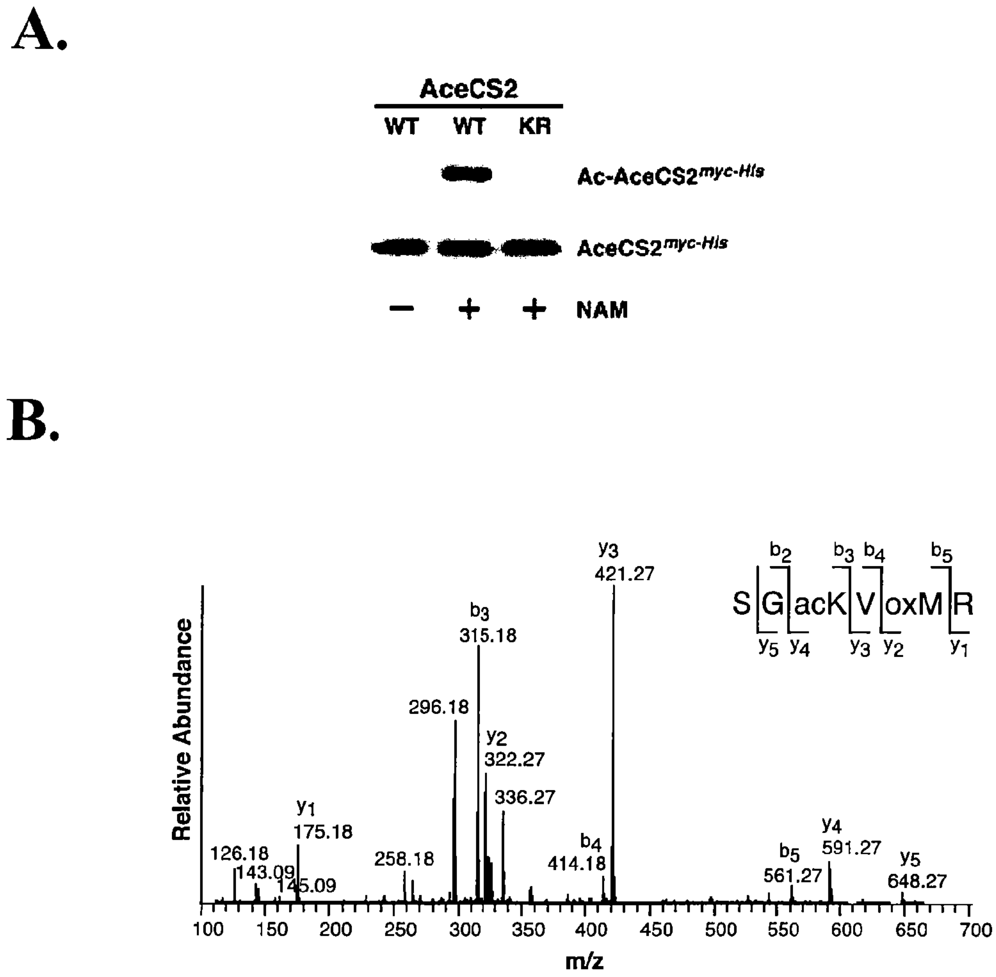
FIG. 6 shows that inhibition of sirtuin activity by nicotinamide (NAM) results in hyperacetylation of recombinant human AceCS2. (A) Inhibition of bacterial sirtuins by nicotinamide during expression of recombinant human AceCS2 protein causes hyperacetylation of human AceCS2 at Lys642. *E. coli* DH5a bacteria were used to express myc-His-tagged AceCS2:WT or AceCS2:KR. Equal amounts of the purified recombinant proteins were analyzed as in (5A). (B) Liquid chromatography coupled tandem mass spectrometry of tryptic digests of recombinant AceCS2:WT purified from nicotinamide-treated *E. coli* confirmed acetylation of Lys642 (acK). The tandem mass spectrum of the doubly charged ion at m/z 368.1948 is shown. SGacKVoxMR, SEQ ID NO:8. Details are presented in Example 8.

To determine whether human AceCS2 is acetylated in vivo, AceCS2$^{Flag}$ was immunoprecipitated from cells after small interfering RNA (siRNA)-mediated knockdown of SIRT3 and prepared for mass spectrometry. LC-MS/MS analysis of the tryptic digests indicated the presence of an acetylated lysine residue (acK) in position 642 of AceCS2 (FIG. 4).

Example 7

Hyperacetylation of Human AceCS2 Expressed in *E. coli* Lacking Sirtuin CobB

Like *Salmonella enterica, E. coli* contain the sirtuin CobB. Given a potentially conserved role for sirtuin-mediated deacetylation in the control of acetyl-CoA synthetase proteins throughout evolution, it was tested whether expression of human AceCS2 in an *E. coli* K-12 strain lacking the sirtuin CobB would induce hyperacetylation of AceCS2. Human AceCS2 purified from a CobB-knockout strain reacted stronger with an acetyl-lysine-specific antibody than AceCS2 purified from the parental CobB wild-type strain (FIG. 5A). This acetylation was specific to AceCS2 Lys642, since a mutation of Lys642 to arginine, which cannot be acetylated, abrogated the reactivity with the anti-acetyl-lysine antibody (FIG. 5A;

right lane). The specificity of the acetyl-lysine-specific antibody was further confirmed by immunoblot analysis of synthetic peptides coupled to a carrier protein (FIG. 5B). The acetyl-lysine-specific antibody only reacted with the peptide containing an acetylated K642 residue and showed no reactivity with the non-acetylated K642-containing peptide (FIG. 5B).

Example 8

Inhibition of Sirtuin Activity by Nicotinamide Results In Hyperacetylation Of Recombinant Human AceCS2

The effect of inhibiting sirtuin activity on the acetylation status of human AceCS2 was examined. Treatment of a wild-type *E. coli* strain (DH5 cc; Invitrogen) with the sirtuin inhibitor nicotinamide resulted in the hyperacetylation of recombinant human AceCS2 (FIG. 6A). This increase in acetylation was specific to Lys642 of AceCS2, since nicotinamide treatment did not induce acetylation of a mutant AceCS2 protein carrying an arginine residue in position 642 (FIG. 6A; right lane). Analysis of purified recombinant AceCS2 from nicotinamide-treated bacteria by LC/MS-MS verified acetylation of a single lysine in the active site of AceCS2, Lys642 (FIG. 6B).

Example 9

Reduction of Endogenous SIRT3 Levels Increases the Acetylation Of AceCS2

Figure 7:
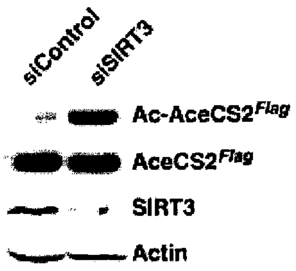
FIG. 7 shows that reduction of endogenous SIRT3 levels by siRNA-mediated knockdown increases the acetylation level of AceCS2$^{Flag}$. Double-stranded siRNAs directed against human SIRT3 (siSIRT3) or firefly luciferase GL3 (siControl) were transfected into HEK293 cells stably expressing AceCS2. Cells were lysed and acetylation of immunoprecipitated AceCS2$^{Flag}$ was analyzed by immunoblotting with antibodies to acetylated lysine (Ac-AceCS2$^{Flag}$). Membranes were stripped and reprobed for total AceCS2 amounts (AceCS2$^{Flag}$). Immunoblotting of total cell extracts with anti-SIRT3 and anti-actin antibodies confirmed the efficiency and specificity of the siRNA treatment. Details are presented in Example 9.
Figure 8:
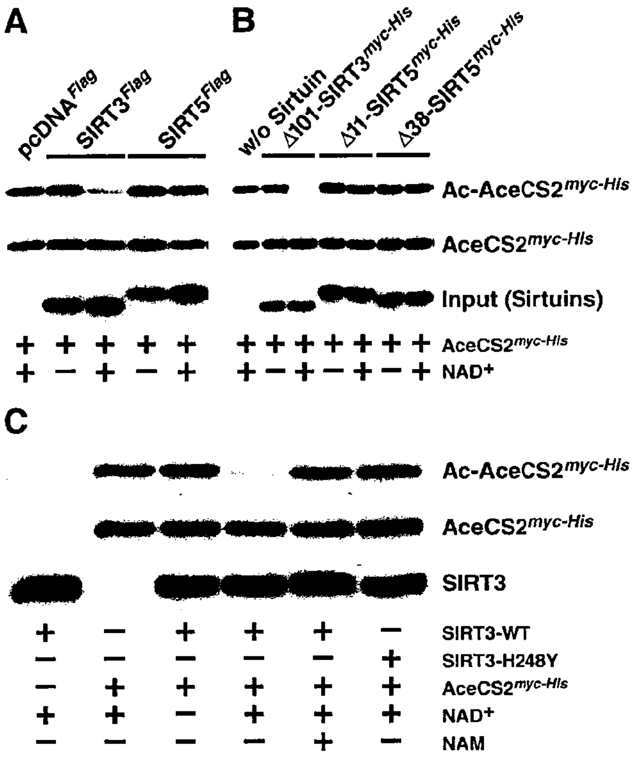
FIG. 8 shows that SIRT3 but not SIRT5 deacetylates AceCS2 in vitro. (A) Recombinant human AceCS2$^{myc\text{-}His}$ purified from nicotinamide-treated *E. coli* was incubated with Flag-tagged SIRT3 or SIRT5 immunoprecipitated from HEK293 cells. As a control, anti-Flag immunoprecipitates from pcDNA$^{Flag}$ expressing HEK293 cells were used in the reactions (left lane). Deacetylation reactions were incubated for 3 h at 32° C. in the presence or absence of nicotinamide adenine dinucleotide ($NAD^+$; 1 mM). All reactions were carried out in the presence of trichostatin A (TSA, 500 nM). Reactions were stopped by the addition of SDS sample buffer, boiled and analyzed by immunoblotting. Acetylated AceCS2$^{myc\text{-}His}$ was detected with acetyl-lysine-specific antibodies (Ac-AceCS2$^{myc\text{-}His}$). Blots were stripped and probed for total levels of AceCS2 with α-myc antibodies (AceCS2$^{myc\text{-}His}$). The presence of Flag-tagged SIRT3 and SIRT5 was verified by immunoblotting with anti-Flag antibodies (lower panel; Input (Sirtuins)). (B) Recombinant human AceCS2 purified from nicotinamide-treated *E. coli* was incubated with purified recombinant sirtuins in the presence or absence of $NAD^+$ (1 mM) and in the presence of TSA (500 nM) for 3 h at 32° C. and analyzed as described in (A). Recombinant SIRT3 or SIRT5 proteins were detected by probing with anti-myc-antibodies (lower panel; Input (Sirtuins)). (C) SIRT3, but not a catalytically inactive mutant of SIRT3, deacetylates AceCS2 in vitro. Deacetylation assays were performed and analyzed as described above. Where indicated, nicotinamide (NAM; 10 mM) was included during the incubation. Details are presented in Example 10.

To further address whether SIRT3 has a role in deacetylating AceCS2 in cells, AceCS2$^{Flag}$-expressing HEK293 cells were treated with siRNAs against SIRT3 or control siRNAs and the acetylation status of immunoprecipitated AceCS2$^{Flag}$ was examined by immunoblotting with antibodies to acetylated lysine (FIG. 7). Acetylation of AceCS2$^{Flag}$ was increased after knockdown of endogenous SIRT3, suggesting that SIRT3 affects AceCS2$^{Flag}$ acetylation in vivo (FIG. 7).

Example 10

SIRT3 Deacetylates AceCS2; SIRT4 and SIRT5 Don't

Acetylation of the active site lysine in *Salmonella enterica* ACS inactivates the enzyme (Starai et al., 2002, Science 298:2390-2). *Salmonella enterica* CobB, which deacetylates ACS, is a class III sirtuin that is most closely related to human SIRT5. SIRT5 localizes to mitochondria and is subject to N-terminal processing (Michishita et al., 2005, *Mol Biol Cell* 16:4623-35). To test whether SIRT5 could deacetylate AceCS2, in vitro deacetylation assays were performed. Immunoprecipitated Flag-tagged sirtuins from HEK293 cells were prepared as described by North et al. (North et al., 2003, *Mol Cell* 11:437-44). While immunoprecipitated Flag-tagged SIRT5 has low but detectable activity on a chemically acetylated H4 peptide (North et al., 2003, Mol Cell 11:437-44), it failed to deacetylate AceCS2 (FIG. 8A). In contrast, immunoprecipitated Flag-tagged SIRT3 deacetylated AceCS2 in a $NAD^+$-dependent manner (FIG. 8A). Flag-tagged SIRT4, another mitochondrial sirtuin with no reported deacetylase activity (North et al., 2003, *Mol Cell* 11:437-44), did not deacetylate AceCS2 (data not shown).

To confirm the findings regarding SIRT3 and SIRT5, recombinant sirtuins were expressed and purified. Based on the finding that SIRT5 is N-terminally truncated (Michishita et al., 2005, *Mol Biol Cell* 16:4623-35) and on the presence of two putative MPP R-2 motifs in its N-terminus, two different recombinant SIRT5 proteins were used, lacking either the first 11 (Δ11-SIRT5$^{myc\text{-}His}$) or 38 (Δ38-SIRT5$^{myc\text{-}His}$) amino acid residues, respectively. Again, while recombinant SIRT3 effectively deacetylated AceCS2, both recombinant SIRT5 proteins failed to do so (FIG. 8B). As expected, deacetylation of AceCS2 by SIRT3 was strictly dependent on the presence of $NAD^+$ (FIG. 8B). Also, the sirtuin inhibitor nicotinamide completely prevented the deacetylation of AceCS2 by SIRT3 and the catalytically inactive SIRT3-H248Y mutant (Schwer et al., 2002, *J Cell Biol* 158:647-57) did not deacetylate AceCS2, despite the presence of $NAD^+$ (FIG. 8C).

Example 11

SIRT3 Coimmunoprecipitates with AceCS2 and Deacetylates AceCS2 in Cells

To determine if SIRT5 deacetylates AceCS2 in cells, AceCS2$^{HA}$ and SIRT3$^{Flag}$ or SIRT5$^{Flag}$ were co-expressed in COS-1 cells. AceCS2HA was immunoprecipitated and the immune complexes were analyzed with antibodies to acetylated lysine (FIG. 9A). Overexpression of SIRT3 decreased the acetylation levels of ectopically expressed AceCS2, while SIRT5 had no effect, despite much higher levels of expression (FIG. 9A).

Interestingly, endogenous SIRT3 co-immunoprecipitated with AceCS2$^{Flag}$ from HEK293 cells (FIG. 9B). Together with the findings described above, this suggests that SIRT3 is the bona fide deacetylase of mitochondrial AceCS2.

Example 12

Acetylation of AceCS2 Reduces its Enzymatic Activity

Based on the finding that nicotinamide treatment of *E. coli* during expression of human AceCS2 significantly increased its levels of acetylation it was examined whether acetylation of AceCS2 at Lys642 controls its acetyl-CoA synthetase activity (FIG. 10A). Measurement of the specific activity of AceCS2 purified from bacteria, treated or not with nicotinamide, indicated that hyperacetylated AceCS2 had a significantly lower specific activity (FIG. 10B). These observations suggested that acetylation of AceCS2 inhibited its enzymatic activity, consistent with what has been shown for ACS in bacteria (Starai et al., 2002, *Science* 298:2390-2).

To further test this hypothesis, hyperacetylated AceCS2 purified from nicotinamide treated *E. coli* was incubated with SIRT3 in the presence of $NAD^+$. This treatment led to a complete deacetylation of AceCS2 (FIG. 10C). No deacetylation of AceCS2 was observed when $NAD^+$ was omitted from the reaction, or when a catalytically inactive SIRT3 mutant (H248Y) was used (FIG. 10C).

Further, measurement of the enzymatic activity of AceCS2 with different levels of acetylation, as described above, showed that deacetylation by SIRT3 was associated with a significant increase in enzymatic activity (FIG. 10D).

In an additional experiment, it was found that incubation of AceCS2 with SIRT3 and $NAD^+$ caused a progressive deacetylation of AceCS2 over time, which could not be observed with the inactive SIRT3-H248Y mutant (FIG. 10E). Again, deacetylation of AceCS2 was associated with a progressive increase in enzymatic activity (FIG. 10F). Based on the data presented herein, it is concluded that the acetylation status of Lys642 controls the activity of human mitochondrial AceCS2.

Example 13

Summary and Discussion

In *Salmonella enterica*, acetylation of ACS by the protein acetyltransferase Pat inactivates the enzyme, while deacetylation by the sirtuin CobB reactivates it (Starai et al., 2002, *Science* 298:2390-2; Starai et al., 2004, *J Mol Biol* 340:1005-12). The acetyl-CoA synthetase reaction, which results in the formation of acetyl-CoA from acetate, ATP and CoA proceeds in two steps. In a first step, acetate is activated to acetyl-adenosine monophosphate (acetyl-AMP). In a second step, acetyl-AMP is converted to acetyl-CoA by the thioester bond forming activity of ACS and acetyl-CoA and AMP are released sequentially (reviewed in Starai et al., 2004, *Cell Mol Life Sci* 61:2020-30). It has been shown that lysine acetylation of the active site lysine (Lys609) of bacterial ACS specifically inhibits the ATP-dependent adenylation of acetate to acetyl-AMP, while the second step of the ACS reaction remains unaffected (Starai, et al., 2002, *Science* 298:2390-2). As illustrated in FIG. 3A, Lys642 of AceCS2 corresponds to the active site lysine Lys609 of ACS from *Salmonella enterica*. Given the conservation of the active site region between ACS and human AceCS2, it is proposed that acetylation of Lys642 of AceCS2 interferes with the first reaction step involving the activation of acetate to acetyl-AMP.

AceCS2 is the first example of a mitochondrial protein being controlled by reversible lysine acetylation and the first target protein for a mitochondrial sirtuin deacetylase. A schematic overview of the regulation of AceCS2 by reversible lysine acetylation is given in FIG. 11. The data presented herein support the model that activation of AceCS2 by SIRT3 is an evolutionarily conserved metabolic control mechanism. The interconversion of acetyl-CoA (in former times known as "activated acetate") and acetate, referred to as the "acetate switch", exists in archaea, eubacteria, and eukaryotes and provides the cell with opportunities to recover $NAD^+$, produce ATP and replenish coenzyme A stores (reviewed in Wolfe, 2005, *Microbiol Mol Biol Rev* 69:12-50). The acetate switch is controlled by the acetate-scavenging enzyme acetyl-CoA synthetase. Metabolic pathways such as energy production in the TCA cycle and cholesterol- and fatty acid biosynthesis require acetyl-CoA as an intermediate.

Yeast critically require acetyl-CoA synthetases for growth but this is not the case for mammalian cells. The majority of acetyl-CoA in mammalian cells is produced in pathways that are not dependent on acetyl-CoA synthetase activity. These are the conversion of pyruvate to acetyl-CoA by pyruvate dehydrogenase and β-oxidation, which results in the formation of acetyl-CoA as an end product. However, in mammals, under some circumstances large amounts of acetate are produced that need to be activated by acetyl-CoA synthetase. For example, under ketogenic conditions such as prolonged fasting or diabetes, the liver releases substantial amounts of acetate into the bloodstream (Buckley and Williamson, 1977, *Biochem J* 166:539-45; Seufert et al., 1974, *Biochem Biophys Res Commun* 57:901-9; Yamashita et al., 2001, *Biochim Biophys Acta* 1532:79-87). In addition, the hepatic acetyl-CoA hydrolase, which produces acetate, is activated under ketogenic conditions (Matsunaga et al., 1985, *Eur J Biochem* 152, 331-6). Utilization of the released acetate in extrahepatic tissues requires the action of acetyl-CoA synthetases. The findings that AceCS2 is abundant in heart and skeletal muscle but absent from the liver and induced under ketogenic conditions, suggest that AceCS2 plays an important role in acetate conversion for energy production under ketogenic conditions (Fujino et al., 2001, *J Biol Chem* 276, 11420-6). Based on the finding that a bacterial sirtuin controls the activity of acetyl-CoA synthetase in *Salmonella enterica* and on the presence of sirtuins in all three kingdoms, a universal connection between central metabolism and sirtuins has been proposed (Starai et al., 2003, *Genetics* 163, 545-55; Starai et al., 2002, *Science* 298, 2390-2). The findings described herein showing that AceCS2 can be inactivated by acetylation of its active site lysine and reactivated by a mitochondrial sirtuin, support these claims and demonstrate the conservation of these pathways from bacteria to mammalian mitochondria.

What is claimed is:

1. A method for identifying an agent that increases the deacetylase activity of a sirtuin 3 (SIRT3) polypeptide, the method comprising the steps of:

(a) contacting a cell expressing a SIRT3 polypeptide and an Acetyl-CoA Synthetase 2 (AceCS2) polypeptide with a candidate agent; and (b) determining the effect, if any, of the candidate agent on the level of acetylated AceCS2 polypeptide in the cell;

wherein said determining comprises:

i) an immunological assay using an antibody specific for the acetylated AceCS2 polypeptide;

ii) detecting acetyl CoA synthetase activity using an enzymatic assay; or iii) detecting an acetylated AceCS2 by mass spectroscopy, wherein a decrease in a first level of acetylated AceCS2 polypeptide in the cell relative to a second level of acetylated AceCS2 polypeptide in a cell, which has not been treated with the candidate agent, is indicative of an agent that increases the deacetylase activity of the SIRT3 polypeptide.

2. The method of claim 1, wherein step (b) comprises an immunological assay using an antibody specific for the acetylated AceCS2 polypeptide.

3. The method of claim 2, wherein the antibody recognizes an acetylated lysine residue of the acetylated AceCS2 polypeptide.

4. The method according to claim 3, wherein the acetylated lysine is selected from the group consisting of:

(i) lysine 642 of human AceCS2, and (ii) a lysine residue corresponding to human lysine 642 in a mammalian homologue of human AceCS2.

5. The method of claim 1, wherein the cell is a mammalian cell.

6. The method of claim 5, wherein the mammalian cell is selected from the group consisting of a heart cell, a muscle cell, and a brain cell.

7. The method of claim 5, wherein the mammalian cell is a human cell.

8. The method of claim 1, further comprising the step of:

(c) identifying a structure or sequence of the candidate agent.

9. The method according to claim 1, wherein step (b) comprises an enzymatic assay detecting acetyl CoA synthetase activity.

10. The method according to claim 1, wherein step (b) comprises detecting an acetylated AceCS2 by mass spectroscopy.

11. A method for identifying an agent that increases the deacetylase activity of a sirtuin 3 (SIRT3) polypeptide, the method comprising the steps of:

(a) contacting a SIRT3 polypeptide and an acetylated Acetyl-CoA Synthetase 2 (AceCS2) polypeptide in an assay mixture comprising $NAD^+$ with a candidate agent; and (b) determining the effect, if any, of the candidate agent on the level of acetylated AceCS2 polypeptide in the assay mixture;

wherein said determining comprises:

i) an immunological assay using an antibody specific for the acetylated AceCS2 polypeptide;

ii) detecting acetyl CoA synthetase activity using an enzymatic assay; or iii) detecting an acetylated AceCS2 by mass spectroscopy, wherein a decrease in a first level of acetylated AceCS2 polypeptide in the assay mixture relative to a second level of acetylated AceCS2 polypeptide in an assay mixture which has not been treated with the candidate agent, is indicative of an agent that increases the deacetylase activity of the SIRT3 polypeptide.

12. The method of claim 11, wherein step (b) comprises an immunological assay using an antibody specific for the acetylated AceCS2 polypeptide.

13. The method of claim 12, wherein the antibody recognizes an acetylated lysine residue of the acetylated AceCS2 polypeptide.

14. The method according to claim 13, wherein the acetylated lysine is selected from the group consisting of:

(i) lysine 642 of human AceCS2, and (ii) a lysine residue corresponding to human lysine 642 in a mammalian homologue of human AceCS2.

15. The method according to claim 11, wherein step (b) comprises an enzymatic assay detecting acetyl CoA synthetase activity.

16. The method according to claim 11, wherein step (b) comprises detecting an acetylated AceCS2 by mass spectroscopy.

17. A method for identifying an agent that modulates the acetylation status of an Acetyl-CoA Synthetase 2 (AceCS2) polypeptide, the method comprising the steps of:

(a) contacting a cell expressing an AceCS2 polypeptide with a candidate agent; and (b) detecting the acetylation level of AceCS2 polypeptide to determine the effect, if any, of the candidate agent on the acetylation status of the AceCS2 polypeptide in the cell;

wherein a difference in a first level of acetylated AceCS2 polypeptide in the cell relative to a second level of acetylated AceCS2 polypeptide in a cell, which has not been treated with the candidate agent, is indicative of an agent that modulates the acetylation status of the AceCS2 polypeptide.

18. A method for identifying an agent that modulates the acetylation status of an Acetyl-CoA Synthetase 2 (AceCS2) polypeptide, the method comprising the steps of:

(a) contacting an AceCS2 polypeptide in an assay mixture with a candidate agent; and (b) detecting the acetylation level of AceCS2 polypeptide to determine the effect, if any, of the candidate agent on the acetylation status of the AceCS2 polypeptide in the assay mixture;

wherein a difference in a first level of acetylated AceCS2 polypeptide in the assay mixture relative to a second level of acetylated AceCS2 polypeptide in assay mixture which has not been treated with the candidate agent, is indicative of an agent that modulates the acetylation status of the AceCS2 polypeptide.

19. A method for identifying an agent that increases the deacetylase activity of a sirtuin 3 (SIRT3) polypeptide, the method comprising the steps of:

(a) contacting a SIRT3 polypeptide and an acetylated Acetyl-CoA Synthetase 2 (AceCS2) polypeptide in an assay mixture comprising $NAD^+$ with a candidate agent; and (b) determining the effect, if any, of the candidate agent on the level of acetylated AceCS2 polypeptide in the assay mixture;

wherein the acetylated AceCS2 polypeptide comprises a $^{14}C$-labeled acetyl group and step (b) is performed by measuring release of the $^{14}C$-labeled acetyl group, wherein a decrease in a first level of acetylated AceCS2 polypeptide in the assay mixture relative to a second level of acetylated AceCS2 polypeptide in an assay mixture which has not been treated with the candidate agent, is indicative of an agent that increases the deacetylase activity of the SIRT3 polypeptide.

* * * * *